US012383587B2

(12) United States Patent
Choi et al.

(10) Patent No.: US 12,383,587 B2
(45) Date of Patent: Aug. 12, 2025

(54) AAV TRIPLE-PLASMID SYSTEM

(71) Applicant: TAKEDA PHARMACEUTICAL COMPANY LIMITED, Osaka (JP)

(72) Inventors: Vivian Choi, Lexington, MA (US); Xing Li, Jamaica Plain, MA (US)

(73) Assignee: TAKEDA PHARMACEUTICAL COMPANY LIMITED, Osaka (JP)

(*) Notice: Subject to any disclaimer, the term of this patent is extended or adjusted under 35 U.S.C. 154(b) by 920 days.

(21) Appl. No.: 17/288,141

(22) PCT Filed: Oct. 24, 2019

(86) PCT No.: PCT/US2019/057916
§ 371 (c)(1),
(2) Date: Apr. 23, 2021

(87) PCT Pub. No.: WO2020/086881
PCT Pub. Date: Apr. 30, 2020

(65) Prior Publication Data
US 2021/0275614 A1    Sep. 9, 2021

Related U.S. Application Data

(60) Provisional application No. 62/750,603, filed on Oct. 25, 2018.

(51) Int. Cl.
*A61K 35/761* (2015.01)
*A61K 38/17* (2006.01)
*C12N 15/11* (2006.01)

(52) U.S. Cl.
CPC ............ *A61K 35/761* (2013.01); *A61K 38/17* (2013.01); *C12N 15/11* (2013.01)

(58) Field of Classification Search
CPC .............................. A61K 35/761; A61K 38/17
See application file for complete search history.

(56) References Cited

U.S. PATENT DOCUMENTS

| 9,840,719 | B2 | 12/2017 | High et al. |
| 2005/0112765 | A1 | 5/2005 | Li |
| 2016/0032319 | A1* | 2/2016 | Wright ............... A61K 48/0091 435/235.1 |
| 2016/0108373 | A1 | 4/2016 | Bennett et al. |
| 2016/0222356 | A1 | 8/2016 | Zhao et al. |
| 2016/0273058 | A1 | 9/2016 | Akashika et al. |
| 2017/0021038 | A1* | 1/2017 | Pan .......................... A61P 27/02 |

(Continued)

FOREIGN PATENT DOCUMENTS

| CN | 104470545 | 3/2015 |
| CN | 105612253 | 5/2016 |

(Continued)

OTHER PUBLICATIONS

Robert et al. Manufacturing of recombinant adeno-associated viruses using mammalian expression platforms. Biotechnology J. 12:1-16. (Year: 2017).*

(Continued)

*Primary Examiner* — Arthur S Leonard
*Assistant Examiner* — Keenan A Bates
(74) *Attorney, Agent, or Firm* — Troutman Pepper Locke LLP

(57) ABSTRACT

A triple-plasmid system for producing recombinant adeno-associated viruses is disclosed.

12 Claims, 17 Drawing Sheets

Specification includes a Sequence Listing.

(56) References Cited

U.S. PATENT DOCUMENTS

| | | | |
|---|---|---|---|
| 2018/0057842 | A1 | 3/2018 | Stanley et al. |
| 2019/0255152 | A1 | 8/2019 | Kim et al. |

FOREIGN PATENT DOCUMENTS

| | | |
|---|---|---|
| CN | 105765066 | 7/2016 |
| JP | 4473346 B2 | 6/2010 |
| JP | 2016517278 A | 6/2016 |
| JP | 2016-525356 | 8/2016 |
| JP | 2018515102 A | 6/2018 |
| WO | 2012158757 A1 | 11/2012 |
| WO | 2013164793 A2 | 11/2013 |
| WO | 2014144486 A2 | 9/2014 |
| WO | 2015031686 A1 | 3/2015 |
| WO | 2016139321 A1 | 9/2016 |
| WO | 2016196507 A1 | 12/2016 |
| WO | 2018080277 | 5/2017 |
| WO | 2019195727 A1 | 10/2019 |

OTHER PUBLICATIONS

Addgene (pLA230 Sequence Analyzer; sequence from Shinkai A et al. https://www.addgene.org/browse/sequence/7054/ (Year: 2024).*

Shinkai A et al. In vivo mutagenesis by *Escherichia coli* DNA polymerase I. lle(709) in motif A functions in base selection. J Biol Chem. 276(50):46759-64 (Year: 2001).*

Trapani et al. Methods in Molecular Biology 1715: Retinal Gene Therapy. Chapter 11: Dual AAV Vectors for Stargardt Disease: 153-175. (Year: 2017).*

Epitope-tagged transcription factor ChIP-seq (pp. 1-4. 2017). https://www.encodeproject.org/documents/35a9f776-dd6a-44e3-8795-50ead83f34f7/@@download/attachment/Guidelines_for_Use_of_Epitope_Tags_in_ChIP-seq_Jan_2017.pdf (Year: 2017).*

Ranjan et al. FLAG tag module for PCR based gene targeting. Journal of Yeast and Fungal Research 1: 165-169. (Year: 2010).*

European Search Report issued Jul. 11, 2022 in connection with EP Application No. 19876857.4.

Xiao et al., "Production of high-titer recombinant adeno-associated virus vectors in the absence of helper adenovirus", Journal of Virology, the American Society for Microbiology, US, vol. 72, No. 3, Mar. 1, 1998, pp. 2224-2232.

English Translation and Japan Office Action for Japanese Patent Application No. 2021-516750 (dated Sep. 22, 2023).

International Search Report mailed Jan. 27, 2020 in connection with PCT/US19/57916.

Written Opinion mailed Jan. 27, 2020 in connection with PCT/US19/57916.

Wang, et al., "A reliable and feasible qPCR strategy for titrating AAV vectors," Medical Science Monitor—Basic Research, Jul. 5, 2013 (Jul. 5, 2013), vol. 19, pp. 187-193.

English Translation and Office Action for Chinese Patent Application No. 201980069110.4 (dated Aug. 17, 2023).

Wright, JF, "Manufacturing and Characterizing AAV-based Vector For Use in Clinical Studies," Gene Therapy 15:840-848 (2008).

Bennicelli et al., "Reversal of Blindness in Animal Models of Leber Congenital Amaurosis Using Optimized AAV2-mediated Gene Transfer," Molecular Therapy 16(3):458-465 (2008).

Hauck et al., "Undetectable Transcription of cap in a Clinical AAV Vector: Implications for Performed Capsid in Immune Responses," Molecular Therapy 17(1):144-152 (2009).

Smith et al., "Packaging of Host Cell and Plasmid DNA into Recombinant Adeno-Associated Virus Particles Produced by Triple Transfection," Molecular Therapy 7(5):S348 (2003).

Ozawa, K., "Gene Therapy Using AAV Vectors," Drug Delivery System 22-6, p. 643-650 (2007) (English abstract only).

Chadeuf et al., "Evidence for Encapsidation of Prokaryotic Sequences During Recombinant Adeno-Associated Virus Production and Their in Vivo Persistence After Vector Delivery," Molecular Therapy 12(4):744-753 (2005).

* cited by examiner

AAV TRIPLE-PLASMID SYSTEM

CROSS-REFERENCE

This application is a 371 National Stage of PCT/US19/57916, filed Oct. 24, 2019, which claims priority U.S. Provisional Patent Application No. 62/750,603, filed Oct. 25, 2018, which are incorporated herein by reference in their entirety.

SEQUENCE LISTING

The instant application contains a Sequence Listing which has been submitted electronically in ASCII format and is hereby incorporated by reference in its entirety. Said ASCII copy, created on Oct. 22, 2019, is named 250478_001858_SL.txt and is 274,165 bytes in size.

BACKGROUND

Adeno-associated virus (AAV) is a DNA parvovirus that infects humans and various other animal species such as primates, bovine, feline, and canines. It belongs to the family Parvoviridae and is placed in the genus *Dependovirus*, because productive infection by AAV occurs only in the presence of a helper virus (e.g., adenovirus or herpes virus). This small non-enveloped virus contains a 4.6 kbases single stranded DNA genome that encodes sets of replication (Rep) and capsid (Cap) proteins. For example, Rep proteins (Rep78, Rep68, Rep52 and Rep40) are involved in replication, rescue and integration of the AAV genome, and Cap proteins (VP1, VP2 and VP3) provides structural function and form the virion capsid. Flanking the Rep and Cap open reading frames at the 5' and 3' ends are 145 bp inverted terminal repeats (ITRs). The ITRs function in cis as origins of nucleic acid replication and as packaging signals for the virus.

There are two stages to the AAV life cycle once infection has occurred: 1) the lytic stage and 2) the lysogenic stage. With the aid of the helper virus, the lytic stage begins. During this stage AAV commences productive infection resulting in genome replication, viral gene expression, and virion production. The case of the adenoviral helper, the adenoviral proteins that provide helper functions regarding AAV expression include E1a, E1b, E2a, E4, and VA RNA. The adenovirus helps regulate cellular gene expression by providing the proper milieu for AAV productive infection. See Daya and Berns *Clinical Microbiology Reviews* October 2008, p. 583-593.

AAV is a versatile virus that can be engineered for gene therapy. Recombinant Adeno-Associated Viral Vector (rAAV), which lacks viral genes in its DNA genome, used of gene therapy is primarily a protein-based nanoparticle engineered to cross the cell membrane in order to traffic and deliver its DNA cargo into the nucleus of a cell. rAAV DNA genome can form circular concatemers persisting as episomes in the nucleus of a transduced cell. As the rAAV DNA does not integrate into the host genome, which contributes to the long-term gene expression and durability, which is one of the reasons rAAV is ideal for gene therapy.

Recombinant forms of AAV (rAAV) have been developed as vectors by replacing all viral genes with a therapeutic transgene expression cassette, while retaining the only cis elements, the ITRs, which is required for vector packaging and DNA replication. See, e.g., U.S. Pat. Nos. 4,797,368; 5,153,414; 5,139,941; 5,252,479; and 5,354,678; and International Publication Nos. WO1991/018088; WO1993/024641 and WO1994/13788. Early methods of rAAV production relied on a two-plasmid system comprising: 1) an AAV helper plasmid (generally encompassing AAV Rep and Cap coding regions, while lacking AAV ITRs so it cannot replicate or package itself) and 2) an ITR-containing plasmid (generally encompassing a selected transgene of interest bounded by AAV ITRs which provides for viral replication and packaging functions). Both the helper plasmid and the ITR-containing plasmid bearing the selected gene can be introduced into suitable cells for production by transient transfection. The transfected cell can then be infected with a helper virus, such as an adenovirus or herpes simplex virus, which transactivates the AAV promoters present on the helper plasmid that direct the transcription and translation of AAV Rep and Cap regions. Regarding the Ad helper virus, the E1a, E1b, E2a, E4, and VA RNA genes can supply the helper functions necessary for rAAV production. Infection of helper virus into producer cells to generate rAAV was effective in producing rAAV; however, a consequence is that it can also produce helper virus particles that can elicit immune responses from the host. In certain platforms, the viral helper genes necessary for AAV manufacturing can be stably transfected into the manufacturing cell line (e.g., HEK293 cells), thereby reducing the possibility of an anti-helper virus immune response by the host immune system coming from trace levels of residual helper virus.

More recently, a triple-plasmid transfection method has been developed. This method uses an AAV serotype-specific Rep and Cap plasmid as well as the transgene-containing plasmid but eliminated the use of helper virus infection by supplying the essential helper viral genes on a third plasmid (i.e., the viral coding sequences were removed or reduced), thus lowering the potential anti-helper virus immune response by the host immune system. Supplying the viral helper genes on the third plasmid greatly decreased helper viral production in the transfected cells, providing only rAAV. Multiplasmid transient transfection of adherent HEK293 cells is a commonly used method for rAAV production.

In a multiplasmid system, it is important to maintain an appropriate plasmid size. Thus, it may be important to add nucleic acid sequences (a.k.a "stuffer sequences") to ensure that the plasmid is of an optimal size. For example, to discourage that the plasmid backbone of the ITR-containing plasmid is not packaged into the vector capsid, a stuffer sequence may need to be added such that the backbone is too large to be effectively packaged into the capsid. However, it is important that the stuffer sequence is "silent" and does not activate the immune system in the small chance that that plasmid does become packaged.

What is needed, therefore, is an improved triple-plasmid based system for producing rAAV. The plasmid system should provide improved transfection and lowered immunogenicity while still retaining optimum expression of the transgene. It is to such a plasmid system that embodiments of the present disclosure are directed.

BRIEF SUMMARY OF THE DISCLOSURE

As specified in the Background Section, there is a great need in the art to improve rAAV plasmid systems for rAAV-based gene therapies. The present disclosure satisfies this and other needs. Embodiments of the present disclosure relate generally to a plasmid system for the production of rAAV and more specifically to a triple-plasmid based system.

In one aspect, the invention is directed to a plasmid system for Recombinant Adeno-Associated Viral Vector (rAAV) production comprising: (i) a transgene-containing plasmid comprising at least one heterologous nucleic acid sequence flanked by a 5' and 3' AAV inverted terminal repeat (ITR) and a stuffer sequence outside of the ITRs; (ii) a plasmid comprising AAV replication (Rep) and capsid (Cap) gene sequences; and (iii) an adenovirus (Ad) helper plasmid.

In certain embodiments, the stuffer sequence increases the size of the transgene-containing plasmid backbone. In certain embodiments, the stuffer sequence increases the size of the transgene-containing plasmid backbone such that the transgene-containing plasmid backbone is discouraged from being packaged into an rAAV capsid. In certain embodiments, the plasmid backbone incorporation into the rAAV is below the limit of detection. In certain embodiments, the backbone of the transgene-containing plasmid is larger than a wild-type AAV genome following the addition of the stuffer sequence.

In certain embodiments, the stuffer sequence is devoid of enhancers, promoters, splicing regulators, noncoding RNAs, antisense sequences, coding sequences, or any combination thereof. In certain embodiments, the stuffer sequence is devoid of enhancers, promoters, splicing regulators, non-coding RNAs, antisense sequences, and coding sequences. In certain embodiments, the stuffer sequence comprises an inert intronic DNA sequence found in the human genome.

In certain embodiments, the stuffer sequence comprises a nucleic acid sequence of between 1000 and 5000 nucleotides in length or a nucleic acid sequence of between 1000 and 2000 nucleotides in length.

In certain embodiments, the stuffer sequence comprises GAPDH intron 2, fragment, or mutant thereof. In certain embodiments, the stuffer sequence comprises an inactivated gentamycin gene.

In certain embodiments, the stuffer sequence comprises a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NO: 9. In certain embodiments, the stuffer sequences comprises SEQ ID NO: 9 or a fragment thereof. In certain embodiments, the fragment is between 800-1000 nucleotides long.

In certain embodiments, the stuffer sequence consists of a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NO: 9. In certain embodiments, the stuffer sequences consists of SEQ ID NO: 9 or a fragment thereof. In certain embodiments, the fragment is between 800-1000 nucleotides long.

In certain embodiments, the transgene-containing plasmid comprises a plasmid with a structure in the same order as FIG. 3A, wherein the eGFP and SEAP transgenes can be replaced with the at least one heterologous nucleic acid sequence.

In certain embodiments, the transgene-containing plasmid comprises a plasmid with a structure in the same order as FIG. 3B, wherein the eGFP transgene can be replaced with the at least one heterologous nucleic acid sequence.

In certain embodiments, the transgene-containing plasmid comprises nucleic acid sequences in the 5' to 3' direction of: a 5' ITR (e.g., SEQ ID NOs: 2 or 43), a promoter (e.g., SEQ ID NO: 4), at least one heterologous nucleic acid sequence, a polyA sequence (e.g., SEQ ID NO: 8), a 3' ITR (e.g., SEQ ID NO: 3), and the stuffer sequence (e.g., SEQ ID NO: 9), wherein each nucleic acid sequence can be substituted with or encodes a corresponding functional fragment or derivative thereof or a sequence with at least 60%, at least 65%, at least 70%, at least 75%, at least 80%, at least 85%, at least 90%, at least 95%, at least 96%, at least 97%, at least 98%, or at least 99% identity therewith.

In certain embodiments, the transgene-containing plasmid further comprises a DNA titer tag outside the expression cassette but between the 5' ITR and 3' ITR.

In certain embodiments, the transgene-containing plasmid further comprises a DNA titer tag i) upstream of the 3' ITR and downstream of a polyA sequence or ii) upstream of the 3' ITR and downstream of the at least one heterologous nucleic acid sequence; iii) or downstream of the 5' ITR and upstream of the at least one heterologous nucleic acid sequence; or iv) downstream of the 5' ITR and upstream of a promoter for the at least one heterologous nucleic acid sequence; or v) downstream of the 5' ITR and upstream of the 3' ITR.

In certain embodiments, the transgene-containing plasmid further comprises a DNA titer tag i) upstream of a 3' ITR (e.g., SEQ ID NO: 3) and downstream of a polyA sequence (e.g., SEQ ID NO: 8) or ii) upstream of a 3' ITR (e.g., SEQ ID NO: 3) and downstream of the at least one heterologous nucleic acid sequence; iii) or downstream of a 5' ITR (e.g., SEQ ID NOs: 2 or 43) and upstream of the at least one heterologous nucleic acid sequence; or iv) downstream of a 5' ITR (e.g., SEQ ID NOs: 2 or 43) and upstream of a promoter (e.g., SEQ ID NO: 4); or v) downstream of a 5' ITR (e.g., SEQ ID NOs: 2 or 43) and upstream of a 3' ITR (e.g., SEQ ID NO: 3).

In certain embodiments, the transgene-containing plasmid comprises nucleic acid sequences in the 5' to 3' direction of: a 5' ITR (e.g., SEQ ID NO: 2 or 43), a promoter (e.g., SEQ ID NO: 4), at least one heterologous nucleic acid sequence, a polyA sequence (e.g., SEQ ID NO: 8), a 3' ITR (e.g., SEQ ID NO: 3), and the stuffer sequence (e.g., SEQ ID NO: 9), wherein each nucleic acid sequence can be substituted with or encodes a corresponding functional fragment or derivative thereof or a sequence with at least 60%, at least 65%, at least 70%, at least 75%, at least 80%, at least 85%, at least 90%, at least 95%, at least 96%, at least 97%, at least 98%, or at least 99% identity therewith.

In certain embodiments, the transgene-containing plasmid further comprises a DNA titer tag outside the expression cassette but between the 5' ITR and 3' ITR.

In certain embodiments, the transgene-containing plasmid further comprises a DNA titer tag i) upstream of the 3' ITR and downstream of a polyA sequence or ii) upstream of the 3' ITR and downstream of the at least one heterologous nucleic acid sequence; iii) or downstream of the 5' ITR and upstream of the at least one heterologous nucleic acid sequence; or iv) downstream of the 5' ITR and upstream of a promoter for the at least one heterologous nucleic acid sequence; or v) downstream of the 5' ITR and upstream of the 3' ITR.

In certain embodiments, the transgene-containing plasmid further comprises a DNA titer tag i) upstream of a 3' ITR (e.g., SEQ ID NO: 3) and downstream of a polyA sequence (e.g., SEQ ID NO: 8) or ii) upstream of a 3' ITR (e.g., SEQ ID NO: 3) and downstream of the at least one heterologous nucleic acid sequence; iii) or downstream of a 5' ITR (e.g., SEQ ID NOs: 2 or 43) and upstream of the at least one heterologous nucleic acid sequence; or iv) downstream of a 5' ITR (e.g., SEQ ID NOs: 2 or 43) and upstream of a promoter (e.g., SEQ ID NO: 4); or v) downstream of a 5' ITR (e.g., SEQ ID NOs: 2 or 43) and upstream of a 3' ITR (e.g., SEQ ID NO: 3).

In certain embodiments, the AAV Rep gene sequence is from AAV serotype 2, 5, 8, 9, or hybrids thereof. In certain embodiments, the AAV Cap gene sequence is from AAV serotype 2, 5, 8, 9, or hybrids thereof. In certain embodiments, the plasmid comprising the Rep and Cap gene sequences further comprises a promoter. In certain embodiments, the promoter is an AAV promoter. In certain embodiments, the promoter is an AAV P5 promoter.

In certain embodiments, the Ad helper plasmid comprises one or more of Adenovirus genes selected from E1a, E1b, E2a, E4orf6, or VA RNA.

In certain embodiments, the Ad helper plasmid comprises nucleic acid sequences in the 5' to 3' direction of: SEQ ID NOs: 18, 17, 16, and 20, wherein each nucleic acid sequence can be substituted with a corresponding functional fragment or derivative thereof or a sequence with at least 60%, at least 65%, at least 70%, at least 75%, at least 80%, at least 85%, at least 90%, at least 95%, at least 96%, at least 97%, at least 98%, or at least 99% identity therewith.

In certain embodiments, the Ad helper plasmid comprises nucleic acid sequences in the 5' to 3' direction of: SEQ ID NOs: 21, 16, 39, 40, 22, 23, and 20 wherein each nucleic acid sequence can be substituted with or encode a corresponding functional fragment or derivative thereof or a sequence with at least 60%, at least 65%, at least 70%, at least 75%, at least 80%, at least 85%, at least 90%, at least 95%, at least 96%, at least 97%, at least 98%, or at least 99% identity therewith.

In certain embodiments, the Ad helper plasmid comprises a structure in the same order as either construct of FIG. 5.

In certain embodiments, the Ad helper plasmid comprises a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NO: 14.

In certain embodiments, the Ad helper plasmid comprises a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NO: 15.

In certain embodiments, the heterologous nucleic acid sequence is a heterologous gene of interest encoding a peptide, polypeptide, or protein. In certain embodiments, the peptide, polypeptide, or protein is an enzyme, antibody, MHC molecule, T-cell receptor, B-cell receptor, aptamer, avimer, receptor-binding ligand, targeting peptides, a therapeutic agent, or gene editing molecule. In certain embodiments, the heterologous nucleic acid sequenceis a nucleic acid sequence such as an antisense, siRNA, shRNA, miRNA, EGSs, gRNA, sgRNA, ribozyme, or aptamer.

In another aspect, the invention is directed to a host cell comprising any one of the plasmid systems described herein.

In another aspect, the invention is directed to a rAAV produced by any one of the plasmid systems described herein.

In another aspect, the invention is directed to a DNA titer tag allowing for universal vector titering, comprising a nucleic acid tag sequence from about 60 nucleotides to about 100 nucleotides long either upstream or downstream from a nucleic acid sequence of a heterologous nucleic acid sequence within a transgene-containing plasmid, wherein the nucleic acid tag sequence can be used in at least two different transgene-containing plasmids to allow for universal vector genome titering between at least two different types of AAV vectors. In certain embodiments, the nucleic acid tag sequence is about 100 nucleotides long.

In certain embodiments, the nucleic acid tag sequence is upstream from a 3' ITR sequence of the transgene-containing plasmid but not within an expression cassette of the transgene-containing plasmid.

In certain embodiments, the nucleic acid tag sequence is downstream from a 5' ITR sequence of the transgene-containing plasmid but not within an expression cassette of the transgene-containing plasmid.

In certain embodiments, the DNA titer tag comprises any one of nucleic acid sequences of SEQ ID NOS: 61-70.

In another aspect, the invention is directed to a method for producing a rAAV comprising transducing a cell with the any one of the plasmid systems described herein and isolating the rAAV. In another aspect, the invention is directed to a rAAV produced by said method.

In another aspect, the invention is directed to a composition comprising the plasmid system of the invention.

In another aspect, the invention is directed to a pharmaceutical composition comprising the rAAV produced by the plasmid system of the invention.

In another aspect, the invention is directed to a method for delivering or transferring a nucleic acid sequence into a subject's cell, comprising administering the rAAV produced by the plasmid system of the invention to a subject thereby delivering the nucleic acid sequence into the cell. In certain embodiments, the subject's cell is in culture or is present in the subject.

In another aspect, the invention is directed to a method for treating or preventing a disease or disorder in a subject, comprising administering to a subject in need thereof a rAAV produced by the plasmid system of the invention.

In another aspect, the invention is directed to a host cell comprising contacting the host cell with a rAAV produced by the plasmid system of the invention.

These and other objects, features and advantages of the present disclosure will become more apparent upon reading the following specification in conjunction with the accompanying description, claims and drawings.

BRIEF DESCRIPTION OF THE DRAWINGS

FIG. 4A depicts an exemplary AAV Rep-Cap plasmid incorporating different AAV Rep and Cap genes, in accordance with some embodiments of the present disclosure. FIG. 4B depicts an exemplary AAV Rep-Cap plasmid incorporating a promoter from AAV serotype 2.

FIG. 14A depicts an exemplary AAV Rep-Cap plasmid incorporating different AAV Rep and Cap genes, in accordance with some embodiments of the present disclosure. FIG. 14B depicts an exemplary AAV Rep-Cap plasmid incorporating different AAV Rep and Cap genes and incorporating the P5 promoter, in accordance with some embodiments of the present disclosure.

DETAILED DESCRIPTION OF THE DISCLOSURE

Figure 1:
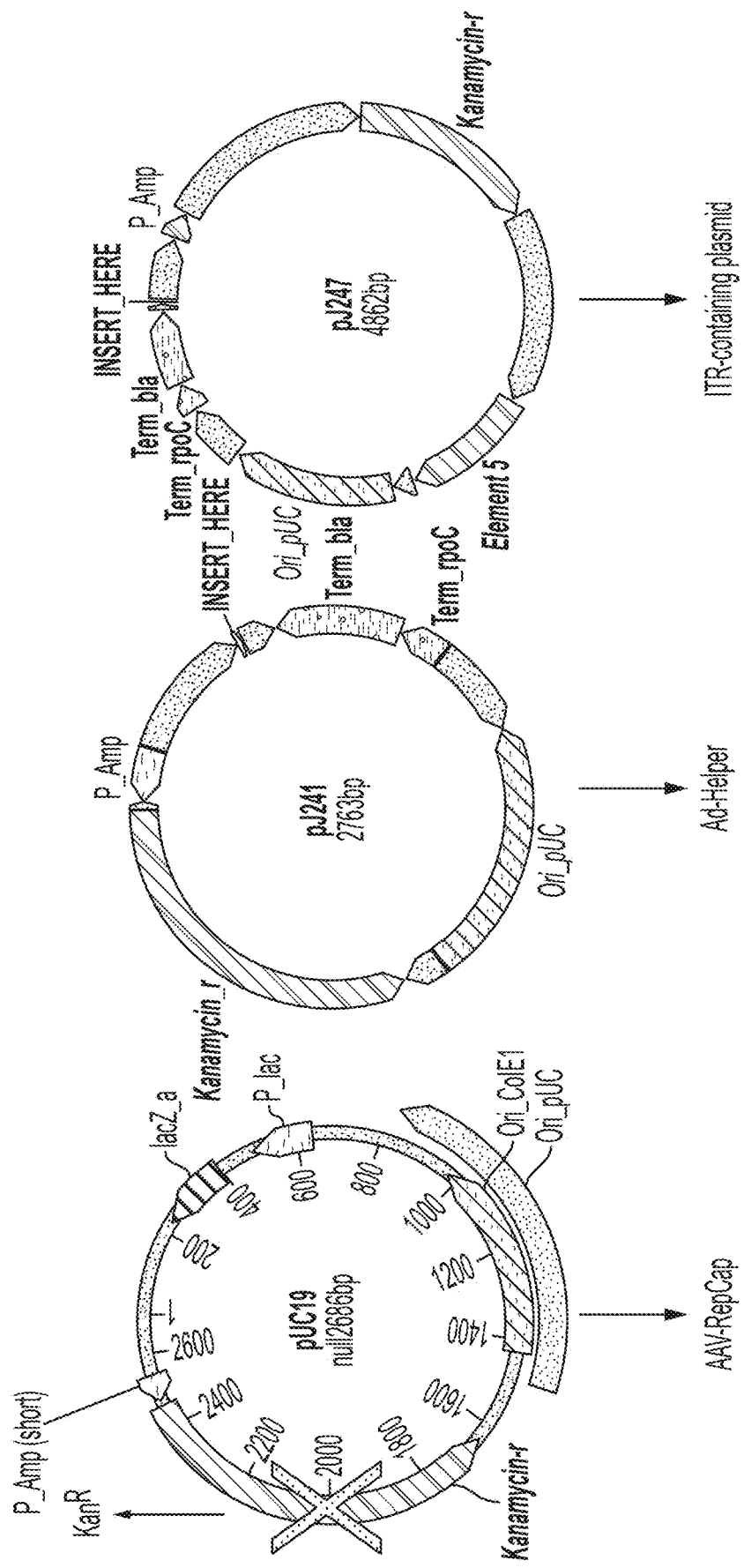
FIG. 1 depicts an exemplary triple-plasmid system for the production of rAAV, in accordance with some embodiments of the present disclosure.
Figure 2:
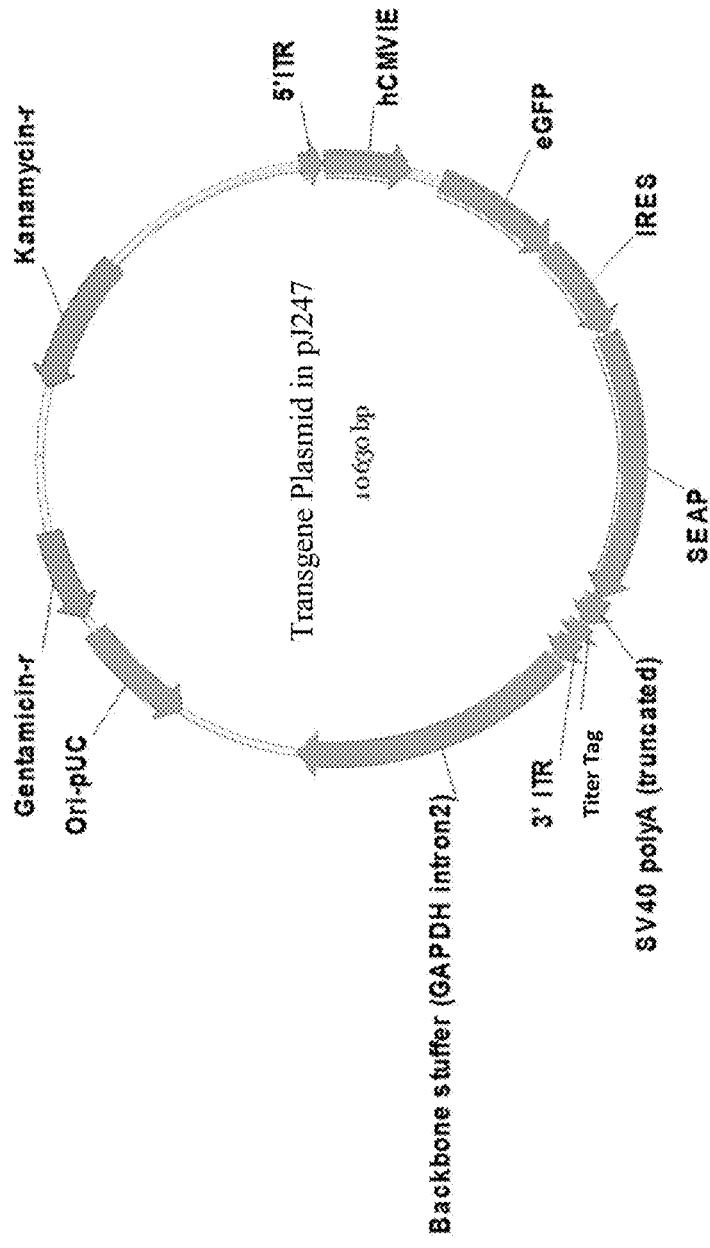
FIG. 2 depicts an exemplary transgene-containing plasmid for rAAV production incorporating eGFP and SEAP as transgenes, in accordance with some embodiments of the present disclosure.

As specified in the Background section, there is a great need in the art to identify technologies for rAAV production to generate rAAV-based gene therapies. The present disclosure satisfies this and other needs. Embodiments of the present disclosure relate generally to a rAAV production and more specifically to a triple-plasmid based system to produce rAAV.

To facilitate an understanding of the principles and features of the various embodiments of the disclosure, various illustrative embodiments are explained below. Although exemplary embodiments of the disclosure are explained in detail, it is to be understood that other embodiments are contemplated. Accordingly, it is not intended that the disclosure is limited in its scope to the details of construction and arrangement of components set forth in the following description or examples. The disclosure is capable of other embodiments and of being practiced or carried out in various ways. Also, in describing the exemplary embodiments, specific terminology will be resorted to for the sake of clarity.

It is intended that each term contemplates its broadest meaning as understood by those skilled in the art and includes all technical equivalents which operate in a similar manner to accomplish a similar purpose. It is to be understood that embodiments of the disclosed technology may be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named. In other words, the terms "a," "an," and "the" do not denote a limitation of quantity, but rather denote the presence of "at least one" of the referenced item.

As used herein, the term "and/or" may mean "and," it may mean "or," it may mean "exclusive-or," it may mean "one,"

it may mean "some, but not all," it may mean "neither," and/or it may mean "both." The term "or" is intended to mean an inclusive "or."

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value. Further, the term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

Throughout this description, various components may be identified having specific values or parameters, however, these items are provided as exemplary embodiments. Indeed, the exemplary embodiments do not limit the various aspects and concepts of the present disclosure as many comparable parameters, sizes, ranges, and/or values may be implemented. The terms "first," "second," and the like, "primary," "secondary," and the like, do not denote any order, quantity, or importance, but rather are used to distinguish one element from another.

It is noted that terms like "specifically," "preferably," "typically," "generally," and "often" are not utilized herein to limit the scope of the claimed disclosure or to imply that certain features are critical, essential, or even important to the structure or function of the claimed disclosure. Rather, these terms are merely intended to highlight alternative or additional features that may or may not be utilized in a particular embodiment of the present disclosure. It is also noted that terms like "substantially" and "about" are utilized herein to represent the inherent degree of uncertainty that may be attributed to any quantitative comparison, value, measurement, or other representation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "50 mm" is intended to mean "about 50 mm".

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

As used herein, the terms "subject", "patient", "individual", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

As used herein, the term "gene therapy" includes any therapeutic approach of providing a nucleic acid encoding a therapeutic gene (e.g., a Factor VIII/IX/X) to a patient to relieve, diminish, or prevent the reoccurrence of one or more symptoms (e.g., clinical factors) associated with a disease or condition. The term encompasses administering any compound, drug, procedure, or regimen comprising a nucleic acid encoding a therapeutic gene, including any modified form of the gene (e.g., a Factor VIII/IX/X variant), for maintaining or improving the health of an individual with the disease or condition. One skilled in the art will appreciate that either the course of gene therapy or the dose of a genetic therapeutic agent can be changed, e.g., based upon the results obtained in accordance with the present disclosure.

As used herein the term "therapeutically effective" applied to dose or amount refers to that quantity of a compound or pharmaceutical composition that when administered to a subject for treating (e.g., preventing or ameliorating) a state, disorder or condition, is sufficient to affect such treatment. For example, a therapeutically effective amount of a drug useful for treating hemophilia can be the amount that is capable of preventing or relieving one or more symptoms associated with hemophilia. The "therapeutically effective amount" will vary depending on the compound or bacteria or analogues administered as well as the disease and its severity and the age, weight, physical condition and responsiveness of the mammal to be treated. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, the term "vector" refers to any vehicle used to transfer a nucleic acid (e.g., encoding a gene therapy construct) into a host cell. In some embodiments, a vector includes a replicon, which functions to replicate the vehicle, along with the target nucleic acid. In some embodiments, a vector is a viral particle for introducing a target nucleic acid (e.g., a codon-altered polynucleotide encoding a therapeutic gene or therapeutic gene variant). Many modified eukaryotic viruses useful for gene therapy are known in the art. For example, adeno-associated viruses (AAVs) are particularly well suited for use in human gene therapy because humans are a natural host for the virus, the native viruses are not known to contribute to any diseases, and the viruses elicit a mild immune response. "Recombinant AAV" (rAAV) and "AAV" are used interchangeably throughout the application.

The term "plasmid" refers to an extrachromosomal circular DNA capable of autonomous replication in a given bacterial cell. Exemplary plasmids include but are not limited to those derived from pBR322, pUC, pUC19, pUC57, pJ241, or pJ247, pBluescript, pREP4, pCEP4, pCI, and p Poly (Lathe et al., Gene 57 (1987), 193-201). Plasmids can also be engineered by standard molecular biology techniques (Sambrook et al., Laboratory Manual, Cold Spring Harbor Laboratory Press, Cold Spring Harbor (1989), N.Y.). It may also comprise a selection gene in order to select or to identify the transfected cells (e.g., by complementation of a cell auxotrophy or by antibiotic resistance), stabilizing elements (e.g., cer sequence) or integrative elements (e.g., LTR viral sequences and transposons).

As used herein, the term "plasmid backbone" refers to a sequence of DNA that typically contains an origin of replication (e.g., SEQ ID NOs: 20 and 26), and an antibiotic selection gene, which are necessary for the specific growth of only the host that is transformed with the proper plasmid. In certain embodiments, these elements are not intended to be packaged in the rAAV capsid.

As used herein, the term "gene" refers to the segment of a DNA molecule that codes for a polypeptide chain (e.g., the coding region). In some embodiments, a gene is positioned by regions immediately preceding, following, and/or intervening the coding region that are involved in producing the polypeptide chain (e.g., regulatory elements such as a promoter, enhancer, polyadenylation sequence, 5'-untranslated region, 3'-untranslated region, or intron).

As used herein, the term "regulatory elements" refers to nucleic acid sequences, such as promoters, enhancers, terminators, polyadenylation sequences, introns, etc . . . , that provide for the expression of a coding sequence in a cell.

As used herein, the term "promoter element" refers to a nucleic acid sequence that assists with controlling expression of a coding sequence. Generally, promoter elements are located 5' of the translation start site of a gene. However, in certain embodiments, a promoter element may be located within an intron sequence, or 3' of the coding sequence. In some embodiments, a promoter useful for gene therapy is derived from the native gene of the target protein. In some embodiments, a promoter useful for gene therapy is specific for expression in a particular cell or tissue of the target organism (e.g., a liver-specific promoter) (Wu Z et al. Molecular Therapy 16(2):280-9. Choi V W et al. Molecular Therapy Methods & Clinical Development 2015. 2:15022), both of which are incorporated herein in their entirety for all intended purposes. In yet other embodiments, one of a plurality of well characterized promoter elements is used in gene therapy described herein.

Non-limiting examples of well-characterized promoter elements include the CMV early promoter (e.g., hCMVie (SEQ ID NO: 4))), the 3-actin promoter, and the methyl CpG binding protein 2 (MeCP2) promoter. In some embodiments, the promoter is a constitutive promoter, which drives substantially constant expression of the target protein. In other embodiments, the promoter is an inducible promoter, which drives expression of the target protein in response to a particular stimulus (e.g., exposure to a particular treatment or agent). For a review of designing promoters for AAV-mediated gene therapy, see Gray et al. (Human Gene Therapy 22:1143-53 (2011)), the contents of which are expressly incorporated by reference in their entirety for all purposes.

As used herein, the term "transgene" broadly refers to any nucleic acid that is introduced into the genome of an animal, including but not limited to genes or nucleic acid having sequences which are perhaps not normally present in the genome, genes which are present but not normally transcribed and translated ("expressed") in a given genome, or any other gene or nucleic acid which one desires to introduce into the genome. This may include genes which may normally be present in the non-transgenic genome, but which one desires to have altered in expression, or which one desires to introduce in a non-mutated form or an altered or variant form. The transgene may be specifically targeted to a defined genetic locus, may be randomly integrated within a chromosome, or it may be extrachromosomally replicating DNA. A transgene may include one or more transcriptional regulatory sequences and any other nucleic acid, such as introns, that may be necessary for optimal expression of a selected nucleic acid. A transgene can be as few as a couple of nucleotides long, but is preferably at least about 50, 100, 150, 200, 250, 300, 350, 400, or 500 nucleotides long or even longer and can be, e.g., an entire viral genome. A transgene can be coding or non-coding sequences, or a combination thereof. A transgene usually comprises a regulatory element that is capable of driving the expression of one or more transgenes under appropriate conditions.

As used herein, the term "heterologous" as it relates to nucleic acid sequences, such as coding sequences and/or control sequences, denotes sequences that are not normally joined together and/or are not normally associated with a particular cell. Thus, a "heterologous" nucleic acid sequence means that the nucleic acid sequence is from an organism other than AAV or is synthetically derived. In certain embodiments, the heterologous nucleic acid sequence (e.g., a heterologous gene of interest) can encode a polypeptide such as, but not limited to, a clotting factor, an enzyme, an antibody or other polypeptide of interes. In certain embodiments, the heterologous nucleic acid sequence can encode an RNA having a structural or therapeutic function such as, but not limited to, an antisense, siRNA, shRNA, miRNA, EGSs, gRNA, sgRNA, ribozyme, or aptamer. Similarly, a cell transformed with a construct which is not normally present in the cell would be considered heterologous for purposes of this invention.

"Operably-linked" refers to the association of two or more nucleic acid sequence elements that are physically linked so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

As used herein, the term "nucleic acid" refers to deoxyribonucleotides or ribonucleotides and polymers thereof in either single- or double-stranded form and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

The term "amino acid" refers to naturally occurring and non-natural amino acids, including amino acid analogs and amino acid mimetics that function in a manner similar to the naturally occurring amino acids. Naturally occurring amino acids include those encoded by the genetic code, as well as those amino acids that are later modified, e.g., hydroxyproline, y-carboxyglutamate, and O-phosphoserine. Naturally occurring amino acids can include, e.g., D- and L-amino acids. The amino acids used herein can also include non-natural amino acids. Amino acid analogs refer to compounds that have the same basic chemical structure as a naturally occurring amino acid, i.e., any carbon that is bound to a hydrogen, a carboxyl group, an amino group, and an R group, e.g., homoserine, norleucine, methionine sulfoxide, or methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "derivative" as used herein refers to a nucleic acid, peptide, or protein or a variant or analog thereof comprising one or more mutations and/or chemical modifications as compared to a corresponding full-length wild type nucleic acid, peptide or protein. Non-limiting examples of chemical modifications involving nucleic acids include, for example, modifications to the base moiety, sugar moiety, phosphate moiety, phosphate-sugar backbone, or a combination thereof.

The nucleic acid sequences that encode mutant gene constructs that may be useful with the plasmid system described herein may be identical to a wildtype (i.e., unmutated) sequence or may be a different coding sequence, which sequence, as a result of the redundancy or degeneracy of the genetic code, encodes the same polypeptides as the wildtype coding sequence. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each variation of a nucleic acid which encodes a same polypeptide is implicit in each described sequence with respect to the expression product, but not with respect to actual gene therapy constructs.

As to amino acid sequences, one of ordinary skill in the art will recognize that individual substitutions, deletions or additions to a nucleic acid or peptide sequence that alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure. Conservative amino acid substitutions providing functionally similar amino acids are well known in the art. Dependent on the functionality of the particular amino acid, e.g., catalytic, structural, or sterically important amino acids, different groupings of amino acid may be considered conservative substitutions for each other.

The terms "identical" or percent (%) "identity," in the context of two or more nucleic acids or peptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection.

As is known in the art, a number of different programs may be used to identify whether a protein (or nucleic acid as discussed below) has sequence identity or similarity to a known sequence. Sequence identity and/or similarity is determined using standard techniques known in the art, including, but not limited to, the local sequence identity algorithm of Smith & Waterman, Adv. Appl. Math., 2:482 (1981), by the sequence identity alignment algorithm of Needleman & Wunsch, J. Mol. Biol., 48:443 (1970), by the search for similarity method of Pearson & Lipman, Proc. Natl. Acad. Sci. U.S.A., 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res., 12:387-395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc, all of which are incorporated by reference.

In accordance with the present disclosure there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); Oligonucleotide Synthesis (M. J. Gait ed. 1984); *Nucleic Acid Hybridization* (B. D. Hames & S. J. Higgins eds. (1985); *Transcription and Translation* (B. D. Hames & S. J. Higgins, eds. (1984); *Animal Cell Culture* (R. I. Freshney, ed. (1986); *Immobilized Cells and Enzymes* (IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994); among others.

Plasmid Systems of the Disclosure

In one aspect, the disclosure provides a triple-plasmid system for engineering and producing Recombinant Adeno Associated Viral Vector (rAAV). In certain embodiments, the three plasmid backbones are all the same. In certain embodiments, at least one of the three plasmid backbones are different. In certain embodiments, all three plasmid backbones are different. In certain embodiments, all three plasmid backbones are different to prevent recombination occurring that can lead to the reconstruction of the complete AAV genome. In certain embodiments, the three plasmids comprise plasmid backbones based on, for example and without limitation, pUC19, pBR322, pUC57, pJ241, or pJ247. In certain embodiments, the three plasmids comprise plasmid backbones based on pUC19, pJ241, and pJ247.

In certain embodiments, one plasmid serves as the transgene-containing plasmid for rAAV production construct, a second plasmid serves as the AAV Rep-Cap construct, and a third plasmid serves as the Adenovirus (Ad) Helper construct. Exemplary plasmids of each type are shown in FIG. 1.

Transgene-Containing Plasmid for rAAV Production

The transgene-containing plasmid for rAAV production is engineered to carry at least one heterologous nucleic acid sequence of interest (e.g., an anti-sense RNA molecule, shRNA, miRNA, a ribozyme, or a gene encoding a polypeptide of interest) in which the internal portion of the AAV genome is replaced with a heterologous nucleic acid sequence of interest within an expression cassette. "Expression cassette" as used herein means a nucleic acid sequence capable of directing expression of a particular heterologous nucleic acid sequence in an appropriate host cell (e.g., mammal), which may include a promoter operably linked to the nucleic acid sequence of interest that may be operably linked to termination signals. The expression cassette including the heterologous nucleic acid sequence of interest may be chimeric. The expression cassette may also be one that is naturally occurring but has been obtained in a recombinant form useful for heterologous expression.

In certain embodiments, the transgene-containing plasmid does not comprise an antibiotic resistance gene. In certain embodiments, the transgene-containing plasmid does not comprise an ampicillin resistance gene (e.g., SEQ ID NOs: 71 and 73). While antibiotic resistance genes are commonly used as selection markers for plasmid production, the inclusion of an antibiotic resistance gene (e.g., ampicillin resistance gene) can raise safety concerns. For example, there can be a horizontal gene transfer to patient's bacteria, which would be prevented if the gene is not present in the plasmid. It is particularly important to avoid using antibiotic selection markers involving antibiotics that are in significant clinical use, in order to avoid unnecessary risk of spread of antibiotic resistance traits to environmental microbes (e.g., ampicillin). One should also avoid using antibiotic resistance genes for antibiotics that cause serious hypersensitivity reactions in patients as there could be residual antibiotic in the pharmaceutical composition (e.g., penicillin and other β-lactam antibiotics).

Exemplary transgene-containing plasmids according to the invention is shown in FIGS. 2, 3A, 3B, 15A, and 15B and SEQ ID NOs: 1, 42, 71, and 73, or a plasmid with at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NOs: 1, 42, 71, and 73. FIGS. 2, 3A, 3B, 15A, and 15B provides an example of the order of the elements of the transgene-containing plasmids of the invention.

The transgene-containing plasmids according to SEQ ID NOs: 71 and 73 are advantageous because they remove all traces of the ampicillin resistance gene and also include an inactivated gentamycin resistance gene (e.g., the start codon from the open reading frame was removed), which acts as an additional stuffer sequence.

The transgene-containing plasmid is constructed using known techniques to at least provide operatively linked components in the direction of transcription, control elements including a transcriptional initiation region, the DNA of interest and a transcriptional termination region. The control elements are selected to be functional in a mammalian cell. The resulting construct, which contains the operatively linked components, is flanked (5' and 3') with functional AAV inverted terminal repeat (ITR) sequences. Termination signals, such as polyadenylation sites, can also be included in the plasmid.

The ITRs have been shown to be the only cis elements required for packaging allowing for complete gutting of viral genes to create rAAV. Even though the rolling-circle DNA replication mechanism primarily amplifies (i.e., replicates) the transgene expression cassette DNA sequence flanked by the ITRs due to the presence of the D sequence within the ITRs, the plasmid DNA backbone (e.g., origin of replication, antibiotic resistance gene expression cassette, etc.,) can also be packaged into the vector capsid, albeit at a lower frequency due to the absence of the flanking D sequence domain. AAV is efficient in packaging a genome size similar to or smaller than the wildtype virus genome (~4.7 kbases). One could discourage the packaging of the plasmid backbone by increasing the size of the backbone to such a degree that it is unfavorable for the backbone to be packaged into the capsid. Enlargement of the backbone can be achieved by additional "stuffer" sequences (i.e., filler component), resulting in a plasmid backbone size larger than the wild-type AAV genome. Without wishing to be bound by theory, it is suggested that the presence of an enlarged plasmid backbone can reduce the probability of the rAAV packaging the plasmid backbone into the vector capsid. In some embodiments, the enlarged plasmid backbone is created by use of the stuffer sequence.

In certain embodiments, the stuffer sequence is silent in terms of biological activity, in that it is devoid of at least one of enhancers, promoters, splicing regulators, noncoding RNAs, antisense sequences, and/or coding sequences. In certain embodiments, each of enhancers, promoters, splicing regulators, noncoding RNAs, antisense sequences, and coding sequences are absent.

In certain embodiments, the stuffer sequence comprises an inert intronic DNA sequence found in the human genome. By utilizing a DNA sequence from the human genome, there will be lower probability that the stuffer sequence will elicit an immune response in case the plasmid becomes packaged into the capsid. It is also important that the stuffer sequence does not include an open reading frame.

The stuffer sequence should be large enough that the size of the plasmid backbone is larger than the optimal packaging size of rAAV such that the plasmid backbone is not packaged into the vector capsid. The stuffer sequence can consist of at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000 or at least 10000 nucleotides. In certain embodiments, the stuffer sequence comprises a nucleic acid of between 1000 and 5000 nucleotides in length. In certain embodiments, the stuffer sequence comprises a nucleic acid of between 1000 and 2000 nucleotides in length. In certain embodiments, the stuffer sequence comprises a nucleic acid of between 800 and 1500 nucleotides in length. In certain embodiments, the stuffer sequence comprises a nucleic acid of between 800 and 1000 nucleotides in length.

In a preferred embodiment, the stuffer sequence comprises human GAPDH intron 2 (NG007073.2). Without wishing to be bound by theory, the use of human GAPDH intron 2 has lower immunogenicity as it is present in the human genome already and thus should not elicit an immune response if it is by chance packaged. GAPDH intron 2 is ideal as a stuffer sequence as it is a single naturally occurring sequence. There is no need to include any additional nucleotides or to link more than one sequence together, which would result in an unnatural buttressing of DNA sequences.

In certain embodiments, the stuffer sequence comprises, consists of, or consists essentially of a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NO: 9 or a fragment thereof. In certain embodiments, the stuffer sequence comprises, consists of, or consists essentially of SEQ ID NO: 9 or a fragment thereof.

In certain embodiments, the stuffer sequence comprises an inactivated gentamycin gene. In certain embodiments, the gentamycin gene is modified so that it is not expressed. For example, the start codon could be removed.

In certain embodiments, the stuffer sequence comprises, consists of, or consists essentially of a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NO: 72 or a fragment thereof. In certain embodiments, the stuffer sequence comprises, consists of, or consists essentially of SEQ ID NO: 72 or a non-functional fragment thereof.

The transgene-containing plasmid can be constructed using ITRs from any of the various AAV serotypes. These ITRs base pair to allow for synthesis of the complementary DNA strand. The ITRs remain functional in such plasmids to allow replication and packaging of the rAAV containing the heterologous nucleic acid sequence of interest. Mutations within the terminal repeat sequences of AAV plasmids are well tolerated in generating functional AAV vectors. See e.g., Samulski et al, 1983; Muzyczka et al, 1984; and U.S. Pat. No. 9,163,259, which of which as incorporated herein in their entirety for all purposes. Even plasmids with one of the two ITRs deleted, the AAV sequences could be rescued, replicated, and infectious virions be produced, as long as the existing ITR in the construct contains the full AAV ITR sequence.

The nucleic acid sequences of AAV ITR regions are known. The ITR need not have the wild-type nucleic acid sequence, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV6, AAV7, AAV8, AAV9, AAV10, AAV11, or a chimera thereof. Furthermore, 5' and 3' ITRs which flank a selected nucleic acid sequence in an AAV vector need not necessarily be identical or derived from the same AAV serotype or isolate, so long as they function as intended, i.e., to allow for excision and rescue of the sequence of interest from a host cell genome. Even though SEQ ID NOs: 2 and 43 is used as an example of the 5' ITR sequence of the rAAV described in this document, it is expected that any 5' ITR sequence that carries the terminal resolution site would produce vectors with the same functionality. Likewise, even though SEQ ID NO: 3 is used as an example of the 3' ITR sequence of the rAAV described in this document, it is expected that any 3' ITR sequence that carries the terminal resolution site would produce vectors with the same functionality.

In certain embodiments, the 5' ITR sequence comprises, consists of, or consists essentially of a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NO: 2 or SEQ ID NO 43 or a functional fragment or derivative thereof. In certain embodiments, the 5' ITR comprises, consists of, or consists essentially of SEQ ID NO: 2 or SEQ ID NO 43, or a functional fragment or derivative thereof.

In certain embodiments, the 3' ITR sequence comprises, consists of, or consists essentially of a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NO: 3 or a functional fragment or derivative thereof. In certain embodiments, the 3' ITR comprises, consists of, or consists essentially of SEQ ID NO: 3, or a functional fragment or derivative thereof.

In certain embodiments, the transgene-containing plasmid comprising the stuffer sequence as described above is operably linked to an expression cassette.

In certain embodiments, the expression cassette comprises a promoter. In certain embodiments, the at least one heterologous nucleic acid sequence (e.g., heterologous gene of interest) is operably linked to a pol II promoter (constitutive, cell-specific, or inducible) such that the heterologous nucleic acid sequence is capable of being expressed in the patient's target cells under appropriate or desirable conditions. Numerous examples of constitutive, cell-specific, and inducible promoters are known in the art, and one of skill could readily select a promoter for a specific intended use, e.g., the selection of the muscle-specific skeletal α-actin promoter or the muscle-specific creatine kinase promoter/enhancer for muscle cell-specific expression, the selection of the constitutive CMV promoter for strong levels of continuous or near-continuous expression (e.g., hCMVie (SEQ ID NO: 4)), or the selection of the inducible ecdysone promoter for induced expression. Induced expression allows the skilled artisan to control the amount of protein that is synthesized. In this manner, it is possible to vary the concentration of therapeutic product. Other examples of well-known inducible promoters are: steroid promoters (e.g., estrogen and androgen promoters) and metallothionein promoters. In certain embodiments, the promoter is a pol III promoter. In certain embodiments, the promoter is a U6 promoter. In certain embodiments, the promoter is an H1 promoter. In certain embodiments, the gene expression cassette is without a promoter.

In certain embodiments, the transgene-containing plasmid is multicistronic, i.e., carries more than one gene. Unlike promoters which will create unique mRNA transcripts for each gene that is expressed, multicistronic plasmids simultaneously express two or more separate proteins from the same mRNA. In such cases, the multiple genes are separated by an element that allows for separate translation for each gene (e.g., internal ribosomal entry sites (IRES) or 2A peptides).

Even though SEQ ID NO: 6 is used as an example of an IRES sequence of the rAAV described in this document, it is expected that any 5' ITR sequence that carries the terminal resolution site would produce vectors with the same functionality.

IRES allow for initiation of translation from an internal region of the mRNA by acting as another ribosome recruitment site. In certain embodiments, the IRES sequence comprises, consists of, or consists essentially of a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NO: 6 or a functional fragment or derivative thereof. In certain embodiments, IRES comprises, consists of, or consists essentially of SEQ ID NO: 6 or a functional fragment or derivative thereof.

In certain embodiments, the transgene-containing plasmid encodes a 2A peptide. 2A peptides (see non-limiting examples in Table 1 below) were created to overcome some of the disadvantages of the IRES element. In particular 2A peptides are "self-cleaving" in that these peptides are thought to function by making the ribosome skip the synthesis of a peptide bond at the C-terminus of a 2A element, leading to separation between the end of the 2A sequence and the next peptide downstream. The "cleavage" occurs between the Glycine and Proline residues found on the C-terminus meaning the upstream cistron will have a few additional residues added to the end, while the downstream cistron will start with the Proline. 2A cleavage is universal in eukaryotic cells, and, some scientists report close to 100% cleavage. The choice of specific 2A peptide will ultimately depend on a number of factors such as cell type or experimental conditions, which one of ordinary skill would be understand which one to choose.

TABLE 1

Examples of four common 2A peptides.

| Peptide | Amino acid sequence* |
|---|---|
| T2A: | (GSG) E G R G S L L T C G D V E E N P G P (SEQ ID NO: 74) |
| P2A: | (GSG) A T N F S L L K Q A G D V E E N P G P (SEQ ID NO: 75) |
| E2A: | (GSG) Q C T N Y A L L K L A G D V E S N P G P (SEQ ID NO: 76) |
| F2A: | (GSG) V K Q T L N F D L L K L A G D V E S N P G P (SEQ ID NO: 77) |

*(GSG) residues can be added to the 5' end of the peptide to improve cleavage efficiency.

Figure 3A:
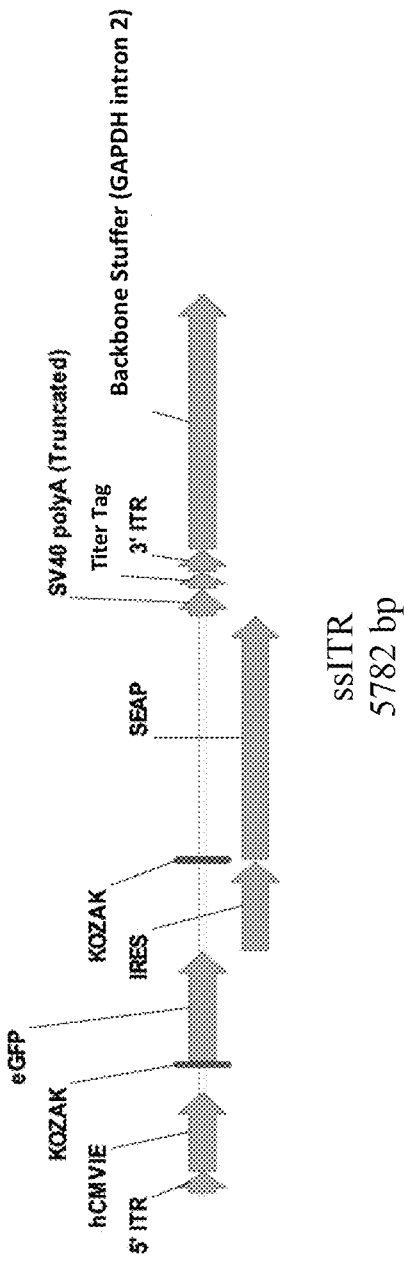
FIGS. 3A-3B: shows exemplary gene constructs of transgene-containing plasmids for single-stranded (ss) (FIG. 3A) and self-complementary (sc) rAAV (FIG. 3B) production.
Figure 3B:
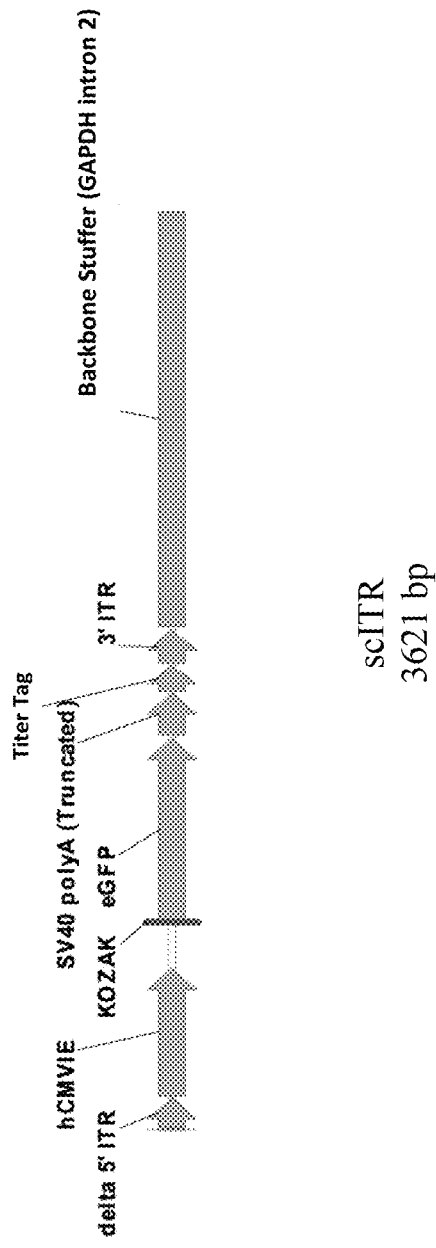

In an embodiment, the plasmid comprises 5' and 3' ITRs from an AAV, wherein the ITRs surround at least one gene. In certain embodiments, a stuffer sequence is located downstream of the 3' ITR. In certain embodiments, the stuffer sequence is upstream of the 5' ITR. ITRs can be from AAV serotypes AAV1, AAV2, AAV3, AAV4, AAV5, AAV6, AAV7, AAV8, AAV9, AAV10, and/or AAV11, or a chimera thereof. In certain embodiments, the ITRs are from AAV serotypes AAV2 and/or AAV5. In certain embodiments, the ITRs can be SEQ ID NO: 2, 3, or 43, or a functional fragment or derivative thereof. In some embodiments, the gene is a reporter gene, such as for example and not limitation, eGFP (e.g., SEQ ID NO: 5) and/or SEAP (e.g., SEQ ID NO: 7). In some embodiments, the stuffer sequence is GAPDH intron 2 or a fragment or variant thereof. In some embodiments, the stuffer sequence is SEQ ID NO: 9 or a fragment thereof. Exemplary gene constructs are shown in FIG. 3 for use in plasmids to generate ssAAV (FIG. 3A) and scAAV (FIG. 3B) rAAV.

Rep-Cap Plasmid

The second plasmid comprises AAV replication (Rep) and capsid (Cap) gene sequences. The AAV Rep-Cap plasmid includes both of the major AAV genes open reading frames (ORFs), Rep gene, and Cap gene. Rep proteins have been shown to possess many functions, including, among others: recognition, binding and nicking of the AAV origin of DNA replication; DNA helicase activity; and modulation of transcription from AAV (or other heterologous) promoters. Cap proteins supply necessary packaging functions and assemble into the viral capsid shell. AAV helper functions are used herein to complement AAV functions in trans that are missing from AAV vectors. Rep and Cap genes are translated to produce multiple distinct proteins (Rep78, Rep68, Rep52, Rep40—required for the AAV life cycle; VP1, VP2, VP3— capsid proteins). The Rep and/or Cap genes can be derived from AAV serotypes AAV1, AAV2, AAV3, AAV4, AAV5, AAV6, AAV7, AAV8, AAV9, AAV10, and/or AAV11, or a chimera thereof. In certain embodiments, the AAV Rep and/or Cap genes encode genetically engineered AAV and/or chemically modified AAV. See e.g., AAV virions mutated to be less immunogenic such as those recited in U.S. Pat. No. 7,259,151, incorporated herein by reference for all intended purposes. The selection of the AAV serotype can be selected on the tropism of the AAV serotype. Table 2 below provides examples, without limitation, of tropism of the most widely used AAV serotypes. The tropism of AAV can also be modified via pseudotyping (i.e., the mixing of a capsid and genome from ITRs from a different viral serotypes). These serotypes are denoted using a slash, so that AAV2/5 indicates a virus containing the genome carrying ITR of serotype 2 packaged in the capsid from serotype 5. Use of these pseudotyped viruses can improve transduction efficiency, as well as alter tropism. For example, neurons that are not efficiently transduced by AAV2, one can use AAV2/5, which is distributed more widely in the brain and shown to have improved transduction efficiency. One can also use hybrid capsids derived from multiple different serotypes, which also alter viral tropism. For example, AAV-DJ, which contains a hybrid capsid derived from eight serotypes, displays a higher transduction efficiency in vitro than any wild type serotype; in vivo, it displays very high infectivity across a broad range of cell types. The mutant AAV-DJ8 displays the properties of AAV-DJ, but with enhanced brain uptake. A number of AAV helper plasmids have been described, such as the commonly used plasmids pAAV/Ad and pIM29+45 which encode both Rep and Cap gene expression products. See, e.g., Samulski et al. (1989) J. Virol. 63:3822-3828; and McCarty et al. (1991) J. Virol. 65:2936-2945 and U.S. Pat. Nos. 5,139,941; 6,001,650; 6,376,237; 7,259,151, each of which are incorporated herein by reference in their entirety for all purposes.

TABLE 2

Tissue Tropism of AAV Serotypes

| Tissue | Optimal Serotype |
|---|---|
| Heart | AAV1, AAV8, AAV9 |
| Kidney | AAV2 |
| Liver | AAV7, AAV8, AAV9 |
| Nervous System | AAV1, AAV2, AAV4, AAV5, AAV8, AAV9 |

TABLE 2-continued

Tissue Tropism of AAV Serotypes

| Tissue | Optimal Serotype |
|---|---|
| Lung | AAV4, AAV5, AAV6, AAV9 |
| Pancreas | AAV8 |
| Photoreceptor Cells | AAV2, AAV5, AAV8 |
| RPE (Retinal Pigment Epithelium) | AAV1, AAV2, AAV4, AAV5, AAV8 |
| Skeletal Muscle | AAV1, AAV6, AAV7, AAV8, AAV9 |

An exemplary Rep-Cap plasmid according to the invention is shown in FIGS. 4A, 4B, 14A, and 14B; and SEQ ID NOs: 24, 31, 33, 35, 37, 41, 59, and 60, or a plasmid with at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NOs: 24, 31, 33, 35, 37, 41, 59, or 60. FIGS. 4A, 4B, 14A, and 14B; provide examples of the order of the elements in the plasmids of AAV Rep-Cap plasmids of the invention.

In certain embodiments, the Rep genes can be derived from AAV serotypes AAV1, AAV2, AAV3, AAV4, AAV5, AAV6, AAV7, AAV8, AAV9, AAV10, and/or AAV11, or a chimera thereof. In certain embodiments, the AAV Rep gene is genetically engineered AAV and/or chemically modified AAV. In certain embodiments, the Rep gene includes genes from AAV serotype 2 (Rep2) and/or Rep5, which includes chimeras (e.g., AAV Rep2/5).

In certain embodiments, the Cap genes can be derived from AAV serotypes AAV1, AAV2, AAV3, AAV4, AAV5, AAV6, AAV7, AAV8, AAV9, AAV10, and/or AAV11, or a chimera thereof. In certain embodiments, the AAV Cap gene is genetically engineered AAV and/or chemically modified AAV. In any of the foregoing embodiments, the Cap gene may be from the same AAV serotype as the Rep gene or a different AAV serotype from the Rep gene. In any of the foregoing embodiments, the plasmid further comprises a Cap gene from any of AAV serotypes 2, 5, 8, and/or 9 (Cap2, Cap5, Cap8, and Cap9, respectively), including chimeric proteins comprising hybrids of Cap proteins from those serotypes.

In certain embodiments, the Rep-Cap plasmid includes, but is not limited to, Rep gene sequence from AAV serotypes 2 and as a chimeric Rep protein combined from more than 1 serotypes, for example Rep2/5, and capsid gene sequence from any AAV capsid serotypes including AAV2, AAV5, AAV8, and/or AAV9.

In certain embodiments, the Rep gene sequence comprises, consists of, or consists essentially of a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NOs: 11, 12, 28, or 30, or a functional fragment or derivative thereof. In certain embodiments, Rep gene sequence comprises, consists of, or consists essentially of SEQ ID NOs: 11, 12, 28, or 30, or a functional fragment or derivative thereof.

In certain embodiments, the Cap gene sequence comprises, consists of, or consists essentially of a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NOs: 13, 29, 32, or 36, or a functional fragment or derivative thereof. In certain embodiments, Cap gene sequence comprises, consists of, or consists essentially of SEQ ID NOs: 13, 29, 32, or 36, or a functional fragment or derivative thereof.

In certain embodiments, the promoter sequence comprises, consists of, or consists essentially of a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NO: 34, or a functional fragment or derivative thereof. In certain embodiments, promoter sequence comprises, consists of, or consists essentially of SEQ ID NO: 34, or a functional fragment or derivative thereof.

Figure 14A:
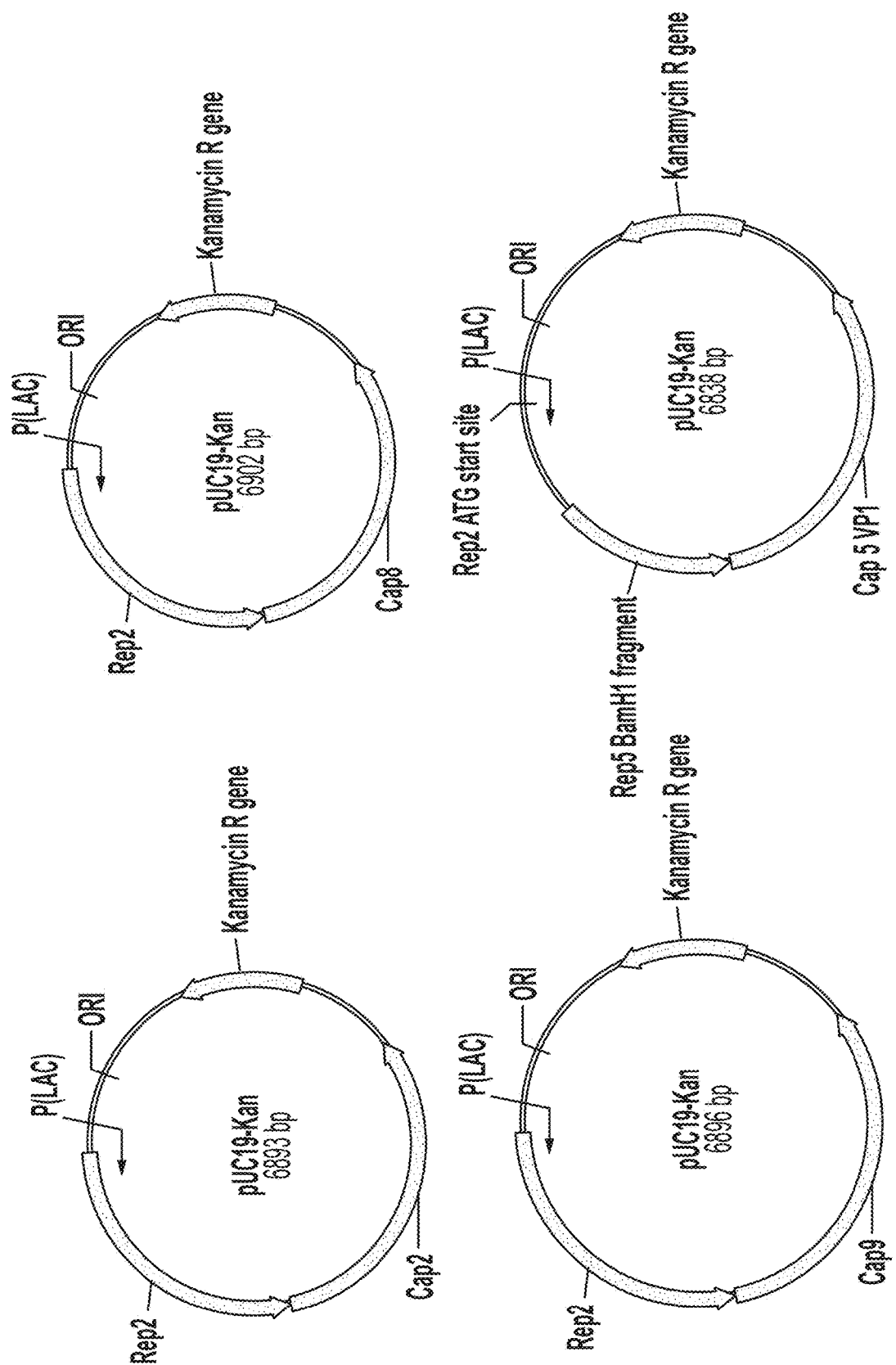
FIGS. 14A-14B.
Figure 14B:
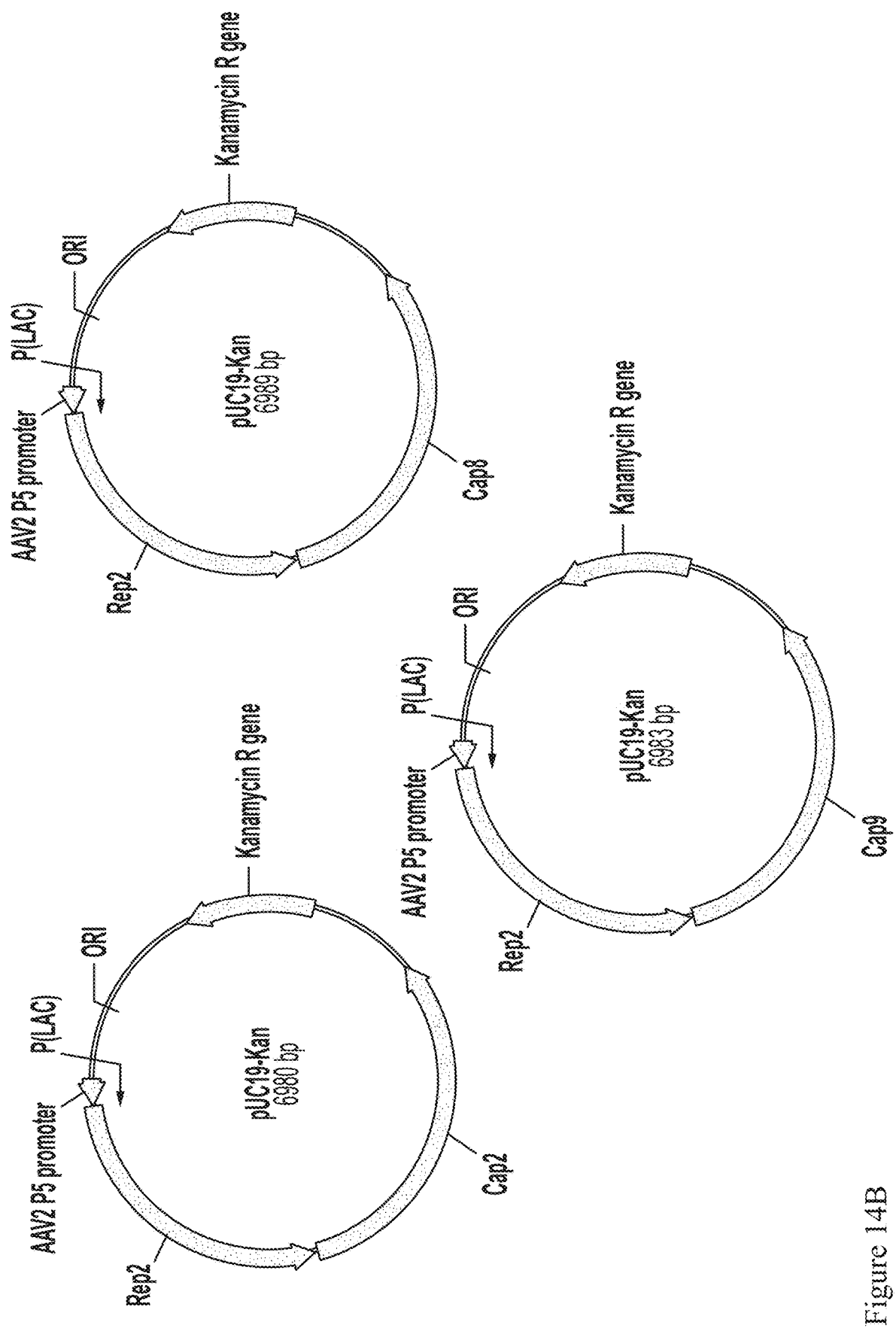
Figure 15A:
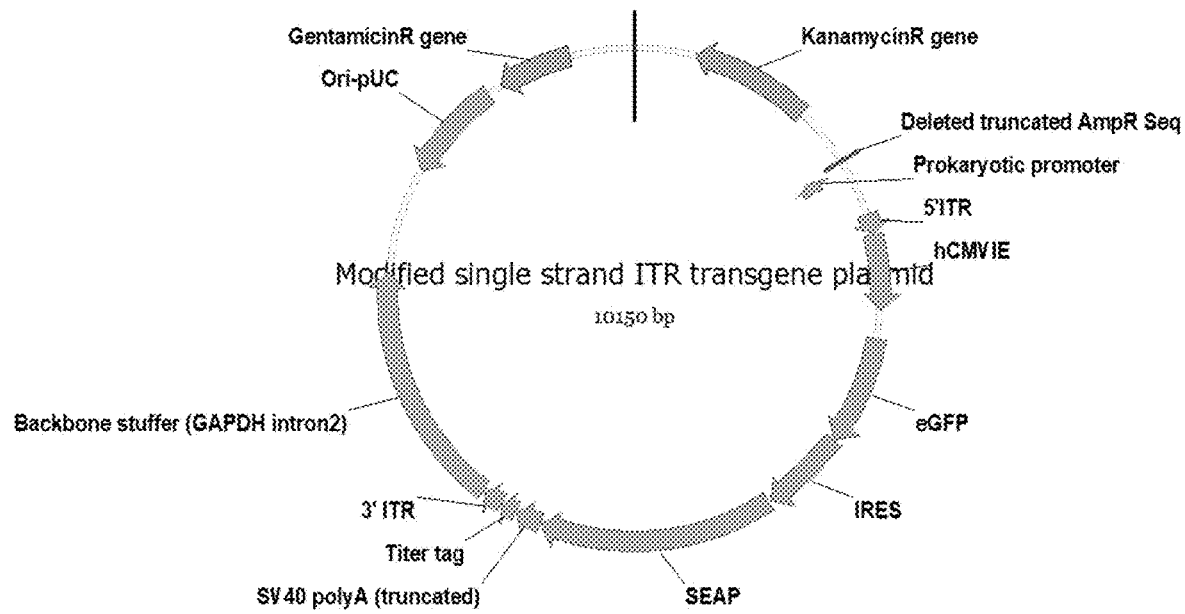
FIG. 15: shows exemplary ene constructs of transgene-containing plasmids for single-stranded (ss) (FIG. 15A) and self-complementary (sc) rAAV (FIG. 15B) production. Both modified plasmids were containing improved plasmid backbones with higher developability.
Figure 15B:
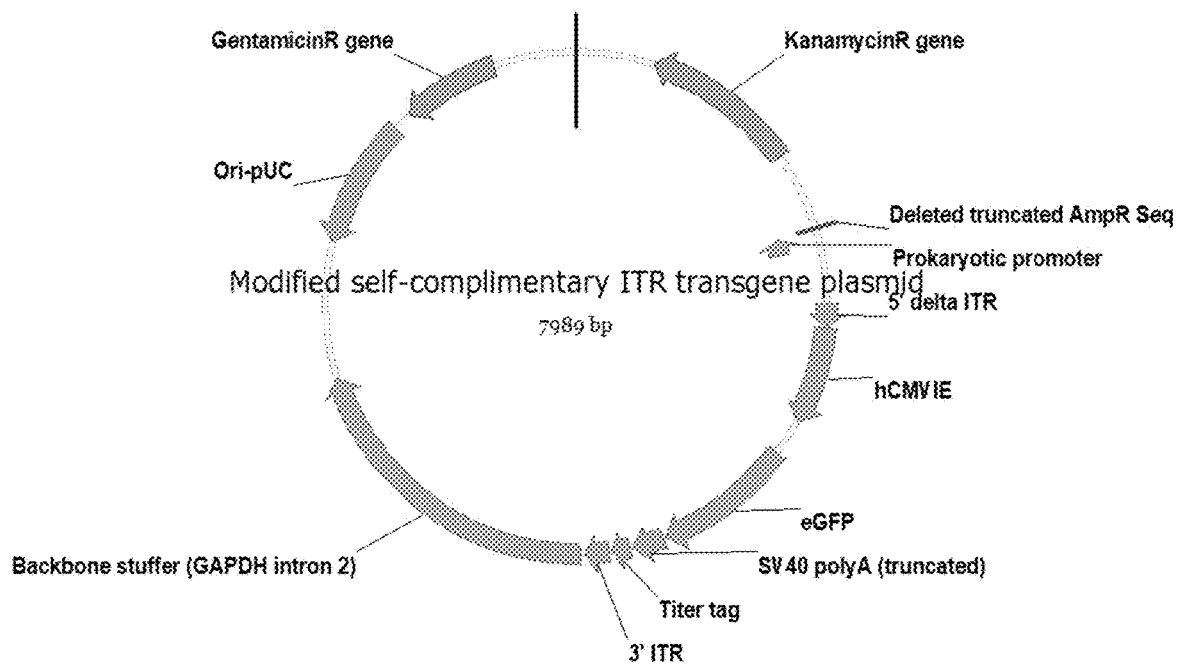
Figure 16A:
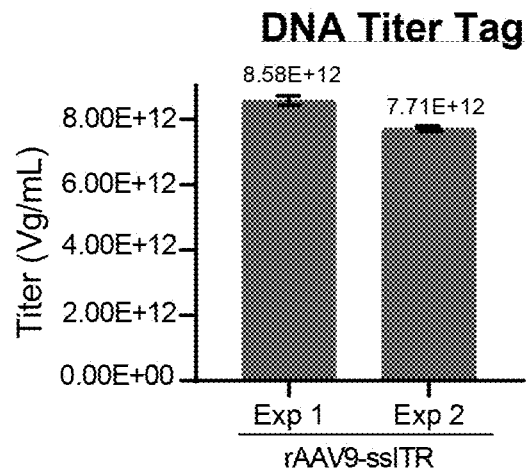
FIGS. 16A-16B: shows that viral genome copy number per ml lysate for the modified single strand ITR (ssITR) transgene plasmid (FIG. 16A) and modified self-complementary ITR (scITR) plasmid (FIG. 16B) using a 100 nucleotide long DNA titer tag for qPCR analysis.
Figure 16B:
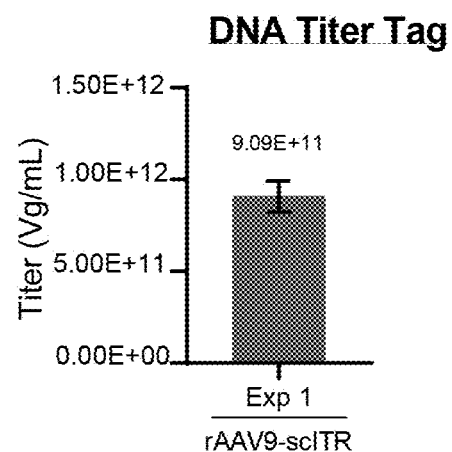

In an embodiment, the Rep-Cap plasmid further comprises an AAV promoter to control expression of the AAV Rep and Cap proteins described herein. The promoter can be any desired promoter, selected by known considerations, such as the level of expression of a nucleic acid functionally linked to the promoter and the cell type in which the vector is to be used. That is, the promoter can be tissue/cell-specific. Promoters can be prokaryotic, eukaryotic, fungal, nuclear, mitochondrial, viral or plant promoters. Promoters can be exogenous or endogenous to the cell type being transduced by the vector. Promoters can include, for example, bacterial promoters, known strong promoters such as SV40 or the inducible metallothionein promoter, or an AAV promoter, such as an AAV P5 promoter. Additionally, chimeric regulatory promoters for targeted gene expression can be utilized. Examples of these regulatory systems, which are known in the art, include the tetracycline based regulatory system which utilizes the tet transactivator protein (tTA), a chimeric protein containing the VP1 6 activation domain fused to the tet repressor of *Escherichia coli*, the EPTG based regulatory system, the CID based regulatory system, and the Ecdysone based regulatory system. Other promoters include promoters derived from actin genes, immunoglobulin genes, cytomegalovirus (CMV) (e.g., hCMVie (SEQ ID NO: 4), adenovirus, bovine papilloma virus, adenoviral promoters, such as the adenoviral major late promoter, an inducible heat shock promoter, respiratory syncytial virus, Rous sarcoma virus (RSV), etc. The promoter can be the promoter of any of the AAV serotypes and can be the p19 promoter or the p40 promoter. In certain embodiments, the promoter can be an AAV2 P5 promoter or an AAV5 P5 promoter or an AAV P5 promoter. Furthermore, smaller fragments of the P5 promoter that retain promoter activity can readily be determined by standard procedures including, for example, constructing a series of deletions in the P5 promoter, linking the deletion to a reporter gene, and determining whether the reporter gene is expressed, i.e., transcribed and/or translated. Examples of potential promoter ca be found in WO2005017101, incorporated by reference herein for all intended purposes. In certain embodiments, the AAV promoter is from AAV serotype 2. Exemplary P5-Rep-Cap plasmids comprising the AAV2 promoter P5 are shown in FIGS. 4B and 14B and in SEQ ID NO: 34.

Suitable plasmid backbones for the Rep-Cap plasmid includes but is not limited to. pHLP19, pUC18, pUC19, and pAAV-RC2, see also plasmid backbones described in U.S. Pat. Nos. 6,001,650 and 6,156,303, the entirety of both incorporated herein by reference for all purposes. In certain embodiments, the Rep-Cap plasmid backbone is pUC19.

Ad Helper Plasmid

In an embodiment, the Ad helper plasmid comprises adenovirus genes including, but not limited to, Ad2 and/or Ad5. In an embodiment, the Ad helper plasmid comprises Ad5 genes. The Ad5 gene sequence is used because Ad5 is an efficient helper virus to rAAV. It is known that the full-complement of adenovirus genes is not required for helper function. In fact, it is more desirable to not have the full compliment. For example, adenovirus mutants incapable of DNA replication and late gene synthesis have been shown to be permissive for AAV replication. Ito et al., (1970) J. Gen. Virol. 9: 243; Ishibashi et al, (1971) Virology 45: 317. Thus, the Ad Helper Plasmid is designed to be of minimal size to only carry the required Ad genes required for rAAV production and to serve as a reduced plasmid size construct. It has been shown that adenoviruses defective in the E1 region, or having a deleted E4 region, are unable to support AAV replication. Thus, E1A and/or E4 regions are likely required for AAV replication, either directly or indirectly. Laughlin et al., (1982) J. Virol. 41: 868; Janik et al., (1981) Proc. Natl. Acad. Sci. USA 78: 1925; Carter et al., (1983) Virology 126: 505. Other characterized Ad mutants include: E1B (Laughlin et al. (1982), supra; Janik et al. (1981), supra; Ostrove et al., (1980) Virology 104: 502); E2A (Handa et al., (1975) J. Gen. Virol. 29: 239; Strauss et al., (1976) J. Virol. 17: 140; Myers et al., (1980) J. Virol. 35: 665; Jay et al., (1981) Proc. Natl. Acad. Sci. USA 78: 2927; Myers et al., (1981) J. Biol. Chem. 256: 567); E2B (Carter, Adeno-Associated Virus Helper Functions, in I CRC Handbook of Parvoviruses (P. Tijssen ed., 1990)); E3 (Carter et al. (1983), supra); and E4 (Carter et al. (1983), supra; Carter (1995)). Although studies of the accessory functions provided by adenoviruses having mutations in the E1B coding region have produced conflicting results, Samulski et al., (1988) J. Virol. 62: 206-210, recently reported that E1B55k is required for AAV virion production, while E1B19k is not. In addition, International Publication WO 97/17458 and Matshushita et al., (1998) Gene Therapy 5: 938-945, describe accessory proteins encoding various Ad genes. Particularly preferred accessory function plasmids comprise an adenovirus VA RNA coding region, an adenovirus E4 ORF6 coding region, an adenovirus E2A 72 kD coding region, an adenovirus E1A coding region, and an adenovirus E1B region lacking an intact E1B55k coding region. Examples of these plasmids are described in International Publication No. WO 01/83797. Each reference recited in this paragraph are incorporated herein by reference in their entirety for all purposes.

Figure 5:
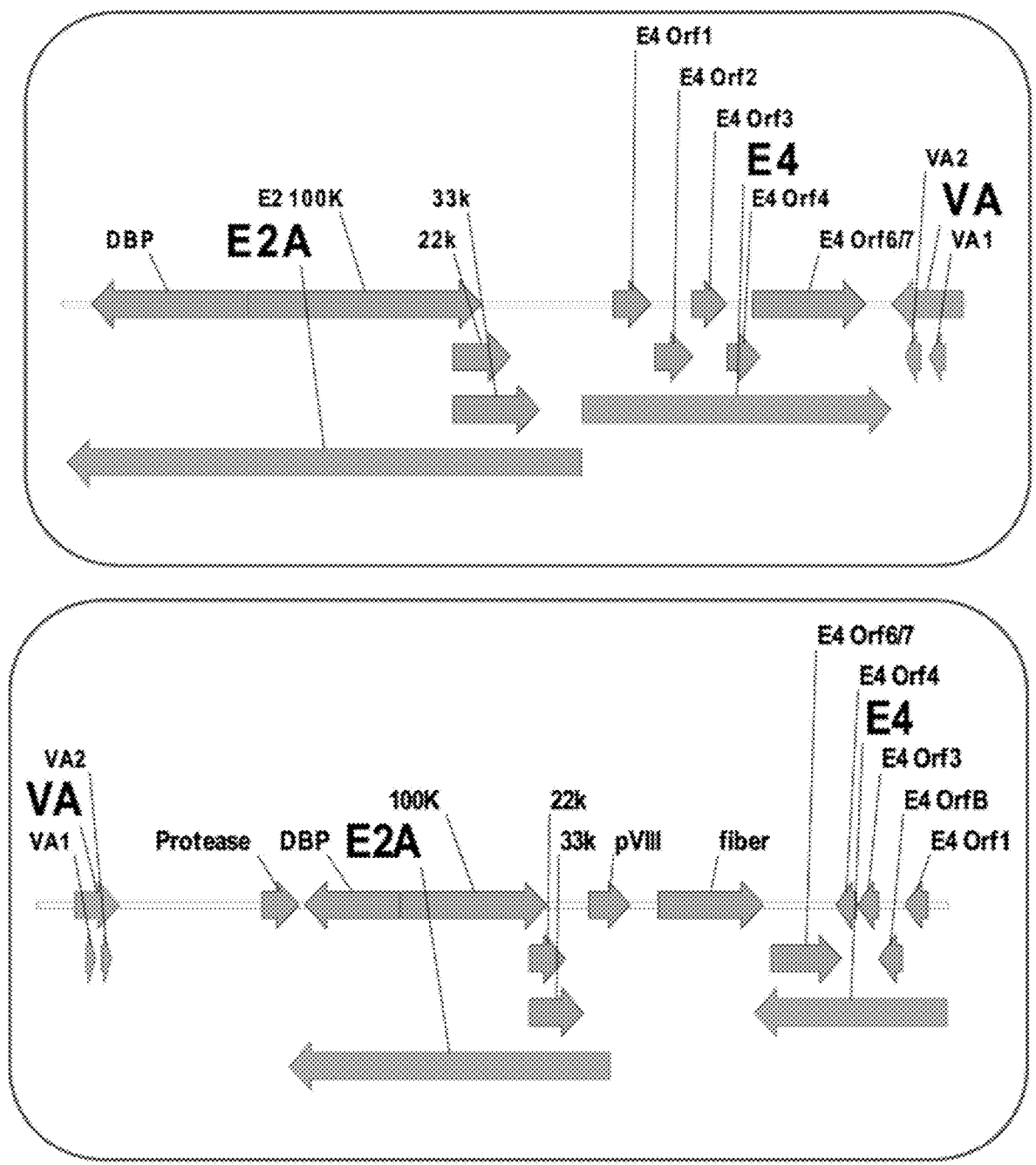
FIG. 5 depicts exemplary Ad Helper Plasmids in short (top panel) and long (bottom panel) embodiments.

Exemplary Ad helper plasmids according to the invention is shown in FIG. 5 and SEQ ID NOs: 14 and 15, or a plasmid with at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NOs: 14 and 15. FIG. 5 provides examples of the order of the elements in the plasmids of Ad helper plasmids of the invention.

In certain embodiments, the Ad helper plasmid can include, without limitation, adenoviral gene sequences for E2a, E4 (orf6), the VA1 RNA gene, and the parvovirus VP capsid gene unit. In certain embodiments, the Ad Helper Plasmid can include VA, E4, and E2A genes. As there is a limitation of how much plasmid can be efficiently transfected to cells for rAAV production, having a reduced size plasmid carrying these Ad genes could help increase the molar content of all three plasmids used in the transfection, thus increasing the probability of producing higher yield rAAV.

In an embodiment, the Ad helper plasmid comprises E2A, E4 ORFs 1, 2, 3, 4, and 6/7, and VA ("short Ad helper plasmid"). An exemplary short Ad Helper Plasmid is shown in the top panel of FIG. 5. The shorter plasmid described here is to reduce "plasmid load" during the step of transfection so that the overall copy number of plasmids of all three plasmids can be increased to give higher number of plasmid templates for gene expression and replication for rAAV production. The reduced plasmid load is surprisingly useful for larger batches. This may not be a crucial parameter in small research scale production but could be much more critical when scaled up. This exemplary short Ad Helper Plasmid is approximately 12 kb. In another embodiment, the Ad Helper Plasmid comprises E2A, E4 ORFs 1, 2, 3, 4, and 6/7, and VA, as well as genes encoding a protease and a fiber and promoter pVIII ("long Ad helper plasmid"). An exemplary long Ad Helper Plasmid is shown in the bottom panel of FIG. 5. This exemplary long Ad Helper Plasmid is approximately 18 kb.

The differences between the short and long constructs are shown in FIG. 5. The orientations of the three essential gene elements are different. The long version carries additional elements from the adenovirus genome that may have functions that influence rAAV production. The short version contains the minimal gene sequence that is known to be able to support rAAV production.

In certain embodiments, the VA sequence comprises, consists of, or consists essentially of a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NOs: 16 or 48-50, or a functional fragment or derivative thereof. In certain embodiments, VA sequence comprises, consists of, or consists essentially of SEQ ID NOs: 16 or 48-50, or a functional fragment or derivative thereof.

In certain embodiments, the E4 sequence comprises, consists of, or consists essentially of a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NOs: 17, 40, 47, or 55-58, or a functional fragment or derivative thereof. In certain embodiments, E4 sequence comprises, consists of, or consists essentially of SEQ ID NOs: 17, 40, 47, or 55-58, or a functional fragment or derivative thereof.

In certain embodiments, the E2A sequence comprises, consists of, or consists essentially of a nucleic acid having at least about 40%, about 50%, about 60%, about 65%, about 70%, about 75%, about 80%, about 85%, about 90%, about 91%, about 92%, about 93%, about 94%, about 95%, about 96%, about 97%, about 98%, or about 99% identity to SEQ ID NOs: 18, 39, 46, or 51, or a functional fragment or derivative thereof. In certain embodiments, E2A sequence comprises, consists of, or consists essentially of SEQ ID NOs: 18, 39, 46, or 51, or a functional fragment or derivative thereof.

Suitable plasmids for the Ad Helper Plasmid include, but are not limited to, pJ241, see also plasmids described in U.S. Pat. Nos. 6,001,650 and 6,156,303, the entirety of both incorporated by reference herein. In certain embodiments, the Ad Helper Plasmid backbone is pUC57.

Additional Genes

In a further embodiment, all three plasmids contain a selection marker. An example of a selection marker includes, but is not limited, to positive selection markers such as drug resistance genes including, but not limited to, G418 (with neor), puromycin (with puror), hygromycin B (with hygr), blasticidin S (with bsrr), mycophenolic acid and 6-thio (guanine) (with gpt) and gancyclovir or 1 (2'-deoxy-2'-fluoro-beta-D-arabinofuranosyl)-5-iodouracil (FIAU) (with HSV-tk), gentamycin, and/or kanamycin (with kanr). In a further embodiment, the drug selection marker on all three plasmids is kanamycin. In certain embodiments, the kanamycin gene comprises or consists of SEQ ID NOs: 19 or 25, or functional fragments or derivatives thereof. In certain embodiments, the gentamycin gene comprises or consists of SEQ ID NOs: 44 or 72, or functional fragments or derivatives thereof.

In an embodiment, one or more of the three plasmids carries one or more reporter genes. Several reporter genes are known in the art and some are commercially available (see, Alam and Cook, supra). The reporter gene can be inserted within a plasmid that is particularly suited for an organism and molecular biology manipulations. Promoters of interest can be inserted into cloning sites so that the expression of the reporter gene is under the control of the promoter (see, Rosenthal, N., Methods Enzymol. 152: 704-720 (1987); and Shiau, A. and Smith, J. M., Gene 67: 295-299 (1988)). Known methods are used to introduce these plasmids into a cell type or whole organism (see, Sambrook et al., Molecular Biology, A Laboratory Manual, Cold Spring Harbor Laboratory Press (1989); and Nolan, In: Molecular Cloning, Cold Spring Harbor Laboratory Press, (1989)). Examples of reporter genes include, without limitation, β-galactosidase (LacZ), firefly luciferase, *Renilla* luciferase, *Gaussia* luciferase, chloramphenicol acetyltransferase (CAT), secreted embryonic alkaline phosphatase (SEAP), cyan fluorescent protein (CFP), green fluorescent protein (GFP), enhanced GFP (eGFP), yellow fluorescent protein (YFP), enhanced YFP (eYFP), blue fluorescent protein (BFP), enhanced BFP (eBFP), red fluorescent protein from the Discosoma coral (DsRed), and/or MmGFP (Zemicka-Goetz et al. (1997) Development 124: 1133-1137) or others familiar to those of ordinary skill. In another embodiment, one or more of the three plasmids carries a reporter construct comprising both eGFP and SEAP, with an internal ribosome entry site (IRES) located between eGFP and SEAP. In such an embodiment, eGFP, which localizes in the nucleus, can be used for determining vector transduction tropism of the rAAV, while SEAP, which is secreted outside of the cell, can permit quantitative measurement of transduction efficiency, either in culture medium in an in vitro setting, or in the subject's bloodstream in an in vivo setting. LacZ can enable color-based selection of desired clones, based on disruption of the lacZ gene by a cloned gene.

In an embodiment, each plasmid comprises a unique DNA titer tag. In certain embodiments, the DNA titer tag only appears in the transgene-containing plasmid. In certain embodiments the DNA titer tag appears in all of the plasmid systems. This unique DNA titer tag can be included to enable universal vector genome titering, e.g., via a qPCR (or ddPCR)-based vector genome titering assay, to quantify the amount of vector present. In certain embodiments, the DNA titer tag can be outside the expression cassette but between the 2 ITR's to ensure that it becomes packaged. For example, the DNA titer tag can be upstream of the 3'ITR sequence. As another example, the DNA titer tag can be downstream of the 5'ITR sequence. In certain embodiments, the DNA titer tag is constructed such that it does not appear endogenously within the subject's genome. For example, the sequence can be compared against the subject's DNA (e.g., via a Blast search or other alignment search tool). The primers used to run the qPCR analysis can also be analyzed to ensure that they do not identify any sequence found in the host cells used to package the virion.

The DNA titer tag can be of a size that allows for efficient qPCR analysis but also takes up the least amount of genome space in the plasmid. In certain embodiments, the DNA titer tag sequence is about 60 nucleotides to about 100 nucleotides in length (e.g. SEQ ID NO: 10) and designed based on a sequence that does not exist in humans or standard laboratory animals. In certain embodiments, the DNA titer tag sequence is about 60 nucleotides to about 80 nucleotides, about 65 nucleotides to about 95 nucleotides, about 70 nucleotides to about 90 nucleotides, or about 75 nucleotides to about 85 nucleotides. In certain embodiments, the DNA titer tag sequence is about 60 nucleotides to about 70 nucleotides, about 65 nucleotides to about 75 nucleotides, about 70 nucleotides to about 80 nucleotides, about 75 nucleotides to about 85 nucleotides, about 80 nucleotides to about 90 nucleotides, about 85 nucleotides to about 95 nucleotides, or about 90 nucleotides to about 100 nucleotides. In certain embodiments, the DNA titer tag sequence is at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides. In certain embodiments, the stretch of DNA titer sequence is 100 nucleotides in length. In certain embodiments, a titer tag of 100 nucleotides can be advantageous in rapid qPCR assays and allow for efficient packaging due to the overall plasmid size and packaging limitations.

Non-limiting examples of nucleic acid sequences that encode DNA titer tags includes SEQ ID NO: 61-70.

Heterologous Nucleic Acid Sequence

Recombinant AAV made by the plasmids of the invention can be administered to one or more cells or tissue of a subject. Thus, the invention embraces the delivery of heterologous nucleic acid sequence that can be useful to modulate the cells or tissue of the subject. For example, rAAV can upregulate or downregulate an activity or product of a cell or tissue.

In certain embodiments, the heterologous nucleic acid sequence can be a heterologous gene of interest encoding one or more peptide, polypeptide, or protein. In certain embodiments, the heterologous nucleic acid sequence can encode a peptide, polypeptide, or protein that binds to a specific target of interest, which can be useful for the treatment or prevention of disease in a subject. Examples of such heterologous nucleic acid sequences and associated peptides, polypeptides, or proteins include, but are not limited to, a gene encoding antibodies, MHC molecules, T-cell receptors, B-cell receptors, aptamers, avimers, receptor-binding ligands, or targeting peptides. Antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies). An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

In certain embodiments, the heterologous nucleic acid sequence (e.g., heterologous gene of interest) can encode a peptide, polypeptide, or protein that can be useful for the treatment or prevention of disease in a subject. For example, the heterologous nucleic acid sequencecan encode a protein X for the treatment of disease Y. Protein X can, for example, substitute for a mutated protein or act to block a mutated protein. Such nucleic acid sequences and associated diseases include, but are not limited to, nucleic acid sequences encoding glucose-6-phosphatase, associated with glycogen storage deficiency type 1A; DNA encoding phosphoenolpyruvate-carboxykinase, associated with Pepck deficiency; DNA encoding galactose-1 phosphate uridyl transferase, associated with galactosemia; DNA encoding phenylalanine hydroxylase, associated with phenylketonuria; DNA encoding branched chain alpha-ketoacid dehydrogenase, associated with Maple syrup urine disease; DNA encoding fumarylacetoacetate hydrolase, associated with tyrosinemia type 1; DNA encoding methylmalonyl-CoA mutase, associated with methylmalonic acidemia; DNA encoding medium chain acyl CoA dehydrogenase, associated with medium chain acetyl CoA deficiency; DNA encoding ornithine transcarbamylase, associated with ornithine transcarbamylase deficiency; DNA encoding argininosuccinic acid synthetase, associated with citrullinemia; DNA encoding low density lipoprotein receptor protein, associated with familial hypercholesterolemia; DNA encoding UDP-glucouronosyltransferase, associated with Crigler-Najjar disease; DNA encoding adenosine deaminase, associated with severe combined immunodeficiency disease; DNA encoding hypoxanthine guanine phosphoribosyl transferase, associated with Gout and Lesch-Nyan syndrome; DNA encoding biotinidase, associated with biotinidase deficiency; DNA encoding alpha-galactosidase-A, associated with Fabry disease; DNA encoding beta-glucocerebrosidase, associated with Gaucher disease; DNA encoding beta-glucuronidase, associated with Sly syndrome; DNA encoding peroxisome membrane protein 70 kDa, associated with Zellweger syndrome; DNA encoding porphobilinogen deaminase, associated with acute intermittent porphyria; DNA encoding alpha-1 antitrypsin for treatment of alpha-1 antitrypsin deficiency (emphysema); DNA encoding Cl-esterase for the treatment of hereditary angioedema (HAE); DNA encoding phenylalanine hydroxylase for the treatment of phenylketonuria; DNA encoding acid alpha-glucosidase for the treatment of with Pompe disease; DNA encoding ATP7B for the treatment of Wilson's disease; DNA encoding alpha-L-iduronidase for the treatment of mucopolysaccharidose type I (MPSI); DNA encoding iduronate sulfatase for the treatment of mucopolysaccharidose type II (MPSII); DNA encoding heparan sulfamidase for the treatment of mucopolysaccharidose type IIIA (MPSIIIA); DNA encoding N-acetylglucosaminidase for the treatment of mucopolysaccharidose type IIIB (MPSIIIB); DNA encoding heparan-alpha-glucosaminide N-acetyltransferase for the treatment of mucopolysaccharidose type IIIC (MPSIIIC); DNA encoding N-acetylglucosamine 6-sulfatase for the treatment of mucopolysaccharidose type IIID (MPSIIID); DNA encoding galactose-6-sulfate sulfatase for the treatment of mucopolysaccharidose type IVA (MPSIVA); DNA encoding beta-galactosidase for the treatment of mucopolysaccharidose type IVB (MPSIVB); DNA encoding N-acetylgalactosamine-4-sulfatase for the treatment of mucopolysaccharidose type VI (MPSVI); DNA encoding beta-glucuronidase for the treatment of mucopolysaccharidose type VII (MPSVII); DNA encoding hyaluronidase for the treatment of mucopolysaccharidose type IX (MPSIX); DNA encoding erythropoietin for treatment of anemia due to thalassemia or to renal failure; DNA encoding vascular endothelial growth factor, DNA encoding angiopoietin-1, and DNA encoding fibroblast growth factor for the treatment of ischemic diseases; DNA encoding thrombomodulin and tissue factor pathway inhibitor for the treatment of occluded blood vessels as seen in, for example, atherosclerosis, thrombosis, or embolisms; DNA encoding aromatic amino acid decarboxylase (AADC), and DNA encoding tyrosine hydroxylase (TH) for the treatment of Parkinson's disease; DNA encoding the beta adrenergic receptor, DNA encoding anti-sense to, or DNA encoding a mutant form of, phospholamban, DNA encoding the sarco(endo)plasmic reticulum adenosine triphosphatase-2 (SERCA2), and DNA encoding the cardiac adenylyl cyclase for the treatment of congestive heart failure; DNA encoding a tumor suppressor gene such as p53 for the treatment of various cancers; DNA encoding a cytokine such as one of the various interleukins for the treatment of inflammatory and immune disorders and cancers; DNA encoding dystrophin or minidystrophin and DNA encoding utrophin or miniutrophin for the treatment of muscular dystrophies; DNA encoding ABCA4 for the treatment of Stargardt's disease; and, DNA encoding insulin for the treatment of diabetes.

In certain embodiments, the heterologous nucleic acid sequence (e.g., heterologous gene of interest) can encode a peptide, polypeptide, or protein that encodes a blood coagulation protein, which proteins may be delivered to the cells of a subject having a blood disorder (e.g., hemophilia). Examples of such nucleic acids and associated peptides, polypeptides, or proteins include, but are not limited to, DNA encoding Factor IX to a subject for treatment of hemophilia B, Factor VIII to a subject for treatment of hemophilia A, Factor VII for treatment of Factor VII deficiency, Factor X for treatment of Factor X deficiency, Factor XI for treatment of Factor XI deficiency, Factor XIII for treatment of Factor XIII deficiency, and Protein C for treatment of Protein C deficiency.

The invention also includes the expression of engineered artificial DNA binding domain peptide, transcriptional activator or transcriptional repressor and nucleases that can interact with the host cell genome to affect up or down gene expression level for genetic and/or acquired diseases.

The invention also includes the expression of heterologous nucleic acid sequences, including but not limited to, antisense, siRNA, shRNA, miRNA, EGSs, gRNA, sgRNA, ribozymes, or aptamers, which could interact with cellular DNA, RNA and/or proteins that can change the gene expression or activities of proteins for genetic and/or acquired diseases.

The invention also includes the expression of intermediate and/or critical raw material for cellular therapy, including but not limited to rAAV, to be used to infect cells to generate genetically engineered cell therapy materials or drug product.

The invention also includes a heterologous nucleic acid sequence that is a gene editing molecule used for modifying a genomic locus of interest (i.e., target) in a cell. Such modifications include, but are not limited to a disruption, deletion, repair, mutation, addition, alteration, or modification of a gene sequence at a target locus in a gene. Examples of gene-editing molecules include, but are not limited to, endonucleases such as zinc finger nucleases (ZFns), transcription activator-like effector nucleases (TALENs), meganucleases, restriction endonucleases, recombinases, and Clustered Regularly Interspersed Short Palindromic Repeats (CRISPR)/CRISPR-associated (Cas) proteins.

Delivery of rAAV

Recombinant AAV described herein, can be used at a therapeutically useful concentration for the treatment and/or prevention of a disease of interest, by administering to a subject in need thereof, an effective amount of the rAAV made by the plasmids of the invention. Subjects to be treated with rAAV made by the plasmids of the present invention can also be administered with other therapeutic agents or devices with known efficacy for treating or preventing the disease.

Delivery of the rAAV to a subject may be by intramuscular injection or by administration into the bloodstream of the subject. Administration into the bloodstream may be by injection into a vein, an artery, or any other vascular conduit the mutant virions into the bloodstream by way of isolated limb perfusion, a technique well known in the surgical arts, the method essentially enabling the artisan to isolate a limb from the systemic circulation prior to administration of the rAAV. Moreover, for certain conditions, it may be desirable to deliver the mutant virions to the CNS of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage, intracerebral ventricular, intracranial, cisterna *magna* injection, intrathecal, intracatorid, intranasal and the like. rAAV or cells transduced in vitro may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection. See, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000, each of which are incorporated herein in their entirety for all purposes. For administration to the eye, methods can include, subretinal, intravitreal, trans-scleral, or intracranial.

TABLE 3

Exemplary Sequences for Use in the Plasmids of the Invention

| Sequence ID | Description |
| --- | --- |
| SEQ ID NO: 1 | Single-strand ITR transgene plasmid |
| SEQ ID NO: 2 | 5' ITR |
| SEQ ID NO: 3 | 3' ITR |
| SEQ ID NO: 4 | hCMVie |
| SEQ ID NO: 5 | eGFP |

TABLE 3-continued

Exemplary Sequences for Use in the Plasmids of the Invention

| Sequence ID | Description |
| --- | --- |
| SEQ ID NO: 6 | IRES |
| SEQ ID NO: 7 | SEAP |
| SEQ ID NO: 8 | SV40 poly A |
| SEQ ID NO: 9 | GAPDH stuffer sequence |
| SEQ ID NO: 10 | DNA titer tag |
| SEQ ID NO: 11 | Rep2/5 |
| SEQ ID NO: 12 | Rep2 |
| SEQ ID NO: 13 | Cap9 |
| SEQ ID NO: 14 | Complete short ad helper plasmid |
| SEQ ID NO: 15 | Complete long Ad helper plasmid |
| SEQ ID NO: 16 | VA gene |
| SEQ ID NO: 17 | E4 gene |
| SEQ ID NO: 18 | E2A |
| SEQ ID NO: 19 | Kanamycin resistance gene (complement) |
| SEQ ID NO: 20 | pUC origin (complement) |
| SEQ ID NO: 21 | P_Amp (complement) |
| SEQ ID NO: 22 | Term_bla (complement) |
| SEQ ID NO: 23 | Rpo_C (complement) |
| SEQ ID NO: 24 | pRep2/5-Cap5 plasmid |
| SEQ ID NO: 25 | Kanamycin resistance gene (complement) |
| SEQ ID NO: 26 | origin of replication; RNaseH cleavage point |
| SEQ ID NO: 27 | lac promoter (complement) |
| SEQ ID NO: 28 | Rep5 BamHI fragment (complement) |
| SEQ ID NO: 29 | Cap5/VP1 fragment (complement) |
| SEQ ID NO: 30 | Start site of Rep2 (complement) |
| SEQ ID NO: 31 | pRep2-Cap2 plasmid |
| SEQ ID NO: 32 | Cap2 |
| SEQ ID NO: 33 | pUC19-Kan-Rep2Cap2 plasmid |
| SEQ ID NO: 34 | AAV2/P5 promoter (complement) |
| SEQ ID NO: 35 | pRep2-Cap8 plasmid |
| SEQ ID NO: 36 | Cap8 gene (complement) |
| SEQ ID NO: 37 | pRep2-Cap9 plasmid |
| SEQ ID NO: 38 | lac promoter |
| SEQ ID NO: 39 | E2A gene (complement) |
| SEQ ID NO: 40 | E4 gene (complement) |
| SEQ ID NO: 41 | pUC19-Kan-Rep2Cap9 plasmid |
| SEQ ID NO: 42 | Self-complementary ITR transgene plasmid |
| SEQ ID NO: 43 | Truncated 5' ITR |
| SEQ ID NO: 44 | Gentamycin resistance gene (complement) |
| SEQ ID NO: 45 | pHelper plasmid |
| SEQ ID NO: 46 | E2A complement |
| SEQ ID NO: 47 | E4 (complement) |
| SEQ ID NO: 48 | VA (complement) |
| SEQ ID NO: 49 | VA2 RNA (complement) |
| SEQ ID NO: 50 | VA1 RNA (complement) |
| SEQ ID NO: 51 | E2A-BP |
| SEQ ID NO: 52 | L4 100K |
| SEQ ID NO: 53 | hAdV2, 33-100kD |
| SEQ ID NO: 54 | Incomplete L4 pVIII |
| SEQ ID NO: 55 | E4 orf 6/7 (complement) |
| SEQ ID NO: 56 | E4 orf 4 (complement) |
| SEQ ID NO: 57 | E4 orf 3 |
| SEQ ID NO: 58 | E4 orf 2 (complement) |
| SEQ ID NO: 59 | pAAV-RC |
| SEQ ID NO: 60 | pUC19-Kan-Rep2Cap8 plasmid |
| SEQ ID NO: 61 | DNA Titer Tag |
| SEQ ID NO: 62 | DNA Titer Tag |
| SEQ ID NO: 63 | DNA Titer Tag |
| SEQ ID NO: 64 | DNA Titer Tag |
| SEQ ID NO: 65 | DNA Titer Tag |
| SEQ ID NO: 66 | DNA Titer Tag |
| SEQ ID NO: 67 | DNA Titer Tag |
| SEQ ID NO: 68 | DNA Titer Tag |
| SEQ ID NO: 69 | DNA Titer Tag |
| SEQ ID NO: 70 | DNA Titer Tag |
| SEQ ID NO: 71 | Single-strand ITS transgene plasmid |
| SEQ ID NO: 72 | Gentamycin resistance gene-inactivated (complement) |
| SEQ ID NO: 73 | Self-complementary ITS transgene plasmid |
| SEQ ID NO: 74 | T2A |
| SEQ ID NO: 75 | P2A |
| SEQ ID NO: 76 | E2A |
| SEQ ID NO: 77 | F2A |

EXAMPLES

The present disclosure is also described and demonstrated by way of the following examples. However, the use of these and other examples anywhere in the specification is illustrative only and in no way limits the scope and meaning of the disclosure or of any exemplified term. Likewise, the disclosure is not limited to any preferred embodiments described here. Indeed, many modifications and variations of the disclosure may be apparent to those skilled in the art upon reading this specification, and such variations can be made without departing from the disclosure in spirit or in scope. The disclosure is therefore to be limited only by the terms of the appended claims along with the full scope of equivalents to which those claims are entitled.

Example 1: In Vitro Expression of Cap Proteins

Figure 4A:
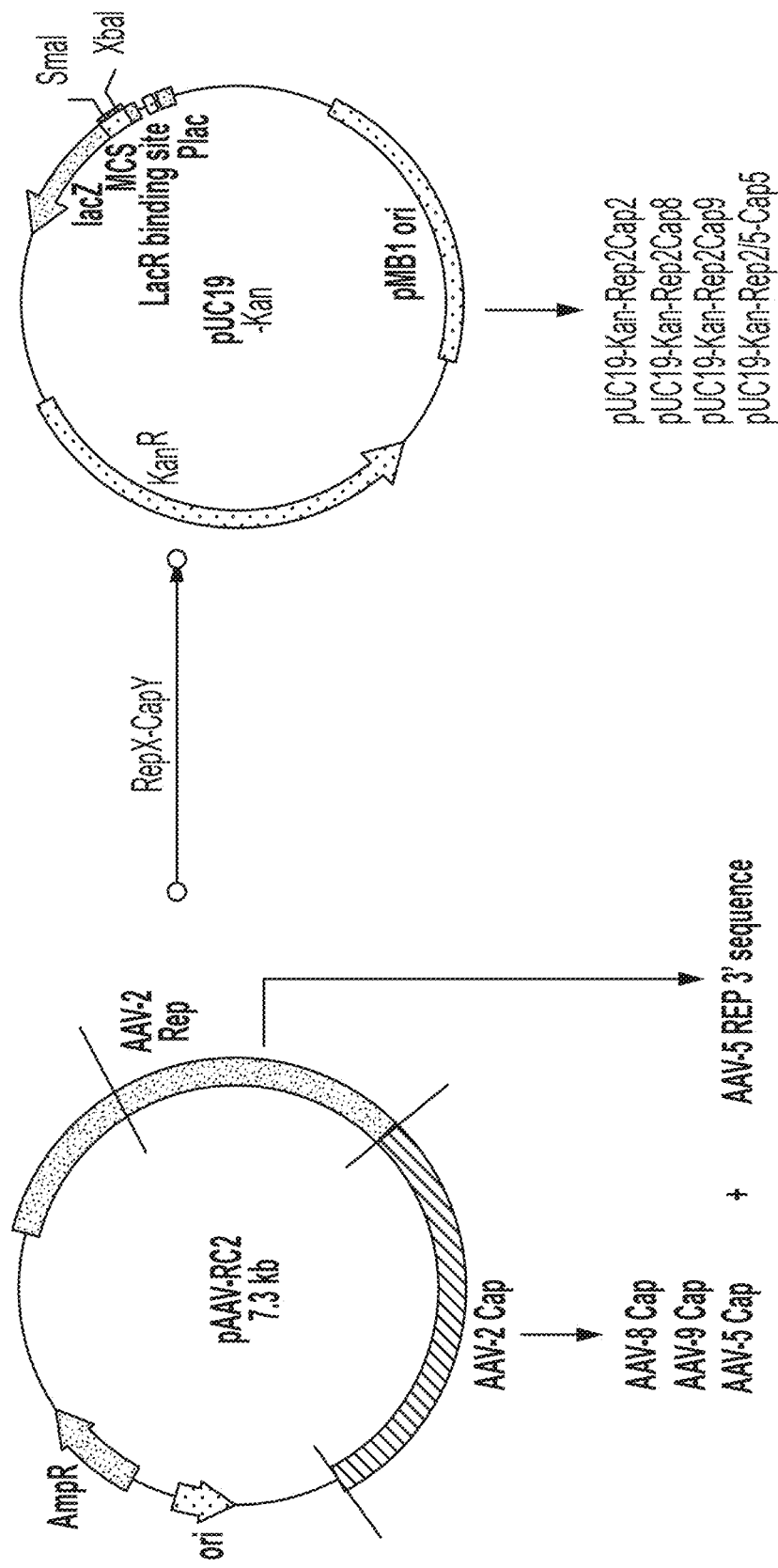
FIGS. 4A-4B.
Figure 4B:
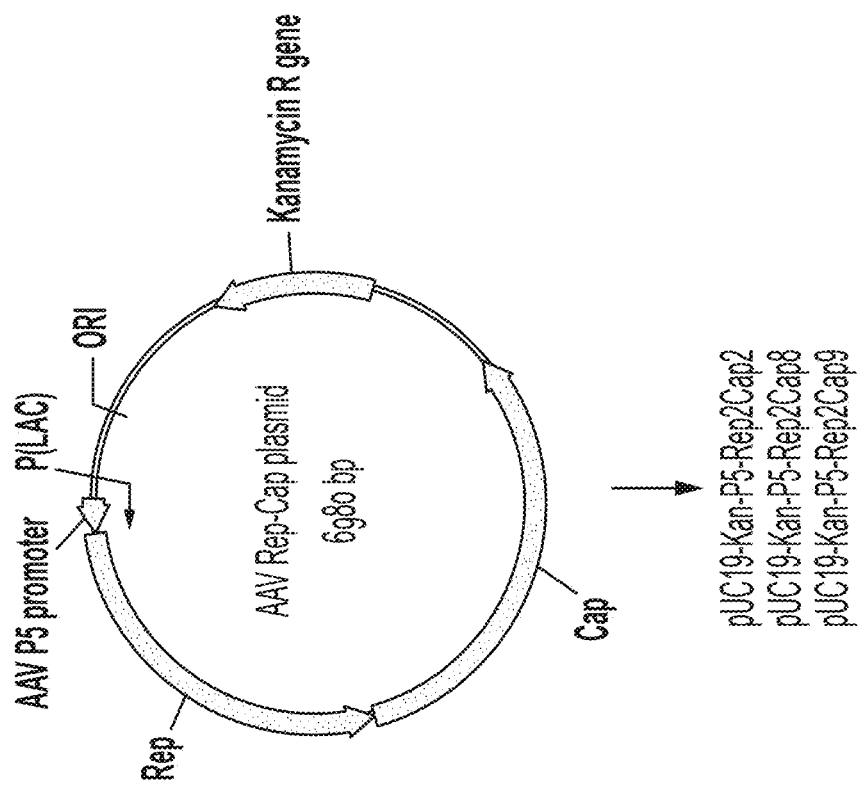

This example investigated the in vitro expression of the capsid proteins in AAV293 (Agilent) cells from pUC19-based plasmids as compared to expression levels of the same capsid proteins from control pAAV-RC2 based plasmids carrying Rep2 and Cap2 genes (Agilent) (FIG. 4A).

A first set of four plasmids with varied Rep and Cap genes were created in the pAAV-RC background, starting with Rep2Cap2-pAAV-RC (i.e., pAAV-RC2 as shown in FIG. 4A). The pAAV-RC2 was used to generate Rep2/5Cap5-pAAV-RC, Rep2Cap8-pAAV-RC, and Rep2Cap9-pAAV-RC (FIG. 4A).

A second set of four plasmids were created in the pUC19-Kan background, with the same replication and capsid proteins as the first set. Thus, Rep2Cap2-pUC19-Kan, Rep2/5Cap5-pUC19-Kan, Rep2Cap8-pUC19-Kan, and Rep2Cap9-pUC19-Kan (FIGS. 4A and 14A).

For the experiments, each of the 8 plasmids were separately transfected along with the Ad Helper plasmid, pHelper (Agilent) (e.g., SEQ ID NO: 45), at a ratio of 1:1.

Figure 6:
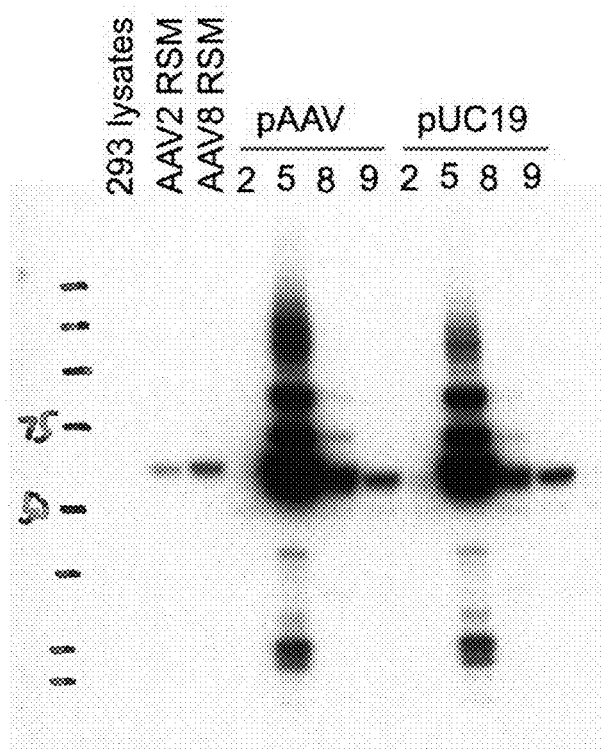
FIG. 6 is a Western blot showing expression levels of Cap proteins from different AAV serotypes from a plasmid according to the disclosure.

Expression levels of the Cap protein from the pUC19-Kan-based plasmids were compared to expression levels of the same Cap protein from the pAAV-RC2-based plasmids via Western blotting using a monoclonal B1 antibody (FIG. 6). Positive controls AAV2 reference standard material (RSM) and AAV8 RSM are reference standard materials containing the AAV2 and AAV8 Cap proteins, while the negative control was a cell lysate from HEK293 without any Cap-bearing plasmid. The expression level of capsid protein was AAV5>AAV8>AAV9>AAV2 for both the pUC19-based plasmids and the pAAV-RC2-based plasmids.

Figure 7:
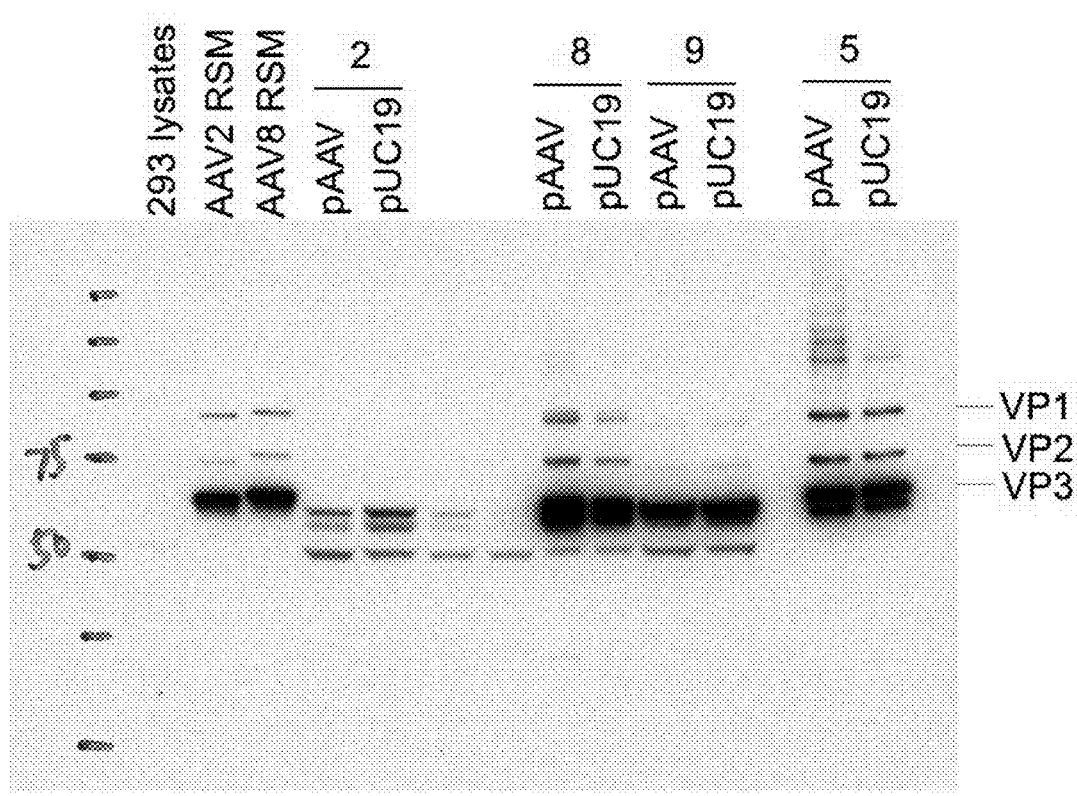
FIG. 7 is a Western blot showing expression levels of Cap proteins from different AAV serotypes from a plasmid according to the disclosure. A Monoclonal B1 clone was used for blot analysis.

FIG. 7 is a Western blot analysis conducted with reduced sample to specifically analyze the amounts of Cap proteins VP1-VP3 more clearly.

Figure 8:
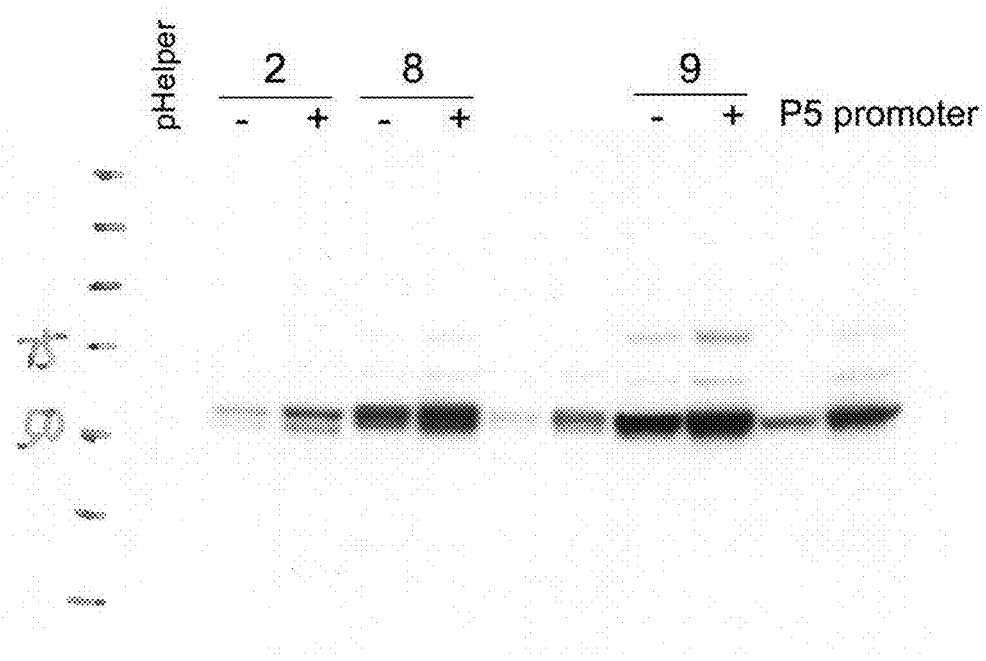
FIG. 8 is a Western blot showing AAV P5-driven expression levels of Cap proteins from different AAV serotypes from a plasmid according to the disclosure. −: plasmid constructs without the P5 promoter; +: plasmid constructs with the P5 promoter. A Monoclonal B1 clone was used for blot analysis.

Next, the AAV2 P5 promoter was added to the Rep2Cap2 pUC19-Kan, Rep2Cap8 pUC19-Kan, and Rep2Cap9 pUC19-Kan plasmids (e.g., FIGS. 4B and 14B). FIG. 8 shows expression levels of Cap proteins from AAV serotypes 2, 8 and 9 expressed using the P5 promoter tested under the same conditions as described above in comparison with those without the P5 promoter. It was found that the P5 promoter gives higher levels of capsid protein expression. The transgene-containing plasmid and Ad helper plasmid were administered at a ratio of 1:1.

Example 2: Functional Testing of Short and Long Ad Helper Plasmids

The purpose of this example was to test the function of a short Ad helper plasmid and a long Ad helper plasmid versus the commercial pHelper. Each plasmid was tested individually to ensure each one is functional before using them in combination.

Figure 9:
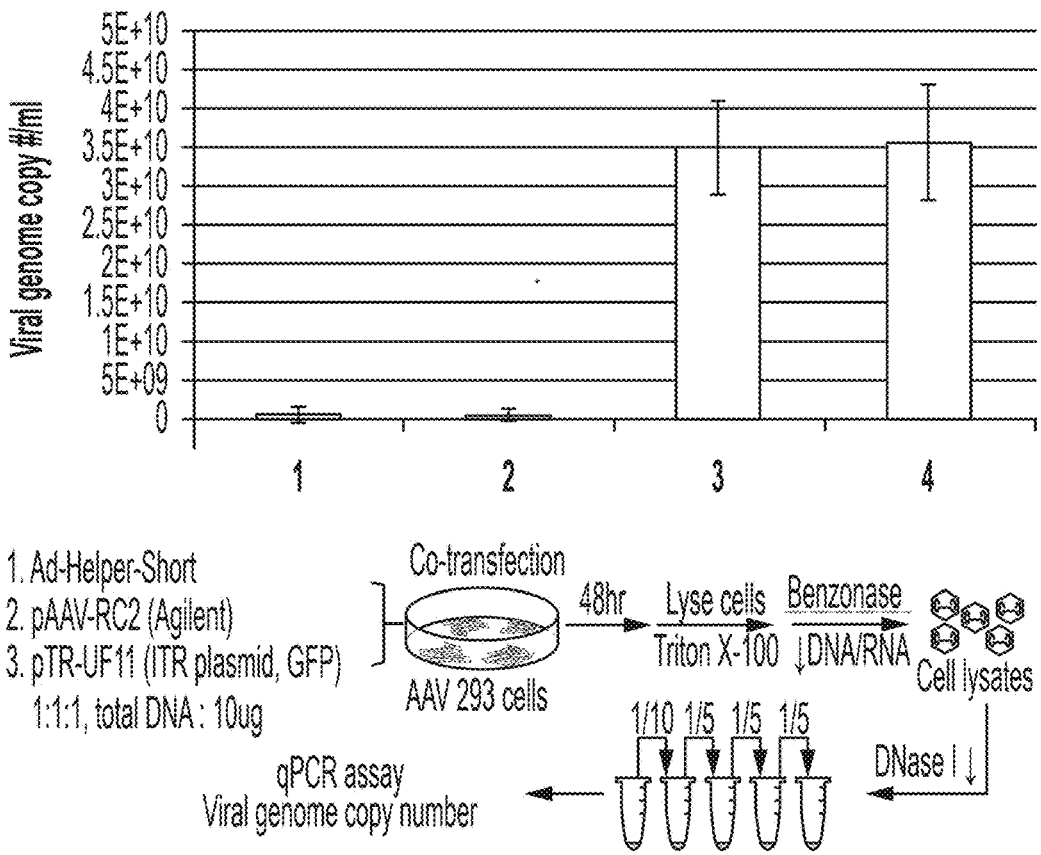
FIG. 9 shows the results of a qPCR assay of viral genome copy number using a short Ad Helper Plasmid according to the disclosure. 1: Negative Control 1 (pHelper+pAAV-RC2 (Agilent)); 2: Negative Control 2 (pHelper+pTRUF11); 3: Positive control (pHelper+pAAV-RC2+pTRUF11); 4: Short Ad Helper Test (Short-Helper (SEQ ID NO: 14)+pAAV-RC2+pTRUF11).

FIG. 9 shows the positive test results using the short Ad helper plasmid (SEQ ID NO: 14) in the HEK293 host cell system. The short Ad helper plasmid (SEQ ID NO: 14) was tested by co-transfecting the short helper plasmid along with a pTRUF11 transgene-containing plasmid carrying GFP as the transgene between the ITRs and the Agilent RC2 plasmid carrying AAV Rep2 and Cap2 genes. The negative controls consisted of 1) a commercial Ad helper plasmid (pHelper) and the Agilent plasmid RC2 and 2) pHelper and pTRUF11; the positive control consisted of pHelper, pTRUF11, and Agilent RC2 plasmid. After 48 hours, the HEK293 cells were lysed with Triton X-100 and treated with benzonase nuclease to degrade DNA and RNA. The cell lysates, containing AAV particles, were treated with DNase I and serially diluted before undergoing qPCR to determine the viral genome copy number per ml cell lysate. FIG. 9 shows the results of the qPCR assay, with columns 1 and 2 representing the negative controls, column 3 showing the positive control, and column 4 showing the viral genome copy number obtained when the short Ad helper plasmid was used together with 2 other plasmids to produce rAAV.

Figure 10:
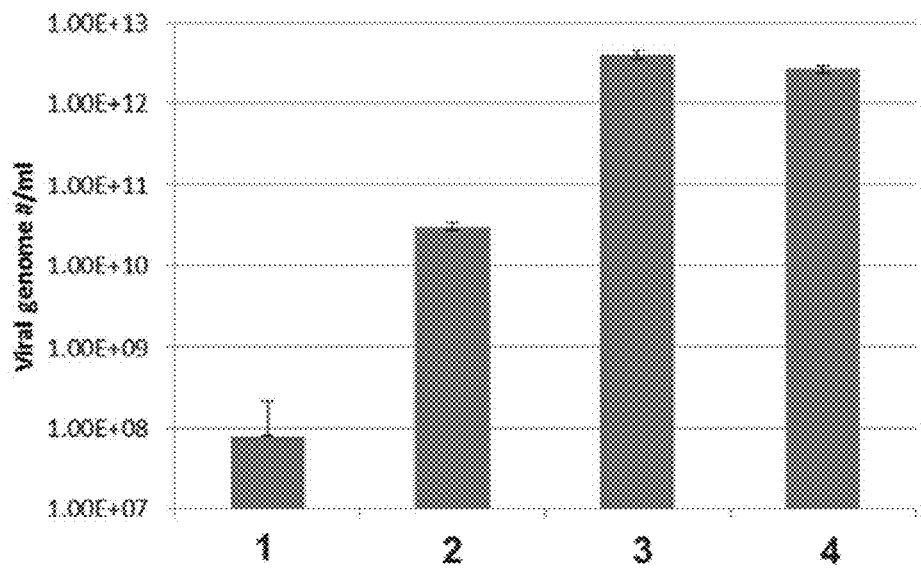
FIG. 10 shows the results of a qPCR assay of viral genome copy number using a long Ad Helper Plasmid according to the disclosure. 1: Negative Control 1 (pTRUF11+pAAV-RC2 (Rep2Cap2 (Agilent)); 2: Positive Control 2 (pHelper+pAAV-RC2+pTRUF11); 3: Short Ad Helper Test (Short-Helper (SEQ ID NO: 14)+pUC19-Rep2Cap8+pITRss (SEQ ID NO: 1)); 4: Long Ad Helper Test (Long-Helper (SEQ ID NO: 15)+pUC19-Rep2Cap8+pITRss (SEQ ID NO: 1)).

A similar experiment was performed to test a long Ad helper plasmid (SEQ ID NO: 15) according to the disclosure (FIG. 10). FIG. 10 shows the viral genome copy number per ml cell lysate, as determined by qPCR, of a negative control (column 1), a positive control (column 2), the short Ad helper plasmid (SEQ ID NO: 14)+Rep-Cap bearing plasmid+ITR-GFP bearing plasmid (column 3), and the long Ad Helper Plasmid+Rep-Cap bearing plasmid+ITR-GFP bearing plasmid (column 4). Therefore, the long Ad Helper Plasmid also resulted in the production of AAV.

Example 3: rAAV Virion Production Using the Triple-Plasmid System

Figure 11:
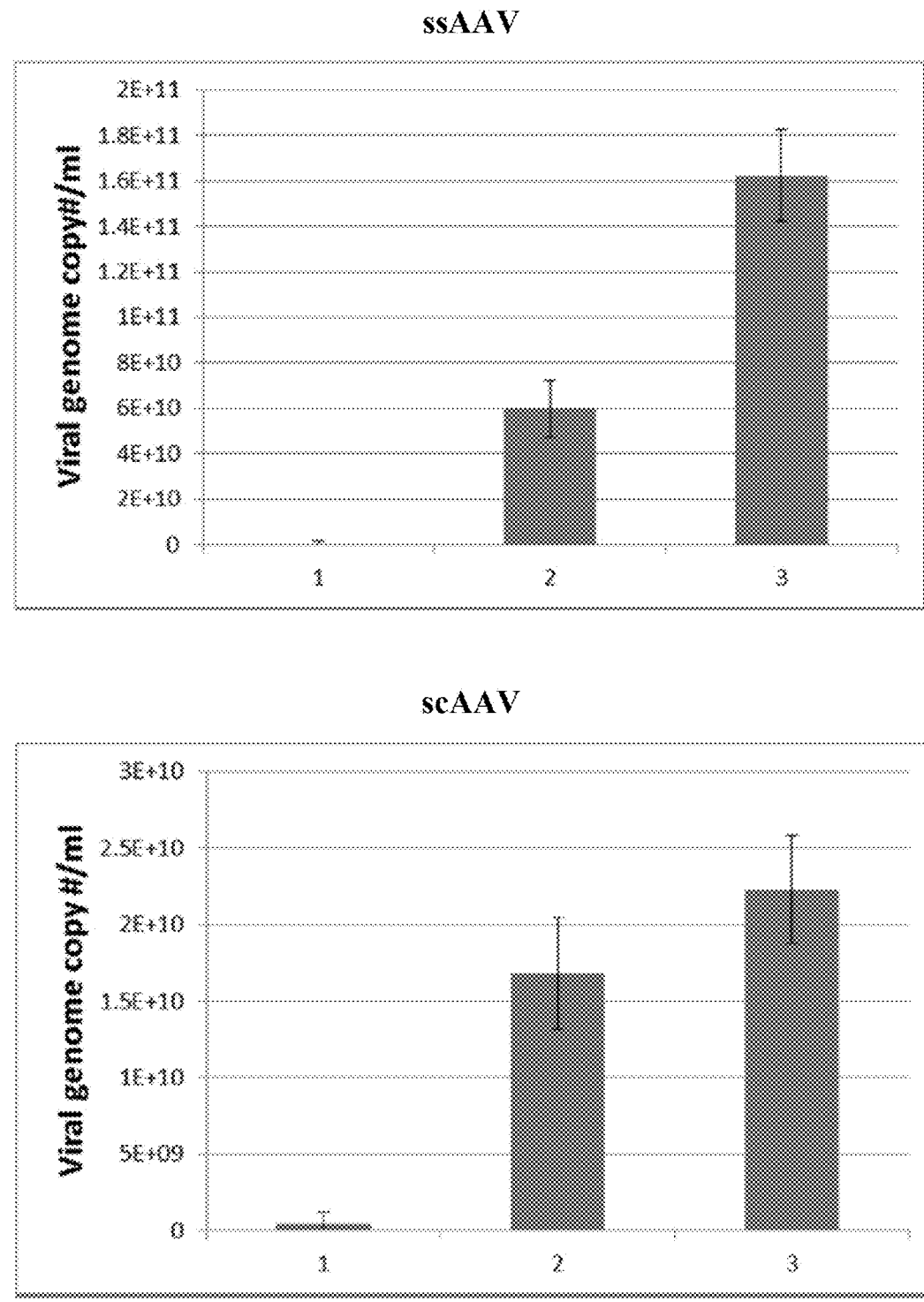
FIG. 11 shows the viral genome copy number per ml cell lysate for rAAV containing a single-stranded (top panel) or self-complementary (bottom panel) DNA genome produced using the corresponding transgene-containing plasmids for rAAV production. For the top panel: 1: Negative Control (pHelper+AAV-RC2); 2: Positive Control (pHelper+pAAV-RC2+pTRUF 11); 3: ssITR (pHelper+pAAV-RC2+ssITR) (SEQ ID NO: 1). For the bottom panel: 1: Negative Control (pHelper+AAV-RC2); 2: Positive Control (pHelper+pAAV-RC2+pTRUF11); 3: scITR (pHelper+pAAV-RC2+scITR (SEQ ID NO: 42).

The ability of the single strand (ss)- and self-complementary (sc)-ITR-bearing plasmids according to the disclosure to form rAAV virions was tested. In this experiment, the plasmids were co-transfected into HEK293 cells (Agilent). For each transfection, Ad-helper plasmid, Rep-Cap plasmid, and transgene-containing plasmid were used at 1:1:1 molar ratio and 10 ug of total DNA was used per 10 cm plate. The negative control was the commercially available Ad helper plasmid (Agilent) and the commercially available Rep-Cap-bearing plasmid (Agilent), while the positive control used a different ITR-bearing plasmid (ATCC). The top panel of FIG. 11 shows the viral genome copy number per ml cell lysate for the ss-ITR-bearing plasmid (measured by qPCR as above), while the bottom panel shows the viral genome copy number per ml cell lysate for the sc-ITR-bearing plasmid. In both panels, column 1 shows the copy number for the negative control, column 2 represents the positive control, and column 3 represents the plasmid according to the disclosure.

Figure 12:
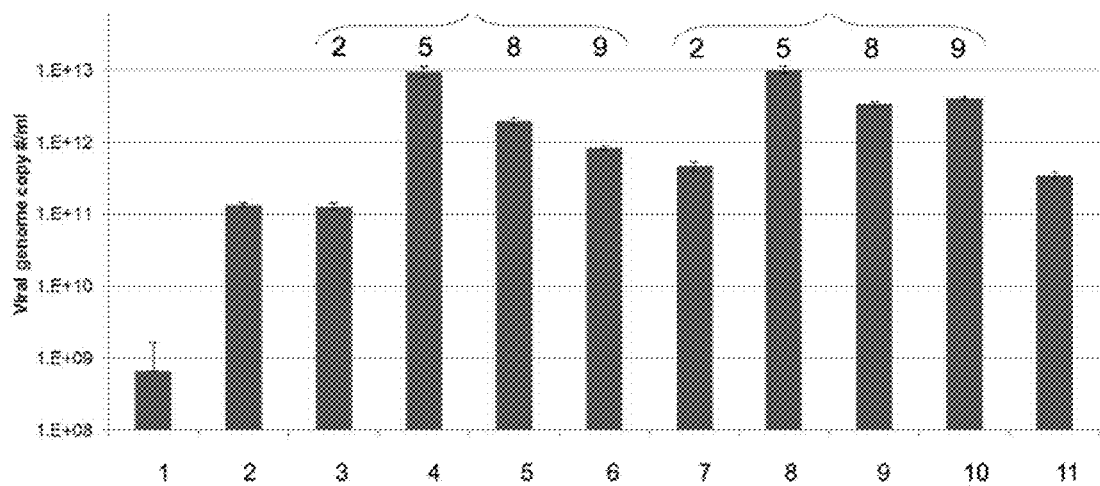
FIG. 12 shows the viral genome copy number per ml cell lysate of multiple capsid serotypes for a triple-plasmid system according to the disclosure, along with positive and negative controls. 1: Negative Control (pHelper+pTRUF11); 2: Positive Control (pHelper+pTRUF11+pAAV-RC2); 3: pHelper+pTRUF11+pUC19-P5-Rep2Cap2 (SEQ ID NO: 31); 4: pHelper+pTRUF11+pUC19-Rep2/5Cap5 (SEQ ID NO: 24); 5: pHelper+pTRUF11+pUC19-P5-Rep2Cap8 (SEQ ID NO: 35); 6: pHelper+pTRUF11+pUC19-P5-Rep2Cap9 (SEQ ID NO: 37); 7: Short-Helper (SEQ ID NO: 14)+ssITR (SEQ ID NO: 1)+pUC19-P5-Rep2Cap2 (SEQ ID NO: 31); 8: Short-Helper (SEQ ID NO: 14)+ssITR (SEQ ID NO: 1)+pUC19-Rep2/5Cap5 (SEQ ID NO: 24); 9: Short-Helper (SEQ ID NO: 14)+ssITR (SEQ ID NO: 1)+pUC19-P5-Rep2Cap8 (SEQ ID NO: 35); 10: Short-Helper (SEQ ID NO: 14)+ssITR (SEQ ID NO: 1)+pUC19-P5-Rep2Cap9 (SEQ ID NO: 37); 11: Short-Helper (SEQ ID NO: 14)+ssITR (SEQ ID NO: 1)+pAAV-RC2.
Figure 13A:
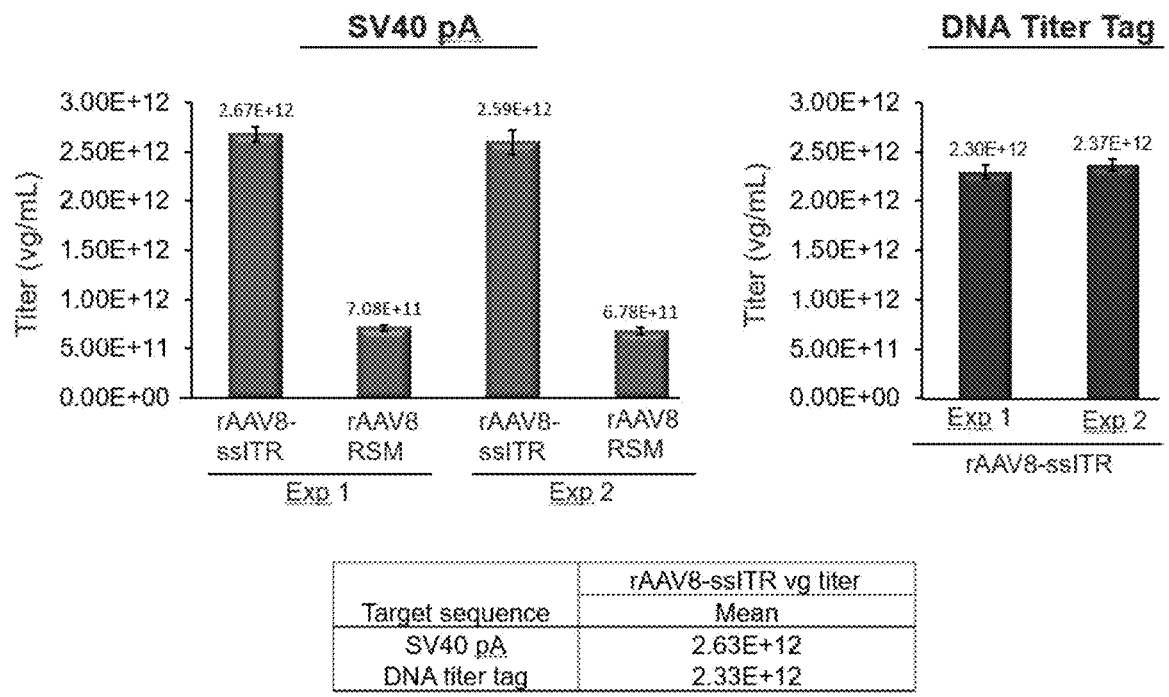
FIG. 13A-13B shows that viral genome copy number per ml lysate for the single strand ITR (ssITR) transgene plasmid (FIG. 13A) and self complementary ITR (scITR) plasmid using both SV40 polyA and a 100 nucleotide long DNA titer tag for qPCR analysis.
Figure 13B:
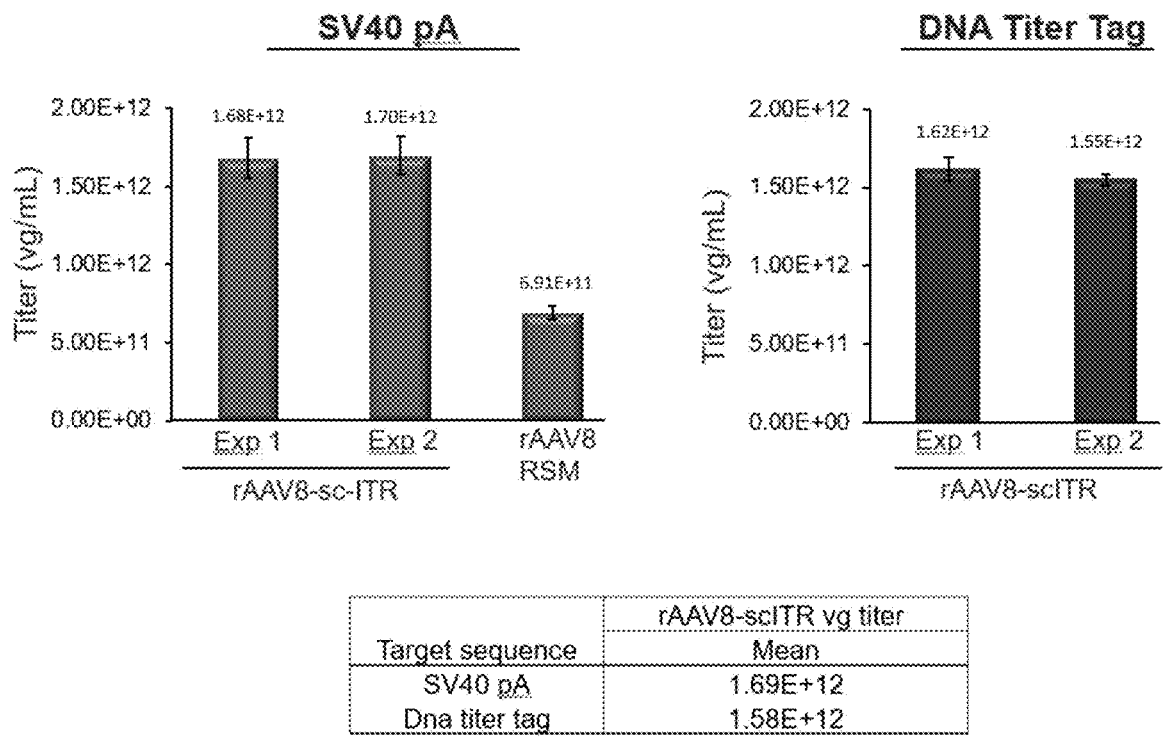

Next, three plasmids according to the disclosure were co-transfected into HEK293 cells (again, 1:1:1 ratio) for qPCR assays. The negative control (column 1 of FIG. 12) was a commercially available Ad helper plasmid and a ITR-bearing plasmid. The positive control (column 2 of FIG. 12) included a commercially available Rep-Cap-bearing plasmid. Columns 3-6 correspond to AAV genome copy numbers from cells transfected with the same commercially available Ad helper plasmid and ITR-bearing plasmid along with a pUC19-based plasmid encoding Rep and Cap proteins from AAV serotypes 2, 5, 8, or 9 (noted across the top of the figure). Columns 7-10 of FIG. 12 correspond to AAV genome copy numbers from cells transfected with Ad helper plasmids, pUC19-based Rep-Cap-bearing plasmids, and ITR-bearing plasmids according to the disclosure. Column 11 of FIG. 12 is another positive control corresponding to AAV genome copy number from cells transfected with an Ad helper plasmid and ss-ITR plasmid according to the disclosure and a commercially available Rep-Cap-bearing plasmid.

Example 4: Purification and Production of rAAVs

HEK293 cells were co-transfected with a plasmid system comprising three plasmids according to the disclosure. The cells were chemically lysed, and the cell pellet and medium were collected. The cell lysate was clarified and treated with benzonase. The clarified lysate was run on an appropriate affinity column (e.g., for a plasmid system comprising AAV8 capsid, the affinity column was AVB; for a plasmid system comprising AAV9, the affinity column was AAV9-POROS CaptureSelect). Following a buffer exchange, the rAAV was eluted from the column. The rAAV was then characterized, by way of example and not limitation, by qPCR to determine the viral genome copy number (see FIGS. 9-13, 16). The rAAV can further be evaluated by silver stain to determine purity and identity, by Limulus amebocyte lysate (LAL) assay to measure endotoxin activity and microbial contamination, and by an in vitro transduction assay to determine biological activity. Other characterization assays include alkaline electrophoresis to test the size and integrity of the viral genome, ELISA to examine the capsids, infectious center assays to determine the infectivity of the rAAV particles, and electron microscopy to observe the rAAV particles. Western blotting for specific proteins may also be performed by using appropriate antibodies (see FIGS. 6-8).

Example 5: Use of Tag to Titer Vector Genome

While sequences such as polyA sequences can be used for qPCR quantification, it is not ideal to use such sequences for universal titering. For example, each transgene may use a different polyA sequence (e.g., SV40, bGH polyA, etc.,), thereby precluding its use to quantitate vectors across all transgene platforms. Therefore, a separate DNA titer tag outside the transgene cassette (i.e., not transcribed as part of the transgene mRNA transcript) was tested for its ability to universally quantitate any transgene cassette.

A 100 nucleotides DNA titer tag was included upstream of the 3' ITR sequence. This same titer tag can be used in any transgene-containing plasmid for rAAV production to allow for universal vector genome titering via qPCR techniques, which can be used as a single reference standard for any project. The qPCR titration results were compared for the same batch of AAV using either SV40 polyA or the 100 nucleotides DNA titer tag as the target sequence.

Two different viral vectors: rAAV8-ssITR (SEQ ID NO: 1) and rAAV8-scITR (SEQ ID NO: 42) were produced with the transgene-containing plasmid being either single-stranded (SEQ ID NO: 1) or self-complementary (SEQ ID NO: 42) transgene-containing plasmids. Similar qPCR titers were obtained using the two different target sequences, indicating the 100 nucleotides DNA titer tag works equally well as the SV40 polyA, which has been widely used in the field for qPCR-based vector titration (FIG. 13A (rAAV8-ssITR) and 13B (rAAV8-scITR)).

Example 6: Use of Tag to Titer Vector Genome

To further confirm the utility of the DNA titer tag, the same 100 nucleotides DNA titer tag used in Example 5 was included upstream of the 3' ITR sequence in two additional viral vectors: rAAV9-ssITR (SEQ ID NO: 71) and rAAV9-scITR (SEQ ID NO: 73).

While several possible embodiments are disclosed above, embodiments of the present disclosure are not so limited. These exemplary embodiments are not intended to be exhaustive or to unnecessarily limit the scope of the disclosure, but instead were chosen and described in order to explain the principles of the present disclosure so that others skilled in the art may practice the disclosure. Indeed, various modifications of the disclosure in addition to those described herein will become apparent to those skilled in the art from the foregoing description. Such modifications are intended to fall within the scope of the appended claims. Further, the terminology employed herein is used for the purpose of describing exemplary embodiments only and the terminology is not intended to be limiting since the scope of the various embodiments of the present disclosure will be limited only by the appended claims and equivalents thereof. The scope of the disclosure is therefore indicated by the following claims, rather than the foregoing description and above-discussed embodiments, and all changes that come within the meaning and range of equivalents thereof are intended to be embraced therein.

All patents, applications, publications, test methods, literature, and other materials cited herein are hereby incorporated by reference in their entirety as if physically present in this specification.

What is claimed is:

1. A plasmid system for Recombinant Adeno-Associated Viral Vector (rAAV) production comprising the following three plasmids:
   (i) a transgene-containing plasmid comprising at least one heterologous nucleic acid flanked by a 5' and 3' AAV inverted terminal repeat (ITR) and a stuffer sequence outside of the ITRs, wherein the stuffer sequence comprises a nucleic acid having at least 40% identity to SEQ ID NO: 9;
   (ii) a plasmid comprising AAV replication (Rep) and capsid (Cap) gene sequences; and
   (iii) an adenovirus (Ad) helper plasmid,
   wherein the backbone of the transgene-containing plasmid is larger than a wild-type AAV genome, and wherein the transgene-containing plasmid further comprises a DNA titer tag having a length of between about 60 nucleotides to about 100 nucleotides.

2. The plasmid system of claim 1, wherein the transgene-containing plasmid is not packaged into an rAAV capsid.

3. The plasmid system of claim 1, wherein the stuffer sequence comprises a nucleic acid sequence of between 1000 and 2600 nucleotides in length.

4. The plasmid system of claim 1, wherein the stuffer sequence comprises GAPDH intron 2, fragment, or mutant thereof.

5. The plasmid system of claim 1, wherein the stuffer sequence comprises SEQ ID NO: 9.

6. The plasmid system of claim 1, wherein the transgene-containing plasmid comprises nucleic acid sequences in the 5' to 3' direction of: SEQ ID NO: 2, SEQ ID NO: 4, at least one heterologous nucleic acid, SEQ ID NO: 8, SEQ ID NO: 3, and the stuffer sequence.

7. The plasmid system of claim 1, wherein the transgene-containing plasmid comprises:
   a) the DNA titer tag i) upstream of the 3' ITR and downstream of a polyA sequence or ii) upstream of the 3' ITR and downstream of the at least one heterologous nucleic acid; iii) or downstream of the 5' ITR and upstream of the at least one heterologous nucleic acid sequence; or iv) downstream of the 5' ITR and upstream of a promoter for the at least one heterologous nucleic acid sequence; or v) downstream of the 5' ITR and upstream of the 3' ITR; or
   b) the DNA titer tag i) upstream of SEQ ID NO: 3 and downstream of SEQ ID NO: 8 or ii) upstream of SEQ ID NO: 3 and downstream of the at least one heterologous nucleic acid sequence; iii) or downstream of SEQ ID NO: 2 or SEQ ID NO: 43 and upstream of the at least one heterologous nucleic acid sequence; or iv) downstream of SEQ ID NO: 2 and upstream of SEQ ID NO: 4; or v) downstream of SEQ ID NO: 2 or SEQ ID NO: 43 and upstream of SEQ ID NO: 3.

8. The plasmid system of claim 1, wherein the transgene containing plasmid comprises nucleic acid sequences in the 5' to 3' direction of: SEQ ID NO: 43, SEQ ID NO:4, at least one heterologous nucleic acid sequence, SEQ ID NO: 8, SEQ ID NO: 3, and the stuffer sequence.

9. The plasmid system of claim 8, wherein the transgene-containing plasmid comprises the DNA titer tag outside the expression cassette but between the 5' ITR and 3' ITR.

10. A host cell comprising the plasmid system of claim 1.

11. A method for producing a Recombinant Adeno-Associated Viral Vector (rAAV) comprising transducing a cell with the plasmid system of claim 1 and isolating the rAAV.

12. A composition comprising the plasmid system of claim 1.

* * * * *

SEQUENCE LISTING

```
<160> NUMBER OF SEQ ID NOS: 77

<210> SEQ ID NO 1
<211> LENGTH: 10630
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (6316)..(6415)
<223> OTHER INFORMATION: a, c, t, g, unknown or other
<220> FEATURE:
```

```
<221> NAME/KEY: misc_feature
<222> LOCATION: (6316)..(6415)
<223> OTHER INFORMATION: This region may encompass 60-100 nucleotides

<400> SEQUENCE: 1
tagggaaata ggccaggttt tcaccgtaac acgccacatc ttgcgaatat atgtgtagaa      60
actgccggaa atcgtcgtgt gcactcatgg aaaacggtgt aacaagggtg aacactatcc     120
catatcacca gctcaccgtc tttcattgcc atacggaact ccggatgagc attcatcagg     180
cgggcaagaa tgtgaataaa ggccggataa aacttgtgct tatttttctt tacggtcttt     240
aaaaaggccg taatatccag ctgaacggtc tggttatagg tacattgagc aactgactga     300
aatgcctcaa aatgttcttt acgatgccat tgggatatat caacggtggt atatccagtg     360 attttttct ccattttttt ttcctccttt agaaaaactc atcgagcatc aaatgaaact      420
gcaatttatt catatcagga ttatcaatac catattttg aaaaagccgt ttctgtaatg      480
aaggagaaaa ctcaccgagg cagttccata ggatggcaag atcctggtat cggtctgcga     540
ttccgactcg tccaacatca atacaaccta ttaatttccc ctcgtcaaaa ataaggttat     600
caagtgagaa atcaccatga gtgacgactg aatccggtga agtggcaaa agtttatgca     660 tttctttcca gacttgttca acaggccagc cattacgctc gtcatcaaaa tcactcgcat     720
caaccaaacc gttattcatt cgtgattgcg cctgagcgag gcgaaatacg cgatcgctgt     780
taaaaggaca attacaaaca ggaatcgagt gcaaccggcg caggaacact gccagcgcat     840
caacaatatt ttcacctgaa tcaggatatt cttctaatac ctggaacgct gtttttccgg     900
ggatcgcagt ggtgagtaac catgcatcat caggagtacg gataaaatgc ttgatggtcg     960
gaagtggcat aaattccgtc agccagttta gtctgaccat ctcatctgta acatcattgg    1020
caacgctacc tttgccatgt ttcagaaaca actctggcgc atcgggcttc ccatacaagc    1080
gatagattgt cgcacctgat tgcccgacat tatcgcgagc ccatttatac ccatataaat    1140
cagcatccat gttggaattt aatcgcggcc tcgacgtttc ccgttgaata tggctcattt    1200 tttttcctc ctttaccaat gcttaatcag tgaggcacct atctcagcga tctgtctatt    1260
tcgttcatcc atagttgcct gactccccgt cgtgtagata actacgatac gggagggctt    1320
accatctggc cccagcgctg cgatgatacc gcgagaacca cgctcaccgg ctccggattt    1380
atcagcaata aaccagccag ccggaagggc cgagcgcaga agtggtcctg caactttatc    1440
cgcctccatc cagtctatta attgttgccg ggaagctaga gtaagtagtt cgccagttaa    1500
tagtttgcgc aacgttgttg ccatcgctac aggcatcgtg gtgtcacgct cgtcgtttgg    1560
tatggcttca ttcagctccg gttcccaacg atcaaggcga gttacatgat cccccatgtt    1620
gtgcacgttg tcagaagtaa gttggccgca gtgttatcac tcatggttat ggcagcactg    1680
cataattctc ttactgtcat gccatccgta agatgctttt ctgtgactgg tgagtactca    1740
accaagtcat tctgagaata gtgtatgcgg cgaccgagtt gctcttgccc ggcgtcaata    1800
cgggataata ccgcgccaca tagcagaact ttaaaagtgc tcatcattgg aaaacgttct    1860
tcggggcgaa aactctcaag gatcttaccg ctgttgagat ccagttcgat gtaacccact    1920
cgtgcaccca actgatcttc agcatctttt actttcacca gcgtttctgg gtgagcaaaa    1980
acaggaaggc aaaatgccgc aaaaaaggga ataagggcga cacggaaatg ttgaatactc    2040
atattcttcc ttttcaata ttattgaagc atttatcagg gttattgtct catgagcgga    2100
tacatatttg aatgtattta gaaaaataaa caaatagggg tcagtgttac aaccaattaa    2160
ccaattctga acattatcgc gagcccattt atacctgaat atggctcata acacccttg     2220
```

```
tttgcctggc ggcagtagcg cggtggtccc acctgacccc atgccgaact cagaagtgaa    2280
acgccgtagc gccgatggta gtgtggggac tccccatgcg agagtaggga actgccaggc    2340
atcaaataaa acgaaaggct cagtcgaaag actgggcctt tcgcccgggc taattgaggg    2400
gtgtcgccct tattcgactc ggggctcgag ctgcgcgctc gctcgctcac tgaggccgcc    2460
cgggcaaagc ccgggcgtcg gcgacctttt ggtcgcccgg cctcagtgag cgagcgagcg    2520
cgcagagagg gagtggccaa ctccatcact agggggttcct ttaattaaac gcgtttacat    2580
aacttacggt aaatggcccg cctggctgac cgcccaacga cccccgccca ttgacgtcaa    2640
taatgacgta tgttcccata gtaacgccaa tagggacttt ccattgacgt caatgggtgg    2700
actatttacg gtaaactgcc cacttggcag tacatcaagt gtatcatatg ccaagtacgc    2760
cccctattga cgtcaatgac ggtaaatggc ccgcctggca ttatgcccag tacatgacct    2820
tatgggactt tcctacttgg cagtacatct acgtattagt catcgctatt accatggtga    2880
tgcggttttg gcagtacatc aatgggcgtg atagcggtt tgactcacgg ggatttccaa    2940
gtctccaccc cattgacgtc aatgggagtt tgttttggca ccaaaatcaa cgggactttc    3000
caaaatgtcg taacaactcc gccccattga cgcaaatggg cggtaggcgt gtacggtggg    3060
aggtctatat aggcgcgccg aactgaaaaa ccagaaagtt aactggtaag tttagtcttt    3120
ttgtctttta tttcaggtcc cggatccggt ggtggtgcaa atcaaagaac tgctcctcag    3180
tggatgttgc ctttacttct aggcctgtac ggaagtgtta cttctgctct aaaagctcct    3240
gcagggaatt cgccaccatg gtgagcaagg gcgaggagct gttcaccggg gtggtgccca    3300
tcctggtcga gctggacggc gacgtaaacg gccacaagtt cagcgtgtcc ggcgagggcg    3360
agggcgatgc cacctacggc aagctgaccc tgaagttcat ctgcaccacc ggcaagctgc    3420
ccgtgccctg gcccacectc gtgaccaccc tgacctacgg cgtgcagtgc ttcagccgct    3480
accccgacca catgaagcag cacgacttct tcaagtccgc catgcccgaa ggctacgtcc    3540
aggagcgcac catcttcttc aaggacgacg gcaactacaa gacccgcgcc gaggtgaagt    3600
tcgagggcga cacccctggtg aaccgcatcg agctgaaggg catcgacttc aaggaggacg    3660
gcaacatcct ggggcacaag ctggagtaca actacaacag ccacaacgtc tatatcatgg    3720
ccgacaagca gaagaacggc atcaaggtga acttcaagat ccgccacaac atcgaggacg    3780
gcagcgtgca gctcgccgac cactaccagc agaacacccc catcggcgac ggccccgtgc    3840
tgctgcccga caaccactac ctgagcaccc agtccgccct gagcaaagac cccaacgaga    3900
agcgcgatca catggtcctg ctggagttcg tgaccgccgc cgggatcact ctcggcatgg    3960
acgagctgta caagtaatag actagtgccc ctctccctcc ccccccccta cgttactgg    4020 ccgaagccgc ttggaataag gccggtgtgc gtttgtctat atgttatttt ccaccatatt    4080
gccgtctttt ggcaatgtga gggcccggaa acctggccct gtcttcttga cgagcattcc    4140 tagggggtctt tccctctcg ccaaaggaat gcaaggtctg ttgaatgtcg tgaaggaagc    4200
agttcctctg gaagcttctt gaagacaaac aacgtctgta gcgaccctttt gcaggcagcg    4260 gaaccccccca cctggcgaca ggtgcctctg cggccaaaag ccacgtgtat aagatacacc    4320
tgcaaaggcg gcacaacccc agtgccacgt tgtgagttgg atagttgtgg aaagagtcaa    4380
atggctcacc tcaagcgtat tcaacaaggg gctgaaggat gcccagaagg taccccattg    4440
tatgggatct gatctggggc ctcggtgcac atgctttaca tgtgtttagt cgaggttaaa    4500
aaacgtctag gccccccgaa ccacggggac gtggttttcc tttgaaaaac acgatgataa    4560
```

-continued

```
taccggtgcc accatgctgc tgctgctgct gctgctgggc ctgaggctac agctctccct    4620
gggcatcatc ccagttgagg aggagaaccc ggacttctgg aaccgcgagg cagccgaggc    4680
cctgggtgcc gccaagaagc tgcagcctgc acagacagcc gccaagaacc tcatcatctt    4740
cctgggcgat gggatggggg tgtctacggt gacagctgcc aggatcctaa aagggcagaa    4800
gaaggacaaa ctggggcctg agataccct ggccatggac cgcttcccat atgtggctct    4860
gtccaagaca tacaatgtag acaaacatgt gccagacagt ggagccacag ccacggccta    4920
cctgtgcggg gtcaagggca acttccagac cattggcttg agtgcagccg cccgctttaa    4980
ccagtgcaac acgacacgcg gcaacgaggt catctccgtg atgaatcggg ccaagaaagc    5040
agggaagtca gtgggagtgg taaccaccac acgagtgcag cacgcctcgc cagccggcac    5100
ctacgcccac acgtgaacc gcaactggta ctcggacgcc gacgtgcctg cctcggcccg    5160
ccaggagggg tgccaggaca tcgctacgca gctcatctcc aacatggaca ttgacgtgat    5220
cctaggtgga ggccgaaagt acatgtttcg catgggaacc ccagaccctg agtacccaga    5280
tgactacagc caaggtggga ccaggctgga cgggaagaat ctggtgcagg aatggctggc    5340
gaagcgccag ggtgcccggt atgtgtggaa ccgcactgag ctcatgcagg cttccctgga    5400
cccgtctgtg acccatctca tgggtctctt tgagcctgga gacatgaaat acgagatcca    5460
ccgagactcc acactggacc cctccctgat ggagatgaca gaggctgccc tgcgcctgct    5520
gagcaggaac ccccgcggct tcttcctctt cgtggagggt ggtcgcatcg accatggtca    5580
tcatgaaagc agggcttacc gggcactgac tgagacgatc atgttcgacg acgccattga    5640
gagggcgggc cagctcacca gcgaggagga cacgctgagc ctcgtcactg ccgaccactc    5700
ccacgtcttc tccttcggag gctaccccct gcgagggagc tccatcttcg ggctggcccc    5760
tggcaaggcc cggacagga aggcctacac ggtcctccta tacggaaacg gtccaggcta    5820
tgtgctcaag gacggcgccc ggccggatgt taccgagagc gagagcggga gccccgagta    5880
tcggcagcag tcagcagtgc ccctggacga agagacccac gcaggcgagg acgtggcggt    5940
gttcgcgcgc ggcccgcagg cgcacctggt tcacggcgtg caggagcaga ccttcatagc    6000
gcacgtcatg gccttcgccg cctgcctgga gccctacacc gcctgcgacc tggcgccccc    6060
cgccggcacc accgacgccg cgcacccggg ttactctaga gtcggggcgg ccggccgctt    6120
cgagcagaca tgagtcgaca gatcttttaa aaaacctccc acacaattgt tgttgttaac    6180
ttgtttattg cagcttataa tggttacaaa taaagcaata gcatcacaaa tttcacaaat    6240
aaagcatttt tttcactgca ttctagttgt ggtttgtcca aactcatcaa tgtatcttat    6300
catgtctgtt taaacnnnnn nnnnnnnnnn nnnnnnnnnn nnnnnnnnnn nnnnnnnnnn    6360
nnnnnnnnnn nnnnnnnnnn nnnnnnnnnn nnnnnnnnnn nnnnnnnnnn nnnnnattta    6420
aataggaacc cctagtgatg gagttggcca ctccctctct gcgcgctcgc tcgctcactg    6480
aggccgggcg accaaaggtc gcccgacgcc cgggctttgc ccgggcggcc tcagtgagcg    6540
agcgagcgcg cagagagtat acatcgatgt gagttcgcgg gtggctgggg ggccctgggc    6600
tgcgaccgcc cccgaaccgc gtctacgagc cttgcgggct ccgggtcttt gcagtcgtat    6660
ggggggcaggg tagctgttcc ccgcaaggag agctcaaggt cagcgctcgg acctggcgga    6720
gccccgcacc caggctgtgg cgccctgtgc agctccgccc ttgcggcgcc atctgcccgg    6780
agcctccttc ccctagtccc cagaaacagg aggtccctac tcccgcccga gatcccgacc    6840
cggacccta ggtgggggac gctttctttc ctttcgcgct ctgcggggtc acgtgtcgca    6900
gaggagcccc tccccacgg cctccggcac cgcaggcccc gggatgctag tgcgcagcgg    6960
```

```
gtgcatccct gtccggatgc tgcgcctgcg gtagagcggc cgccatgttg caaccgggaa   7020
ggaaatgaat gggcagccgt taggaaagcc tgccggtgac taaccctgcg ctcctgcctc   7080
gatgggtgga gtcgcgtgtg gcggggaagt caggtggagc gaggctagct ggcccgattt   7140
ctcctccggg tgatgctttt cctagattat tctctggtaa atcaaagaag tgggtttatg   7200
gaggtcctct tgtgtcccct ccccgcagag gtgtggtggc tgtggcatgg tgccaagccg   7260
ggagaagctg agtcatgggt agttggaaaa ggacatttcc accgcaaaat ggccctctg   7320 gtggtggccc cttcctgcag cgccggctca cctcacggcc ccgcccttcc cctgccagcc   7380
tagcgttgac ccgaccccaa aggccaggct gtaaatgtca ccgggaggat tgggtgtctg   7440
ggcgcctcgg ggaacctgcc cttctcccca ttccgtcttc cggaaaccag atctcccacc   7500 gcacccctggt ctgaggttaa atatagctgc tgacctttct gtagctgggg gcctgggctg   7560
gggctctctc ccatcccttc tccccacaca catgcactta cctgtgctcc cactcctgat   7620
ttctggaaaa gagctaggaa ggacaggcaa cttggcaaat caaagccctg ggactagggg   7680
gttaaaatac agcttcccct cttcccaccc gccccagtct ctgtcccttt tgtaggaggg   7740
acttagagaa ggggtgggct tgccctgtcc agttaatttc tgacctttac tcctgccctt   7800
tgagtttgat gatgctgagt gtacaagcgt tttctcccta aagggtgcag ctgagctagg   7860
cagcagcaag cattcctggg gtggcatagt ggggtggtga ataccatgta caaagcttgt   7920
gcccagactg tgggtggcag tgccccacat ggccgcttct cctggaaggg cttcgtatga   7980 ctggggtgt tgggcagccc tggagccttc agttgcagcc atgccttaag ccaggccagc   8040
ctggcaggga agctcaaggg agataaaatt caacctcttg ggccctcctg ggggtaagga   8100
gatgctgcat tcgccctctt aatggggagg tggcctaggg ctgctcacat attctggagg   8160
agcctcccct cctcatgcct tcttgcctct tgtctcttag gcatgcaaaa gagtcgaata   8220
agggcgacac aaaatttatt ctaaatgcat aataaatact gataacatct tatagtttgt   8280
attatatttt gtattatcgt tgacatgtat aattttgata tcaaaaactg attttcccctt   8340 tattattttc gagatttatt ttcttaattc tctttaacaa actagaaata ttgtatatac   8400
aaaaaatcat aaataataga tgaatagttt aattataggt gttcatcaat cgaaaaagca   8460
acgtatctta tttaaagtgc gttgcttttt tctcatttat aaggttaaat aattctcata   8520
tatcaagcaa agtgacaggc gcccttaaat attctgacaa atgctctttc cctaaactcc   8580
ccccataaaa aaacccgccg aagcgggttt ttacgttatt tgcggattaa cgattactcg   8640
ttatcagaac cgcccagggg gcccgagctt aagactggcc gtcgttttac aacacagaaa   8700
gagtttgtag aaacgcaaaa aggccatccg tcagggggcct tctgcttagt ttgatgcctg   8760
gcagttccct actctcgcct tccgcttcct cgctcactga ctcgctgcgc tcggtcgttc   8820
ggctgcggcg agcggtatca gctcactcaa aggcggtaat acggttatcc acagaatcag   8880
gggataacgc aggaaagaac atgtgagcaa aaggccagca aaaggccagg aaccgtaaaa   8940
aggccgcgtt gctggcgttt ttccataggc tccgccccc tgacgagcat cacaaaaatc   9000
gacgctcaag tcagaggtgg cgaaacccga caggactata aagataccag gcgtttcccc   9060
ctggaagctc cctcgtgcgc tctcctgttc cgaccctgcc gcttaccgga tacctgtccg   9120
cctttctccc ttcgggaagc gtggcgcttt ctcatagctc acgctgtagg tatctcagtt   9180
cggtgtaggt cgttcgctcc aagctgggct gtgtgcacga accccccgtt cagcccgacc   9240
gctgcgcctt atccggtaac tatcgtcttg agtccaaccc ggtaagacac gacttatcgc   9300
```

```
cactggcagc agccactggt aacaggatta gcagagcgag gtatgtaggc ggtgctacag      9360
agttcttgaa gtggtgggct aactacggct acactagaag aacagtattt ggtatctgcg      9420
ctctgctgaa gccagttacc ttcggaaaaa gagttggtag ctcttgatcc ggcaaacaaa      9480
ccaccgctgg tagcggtggt ttttttgttt gcaagcagca gattacgcgc agaaaaaaag      9540
gatctcaaga agatcctttg atcttttcta cggggtctga cgctcagtgg aacgacgcgc      9600
gcgtaactca cgttaaggga ttttggtcat gagcttgcgc cgtcccgtca agtcagcgta      9660
atgctctgct taggtggcgg tacttgggtc gatatcaaag tgcatcactt cttcccgtat      9720
gcccaacttt gtatagagag ccactgcggg atcgtcaccg taatctgctt gcacgtagat      9780
cacataagca ccaagcgcgt tggcctcatg cttgaggaga ttgatgagcg cggtggcaat      9840
gccctgcctc cggtgctcgc cggagactgc gagatcatag atatagatct cactacgcgg      9900
ctgctcaaac ttgggcagaa cgtaagccgc gagagcgcca acaaccgctt cttggtcgaa      9960
ggcagcaagc gcgatgaatg tcttactacg gagcaagttc ccgaggtaat cggagtccgg     10020
ctgatgttgg gagtaggtgg ctacgtcacc gaactcacga ccgaaaagat caagagcagc     10080
ccgcatggat ttgacttggt cagggccgag cctacatgtg cgaatgatgc ccatacttga     10140
gccacctaac tttgttttag gcgactgccc tgctgcgta acatcgttgc tgctccataa     10200
catcaaacat cgacccacgg cgtaacgcgc ttgctgcttg gatgcccgag gcatagactg     10260
tacaaaaaaa cagtcataac aagccatgaa aaccgccact gcgccgttac caccgctgcg     10320
ttcggtcaag gttctggacc agttgcgtga gcgcattttt ttttcctcct cggcgtttac     10380
gccccgccct gccactcatc gcagtactgt tgtaattcat taagcattct gccgacatgg     10440
aagccatcac agacggcatg atgaacctga atcgccagcg gcatcagcac cttgtcgcct     10500
tgcgtataat atttgcccat agtgaaaacg ggggcgaaga agttgtccat attggccacg     10560
tttaaatcaa aactggtgaa actcacccag ggattggcgc tgacgaaaaa catattctca     10620 ataaacccttt                                                           10630

<210> SEQ ID NO 2
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
ctgcgcgctc gctcgctcac tgaggccgcc cgggcaaagc ccgggcgtcg ggcgaccttt       60
ggtcgcccgg cctcagtgag cgagcgagcg cgcagagagg gagtggccaa ctccatcact      120
aggggttcct                                                            130

<210> SEQ ID NO 3
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
aggaacccct agtgatggag ttggccactc cctctctgcg cgctcgctcg ctcactgagg       60
ccgggcgacc aaaggtcgcc cgacgcccgg gctttgcccg gcggcctcag tgagcgagc      120 gagcgcgcag aga                                                        133
```

```
<210> SEQ ID NO 4
<211> LENGTH: 503
<212> TYPE: DNA
<213> ORGANISM: Human cytomegalovirus

<400> SEQUENCE: 4
acgcgtttac ataacttacg gtaaatggcc cgcctggctg accgcccaac gacccccgcc    60
cattgacgtc aataatgacg tatgttccca tagtaacgcc aatagggact ttccattgac   120
gtcaatgggt ggactattta cggtaaactg cccacttggc agtacatcaa gtgtatcata   180
tgccaagtac gccccctatt gacgtcaatg acggtaaatg gcccgcctgg cattatgccc   240
agtacatgac cttatgggac tttcctactt ggcagtacat ctacgtatta gtcatcgcta   300
ttaccatggt gatgcggttt tggcagtaca tcaatgggcg tggatagcgg tttgactcac   360
ggggatttcc aagtctccac cccattgacg tcaatgggag tttgttttgg caccaaaatc   420
aacgggactt tccaaaatgt cgtaacaact ccgccccatt gacgcaaatg ggcggtaggc   480
gtgtacggtg ggaggtctat ata                                            503

<210> SEQ ID NO 5
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagtaa   720
tag                                                                  723

<210> SEQ ID NO 6
<211> LENGTH: 575
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gcccctctcc ctcccccccc cctaacgtta ctggccgaag ccgcttggaa taaggccggt    60
gtgcgtttgt ctatatgtta ttttccacca tattgccgtc ttttggcaat gtgagggccc   120
```

| | |
|---|---|
| ggaaacctgg ccctgtcttc ttgacgagca ttcctagggg tctttcccct ctcgccaaag | 180 |
| gaatgcaagg tctgttgaat gtcgtgaagg aagcagttcc tctggaagct tcttgaagac | 240 |
| aaacaacgtc tgtagcgacc ctttgcaggc agcggaaccc cccacctggc gacaggtgcc | 300 |
| tctgcggcca aaagccacgt gtataagata cacctgcaaa ggcggcacaa ccccagtgcc | 360 |
| acgttgtgag ttggatagtt gtggaaagag tcaaatggct cacctcaagc gtattcaaca | 420 |
| aggggctgaa ggatgcccag aaggtacccc attgtatggg atctgatctg ggcctcggt | 480 |
| gcacatgctt tacatgtgtt tagtcgaggt taaaaaacgt ctaggccccc cgaaccacgg | 540 |
| ggacgtggtt ttcctttgaa aaacacgatg ataat | 575 |

<210> SEQ ID NO 7
<211> LENGTH: 1560
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

| | |
|---|---|
| atgctgctgc tgctgctgct gctgggcctg aggctacagc tctccctggg catcatccca | 60 |
| gttgaggagg agaacccgga cttctggaac cgcgaggcag ccgaggccct gggtgccgcc | 120 |
| aagaagctgc agcctgcaca gacagccgcc aagaacctca tcatcttcct gggcgatggg | 180 |
| atgggggtgt ctacggtgac agctgccagg atcctaaaag ggcagaagaa ggacaaactg | 240 |
| gggcctgaga tacccctggc catggaccgc ttcccatatg tggctctgtc caagacatac | 300 |
| aatgtagaca acatgtgcc agacagtgga gccacagcca cggcctacct gtgcggggtc | 360 |
| aagggcaact tccagaccat tggcttgagt gcagccgccc gctttaacca gtgcaacacg | 420 |
| acacgcggca acgaggtcat ctccgtgatg aatcgggcca agaaagcagg gaagtcagtg | 480 |
| ggagtggtaa ccaccacacg agtgcagcac gcctcgccag ccggcaccta cgcccacacg | 540 |
| gtgaaccgca actggtactc ggacgccgac gtgcctgcct cggcccgcca ggagggggtgc | 600 |
| caggacatcg ctacgcagct catctccaac atggacattg acgtgatcct aggtggaggc | 660 |
| cgaaagtaca tgtttcgcat gggaaccca gaccctgagt acccagatga ctacagccaa | 720 |
| ggtgggacca ggctgacgg gaagaatctg gtgcaggaat ggctggcgaa gcgccagggt | 780 |
| gcccggtatg tgtggaaccg cactgagctc atgcaggctt ccctgaccc gtctgtgacc | 840 |
| catctcatgg gtctctttga gcctggagac atgaaatacg agatccaccg agactccaca | 900 |
| ctggacccct ccctgatgga gatgacagag gctgccctgc gcctgctgag caggaacccc | 960 |
| cgcggcttct tcctcttcgt ggagggtggt cgcatcgacc atggtcatca tgaaagcagg | 1020 |
| gcttaccggg cactgactga gacgatcatg ttcgacgacg ccattgagag ggcgggccag | 1080 |
| ctcaccagcg aggaggacac gctgagcctc gtcactgccg accactccca cgtcttctcc | 1140 |
| ttcggaggct acccctgcg agggagctcc atcttcgggc tggcccctgg caaggcccgg | 1200 |
| gacaggaagg cctacacggt cctcctatac ggaaacggtc caggctatgt gctcaaggac | 1260 |
| ggcgcccggc cggatgttac cgagagcgag agcgggagcc ccgagtatcg gcagcagtca | 1320 |
| gcagtgcccc tggacgaaga gacccacgca ggcgaggacg tggcggtgtt cgcgcgcggc | 1380 |
| ccgcaggcgc acctggttca cggcgtgcag gagcagacct tcatagcgca cgtcatggcc | 1440 |
| ttcgccgcct gctggagcc ctacaccgcc tgcgacctgg cgccccccgc cggcaccacc | 1500 |
| gacgccgcgc acccgggtta ctctagagtc ggggcggccg ccgcttcga gcagacatga | 1560 |

<210> SEQ ID NO 8
<211> LENGTH: 168
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

| | | | |
|---|---|---|---|
| agatctttta aaaaacctcc cacacaattg ttgttgttaa cttgtttatt gcagcttata | 60 |
| atggttacaa ataaagcaat agcatcacaa atttcacaaa taaagcattt ttttcactgc | 120 |
| attctagttg tggtttgtcc aaactcatca atgtatctta tcatgtct | 168 |

<210> SEQ ID NO 9
<211> LENGTH: 1632
<212> TYPE: DNA
<213> ORGANISM: Homo sapiens

<400> SEQUENCE: 9

| | | | |
|---|---|---|---|
| gtgagttcgc gggtggctgg ggggccctgg gctgcgaccg cccccgaacc gcgtctacga | 60 |
| gccttgcggg ctccgggtct ttgcagtcgt atgggggcag ggtagctgtt ccccgcaagg | 120 |
| agagctcaag gtcagcgctc ggacctggcg gagccccgca cccaggctgt ggcgccctgt | 180 |
| gcagctccgc ccttgcggcg ccatctgccc ggagcctcct tccccctagtc cccagaaaca | 240 |
| ggaggtccct actcccgccc gagatcccga cccggacccc taggtggggg acgctttctt | 300 |
| tcctttcgcg ctctgcgggg tcacgtgtcg cagaggagcc cctccccac ggcctccggc | 360 |
| accgcaggcc ccgggatgct agtgcgcagc gggtgcatcc ctgtccggat gctgcgcctg | 420 |
| cggtagagcg gccgccatgt tgcaaccggg aaggaaatga atgggcagcc gttaggaaag | 480 |
| cctgccggtg actaaccctg cgctcctgcc tcgatgggtg gagtcgcgtg tggcggggaa | 540 |
| gtcaggtgga gcgaggctag ctggcccgat ttctcctccg ggtgatgctt ttcctagatt | 600 |
| attctctggt aaatcaaaga agtgggttta tggaggtcct cttgtgtccc ctccccgcag | 660 |
| aggtgtggtg gctgtggcat ggtgccaagc cgggagaagc tgagtcatgg gtagttggaa | 720 |
| aaggacattt ccaccgcaaa atggcccctc tggtggtggc cccttcctgc agcgccggct | 780 |
| cacctcacgg ccccgccctt cccctgccag cctagcgttg acccgacccc aaaggccagg | 840 |
| ctgtaaatgt caccggagg attgggtgtc tgggcgcctc ggggaacctg cccttctccc | 900 |
| cattccgtct tccggaaacc agatctccca ccgcaccctg gtctgaggtt aaatatagct | 960 |
| gctgaccttt ctgtagctgg gggcctgggc tgggctctc tcccatccct tctccccaca | 1020 |
| cacatgcact tacctgtgct cccactcctg atttctggaa aagagctagg aaggacaggc | 1080 |
| aacttggcaa atcaaagccc tgggactagg gggttaaaat acagcttccc ctcttcccac | 1140 |
| ccgcccagt ctctgtccct tttgtaggag ggacttagag aaggggtggg cttgccctgt | 1200 |
| ccagttaatt tctgaccttt actcctgccc tttgagtttg atgatgctga gtgtacaagc | 1260 |
| gtttctccc taagggtgc agctgagcta ggcagcagca agcattcctg gggtggcata | 1320 |
| gtggggtggt gaataccatg tacaaagctt gtgcccagac tgtgggtggc agtgccccac | 1380 |
| atggccgctt ctcctggaag ggcttcgtat gactgggggt gttgggcagc cctggagcct | 1440 |
| tcagttgcag ccatgcctta agccaggcca gcctggcagg gaagctcaag ggagataaaa | 1500 |
| ttcaacctct tgggccctcc tgggggtaag gagatgctgc attcgccctc ttaatgggga | 1560 |
| ggtggcctag ggctgctcac atattctgga ggagcctccc ctcctcatgc cttcttgcct | 1620 | cttgtctctt ag                                                           1632

<210> SEQ ID NO 10
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(100)
<223> OTHER INFORMATION: a, c, t, g, unknown or other
<220> FEATURE:
<221> NAME/KEY: misc_feature
<222> LOCATION: (1)..(100)
<223> OTHER INFORMATION: This sequence may encompass 60-100 nucleotides

<400> SEQUENCE: 10
nnnnnnnnnn nnnnnnnnnn nnnnnnnnnn nnnnnnnnnn nnnnnnnnnn nnnnnnnnnn        60
nnnnnnnnnn nnnnnnnnnn nnnnnnnnnn nnnnnnnnnn                             100

<210> SEQ ID NO 11
<211> LENGTH: 1845
<212> TYPE: DNA
<213> ORGANISM: Adeno-associated virus

<400> SEQUENCE: 11
atgccggggt tttacgagat tgtgattaag gtccccagcg accttgacga gcatctgccc         60
ggcatttctg acagctttgt gaactgggtg gccgagaagg aatgggagtt gccgccagat        120
tctgacatgg atctgaatct gattgagcag gcaccctga ccgtggccga gaagctgcag        180
cgcgactttc tgacggaatg cgcgcgtgtg agtaaggccc cggaggccct tttctttgtg        240
caatttgaga agggagagag ctacttccac atgcacgtgt cgtggaaac caccggggtg        300 aaatccatgg ttttgggacg tttcctgagt cagattcgcg aaaaactgat tcagagaatt        360
taccgcggga tcgagccgac tttgccaaac tggttcgcgg tcacaaagac cagaaatggc        420
gccggaggcg ggaacaaggt ggtggatgag tgctacatcc ccaattactt gctccccaaa        480
acccagcctg agctccagtg ggcgtggact aatatggaac agtatttaag cgcctgtttg        540
aatctcacgg agcgtaaacg gttggtggcg cagcatctga cgcacgtgtc gcagacgcag        600
gagcagaaca aagagaatca gaatcccaat tctgatgcgc cggtgatcag atcaaaaact        660
tcagccaggt acatggagct ggtcgggtgg ctcgtggaca aggggattac ctcggagaag        720
cagtggatcc aggaaaatca ggagagctac ctctccttca ctccaccgg caactctcgg        780 agccagatca aggccgcgct cgacaacgcg accaaaatta tgagtctgac aaaaagcgcg        840
gtggactacc tcgtggggag ctccgttccc gaggacattt caaaaaacag aatctggcaa        900 attttttgaga tgaatggcta cgacccggcc tacgcgggat ccatcctcta cggctggtgt        960
cagcgctcct tcaacaagag gaacaccgtc tggctctacg acccgccac gaccggcaag       1020 accaacatcg cggaggccat cgcccacact gtgccctttt acggctgcgt gaactggacc       1080
aatgaaaact ttccctttaa tgactgtgtg gacaaaatgc tcatttggtg ggaggaggga       1140
aagatgacca caaggtggt tgaatccgcc aaggccatcc tgggggctc aaaggtgcgg       1200 gtcgatcaga aatgtaaatc tctgttcaa attgattcta ccctgtcat tgtaacttcc       1260 aatacaaaca tgtgtgtggt ggtggatggg aattccacga cctttgaaca ccagcagccg       1320
ctggaggacc gcatgttcaa atttgaactg actaagcggc tcccgccaga ttttggcaag       1380

```
attactaagc aggaagtcaa ggactttttt gcttgggcaa aggtcaatca ggtgccggtg    1440
actcacgagt ttaaagttcc cagggaattg gcgggaacta aagggcgga gaaatctcta    1500 aaacgcccac tgggtgacgt caccaatact agctataaaa gtctggagaa gcgggccagg    1560
ctctcatttg ttcccgagac gcctcgcagt tcagacgtga ctgttgatcc cgctcctctg    1620
cgaccgctca attggaattc aaggtatgat tgcaaatgtg actatcatgc tcaatttgac    1680
aacatttcta acaaatgtga tgaatgtgaa tatttgaatc ggggcaaaaa tggatgtatc    1740
tgtcacaatg taactcactg tcaaatttgt catgggattc cccctggga aaaggaaaac    1800 ttgtcagatt ttggggattt tgacgatgcc aataaagaac agtaa               1845
```

<210> SEQ ID NO 12
<211> LENGTH: 1866
<212> TYPE: DNA
<213> ORGANISM: Adeno-associated virus

<400> SEQUENCE: 12

```
atgccggggt tttacgagat tgtgattaag gtccccagcg accttgacga gcatctgccc     60
ggcatttctg acagctttgt gaactgggtg gccgagaagg aatgggagtt gccgccagat    120
tctgacatga tctgaatct gattgagcag gcacccctga ccgtggccga gaagctgcag    180
cgcgactttc tgacggaatg gcgccgtgtg agtaaggccc cggaggccct tttctttgtg    240
caatttgaga agggagagag ctacttccac atgcacgtgc tcgtggaaac caccggggtg    300
aaatccatgg tttgggacg tttcctgagt cagattcgcg aaaaactgat tcagagaatt    360
taccgcggga tcgagccgac tttgccaaac tggttcgcgg tcacaaagac cagaaatggc    420
gccggaggcg ggaacaaggt ggtggatgag tgctacatcc ccaattactt gctccccaaa    480
acccagcctg agctccagtg ggcgtggact aatatggaac agtatttaag cgcctgtttg    540
aatctcacgg agcgtaaacg gttggtggcg cagcatctga cgcacgtgtc gcagacgcag    600
gagcagaaca aagagaatca gaatcccaat tctgatgcgc cggtgatcag atcaaaaact    660
tcagccaggt acatggagct ggtcgggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg gcctgcaac taccgggaag   1020 accaacatcg cggaggccat agcccacact gtgcccttct acgggtgcgt aaactggacc   1080
aatgagaact ttccccttca acgactgtgtc gacaagatgg tgatctggtg ggaggagggg   1140
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttccctg cagacaatgc gagagaatga atcagaattc aaatatctgc   1680
```

-continued

| | |
|---|---|
| ttcactcacg gacagaaaga ctgtttagag tgctttcccg tgtcagaatc tcaacccgtt | 1740 |
| tctgtcgtca aaaggcgta tcagaaactg tgctacattc atcatatcat gggaaaggtg | 1800 |
| ccagacgctt gcactgcctg cgatctggtc aatgtggatt tggatgactg catctttgaa | 1860 |
| caataa | 1866 |

<210> SEQ ID NO 13
<211> LENGTH: 2211
<212> TYPE: DNA
<213> ORGANISM: Adeno-associated virus

<400> SEQUENCE: 13

| | |
|---|---|
| atggctgccg atggttatct tccagattgg ctcgaggaca accttagtga aggaattcgc | 60 |
| gagtggtggg ctttgaaacc tggagcccct caacccaagg caaatcaaca acatcaagac | 120 |
| aacgctcgag gtcttgtgct tccgggttac aaataccttg acccggcaa cggactcgac | 180 |
| aaggggggagc cggtcaacgc agcagacgcg gcggccctcg agcacgacaa ggcctacgac | 240 |
| cagcagctca aggccggaga caacccgtac ctcaagtaca accacgccga cgccgagttc | 300 |
| caggagcggc tcaaagaaga tacgtctttt gggggcaacc tcgggcgagc agtcttccag | 360 |
| gccaaaaaga ggcttcttga acctcttggt ctggttgagg aagcggctaa gacggctcct | 420 |
| ggaaagaaga ggcctgtaga gcagtctcct caggaaccgg actcctccgc gggtattggc | 480 |
| aaatcgggtg cacagcccgc taaaaagaga ctcaatttcg gtcagactgg cgacacagag | 540 |
| tcagtcccag accctcaacc aatcggagaa cctcccgcag ccccctcagg tgtgggatct | 600 |
| cttacaatgg cttcaggtgg tggcgcacca gtggcagaca ataacgaagg tgccgatgga | 660 |
| gtgggtagtt cctcgggaaa ttggcattgc gattcccaat ggctggggga cagagtcatc | 720 |
| accaccagca cccgaacctg ggcctgcccc acctacaaca tcacctcta caagcaaatc | 780 |
| tccaacagca catctggagg atcttcaaat gacaacgcct acttcggcta cagcaccccc | 840 |
| tgggggtatt ttgacttcaa cagattccac tgccacttct caccacgtga ctggcagcga | 900 |
| ctcatcaaca caactggggg attccggcct aagcgactca acttcaagct cttcaacatt | 960 |
| caggtcaaag aggttacgga caacaatgga gtcaagacca tcgccaataa ccttaccagc | 1020 |
| acggtccagg tcttcacgga ctcagactat cagctcccgt acgtgctcgg tcggctcac | 1080 |
| gagggctgcc tcccgccgtt cccagcggac gttttcatga ttcctcagta cgggtatctg | 1140 |
| acgcttaatg atggaagcca ggccgtgggt cgttcgtcct tttactgcct ggaatatttc | 1200 |
| ccgtcgcaaa tgctaagaac gggtaacaac ttccagttca gctacgagtt tgagaacgta | 1260 |
| cctttccata gcagctacgc tcacagccaa agcctggacc gactaatgaa tccactcatc | 1320 |
| gaccaatact tgtactatct ctcaagagact attaacggtt ctggacagaa tcaacaaacg | 1380 |
| ctaaaattca gtgtggccgg acccagcaac atggctgtcc agggaagaaa ctacatacct | 1440 |
| ggacccagct accgacaaca acgtgtctca accactgtga ctcaaaacaa caacagcgaa | 1500 |
| tttgcttggc ctggagcttc ttcttgggct ctcaatggac gtaatagctt gatgaatcct | 1560 |
| ggacctgcta tggccagcca caaagaagga gaggaccgtt tctttcctt gtctggatct | 1620 |
| ttaattttg gcaaacaagg aactggaaga gacaacgtgg atgcggacaa agtcatgata | 1680 |
| accaacgaag aagaaattaa aactactaac ccggtagcaa cggagtccta tggacaagtg | 1740 |
| gccacaaacc accagagtgc ccaagcacag gcgcagaccg gctgggttca aaaccaagga | 1800 |
| atacttccgg gtatggtttg gcaggacaga gatgtgtacc tgcaaggacc catttgggcc | 1860 |

```
aaaattcctc acacggacgg caactttcac ccttctccgc tgatgggagg gtttggaatg     1920
aagcacccgc ctcctcagat cctcatcaaa aacacacctg tacctgcgga tcctccaacg     1980
gccttcaaca aggacaagct gaactctttc atcacccagt attctactgg ccaagtcagc     2040
gtggagatcg agtgggagct gcagaaggaa acagcaagc gctggaaccc ggagatccag      2100
tacacttcca actattacaa gtctaataat gttgaatttg ctgttaatac tgaaggtgta     2160
tatagtgaac cccgccccat ggcaccaga tacctgactc gtaatctgta a               2211
```

<210> SEQ ID NO 14
<211> LENGTH: 12003
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
aaaaggatct caagaagatc ctttgatctt ttctacgggg tctgacgctc agtggaacga       60
cgcgcgcgta actcacgtta agggatttg gtcatgagct tgcgccgtcc cgtcaagtca      120
gcgtaatgct ctgcttttag aaaaactcat cgagcatcaa atgaaactgc aatttattca     180
tatcaggatt atcaatacca tatttttgaa aaagccgttt ctgtaatgaa ggagaaaact     240
caccgaggca gttccatagg atggcaagat cctggtatcg gtctgcgatt ccgactcgtc     300
caacatcaat acaacctatt aatttcccct cgtcaaaaat aaggttatca agtgagaaat     360
caccatgagt gacgactgaa tccggtgaga atggcaaaag tttatgcatt tctttccaga     420
cttgttcaac aggccagcca ttacgctcgt catcaaaatc actcgcatca accaaaccgt     480
tattcattcg tgattgcgcc tgagcgaggc gaaatacgcg atcgctgtta aaaggacaat     540
tacaaacagg aatcgagtgc aaccggcgca ggaacactgc cagcgcatca acaatatttt     600
cacctgaatc aggatattct tctaatacct ggaacgctgt ttttccgggg atcgcagtgg     660
tgagtaacca tgcatcatca ggagtacgga taaaatgctt gatggtcgga agtggcataa     720
attccgtcag ccagtttagt ctgaccatct catctgtaac atcattggca acgctacctt     780
tgccatgttt cagaaacaac tctggcgcat cgggcttccc atacaagcga tagattgtcg     840
cacctgattg cccgacatta tcgcgagccc atttataccc atataaatca gcatccatgt     900
tggaatttaa tcgcggcctc gacgtttccc gttgaatatg gctcatattc ttccttttc      960 aatattattg aagcatttat cagggttatt gtctcatgag cggatacata tttgaatgta     1020
tttagaaaaa taaacaaata ggggtcagtg ttacaaccaa ttaaccaatt ctgaacatta    1080
tcgcgagccc atttatacct gaatatggct cataacaccc cttgtttgcc tggcggcagt    1140
agcgcggtgg tcccacctga ccccatgccg aactcagaag tgaaacgccg tagcgccgat    1200
ggtagtgtgg ggactcccca tgcgagagta gggaactgcc aggcatcaaa taaaacgaaa    1260
ggctcagtcg aaagactggg cctttcgccc gggctaatta gggggtgtcg cccttcgctg    1320 aagggggtgcg cggatccgta tacgtttaaa cgcggccgcg gtacccaact ccatgctcaa    1380
cagtccccag gtacagccca ccctgcgtcg caaccaggaa cagctctaca gcttcctgga    1440
gcgccactcg ccctacttcc gcagccacag tgcgcagatt aggagcgcca cttcttttg     1500 tcacttgaaa aacatgtaaa aataatgtac tagagacact ttcaataaag gcaaatgctt    1560
ttatttgtac actctcgggt gattatttac ccccaccctt gccgtctgcg ccgtttaaaa    1620
atcaaagggg ttctgccgcg catcgctatg cgccactggc agggacacgt tgcgatactg    1680
```

```
gtgtttagtg ctccacttaa actcaggcac aaccatccgc ggcagctcgg tgaagttttc    1740
actccacagg ctgcgcacca tcaccaacgc gtttagcagg tcgggcgccg atatcttgaa    1800
gtcgcagttg gggcctccgc cctgcgcgcg cgagttgcga tacacagggt tgcagcactg    1860
gaacactatc agcgccgggt ggtgcacgct ggccagcacg ctcttgtcgg agatcagatc    1920
cgcgtccagg tcctccgcgt tgctcagggc gaacggagtc aactttggta gctgccttcc    1980 caaaagggc gcgtgcccag gctttgagtt gcactcgcac cgtagtggca tcaaaaggtg    2040
accgtgcccg gtctgggcgt taggatacag cgcctgcata aaagccttga tctgcttaaa    2100
agccacctga gcctttgcgc cttcagagaa gaacatgccg caagacttgc cggaaaactg    2160
attggccgga caggccgcgt cgtgcacgca gcaccttgcg tcggtgttgg agatctgcac    2220
cacatttcgg ccccaccggt tcttcacgat cttggccttg ctagactgct ccttcagcgc    2280
gcgctgcccg ttttcgctcg tcacatccat ttcaatcacg tgctccttat ttatcataat    2340
gcttccgtgt agacacttaa gctcgccttc gatctcagcg cagcggtgca gccacaacgc    2400
gcagcccgtg ggctcgtgat gcttgtaggt cacctctgca aacgactgca ggtacgcctg    2460
caggaatcgc cccatcatcg tcacaaaggt cttgttgctg gtgaaggtca gctgcaaccc    2520
gcggtgctcc tcgttcagcc aggtcttgca tacggccgcc agagcttcca cttggtcagg    2580
cagtagtttg aagttcgcct ttagatcgtt atccacgtgg tacttgtcca tcagcgcgcg    2640
cgcagcctcc atgcccttct cccacgcaga cacgatcggc acactcagcg ggttcatcac    2700
cgtaatttca ctttccgctt cgctgggctc ttcctcttcc tcttgcgtcc gcataccacg    2760
cgccactggg tcgtcttcat tcagccgccg cactgtgcgc ttacctcctt gccatgctt    2820 gattagcacc ggtgggttgc tgaaacccac catttgtagc gccacatctt ctctttcttc    2880
ctcgctgtcc acgattacct ctggtgatgg cgggcgctcg ggcttgggag aagggcgctt    2940 cttttcttc ttgggcgcaa tggccaaatc cgccgccgag gtcgatggcc gcgggctggg    3000
tgtgcgcggc accagcgcgt cttgtgatga gtcttcctcg tcctcggact cgatacgccg    3060
cctcatccgc ttttttgggg gcgcccgggg aggcggcggc gacggggacg gggacgacac    3120
gtcctccatg gttgggggac gtcgcgccgc accgcgtccg cgctcggggg tggtttcgcg    3180
ctgctcctct tcccgactgg ccatttcctt ctcctatagg cagaaaaaga tcatggagtc    3240
agtcgagaag aaggacagcc taaccgcccc ctctgagttc gccaccaccg cctccaccga    3300
tgccgccaac gcgcctacca ccttccccgt cgaggcaccc ccgcttgagg aggaggaagt    3360
gattatcgag caggacccag gttttgtaag cgaagacgac gaggaccgct cagtaccaac    3420
agaggataaa aagcaagacc aggacaacgc agaggcaaac gaggaacaag tcgggcgggg    3480
ggacgaaagg catggcgact acctagatgt gggagacgac gtgctgttga agcatctgca    3540
gcgccagtgc gccattatct gcgacgcgtt gcaagagcgc agcgatgtgc ccctcgccat    3600
agcggatgtc agccttgcct acgaacgcca cctattctca ccgcgcgtac ccccaaacg    3660 ccaagaaaac ggcacatgcg agcccaaccc gcgcctcaac ttctacccccg tatttgccgt    3720 gccagaggtg cttgccacct atcacatctt tttccaaaac tgcaagatac ccctatcctg    3780
ccgtgccaac cgcagccgag cggacaagca gctggccttg cggcagggcg ctgtcatacc    3840
tgatatcgcc tcgctcaacg aagtgccaaa aatctttgag ggtcttggac gcgacgagaa    3900
gcgcgcggca aacgctctgc aacaggaaaa cagcgaaaat gaaagtcact ctggagtgtt    3960
ggtggaactc gagggtgaca acgcgcgcct agccgtacta aaacgcagca tcgaggtcac    4020
ccactttgcc tacccggcac ttaacctacc ccccaaggtc atgagcacag tcatgagtga    4080
```

```
gctgatcgtg cgccgtgcgc agccctgga gagggatgca aatttgcaag aacaaacaga    4140
ggagggccta cccgcagttg gcgacgagca gctagcgcgc tggcttcaaa cgcgcgagcc    4200
tgccgacttg gaggagcgac gcaaactaat gatggccgca gtgctcgtta ccgtggagct    4260
tgagtgcatg cagcggttct ttgctgaccc ggagatgcag cgcaagctag aggaaacatt    4320
gcactacacc tttcgacagg gctacgtacg ccaggcctgc aagatctcca acgtggagct    4380
ctgcaacctg gtctcctacc ttggaatttt gcacgaaaac cgccttgggc aaaacgtgct    4440
tcattccacg ctcaagggcg aggcgcgccg cgactacgtc cgcgactgcg tttacttatt    4500
tctatgctac acctggcaga cggccatggg cgtttggcag cagtgcttgg aggagtgcaa    4560
cctcaaggag ctgcagaaac tgctaaagca aacttgaag gacctatgga cggccttcaa    4620
cgagcgctcc gtgccgcgc acctggcgga catcattttc cccgaacgcc tgcttaaaac    4680
cctgcaacag ggtctgccag acttcaccag tcaaagcatg ttgcagaact taggaactt    4740 tatcctagag cgctcaggaa tcttgcccgc cacctgctgt gcacttccta gcgactttgt    4800
gcccattaag taccgcgaat gccctccgcc gctttgggc cactgctacc ttctgcagct    4860
agccaactac cttgcctacc actctgacat aatggaagac gtgagcggtg acggtctact    4920
ggagtgtcac tgtcgctgca acctatgcac cccgcaccgc tccctggttt gcaattcgca    4980
gctgcttaac gaaagtcaaa ttatcggtac ctttgagctg cagggtccct cgcctgacga    5040
aaagtccgcg gctccggggt tgaaactcac tccggggctg tggacgtcgg cttaccttcg    5100
caaatttgta cctgaggact accacgccca cgagattagg ttctacgaag accaatcccg    5160
cccgccaaat gcggagctta ccgcctgcgt cattacccag ggccacattc ttggccaatt    5220
gcaagccatc aacaaagccc gccaagagtt tctgctacga aagggacggg gggtttactt    5280 ggaccccag tccggcgagg agctcaaccc aatcccccg ccgccgcagc cctatcagca    5340
gcagccgcgg gcccttgctt ccaggatgg cacccaaaaa gaagctgcag ctgccgccgc    5400
cacccacgga cgaggaggaa tactgggaca gtcaggcaga ggaggttttg gacgaggagg    5460
aggaggacat gatggaagac tgggagagcc tagacgagga agcttccgag gtcgaagagg    5520
tgtcagacga aacaccgtca ccctcggtcg cattcccctc gccggcgccc agaaatcgg    5580 caaccggttc cagcatggct acaacctccg ctcctcaggc gccgccggca ctgcccgttc    5640
gccgacccaa ccgtagatgg gacaccactg gaaccagggc cggtaagtcc aagcagccgc    5700
cgccgttagc ccaagagcaa caacagcgcc aaggctaccg ctcatggcgc gggcacaaga    5760
acgccatagt tgcttgcttg caagactgtg ggggcaacat ctccttcgcc cgccgctttc    5820
ttctctacca tcacggcgtg gccttcccc gtaacatcct gcattactac cgtcatctct    5880
acagcccata ctgcaccggc ggcagcgca gcggcagcaa cagcagcggc cacacagaag    5940
caaaggcgac cggatagcaa gactctgaca aagcccaaga atccacagc ggcggcagca    6000 gcaggaggag gagcgctgcg tctggcgccc aacgaacccg tatcgacccg cgagcttaga    6060
aacaggattt ttcccactct gtatgctata tttcaacaga gcaggggcca agaacaagag    6120
ctgaaaataa aaacaggtc tctgcgatcc ctcacccgca gctgcctgta tcacaaaagc    6180
gaagatcagc ttcggcgcac gctggaagac gcggaggctc tcttcagtaa atactgcgcg    6240
ctgactctta aggactagtt tcgcgccctt tctcaaattt aagcgcgaaa actacgtcat    6300
ctccagcggc cacacccggc gccagcacct gtcgtcagcg ccattatgag caaggaaatt    6360
cccacgccct acatgtggag ttaccagcca caaatgggac ttgcggctgg agctgcccaa    6420
```

```
gactactcaa cccgaataaa ctacatgagc gcgggacccc acatgatatc ccgggtcaac    6480
ggaatccgcg cccaccgaaa ccgaattctc ttggaacagg cggctattac caccacacct    6540
cgtaataacc ttaatccccg tagttggccc gctgccctgg tgtaccagga aagtcccgct    6600
cccaccactg tggtacttcc cagagacgcc caggccgaag ttcagatgac taactcaggg    6660
gcgcagcttg cgggcggctt tcgtcacagg gtgcggtcgc ccgggcgacg taggttttag    6720
ggcggagtaa cttgtatgtg ttgggaattg tagttttctt aaaatgggaa gttacgtaac    6780
gtgggaaaac ggaagtgacg atttgaggaa gttgtgggtt ttttggcttt cgtttctggg    6840
cgtaggttcg cgtgcggttt tctgggtgtt ttttgtggac tttaaccgtt acgtcatttt    6900
ttagtcctat atatactcgc tctgcacttg ccccttttt acactgtgac tgattgagct     6960
ggtgccgtgt cgagtggtgt tttttaata ggttttcttt tttactggta aggctgactg     7020
ttatggctgc cgctgtggaa gcgctgtatg ttgttctgga gcgggagggt gctattttgc    7080
ctaggcagga gggttttttca ggtgtttatg tgttttttctc tcctattaat tttgttatac   7140
ctcctatggg ggctgtaatg ttgtctctac gcctgcgggt atgtattccc ccgggctatt    7200
tcggtcgctt tttagcactg accgatgtga atcaacctga tgtgtttacc gagtcttaca    7260
ttatgactcc ggacatgacc gaggagctgt cggtggtgct ttttaatcac ggtgaccagt    7320 tttttttacgg tcacgccggc atggccgtag tccgtcttat gcttataagg gttgtttttc   7380
ctgttgtaag acaggcttct aatgtttaaa tgttttttttg ttatttttatt ttgtgtttat  7440 gcagaaaccc gcagacatgt ttgagagaaa aatggtgtct ttttctgtgg tggttccgga   7500
gcttacctgc ctttatctgc atgagcatga ctacgatgtg ctttcttttt tgcgcgaggc   7560
tttgcctgat tttttgagca gcaccttgca ttttatatcg ccgcccatgc aacaagctta   7620
catcggggct acgctggtta gcatagctcc gagtatgcgt gtcataatca gtgtgggttc    7680
ttttgtcatg gttcctggcg gggaagtggc cgcgctggtc cgtgcagacc tgcacgatta    7740
tgttcagctg gccctgcgaa gggacctacg ggatcgcgt atttttgtta atgttccgct     7800
tttgaatctt atacaggtct gtgaggaacc tgaattttttg caatcatgat cgctgcttg    7860 aggctgaagg tggagggcgc tctggagcag attttttacaa tggccggact taatattcgg   7920
gatttgctta gagatatatt gagaaggtgg cgagatgaga attatttggg catggttgaa    7980
ggtgctggaa tgtttataga ggagattcac cctgaagggt ttagccttta cgtccacttg   8040
gacgtgaggg ccgtttgcct tttggaagcc attgtgcaac atcttacaaa tgccattatc   8100
tgttctttgg ctgtagagtt tgaccacgcc accgagggg agcgcgttca cttaatagat    8160
cttcattttg aggttttgga taatctttttg gaataaaaaa aaaaacatgg ttcttccagc   8220
tcttcccgct cctcccgtgt gtgactcgca gaacgaatgt gtaggttggc tgggtgtggc   8280
ttattctgcg gtggtggatg ttatcagggc agcggcgcat gaaggagttt acatagaacc    8340
cgaagccagg gggcgcctgg atgctttgag agagtggata tactacaact actacacaga    8400
gcgatctaag cggcgagacc ggagacgcag atctgtttgt cacgcccgca cctggttttg    8460
cttcaggaaa tatgactacg tccggcgttc catttggcat gacactacga ccaacacgat    8520
ctcggttgtc tcggcgcact ccgtacagta gggatcgtct acctccttt gagacagaaa    8580 cccgcgctac catactggag gatcatccgc tgctgcccga atgtaacact tgacaatgc    8640 acaacgtgag ttacgtgcga ggtcttcct gcagtgtggg atttacgctg attcaggaat    8700
gggttgttcc ctgggatatg gttctaacgc gggaggagct tgtaatcctg aggaagtgta   8760
tgcacgtgtg cctgtgttgt gccaacattg atatcatgac gagcatgatg atccatggtt  8820
```

```
acgagtcctg ggctctccac tgtcattgtt ccagtcccgg ttccctgcag tgtatagccg    8880
gcgggcaggt tttggccagc tggtttagga tggtggtgga tggcgccatg tttaatcaga    8940
ggtttatatg gtaccgggag gtggtgaatt acaacatgcc aaaagaggta atgtttatgt    9000
ccagcgtgtt tatgaggggt cgccacttaa tctacctgcg cttgtggtat gatggccacg    9060
tgggttctgt ggtccccgcc atgagctttg gatacagcgc cttgcactgt gggattttga    9120
acaatattgt ggtgctgtgc tgcagttact gtgctgattt aagtgagatc agggtgcgct    9180
gctgtgcccg gaggacaagg cgccttatgc tgcgggcggt gcgaatcatc gctgaggaga    9240
ccactgccat gttgtattcc tgcaggacgg agcggcggcg cagcagtttt attcgcgcgc    9300
tgctgcagca ccaccgccct atcctgatgc acgattatga ctctaccccc atgtaggcgt    9360
ggacttctcc ttcgccgccc gttaagcaac cgcaagttgg acagcagcct gtggctcagc    9420
agctggacag cgacatgaac ttaagtgagc tgcccgggga gtttattaat atcactgatg    9480
agcgtttggc tcgacaggaa accgtgtgga atataacacc taagaatatg tctgttaccc    9540
atgatatgat gcttttaag gccagccggg gagaaaggac tgtgtactct gtgtgttggg    9600
agggaggtgg caggttgaat actagggttc tgtgagtttg attaaggtac ggtgatctgt    9660
ataagctatg tggtggtggg gctatactac tgaatgaaaa atgacttgaa attttctgca    9720
attgaaaaat aaacacgttg aaacataaca caaacgattc tttattcttg ggcaatgtat    9780 gaaaagtgt aagaggatgt ggcaaatatt tcattaatgt agttgtggcc agaccagtcc    9840
catgaaaatg acatagagta tgcacttgga gttgtgtctc ctgtttcctg tgtaccgttt    9900
agtgtaattc aaccgcggat gtcgcccctc ctgacgcggt aggaggaggg gagggtgccc    9960
tgcatgtctg ccgctgctct tgctcttgcc gctgctgagg aggggggcgc atctgccgca   10020
gcaccggatg catctgggaa aagcaaaaaa ggggctcgtc cctgtttccg gaggaatttg   10080
caagcggggt cttgcatgac ggggaggcaa accccgttc gccgcagtcc ggccggtccg   10140
agactcgaac cggggtccc gcgactcaac ccttggaaaa taaccctccg gctacaggga   10200
gcgagccact taatgctttc gctttccagc ctaaccgctt acgctgcgcg cggccagtgg   10260
ccaaaaaagc tagcgcagca gccgccgcgc ctggaaggaa gccaaaagga gcactccccc   10320
gttgtctgac gtcgcacacc tgggttcgac acgcgggcgg taaccgcatg gatcacggcg   10380
gacggccgga tacggggctc gaaccccggt cgtccgccat gatacccttg cgaatttatc   10440
caccagacca cggaagagtg cccgcttaca ggctctcctt ttgcacggtc tagagcgtca   10500
acgattgcgc gcgcctgacc ggccagagcg tcccgaccat ggagcacttt ttgccgctgc   10560
gcaacatctg gaaccgcgtc cgcgactttc cgcgcgcctc caccaccgcc gccggcatca   10620
cctggatgtc caggtacatc tacgatatc atttaattaa gtactgtcga cgcgtacaaa   10680
acgtcaaaag ggcgacacaa aatttattct aaatgcataa taaatactga taacatctta   10740
tagtttgtat tatattttgt attatcgttg acatgtataa ttttgatatc aaaaactgat   10800 tttccctta ttatttcga gatttatttt cttaattctc tttaacaaac tagaaatatt   10860
gtatatacaa aaaatcataa ataatagatg aatagtttaa ttataggtgt tcatcaatcg   10920
aaaaagcaac gtatcttatt taagtgcgt tgctttttc tcatttataa ggttaaataa   10980
ttctcatata tcaagcaaag tgacaggcgc ccttaaatat tctgacaaat gctctttccc   11040
taaactcccc ccataaaaaa acccgccgaa gcgggttttt acgttatttg cggattaacg   11100
attactcgtt atcagaaccg cccaggggggc ccgagcttaa gactggccgt cgttttacaa   11160
```

```
cacagaaaga gtttgtagaa acgcaaaaag gccatccgtc aggggccttc tgcttagttt    11220
gatgcctggc agttccctac tctcgccttc cgcttcctcg ctcactgact cgctgcgctc    11280
ggtcgttcgg ctgcggcgag cggtatcagc tcactcaaag gcggtaatac ggttatccac    11340
agaatcaggg gataacgcag gaaagaacat gtgagcaaaa ggccagcaaa aggccaggaa    11400
ccgtaaaaag gccgcgttgc tggcgttttt ccataggctc cgcccccctg acgagcatca    11460
caaaaatcga cgctcaagtc agaggtggcg aaacccgaca ggactataaa gataccaggc    11520
gtttccccct ggaagctccc tcgtgcgctc tcctgttccg accctgccgc ttaccggata    11580
cctgtccgcc tttctccctt cgggaagcgt ggcgctttct catagctcac gctgtaggta    11640
tctcagttcg gtgtaggtcg ttcgctccaa gctgggctgt gtgcacgaac cccccgttca    11700
gcccgaccgc tgcgccttat ccggtaacta tcgtcttgag tccaacccgg taagacacga    11760
cttatcgcca ctggcagcag ccactggtaa caggattagc agagcgaggt atgtaggcgg    11820
tgctacagag ttcttgaagt ggtgggctaa ctacggctac actagaagaa cagtatttgg    11880
tatctgcgct ctgctgaagc cagttacctt cggaaaaaga gttggtagct cttgatccgg    11940
caaacaaacc accgctggta gcggtggttt ttttgtttgc aagcagcaga ttacgcgcag    12000
aaa                                                                  12003

<210> SEQ ID NO 15
<211> LENGTH: 17817
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
ttagaaaaac tcatcgagca tcaaatgaaa ctgcaattta ttcatatcag gattatcaat      60
accatatttt tgaaaaagcc gtttctgtaa tgaaggagaa aactcaccga ggcagttcca     120
taggatggca agatcctggt atcggtctgc gattccgact cgtccaacat caatacaacc     180
tattaatttc ccctcgtcaa aaataaggtt atcaagtgag aaatcaccat gagtgacgac     240
tgaatccggt gagaatggca aaagtttatg catttctttc cagacttgtt caacaggcca     300
gccattacgc tcgtcatcaa aatcactcgc atcaaccaaa ccgttattca ttcgtgattg     360
cgcctgagcg aggcgaaata cgcgatcgct gttaaaagga caattacaaa caggaatcga     420
gtgcaaccgg cgcaggaaca ctgccagcgc atcaacaata ttttcacctg aatcaggata     480
ttcttctaat acctggaacg ctgttttccc ggggatcgca gtggtgagta accatgcatc     540
atcaggagta cggataaaat gcttgatggt cggaagtggc ataaattccg tcagccagtt     600
tagtctgacc atctcatctg taacatcatt ggcaacgcta cctttgccat gtttcagaaa     660
caactctggc gcatcgggct tcccatacaa gcgatagatt gtcgcacctg attgcccgac     720
attatcgcga gcccatttat acccatataa atcagcatcc atgttggaat ttaatcgcgg     780
cctcgacgtt tcccgttgaa tatggctcat attcttcctt tttcaatatt attgaagcat     840
ttatcagggt tattgtctca tgagcggata catatttgaa tgtatttaga aaaataaaca     900
aataggggtc agtgttacaa ccaattaacc aattctgaac attatcgcga gcccatttat     960
acctgaatat ggctcataac accccttgtt tgcctggcgg cagtagcgcg tggtcccac    1020 ctgaccccat gccgaactca gaagtgaaac gccgtagcgc cgatggtagt gtgggactc    1080 cccatgcgag agtagggaac tgccaggcat caaataaaac gaaaggctca gtcgaaagac    1140
```

```
tgggcctttc gcccgggcta attaggggggt gtcgcccttc gctgaagggg tgaccgtata    1200
cgtttaaact taattaatcg acagaagcac catgtccttg ggtccggcct gctgaatgcg    1260
caggcggtcg gccatgcccc aggcttcgtt ttgacatcgg cgcaggtctt tgtagtagtc    1320
ttgcatgagc ctttctaccg gcacttcttc ttctccttcc tcttgtcctg catctcttgc    1380
atctatcgct gcggcggcgg cggagtttgg ccgtaggtgg cgccctcttc ctcccatgcg    1440
tgtgaccccg aagcccctca tcggctgaag cagggctagg tcggcgacaa cgcgctcggc    1500
taatatggcc tgctgcacct gcgtgagggt agactggaag tcatccatgt ccacaaagcg    1560
gtggtatgcg cccgtgttga tggtgtaagt gcagttggcc ataacggacc agttaacggt    1620
ctggtgaccc ggctgcgaga gctcggtgta cctgagacgc gagtaagccc tcgagtcaaa    1680
tacgtagtcg ttgcaagtcc gcaccaggta ctggtatccc accaaaaagt gcggcggcgg    1740
ctggcggtag aggggccagc gtagggtggc cggggctccg ggggcgagat cttccaacat    1800
aaggcgatga tatccgtaga tgtacctgga catccaggtg atgccggcgg cggtggtgga    1860
ggcgcgcgga aagtcgcgga cgcggttcca gatgttgcgc agcggcaaaa agtgctccat    1920
ggtcgggacg ctctggccgg tcaggcgcgc gcaatcgttg acgctctaga ccgtgcaaaa    1980
ggagagcctg taagcgggca ctcttccgtg gtctggtgga taaattcgca agggtatcat    2040
ggcggacgac cggggttcga gccccgtatc cggccgtccg ccgtgatcca tgcggttacc    2100
gcccgcgtgt cgaacccagg tgtgcgacgt cagacaacgg gggagtgctc cttttggctt    2160
ccttccaggc gcggcggctg ctgcgctagc ttttttggcc actggccgcg cgcagcgtaa    2220
gcggttaggc tggaaagcga aagcattaag tggctcgctc cctgtagccg gagggttatt    2280
ttccaagggt tgagtcgcgg gaccccggt tcgagtctcg gaccggccgg actgcggcga     2340
acggggggttt gcctccccgt catgcaagac cccgcttgca aattcctccg gaaacaggga    2400
cgagccccctt ttttgctttt cccagatgca tccggtgctg cggcagatgc gccccctcc    2460
tcagcagcga caagagcaag agcagcggca gacatgcagg gcaccctccc ctcctcctac    2520
cgcgtcagga ggggcgacat ccgcggttga cgcggcagca gatggtgatt acgaaccccc    2580
gcggcgccgg gcccggcact acctggactt ggaggagggc gagggcctgg cgcggctagg    2640
agcgccctct cctgagcggt acccaagggt gcagctgaag cgtgatacgc gtgaggcgta    2700
cgtgccgcgg cagaacctgt ttcgcgaccg cgagggagag gagcccgagg agatgcggga    2760
tcgaaagttc cacgcagggc gcgagctgcg gcatggcctg aatcgcgagc ggttgctgcg    2820
cgaggaggac tttgagcccg acgcgcgaac cgggattagt cccgcgcgcg cacacgtggc    2880
ggccgccgac ctggtaaccg catacgagca gacggtgaac caggagatta actttcaaaa    2940
aagctttaac aaccacgtgc gtacgcttgt ggcgcgcgag gaggtggcta taggactgat    3000
gcatctgtgg gactttgtaa gcgcgctgga gcaaaaccca aatagcaagc cgctcatggc    3060
gcagctgttc cttatagtgc agcacagcag ggacaacgag gcattcaggg atgcgctgct    3120
aaacatagta gagcccgagg gccgctggct gctcgatttg ataaacatcc tgcagagcat    3180
agtggtgcag gagcgcagct tgagcctggc tgacaaggtg ccgccatca actattccat     3240
gcttagcctg ggcaagtttt acgcccgcaa gatataccat accccttacg ttcccataga    3300
caaggaggta aagatcgagg ggttctacat gcgcatggcg ctgaaggtgc ttaccttgag    3360
cgacgacctg ggcgtttatc gcaacgagcg catccacaag gccgtgagcg tgagccggcg    3420
gcgcgagctc agcgaccgcg agctgatgca cagcctgcaa agggcctgg ctggcacggg     3480
cagcggcgat agagaggccg agtcctactt tgacgcgggc gctgacctgc gctgggcccc    3540
```

-continued

```
aagccgacgc gccctggagg cagctggggc cggacctggg ctggcggtgg cacccgcgcg    3600
cgctggcaac gtcggcggcg tggaggaata tgacgaggac gatgagtacg agccagagga    3660
cggcgagtac taagcggtga tgtttctgat cagatgatgc aagacgcaac ggacccggcg    3720
gtgcgggcgg cgctgcagag ccagccgtcc ggccttaact ccacggacga ctggcgccag    3780
gtcatggacc gcatcatgtc gctgactgcg cgcaatcctg acgcgttccg gcagcagccg    3840
caggccaacc ggctctccgc aattctggaa gcggtggtcc cggcgcgcgc aaaccccacg    3900
cacgagaagg tgctggcgat cgtaaacgcg ctggccgaaa acagggccat ccggcccgac    3960
gaggccggcc tggtctacga cgcgctgctt cagcgcgtgg ctcgttacaa cagcggcaac    4020
gtgcagacca acctggaccg gctggtgggg gatgtgcgcg aggccgtggc gcagcgtgag    4080
cgcgcgcagc agcagggcaa cctgggctcc atggttgcac taaacgcctt cctgagtaca    4140
cagcccgcca acgtgccgcg gggacaggag gactacacca actttgtgag cgcactgcgg    4200
ctaatggtga ctgagacacc gcaaagtgag gtgtaccagt ctgggccaga ctatttttc    4260 cagaccagta gacaaggcct gcagaccgta aacctgagcc aggctttcaa aaacttgcag    4320
gggctgtggg ggtgcgggc tcccacaggc gaccgcgcga ccgtgtctag cttgctgacg    4380
cccaactcgc gcctgttgct gctgctaata gcgcccttca cggacagtgg cagcgtgtcc    4440
cgggacacat acctaggtca cttgctgaca ctgtaccgcg aggccatagg tcaggcgcat    4500
gtggacgagc atactttcca ggagattaca agtgtcagcc gcgcgctggg gcaggaggac    4560
acgggcagcc tggaggcaac cctaaactac ctgctgacca accggcggca gaagatcccc    4620
tcgttgcaca gtttcgcacc ctttggcgca tcccattctc cagtaacttt atgtccatgg    4680
gcgcactcac agacctgggc caaaaccttc tctacgccaa ctccgcccac gcgctagaca    4740
tgacttttga ggtggatccc atggacgagc ccacccttct ttatgttttg tttgaagtct    4800
ttgacgtggt ccgtgtgcac cggccgcacc gcggcgtcat cgaaaccgtg tacctgcgca    4860
cgcccttctc ggccggcaac gccacaacat aaagaagcaa gcaacatcaa caacagctgc    4920
cgccatgggc tccagtgagc aggaactgaa agccattgtc aaagatcttg gttgtgggcc    4980 atatttttg ggcacctatg acaagcgctt tccaggcttt gtttctccac acaagctcgc    5040
ctgcgccata gtcaatacgg ccggtcgcga gactgggggc gtacactgga tggccttttgc    5100 ctggaacccg cactcaaaaa catgctacct ctttgagccc tttggctttt ctgaccagcg    5160
actcaagcag gtttaccagt ttgagtacga gtcactcctg cgccgtagcg ccattgcttc    5220
ttcccccgac cgctgtataa cgctggaaaa gtccacccaa agcgtacagg ggcccaactc    5280
ggccgcctgt ggactattct gctgcatgtt tctccacgcc tttgccaact ggccccaaac    5340
tcccatggat cacaacccca ccatgaacct tattaccggg gtacccaact ccatgctcaa    5400
cagtccccag gtacagccca ccctgcgtcg caaccaggaa cagctctaca gcttcctgga    5460
gcgccactcg ccctacttcc gcagccacag tgcgcagatt aggagcgcca cttctttttg    5520
tcacttgaaa aacatgtaaa aataatgtac tagagacact ttcaataaag gcaaatgctt    5580
ttatttgtac actctcgggt gattatttac ccccacccct gccgtctgcg ccgtttaaaa    5640
atcaaagggg ttctgccgcg catcgctatg cgccactggc agggacacgt tgcgatactg    5700
gtgtttagtg ctccacttaa actcaggcac aaccatccgc ggcagctcgg tgaagttttc    5760
actccacagg ctgcgcacca tcaccaacgc gtttagcagg tcgggcgccg atatcttgaa    5820
gtcgcagttg gggcctccgc cctgcgcgcg cgagttgcga tacacagggt tgcagcactg    5880
```

```
gaacactatc agcgccgggt ggtgcacgct ggccagcacg ctcttgtcgg agatcagatc    5940
cgcgtccagg tcctccgcgt tgctcagggc gaacggagtc aactttggta gctgccttcc    6000
caaaaagggc gcgtgcccag gctttgagtt gcactcgcac cgtagtggca tcaaaaggtg    6060
accgtgcccg gtctgggcgt taggatacag cgcctgcata aaagccttga tctgcttaaa    6120
agccacctga gcctttgcgc cttcagagaa gaacatgccg caagacttgc cggaaaactg    6180
attggccgga caggccgcgt cgtgcacgca gcaccttgcg tcggtgttgg agatctgcac    6240
cacatttcgg ccccaccggt tcttcacgat cttggccttg ctagactgct ccttcagcgc    6300
gcgctgcccg ttttcgctcg tcacatccat ttcaatcacg tgctccttat ttatcataat    6360
gcttccgtgt agacacttaa gctcgccttc gatctcagcg cagcggtgca gccacaacgc    6420
gcagcccgtg ggctcgtgat gcttgtaggt cacctctgca aacgactgca ggtacgcctg    6480
caggaatcgc cccatcatcg tcacaaaggt cttgttgctg gtgaaggtca gctgcaaccc    6540
gcggtgctcc tcgttcagcc aggtcttgca tacggccgcc agagcttcca cttggtcagg    6600
cagtagtttg aagttcgcct ttagatcgtt atccacgtgg tacttgtcca tcagcgcgcg    6660
cgcagcctcc atgcccttct cccacgcaga cacgatcggc acactcagcg ggttcatcac    6720
cgtaatttca ctttccgctt cgctgggctc ttcctcttcc tcttgcgtcc gcataccacg    6780
cgccactggg tcgtcttcat tcagccgccg cactgtgcgc ttacctcctt tgccatgctt    6840
gattagcacc ggtgggttgc tgaaacccac catttgtagc gccacatctt ctctttcttc    6900
ctcgctgtcc acgattacct ctggtgatgg cgggcgctcg ggcttgggag aagggcgctt    6960 cttttcttc ttgggcgcaa tggccaaatc cgccgccgag gtcgatggcc gcgggctggg    7020
tgtgcgcggc accagcgcgt cttgtgatga gtcttcctcg tcctcggact cgatacgccg    7080
cctcatccgc ttttttgggg gcgcccgggg aggcggcggc gacggggacg gggacgacac    7140
gtcctccatg gttgggggac gtcgcgccgc accgcgtccg cgctcggggg tggtttcgcg    7200
ctgctcctct tcccgactgg ccatttcctt tcctataggcagaaaaaga tcatggagtc    7260 agtcgagaag aaggacagcc taaccgcccc ctctgagttc gccaccaccg cctccaccga    7320
tgccgccaac gcgcctacca ccttccccgt cgaggcaccc ccgcttgagg aggaggaagt    7380
gattatcgag caggacccag gttttgtaag cgaagacgac gaggaccgct cagtaccaac    7440
agaggataaa aagcaagacc aggacaacgc agaggcaaac gaggaacaag tcgggcgggg    7500
ggacgaaagg catggcgact acctagatgt gggagacgac gtgctgttga agcatctgca    7560
gcgccagtgc gccattatct gcgacgcgtt gcaagagcgc agcgatgtgc ccctcgccat    7620
agcggatgtc agccttgcct acgaacgcca cctattctca ccgcgcgtac cccccaaacg    7680
ccaagaaaac ggcacatgcg agcccaaccc gcgcctcaac ttctacccccg tatttgccgt    7740 gccagaggtg cttgccacct atcacatctt tttccaaaac tgcaagatac ccctatcctg    7800
ccgtgccaac cgcagccgag cggacaagca gctggcttg cggcagggcg ctgtcatacc    7860
tgatatcgcc tcgctcaacg aagtgccaaa aatctttgag ggtcttggac gcgacgagaa    7920
gcgcgcggca aacgctctgc aacaggaaaa cagcgaaaat gaaagtcact ctggagtgtt    7980
ggtggaactc gagggtgaca acgcgcgcct agccgtacta aaacgcagca tcgaggtcac    8040
ccactttgcc tacccggcac ttaacctacc ccccaaggtc atgagcacag tcatgagtga    8100
gctgatcgtg cgccgtgcgc agcccctgga gagggatgca aatttgcaag aacaaacaga    8160
ggagggccta cccgcagttg gcgacgagca gctagcgcgc tggcttcaaa cgcgcgagcc    8220
tgccgacttg gaggagcgac gcaaactaat gatggccgca gtgctcgtta ccgtggagct    8280
```

```
tgagtgcatg cagcggttct ttgctgaccc ggagatgcag cgcaagctag aggaaacatt    8340
gcactacacc tttcgacagg gctacgtacg ccaggcctgc aagatctcca acgtggagct    8400
ctgcaacctg gtctcctacc ttggaatttt gcacgaaaac cgccttgggc aaaacgtgct    8460
tcattccacg ctcaagggcg aggcgcgccg cgactacgtc cgcgactgcg tttacttatt    8520
tctatgctac acctggcaga cggccatggg cgtttggcag cagtgcttgg aggagtgcaa    8580
cctcaaggag ctgcagaaac tgctaaagca aaacttgaag gacctatgga cggccttcaa    8640
cgagcgctcc gtggccgcgc acctggcgga catcattttc cccgaacgcc tgcttaaaac    8700
cctgcaacag ggtctgccag acttcaccag tcaaagcatg ttgcagaact ttaggaactt    8760
tatcctagag cgctcaggaa tcttgcccgc cacctgctgt gcacttccta gcgactttgt    8820
gcccattaag taccgcgaat gccctccgcc gctttggggc cactgctacc ttctgcagct    8880
agccaactac cttgcctacc actctgacat aatggaagac gtgagcggtg acggtctact    8940
ggagtgtcac tgtcgctgca acctatgcac cccgcaccgc tccctggttt gcaattcgca    9000
gctgcttaac gaaagtcaaa ttatcggtac ctttgagctg cagggtccct cgcctgacga    9060
aaagtccgcg gctccggggt tgaaactcac tccggggctg tggacgtcgg cttaccttcg    9120
caaatttgta cctgaggact accacgccca cgagattagg ttctacgaag accaatcccg    9180
cccgccaaat gcggagctta ccgcctgcgt cattacccag ggccacattc ttggccaatt    9240
gcaagccatc aacaaagccc gccaagagtt tctgctacga aagggacggg gggtttactt    9300
ggaccccccag tccggcgagg agctcaaccc aatcccccccg ccgccgcagc cctatcagca    9360
gcagccgcgg gcccttgctt cccaggatgg cacccaaaaa gaagctgcag ctgccgccgc    9420
cacccacgga cgaggaggaa tactgggaca gtcaggcaga ggaggttttg gacgaggagg    9480
aggaggacat gatggaagac tgggagagcc tagacgagga agcttccgag gtcgaagagg    9540
tgtcagacga acaccgtca ccctcggtcg cattcccctc gccggcgccc cagaaatcgg    9600
caaccggttc cagcatggct acaacctccg ctcctcaggc gccgccggca ctgcccgttc    9660
gccgacccaa ccgtagatgg gacaccactg gaaccagggc cggtaagtcc aagcagccgc    9720
cgccgttagc ccaagagcaa caacagcgcc aaggctaccg ctcatggcgc gggcacaaga    9780
acgccatagt tgcttgcttg caagactgtg ggggcaacat ctccttcgcc cgccgctttc    9840
ttctctacca tcacggcgtg gccttccccc gtaacatcct gcattactac cgtcatctct    9900
acagcccata ctgcaccggc ggcagcggca gcggcagcaa cagcagcggc cacacagaag    9960
caaaggcgac cggatagcaa gactctgaca aagcccaaga aatccacagc ggcggcagca    10020
gcaggaggag gagcgctgcg tctggcgccc aacgaacccg tatcgacccg cgagcttaga    10080
aacaggattt ttccccactct gtatgctata tttcaacaga gcaggggcca agaacaagag    10140
ctgaaaataa aaaacaggtc tctgcgatcc ctcacccgca gctgcctgta tcacaaaagc    10200
gaagatcagc ttcggcgcac gctggaagac gcggaggctc tcttcagtaa atactgcgcg    10260
ctgactctta aggactagtt tcgcgccctt tctcaaattt aagcgcgaaa actacgtcat    10320
ctccagcggc cacacccggc gccagcacct gtcgtcagcg ccattatgag caaggaaatt    10380
cccacgccct acatgtggag ttaccagcca caaatgggac ttgcggctgg agctgccaa    10440
gactactcaa cccgaataaa ctacatgagc gcgggacccc acatgatatc ccgggtcaac    10500
ggaatccgcg cccaccgaaa ccgaattctc ttggaacagg cggctattac caccacacct    10560
cgtaataacc ttaatccccg tagttggccc gctgccctgg tgtaccagga aagtcccgct    10620
```

```
cccaccactg tggtacttcc cagagacgcc caggccgaag ttcagatgac taactcaggg    10680
gcgcagcttg cgggcggctt tcgtcacagg gtgcggtcgc ccgggcaggg tataactcac    10740
ctgacaatca gagggcgagg tattcagctc aacgacgagt cggtgagctc ctcgcttggt    10800
ctccgtccgg acgggacatt tcagatcggg gcgccggcc gtccttcatt cacgcctcgt     10860
caggcaatcc taactctgca gacctcgtcc tctgagccgc gctctggagg cattggaact    10920
ctgcaattta ttgaggagtt tgtgccatcg gtctacttta accccttctc gggacctccc    10980
ggccactatc cggatcaatt tattcctaac tttgacgcgg taaaggactc ggcggacggc    11040
tacgactgaa tgttaagtgg agaggcagag caactgcgcc tgaaacacct ggtccactgt    11100
cgccgccaca agtgctttgc ccgcgactcc ggtgagtttt gctactttga attgcccgag    11160
gatcatatcg agggcccggc gcacggcgtc cggcttaccg cccagggaga gcttgcccgt    11220
agcctgattc gggagtttac ccagcgcccc ctgctagttg agcgggacag gggaccctgt    11280
gttctcactg tgatttgcaa ctgtcgatct tattcccttt aactaataaa aaaaaataat    11340
aaagcatcac ttacttaaaa tcagttagca aatttctgtc cagtttattc agcagcacct    11400
ccttgccctc ctcccagctc tggtattgca gcttcctcct ggctgcaaac tttctccaca    11460
atctaaatgg aatgtcagtt tcctcctgtt cctgtccatc cgcacccact atcttcatgt    11520
tgttgcagat gaagcgcgca agaccgtctg aagataccttcaaccccgtg tatccatatg     11580 acacggaaac cggtcctcca actgtgcctt ttcttactcc tcccttgta tcccccaatg     11640 ggtttcaaga gagtccccct ggggtactct cttgcgcct atccgaacct ctagttacct     11700
ccaatggcat gcttgcgctc aaaatgggca acggcctctc tctggacgag gccggcaacc    11760
ttacctccca aaatgtaacc actgtgagcc cacctctcaa aaaaaccaag tcaaacataa    11820
acctggaaat atctgcaccc ctcacagtta cctcagaagc cctaactgtg gctgccgccg    11880
cacctctaat ggtcgcgggc aacacactca ccatgcaatc acaggccccg ctaaccgtgc    11940
acgactccaa acttagcatt gccacccaag gaccccctcac agtgtcagaa ggaaaagctag   12000 ccctgcaaac atcaggcccc ctcaccacca ccgatagcag taccccttact atcactgcct   12060 caccccctct aactactgcc actggtagct tgggcattga cttgaaagag cccatttata    12120
cacaaaatgg aaaactagga ctaaagtacg gggctccttt gcatgtaaca gacgacctaa    12180
acactttgac cgtagcaact ggtccaggtg tgactattaa taatacttcc ttgcaaacta    12240
aagttactgg agccttgggt tttgattcac aaggcaatat gcaacttaat gtagcaggag    12300
gactaaggat tgattctcaa aacagacgcc ttatacttga tgttagttat ccgtttgatg     12360
ctcaaaacca actaaatcta agactaggac agggccctct ttttataaac tcagcccaca   12420
acttggatat taactacaac aaaggccttt acttgtttac agcttcaaac aattccaaaa    12480
agcttgaggt taacctaagc actgccaagg ggttgatgtt tgacgctaca gccatagcca    12540
ttaatgcagg agatgggctt gaatttggtt cacctaatgc accaaacaca aatcccctca   12600
aaacaaaaat tggccatggc ctagaatttg attcaaacaa ggctatggtt cctaaactag    12660
gaactggcct tagttttgac agcacaggtg ccattacagt aggaaacaaa ataatgata    12720 agctaacttt gtggaccaca ccagctccat ctcctaactg tagactaaat gcagagaaag    12780
atgctaaact cactttggtc ttaacaaaat gtggcagtca atacttgct acagtttcag     12840 ttttggctgt taaaggcagt ttggctccaa tatctggaac agttcaaagt gctcatctta    12900
ttataagatt tgacgaaaat ggagtgctac taaacaattc cttcctggac ccagaatatt    12960
ggaactttag aaatggagat cttactgaag gcacagccta tacaaacgct gttggattta    13020
```

```
tgcctaacct atcagcttat ccaaaatctc acggtaaaac tgccaaaagt aacattgtca   13080
gtcaagttta cttaaacgga gacaaaacta aacctgtaac actaaccatt acactaaacg   13140
gtacacagga acaggagac acaactccaa gtgcatactc tatgtcattt tcatgggact    13200
ggtctggcca caactacatt aatgaaatat ttgccacatc ctcttacact ttttcataca   13260
ttgcccaaga ataaagaatc gtttgtgtta tgtttcaacg tgtttatttt tcaattgcag   13320
aaaatttcaa gtcattttc attcagtagt atagccccac caccacatag cttatacaga    13380
tcaccgtacc ttaatcaaac tcacagaacc ctagtattca acctgccacc tccctcccaa   13440
cacacagagt acacagtcct ttctccccgg ctggccttaa aaagcatcat atcatgggta   13500
acagacatat tcttaggtgt tatattccac acggtttcct gtcgagccaa acgctcatca   13560
gtgatattaa taaactcccc gggcagctca cttaagttca tgtcgctgtc cagctgctga   13620
gccacaggct gctgtccaac ttgcggttgc ttaacgggcg gcgaaggaga agtccacgcc   13680
tacatggggg tagagtcata atcgtgcatc aggatagggc ggtggtgctg cagcagcgcg   13740
cgaataaact gctgccgccg ccgctccgtc ctgcaggaat acaacatggc agtggtctcc   13800
tcagcgatga ttcgcaccgc ccgcagcata aggcgccttg tcctccgggc acagcagcgc   13860
accctgatct cacttaaatc agcacagtaa ctgcagcaca gcaccacaat attgttcaaa   13920
atcccacagt gcaaggcgct gtatccaaag ctcatggcgg ggaccacaga acccacgtgg   13980
ccatcatacc acaagcgcag gtagattaag tggcgacccc tcataaacac gctggacata   14040
aacattacct cttttggcat gttgtaattc accacctccc ggtaccatat aaacctctga   14100
ttaaacatgg cgccatccac caccatccta aaccagctgg ccaaaacctg cccgccggct   14160
atacactgca gggaaccggg actgaacaa tgacagtgga gagcccagga ctcgtaacca    14220
tggatcatca tgctcgtcat gatatcaatg ttggcacaac acaggcacac gtgcatacac   14280
ttcctcagga ttacaagctc ctcccgcgtt agaaccatat cccagggaac aacccattcc   14340
tgaatcagcg taaatcccac actgcaggga agacctcgca cgtaactcac gttgtgcatt   14400
gtcaaagtgt tacattcggg cagcagcgga tgatcctcca gtatggtagc gcgggtttct   14460
gtctcaaaag gaggtagacg atccctactg tacggagtgc gccgagacaa ccgagatcgt   14520
gttggtcgta gtgtcatgcc aaatggaacg ccggacgtag tcatatttcc tgaagcaaaa   14580
ccaggtgcgg gcgtgacaaa cagatctgcg tctccggtct cgccgcttag atcgctctgt   14640
gtagtagttg tagtatatcc actctctcaa agcatccagg cgcccctgg cttcgggttc    14700 tatgtaaact ccttcatgcg ccgctgccct gataacatcc accaccgcag aataagccac   14760
acccagccaa cctacacatt cgttctgcga gtcacacacg ggaggagcgg gaagagctgg   14820
aagaaccatg ttttttttt tattccaaaa gattatccaa aacctcaaaa tgaagatcta    14880
ttaagtgaac gcgctcccct ccggtggcgt ggtcaaactc tacagccaaa gaacagataa   14940
tggcatttgt aagatgttgc acaatggctt ccaaaaggca aacggccctc acgtccaagt   15000
ggacgtaaag gctaaaccct tcagggtgaa tctcctctat aaacattcca gcaccttcaa   15060
ccatgcccaa ataattctca tctcgccacc ttctcaatat atctctaagc aaatcccgaa   15120
tattaagtcc ggccattgta aaaatctgct ccagagcgcc ctccaccttc agcctcaagc   15180
agcgaatcat gattgcaaaa attcaggttc ctcacagacc tgtataagat tcaaaagcgg   15240
aacattaaca aaaataccgc gatccgctag gtcccttcgc agggccagct gaacataatc   15300
gtgcaggtct gcacggacca gcgcggccac ttccccgcca ggaaccatga caaaagaacc   15360
```

```
cacactgatt atgacacgca tactcggagc tatgctaacc agcgtagccc cgatgtaagc    15420
ttgttgcatg ggcggcgata taaaatgcaa ggtgctgctc aaaaaatcag gcaaagcctc    15480
gcgcaaaaaa gaaagcacat cgtagtcatg ctcatgcaga taaaggcagg taagctccgg    15540
aaccaccaca gaaaagacac ccattttct ctcaaacatg tctgcgggtt tctgcataaa     15600
cacaaaataa aataacaaaa aaacatttaa acattagaag cctgtcttac aacaggaaaa    15660
acaaccctta taagcataag acggactacg gccatgccgg cgtgaccgta aaaaactgg     15720 tcaccgtgat taaaaagcac caccgacagc tcctcggtca tgtccggagt cataatgtaa    15780
gactcggtaa acacatcagg ttgattcaca tcggtcagtg ctaaaaagcg accgaaatag    15840
cccgggggaa tacatacccg caggcgtaga gacaacatta cagcccccat aggaggtata    15900
acaaaattaa taggagagaa aaacacataa acacctgaaa aaccctcctg cctaggcaaa    15960
atagcaccct cccgctccag aacaacatac agcgcttcca cagcggcagc cataacagtc    16020
agccttacca gtaaaaaaga aaacctatta aaaaaacacc actcgacacg gcaccagctc    16080
aatcagtcac agtgtaaaaa agggccaagt gcagagcgag tatatatagg actaaaaaat    16140
gacgtaacgg ttaaagtcca caaaaaacac ccagaaaacc gcacgcgaac ctacgcccag    16200
aaacgaaagc caaaaaaccc acaacttcct caaatcgtca cttccgtttt cccacgttac    16260
gtaacttccc attttaagaa aactacaatt cccaacacat acaagttact ccgccctaaa    16320
acctacgtca acgttattta aatgtcgacg cgtacaaaac gtcaaagggg cgacacaaaa    16380
tttattctaa atgcataata aatactgata acatcttata gtttgtatta tattttgtat    16440
tatcgttgac atgtataatt ttgatatcaa aaactgattt tccctttatt attttcgaga    16500 tttatttct taattctctt taacaaacta gaaatattgt atatacaaaa aatcataaat    16560
aatagatgaa tagtttaatt ataggtgttc atcaatcgaa aaagcaacgt atcttattta    16620
aagtgcgttg cttttttctc atttataagg ttaaataatt ctcatatatc aagcaaagtg    16680
acaggcgccc ttaaatattc tgacaaatgc tcttcccta aactcccccc ataaaaaac     16740 ccgccgaagc gggttttac gttatttgcg gattaacgat tactcgttat cagaaccgcc    16800
cagggggccc gagcttaaga ctggccgtcg ttttacaaca cagaaagagt ttgtagaaac    16860 gcaaaaggc catccgtcag gggccttctg cttagtttga tgcctggcag ttccctactc     16920
tcgccttccg cttcctcgct cactgactcg ctgcgctcgg tcgttcggct gcggcgagcg    16980
gtatcagctc actcaaaggc ggtaatacgg ttatccacag aatcagggga taacgcagga    17040
aagaacatgt gagcaaaagg ccagcaaaag gccaggaacc gtaaaaaggc cgcgttgctg    17100 gcgttttcc ataggctccg ccccctgac gagcatcaca aaaatcgacg ctcaagtcag    17160
aggtggcgaa acccgacagg actataaaga taccaggcgt ttccccctgg aagctccctc    17220
gtgcgctctc ctgttccgac cctgccgctt accggatacc tgtccgcctt tctcccttcg    17280
ggaagcgtgg cgctttctca tagctcacgc tgtaggtatc tcagttcggt gtaggtcgtt    17340
cgctccaagc tgggctgtgt gcacgaaccc cccgttcagc ccgaccgctg cgccttatcc    17400
ggtaactatc gtcttgagtc caacccggta agacacgact tatcgccact ggcagcagcc    17460
actggtaaca ggattagcag agcgaggtat gtaggcggtg ctacagagtt cttgaagtgg    17520
tgggctaact acggctacac tagaagaaca gtatttggta tctgcgctct gctgaagcca    17580
gttaccttcg gaaaaagagt tggtagctct tgatccggca aacaaaccac cgctggtagc    17640
ggtggttttt tgtttgcaa gcagcagatt acgcgcagaa aaaaggatc tcaagaagat     17700 cctttgatct tttctacggg gtctgacgct cagtggaacg acgcgcgcgt aactcacgtt    17760
```
aagggatttt ggtcatgagc ttgcgccgtc ccgtcaagtc agcgtaatgc tctgctt    17817

<210> SEQ ID NO 16
<211> LENGTH: 743
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
tgatatccgt agatgtacct ggacatccag gtgatgccgg cggcggtggt ggaggcgcgc    60
ggaaagtcgc ggacgcggtt ccagatgttg cgcagcggca aaagtgctc catggtcggg   120
acgctctggc cggtcaggcg cgcgcaatcg ttgacgctct agaccgtgca aaggagagc   180
ctgtaagcgg gcactcttcc gtggtctggt ggataaattc gcaagggtat catggcggac   240
gaccggggtt cgagcccgt atccggccgt ccgccgtgat ccatgcggtt accgcccgcg   300
tgtcgaaccc aggtgtgcga cgtcagacaa cgggggagtg ctcctttttgg cttccttcca   360
ggcgcggcgg ctgctgcgct agcttttttg gccactggcc gcgcgcagcg taagcggtta   420
ggctggaaag cgaaagcatt aagtggctcg ctccctgtag ccggagggtt attttccaag   480
ggttgagtcg cgggaccccc ggttcgagtc tcggaccggc cggactgcgg cgaacggggg   540
tttgcctccc cgtcatgcaa gaccccgctt gcaaattcct ccggaaacag ggacgagccc   600
cttttttgct tttcccagat gcatccggtg ctgcggcaga tgcgccccc tcctcagcag   660
cggcaagagc aagagcagcg gcagacatgc agggcaccct cccctcctcc taccgcgtca   720
ggagggcga catccgcggt tga                                             743

<210> SEQ ID NO 17
<211> LENGTH: 3201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
cgacgtaggt tttagggcgg agtaacttgt atgtgttggg aattgtagtt ttcttaaaat    60
gggaagttac gtaacgtggg aaaacggaag tgacgatttg aggaagttgt gggttttttg   120
gctttcgttt ctgggcgtag gttcgcgtgc ggttttctgg gtgttttttg tggactttaa   180
ccgttacgtc attttttagt cctatatata ctcgctctgc acttggccct tttttacact   240
gtgactgatt gagctggtgc cgtgtcgagt ggtgtttttt taataggttt tcttttttac   300
tggtaaggct gactgttatg gctgccgctg tggaagcgct gtatgttgtt ctggagcggg   360
agggtgctat tttgcctagg caggaggggtt tttcaggtgt ttatgtgttt ttctctccta   420
ttaattttgt tataccttct atggggggctg taatgttgtc tctacgcctg cgggtatgta   480
ttcccccggg ctatttcggt cgcttttttag cactgaccga tgtgaatcaa cctgatgtgt   540
ttaccgagtc ttacattatg actccggaca tgaccgagga gctgtcggtg gtgcttttta   600
atcacggtga ccagtttttt tacggtcacg ccggcatggc cgtagtccgt cttatgctta   660
taagggttgt ttttcctgtt gtaagacagg cttctaatgt ttaaatgttt ttttgttatt   720
ttatttgtg tttatgcaga aaccgcaga catgttgag agaaaatgg tgtctttttc   780
tgtggtggtt ccggagctta cctgccttta tctgcatgag catgactacg atgtgctttc   840

-continued

```
tttttttgcgc gaggctttgc ctgatttttt gagcagcacc ttgcatttta tatcgccgcc    900
catgcaacaa gcttacatcg gggctacgct ggttagcata gctccgagta tgcgtgtcat    960
aatcagtgtg ggttcttttg tcatggttcc tggcggggaa gtggccgcgc tggtccgtgc   1020
agacctgcac gattatgttc agctggccct gcgaagggac ctacgggatc gcggtatttt   1080
tgttaatgtt ccgcttttga atcttataca ggtctgtgag gaacctgaat ttttgcaatc   1140
atgattcgct gcttgaggct gaaggtggag ggcgctctgg agcagatttt tacaatggcc   1200
ggacttaata ttcgggattt gcttagagat atattgagaa ggtggcgaga tgagaattat   1260
ttgggcatgg ttgaaggtgc tggaatgttt atagaggaga ttcaccctga agggtttagc   1320
ctttacgtcc acttggacgt gagggccgtt tgccttttgg aagccattgt gcaacatctt   1380
acaaatgcca ttatctgttc tttggctgta gagtttgacc acgccaccgg aggggagcgc   1440
gttcacttaa tagatcttca ttttgaggtt ttggataatc ttttggaata aaaaaaaaaa   1500
catggttctt ccagctcttc ccgctcctcc cgtgtgtgac tcgcagaacg aatgtgtagg   1560
ttggctgggt gtggcttatt ctgcggtggt ggatgttatc agggcagcgg cgcatgaagg   1620
agtttacata gaacccgaag ccaggggggcg cctggatgct ttgagagagt ggatatacta   1680
caactactac acagagcgat ctaagcggcg agaccggaga cgcagatctg tttgtcacgc   1740
ccgcacctgg ttttgcttca ggaaatatga ctacgtccgg cgttccattt ggcatgacac   1800
tacgaccaac acgatctcgg ttgtctcggc gcactccgta cagtagggat cgtctacctc   1860
cttttgagac agaaacccgc gctaccatac tggaggatca tccgctgctg cccgaatgta   1920
acactttgac aatgcacaac gtgagttacg tgcgaggtct tccctgcagt gtgggattta   1980
cgctgattca ggaatgggtt gttccctggg atatggttct aacgcgggag gagcttgtaa   2040
tcctgaggaa gtgtatgcac gtgtgcctgt gttgtgccaa cattgatatc atgacgagca   2100
tgatgatcca tggttacgag tcctgggctc tccactgtca ttgttccagt cccggttccc   2160
tgcagtgtat agccggcggg caggttttgg ccagctggtt taggatggtg gtggatggcg   2220
ccatgtttaa tcagaggttt atatggtacc gggaggtggt gaattacaac atgccaaaag   2280
aggtaatgtt tatgtccagc gtgtttatga ggggtcgcca cttaatctac ctgcgcttgt   2340
ggtatgatgg ccacgtgggt tctgtggtcc ccgccatgag ctttggatac agcgccttgc   2400
actgtgggat tttgaacaat attgtggtgc tgtgctgcag ttactgtgct gatttaagtg   2460
agatcagggt gcgctgctgt gcccggagga caaggcgcct tatgctgcgg gcggtgcgaa   2520
tcatcgctga ggagaccact gccatgttgt attcctgcag gacggagcgg cggcggcagc   2580
agtttattcg cgcgctgctg cagcaccacc gccctatcct gatgcacgat tatgactcta   2640
cccccatgta ggcgtggact tctccttcgc cgcccgttaa gcaaccgcaa gttggacagc   2700
agcctgtggc tcagcagctg gacagcgaca tgaacttaag tgagctgccc ggggagttta   2760
ttaatatcac tgatgagcgt ttggctcgac aggaaaccgt gtggaatata cacctaaga   2820
atatgtctgt tacccatgat atgatgcttt ttaaggccag ccggggagaa aggactgtgt   2880
actctgtgtg ttgggaggga ggtggcaggt tgaatactag ggttctgtga gtttgattaa   2940
ggtacggtga tctgtataag ctatgtggtg gtggggctat actactgaat gaaaaatgac   3000
ttgaaatttt ctgcaattga aaaataaaca cgttgaaaca taacacaaac gattctttat   3060
tcttgggcaa tgtatgaaaa agtgtaagag gatgtggcaa atatttcatt aatgtagttg   3120
tggccagacc agtcccatga aaatgacata gagtatgcac ttggagttgt gtctcctgtt   3180
tcctgtgtac cgtttagtgt a                                             3201
```

<210> SEQ ID NO 18
<211> LENGTH: 5336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

| | | | | | |
|---|---|---|---|---|---|
| caccctgtga | cgaaagccgc | ccgcaagctg | cgcccctgag | ttagtcatct | gaacttcggc | 60 |
| ctgggcgtct | ctgggaagta | ccacagtggt | gggagcggga | ctttcctggt | acaccagggc | 120 |
| agcgggccaa | ctacggggat | taaggttatt | acgaggtgtg | gtggtaatag | ccgcctgttc | 180 |
| caagagaatt | cggtttcggt | gggcgcggat | tccgttgacc | cgggatatca | tgtggggtcc | 240 |
| cgcgctcatg | tagtttattc | gggttgagta | gtcttgggca | gctccagccg | caagtcccat | 300 |
| ttgtggctgg | taactccaca | gtagggcgt | gggaatttcc | ttgctcataa | tggcgctgac | 360 |
| gacaggtgct | ggcgccgggt | gtggccgctg | gagatgacgt | agttttcgcg | cttaaatttg | 420 |
| agaaagggcg | cgaaactagt | ccttaagagt | cagcgcgcag | tatttactga | agagagcctc | 480 |
| cgcgtcttcc | agcgtgcgcc | gaagctgatc | ttcgcttttg | tgatacaggc | agctgcgggt | 540 |
| gagggatcgc | agagacctgt | tttttatttt | cagctcttgt | tcttggcccc | tgctctgttg | 600 |
| aaatatagca | tacagagtgg | gaaaaatcct | gtttctaagc | tcgcgggtcg | atacgggttc | 660 |
| gttgggcgcc | agacgcagcg | ctcctcctcc | tgctgctgcc | gccgctgtgg | atttcttggg | 720 |
| ctttgtcaga | gtcttgctat | ccggtcgcct | ttgcttctgt | gtggccgctg | ctgttgctgc | 780 |
| cgctgccgct | gccgccggtg | cagtatgggc | tgtagagatg | acgtagtaa | tgcaggatgt | 840 |
| tacgggggaa | ggccacgccg | tgatggtaga | aagaaagcg | gcgggcgaag | gagatgttgc | 900 |
| ccccacagtc | ttgcaagcaa | gcaactatgg | cgttcttgtg | cccgcgccat | gagcggtagc | 960 |
| cttgcgctg | ttgttgctct | tgggctaacg | gcggcggctg | cttggactta | ccggccctgg | 1020 |
| ttccagtggt | gtcccatcta | cggttgggtc | ggcgaacggg | cagtgccggc | ggcgcctgag | 1080 |
| gagcggaggt | tgtagccatg | ctggaaccgg | ttgccgattt | ctgggggcgcc | ggcgagggga | 1140 |
| atgcgaccga | gggtgacggt | gtttcgtctg | acacctcttc | gacctcggaa | gcttcctcgt | 1200 |
| ctaggctctc | ccagtcttcc | atcatgtcct | cctcctcctc | gtccaaaacc | tcctctgcct | 1260 |
| gactgtccca | gtattcctcc | tcgtccgtgg | gtggcggcgg | cagctgcagc | ttcttttttgg | 1320 |
| gtgccatcct | gggaagcaag | ggcccgcggc | tgctgctgat | agggctgcgg | cggcgggggg | 1380 |
| attgggttga | gctcctcgcc | ggactggggg | tccaagtaaa | cccccgtcc | cttcgtagc | 1440 |
| agaaactctt | ggcgggcttt | gttgatggct | tgcaattggc | caagaatgtg | gccctgggta | 1500 |
| atgacgcagg | cggtaagctc | cgcatttggc | gggcgggatt | ggtcttcgta | gaacctaatc | 1560 |
| tcgtgggcgt | ggtagtcctc | aggtacaaat | ttgcgaaggt | aagccgacgt | ccacagcccc | 1620 |
| ggagtgagtt | tcaaccccgg | agccgcggac | ttttcgtcag | gcgagggacc | ctgcagctca | 1680 |
| aaggtaccga | taatttgact | ttcgttaagc | agctgcgaat | tgcaaaccag | ggagcggtgc | 1740 |
| gggggtgcata | ggttgcagcg | acagtgacac | tccagtagac | cgtcaccgct | cacgtcttcc | 1800 |
| attatgtcag | agtggtaggc | aaggtagttg | gctagctgca | gaaggtagca | gtggcccaa | 1860 |
| agcggcggag | ggcattcgcg | gtacttaatg | ggcacaaagt | cgctaggaag | tgcacagcag | 1920 |
| gtggcgggca | agattcctga | gcgctctagg | ataaagttcc | taaagttctg | caacatgctt | 1980 |
| tgactggtga | agtctggcag | accctgttgc | agggttttaa | gcaggcgttc | ggggaaaatg | 2040 |

-continued

```
atgtccgcca ggtgcgcggc cacggagcgc tcgttgaagg ccgtccatag gtccttcaag    2100
ttttgcttta gcagtttctg cagctccttg aggttgcact cctccaagca ctgctgccaa    2160
acgcccatgg ccgtctgcca ggtgtagcat agaaataagt aaacgcagtc gcggacgtag    2220
tcgcggcgcg cctcgccctt gagcgtggaa tgaagcacgt tttgcccaag gcggttttcg    2280
tgcaaaattc caaggtagga gaccaggttg cagagctcca cgttggagat cttgcaggcc    2340
tggcgtacgt agccctgtcg aaaggtgtag tgcaatgttt cctctagctt gcgctgcatc    2400
tccgggtcag caaagaaccg ctgcatgcac tcaagctcca cggtaacgag cactgcggcc    2460
atcattagtt tgcgtcgctc ctccaagtcg gcaggctcgc gcgtttgaag ccagcgcgct    2520
agctgctcgt cgccaactgc gggtaggccc tcctctgttt gttcttgcaa atttgcatcc    2580
ctctccaggg gctgcgcacg gcgcacgatc agctcactca tgactgtgct catgaccttg    2640
gggggtaggt taagtgccgg gtaggcaaag tgggtgacct cgatgctgcg ttttagtacg    2700
gctaggcgcg cgttgtcacc ctcgagttcc accaacactc cagagtgact ttcattttcg    2760 ctgtttttcct gttgcagagc gttttgccgcg cgcttctcgt cgcgtccaag accctcaaag    2820
atttttggca cttcgttgag cgaggcgata tcaggtatga cagcgccctg ccgcaaggcc    2880
agctgcttgt ccgctcggct gcggttggca cggcaggata ggggtatctt gcagttttgg    2940
aaaaagatgt gataggtggc aagcacctct ggcacggcaa atacggggta gaagttgagg    3000
cgcgggttgg gctcgcatgt gccgttttct tggcgtttgg ggggtacgcg cggtgagaat    3060
aggtggcgtt cgtaggcaag gctgacatcc gctatggcga ggggcacatc gctgcgctct    3120
tgcaacgcgt cgcagataat ggcgcactgg cgctgcagat gcttcaacag cacgtcgtct    3180
cccacatcta ggtagtcgcc atgccttttcg tccccccgcc cgacttgttc ctcgtttgcc    3240
tctgcgttgt cctggtcttg ctttttatcc tctgttggta ctgagcggtc ctcgtcgtct    3300
tcgcttacaa aacctgggtc ctgctcgata atcacttcct cctcctcaag cgggggtgcc    3360
tcgacgggga aggtggtagg cgcgttggcg gcatcggtgg aggcggtggt ggcgaactca    3420 gaggggggcgg ttaggctgtc cttcttctcg actgactcca tgatcttttt ctgcctatag    3480
gagaaggaaa tggccagtcg ggaagaggag cagcgcgaaa ccaccccccga gcgcggacgc    3540 ggtgcggcgc gacgtccccc aaccatggag gacgtgtcgt cccgtccccc gtcgccgccg    3600 cctcccccggg cgccccaaa aaagcggatg aggcggcgta tcgagtccga ggacgaggaa    3660
gactcatcac aagacgcgct ggtgccgcgc acacccagcc cgcggccatc gacctcggcg    3720 gcggattttgg ccattgcgcc caagaagaaa aagaagcgcc cttctcccaa gcccgagcgc    3780
ccgccatcac cagaggtaat cgtggacagc gaggaagaaa gagaagatgt ggcgctacaa    3840
atggtgggtt tcagcaaccc accggtgcta atcaagcatg gcaaaggagg taagcgcaca    3900
gtgcggcggc tgaatgaaga cgacccagtg gcgcgtggta tgcggacgca agaggaagag    3960
gaagagccca gcgaagcgga aagtgaaatt acgtgatga acccgctgag tgtgccgatc    4020
gtgtctgcgt gggagaaggg catggaggct gcgcgcgcgc tgatggacaa gtaccacgtg    4080
gataacgatc taaaggcgaa cttcaaacta ctgcctgacc aagtggaagc tctggcggcc    4140
gtatgcaaga cctggctgaa cgaggagcac cgcgggttgc agctgacctt caccagcaac    4200
aagacctttg tgacgatgat ggggcgattc ctgcaggcgt acctgcagtc gtttgcagag    4260
gtgacctaca agcatcacga gcccacgggc tgcgcgttgt ggctgcaccg ctgcgctgag    4320
atcgaaggcg agcttaagtg tctacacgga agcattatga taaataagga gcacgtgatt    4380
```

| | |
|---|---|
| gaaatggatg tgacgagcga aaacgggcag cgcgcgctga aggagcagtc tagcaaggcc | 4440 |
| aagatcgtga agaaccggtg gggccgaaat gtggtgcaga tctccaacac cgacgcaagg | 4500 |
| tgctgcgtgc acgacgcggc ctgtccggcc aatcagtttt ccggcaagtc ttgcggcatg | 4560 |
| ttcttctctg aaggcgcaaa ggctcaggtg gcttttaagc agatcaaggc ttttatgcag | 4620 |
| gcgctgtatc ctaacgccca gaccgggcac ggtcaccttt tgatgccact acggtgcgag | 4680 |
| tgcaactcaa agcctgggca cgcgcccttt tgggaaggc agctaccaaa gttgactccg | 4740 |
| ttcgccctga gcaacgcgga ggacctggac gcggatctga tctccgacaa gagcgtgctg | 4800 |
| gccagcgtgc accacccggc gctgatagtg ttccagtgct gcaaccctgt gtatcgcaac | 4860 |
| tcgcgcgcgc agggcggagg ccccaactgc gacttcaaga tatcggcgcc cgacctgcta | 4920 |
| aacgcgttgg tgatggtgcg cagcctgtgg agtgaaaact tcaccgagct gccgcggatg | 4980 |
| gttgtgcctg agtttaagtg gagcactaaa caccagtatc gcaacgtgtc cctgccagtg | 5040 |
| gcgcatagcg atgcgcggca gaacccccttt gatttttaaa cggcgcagac ggcaagggtg | 5100 |
| ggggtaaata atcacccgag agtgtacaaa taaaagcatt tgcctttatt gaaagtgtct | 5160 |
| ctagtacatt attttttacat gttttttcaag tgacaaaaag aagtggcgct cctaatctgc | 5220 |
| gcactgtggc tgcggaagta gggcgagtgg cgctccagga agctgtagag ctgttcctgg | 5280 |
| ttgcgacgca gggtgggctg tacctgggga ctgttgagca tggagttggg taccgc | 5336 |

<210> SEQ ID NO 19
<211> LENGTH: 810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

| | |
|---|---|
| ttagaaaaac tcatcgagca tcaaatgaaa ctgcaattta ttcatatcag gattatcaat | 60 |
| accatatttt tgaaaaagcc gtttctgtaa tgaaggagaa aactcaccga ggcagttcca | 120 |
| taggatggca agatcctggt atcggtctgc gattccgact cgtccaacat caatacaacc | 180 |
| tattaatttc ccctcgtcaa aaataaggtt atcaagtgag aaatcaccat gagtgacgac | 240 |
| tgaatccggt gagaatggca aaagtttatg catttctttc cagacttgtt caacaggcca | 300 |
| gccattacgc tcgtcatcaa aatcactcgc atcaaccaaa ccgttattca ttcgtgattg | 360 |
| cgcctgagcg aggcgaaata cgcgatcgct gttaaaagga caattacaaa caggaatcga | 420 |
| gtgcaaccgg cgcaggaaca ctgccagcgc atcaacaata ttttcacctg aatcaggata | 480 |
| ttcttctaat acctggaacg ctgtttttcc ggggatcgca gtggtgagta accatgcatc | 540 |
| atcaggagta cggataaaat gcttgatggt cggaagtggc ataaattccg tcagccagtt | 600 |
| tagtctgacc atctcatctg taacatcatt ggcaacgcta cctttgccat gtttcagaaa | 660 |
| caactctggc gcatcgggct tcccatacaa gcgatagatt gtcgcacctg attgcccgac | 720 |
| attatcgcga gcccatttat acccatataa atcagcatcc atgttggaat ttaatcgcgg | 780 |
| cctcgacgtt tcccgttgaa tatggctcat | 810 |

<210> SEQ ID NO 20
<211> LENGTH: 674
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
atgtgagcaa aaggccagca aaaggccagg aaccgtaaaa aggccgcgtt gctggcgttt      60
ttccataggc tccgccccc tgacgagcat cacaaaaatc gacgctcaag tcagaggtgg     120
cgaaacccga caggactata agataccag gcgtttcccc ctggaagctc cctcgtgcgc     180
tctcctgttc cgaccctgcc gcttaccgga tacctgtccg cctttctccc ttcgggaagc     240
gtggcgcttt ctcatagctc acgctgtagg tatctcagtt cggtgtaggt cgttcgctcc     300
aagctgggct gtgtgcacga accccccgtt cagcccgacc gctgcgcctt atccggtaac     360
tatcgtcttg agtccaaccc ggtaagacac gacttatcgc cactggcagc agccactggt     420
aacaggatta gcagagcgag gtatgtaggc ggtgctacag agttcttgaa gtggtgggct     480
aactacggct acactagaag aacagtattt ggtatctgcg ctctgctgaa gccagttacc     540
ttcggaaaaa gagttggtag ctcttgatcc ggcaaacaaa ccaccgctgg tagcggtggt     600
tttttttgttt gcaagcagca gattacgcgc agaaaaaaag gatctcaaga agatcctttg     660
atcttttcta cggg                                                       674
```

<210> SEQ ID NO 21
<211> LENGTH: 118
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
tttcaatatt attgaagcat ttatcagggt tattgtctca tgagcggata catatttgaa      60
tgtatttaga aaataaaca aatagggtc agtgttacaa ccaattaacc aattctga         118
```

<210> SEQ ID NO 22
<211> LENGTH: 301
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
tattctaaat gcataataaa tactgataac atcttatagt ttgtattata ttttgtatta      60
tcgttgacat gtataatttt gatatcaaaa actgattttc cctttattat tttcgagatt     120
tattttctta attctcttta acaaactaga aatattgtat atacaaaaaa tcataaataa     180
tagatgaata gtttaattat aggtgttcat caatcgaaaa agcaacgtat cttatttaaa     240
gtgcgttgct tttttctcat ttataaggtt aaataattct catatatcaa gcaaagtgac     300
a                                                                     301
```

<210> SEQ ID NO 23
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
ggcgccctta atattctga caaatgctct ttccctaaac tcccccata aaaaacccg       60
ccgaagcggg ttttacgtt atttgcggat taacgattac tcgttatcag aaccgcccag     120
```

<210> SEQ ID NO 24
<211> LENGTH: 6838
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
ctagagtcga cctgcaggca tgcaagcttg gcgtaatcat ggtcatagct gtttcctgtg      60
tgaaattgtt atccgctcac aattccacac aacatacgag ccggaagcat aaagtgtaaa     120
gcctggggtg cctaatgagt gagctaactc acattaattg cgttgcgctc actgcccgct     180
ttccagtcgg gaaacctgtc gtgccagctg cattaatgaa tcggccaacg cgcgggggaga     240
ggcggtttgc gtattgggcg ctcttccgct tcctcgctca ctgactcgct gcgctcggtc     300
gttcggctgc ggcgagcggt atcagctcac tcaaaggcgg taatacggtt atccacagaa     360
tcagggggata acgcaggaaa gaacatgtga gcaaaaggcc agcaaaaggc caggaaccgt     420
aaaaaggccg cgttgctggc gttttttccat aggctccgcc ccctgacga gcatcacaaa     480
aatcgacgct caagtcagag gtggcgaaac ccgacaggac tataaagata ccaggcgttt     540
ccccctggaa gctccctcgt gcgctctcct gttccgaccc tgccgcttac cggatacctg     600
tccgccttc tccttcggg aagcgtggcg ctttctcata gctcacgctg taggtatctc     660
agttcggtgt aggtcgttcg ctccaagctg ggctgtgtgc acgaacccc cgttcagccc     720
gaccgctgcg ccttatccgg taactatcgt cttgagtcca acccggtaag acacgactta     780
tcgccactgg cagcagccac tggtaacagg attagcagag cgaggtatgt aggcggtgct     840
acagagttct tgaagtggtg gcctaactac ggctacacta aaggacagt atttggtatc     900
tgcgctctgc tgaagccagt taccttcgga aaaagagttg gtagctcttg atccggcaaa     960
caaaccaccg ctggtagcgg tggttttttt gtttgcaagc agcagattac gcgcagaaaa    1020
aaaggatctc aagaagatcc tttgatcttt tctacggggt ctgacgctca gtggaacgaa    1080
aactcacgtt aagggatttt ggtcatgtga ttatcaaaaa ggatcttcac ctagatcctt    1140
ttaaattaaa aatgaagttt taaatcaatc taaagtatat atgagtaaac ttggtctgac    1200
agttagaaaa actcatcgag catcaaatga aactgcaatt tattcatatc aggattatca    1260
ataccatatt tttgaaaaag ccgtttctgt aatgaaggag aaaactcacc gaggcagttc    1320
cataggatgg caagatcctg gtatcggtct gcgattccga ctcgtccaac atcaatacaa    1380
cctattaatt tcccctcgtc aaaaataagg ttatcaagtg agaaatcacc atgagtgacg    1440
actgaatccg gtgagaatgg caaaagttta tgcatttctt tccagacttg ttcaacaggc    1500
cagccattac gctcgtcatc aaaatcactc gcatcaacca accgttatt cattcgtgat    1560
tgcgcctgag cgagacgaaa tacgcgatcg ctgttaaaag gacaattaca acaggaatc    1620
gaatgcaacc ggcgcaggaa cactgccagc gcatcaacaa tattttcacc tgaatcagga    1680
tattcttcta atacctggaa tgctgttttc ccagggatcg cagtggtgag taaccatgca    1740
tcatcaggag tacggataaa atgcttgatg gtcggaagag gcataaattc cgtcagccag    1800
tttagtctga ccatctcatc tgtaacatca ttggcaacgc tacctttgcc atgtttcaga    1860
aacaactctg gcgcatcggg cttcccatac aatcgataga ttgtcgcacc tgattgcccg    1920
acattatcgc gagcccattt ataccccatat aaatcagcat ccatgttgga atttaatcgc    1980
ggcctagagc aagacgtttc ccgttgaata tggctcatac tcttcctttt tcaatattat    2040
```

```
tgaagcattt atcagggtta ttgtctcatg agcggataca tatttgaatg tatttagaaa    2100
aataaacaaa taggggttcc gcgcacattt ccccgaaaag tgccacctga cgtctaagaa    2160
accattatta acatgacatt aacctataaa aataggcgta tcacgaggcc ctttcgtctc    2220
gcgcgtttcg gtgatgacgg tgaaaacctc tgacacatgc agctcccgga gacggtcaca    2280
gcttgtctgt aagcggatgc cgggagcaga caagcccgtc agggcgcgtc agcgggtgtt    2340
ggcgggtgtc ggggctggct taactatgcg gcatcagagc agattgtact gagagtgcac    2400
catatgcggt gtgaaatacc gcacagatgc gtaaggagaa ataccgcat caggcgccat     2460 tcgccattca ggctgcgcaa ctgttgggaa gggcgatcgg tgcgggcctc ttcgctatta    2520
cgccagctgg cgaaaggggg atgtgctgca aggcgattaa gttgggtaac gccagggttt    2580
tcccagtcac gacgttgtaa aacgacggcc agtgaattcg agctcggtac cgtaacaaa     2640 agcttatcga gcggccgcaa gaggcagtat tttactgaca cgaatacacg gtttattgag    2700
ggtatgcgac atgaatgggt taaaggggtc gggtaaggta tcgggttccg ataggtctgg    2760
tggttctgta ttccccggtg ctgtccgggg caaagtccac aaactggggg tcgttgtagt    2820
tgtttgtgta ctggatctct gggttccacc tcttggagtt ttccttcttg agctcccact    2880
ccatctccac ggtgacctgc ccggtgctgt actgggtgat gaagctgctg acgggcacgt    2940
ccgagaagct ggtgatattt ccgggcacag gcgtgttctt gatgagcatc atgggcggtg    3000
ggtgtttgag tccgaatccg cccatggccg gagagggtg aaagtgcgcc cccgtctctg      3060
ggatcttggc ccagatgggt ccttggaggt acacgtccct ctccatccac acgctgccgg    3120
gcacgatttc ctggaggttg tacgtgccgg tcgcgggggc agtggtggag ctctggttgt    3180
tggtggccat ctgcccgccg acgttgtacg ccacgcggtt caccggctgc gtctcgctct    3240
cgctggtgat gagcatgttg ccctcgaggt acgtggcggt ggtgcccggg ttcgccggct    3300
ggctgttgaa gatcatagtg ttctccaggg cataggtgtt gctgccctgg aggttgttgg    3360
tcatgccgtt cggctgcggg ggcacctggt aactcgcgcc ctcgagctcc atcctattgg    3420
tcgtggcgaa ggcgctgaca ctggcgcggt tgaccccgga gcccaggttc cagccctggg    3480
ttcggcccat gggccccggg aaccagtttt tgtaggtgtt ggcgtatctc ccggccaggt    3540
tcttgttgaa ctggactccg ccagtgttat ttgtgctcac gaagcggtac aagtactggt    3600
ccaccagcgg gttggccagc ttgaacaggt tctgactggg agcgaagctg gagtggaagg    3660
gcacctcctc aaagttgtag gtaaactcaa agttgttgcc cgttctcagc atcttgctgg    3720
gaaagtactc taggcagaag aagctgctcc tctcggtggg attttctgtg ttgtcgcggt    3780
tcagcgtcgc gtaaccgtac tgcggcagcg taaagacctg cggagggaag gccggcaggc    3840
atccctcggt cccgttgccg acgacgtagg gcagctggta gtcgtcgtcc gtaaacactt    3900
ggacggtgga ggtgaggttg ttggcgatgg tggtggtgga gtcctgcacc gtgacctctt    3960
tgacttgaat gttgaagatt ttgactctga gggaccgggg tctgaagccc cagtagttgt    4020
tgatgagtct ttgccagtct cgggggctcc agtggctgtg gaagcggtta aagtcaaagt    4080
acccccaggg ggtgctgtat ccaaagtagg cgttggcgtt gcttccgtcg acggagccgc    4140
ttttgatctc tcggtactgg tggttgttgt agctgggcag cacccaggtt cgggtggact    4200
tggtgacgac tctgtccccc atccacgtgg aatcgcaatg ccaatctccc gaggcattgc    4260
ccactccatc ggcaccttgg ttattgtcgc ccaatgggcc gccacctccc gcagacattg    4320
tatcagctcc caaacttgag gctggttggg ctgggatttg cagctgctgg gatccgctgg    4380
```

```
gtccagcttc ggcgtctgac gaggtggaag gcttggagtc ctcttcggtc cgagccttct    4440 ttcttttttgg aaagtggtcg tctatccgct ttccggtagg ggccgtctta gcaccctctt    4500
caaccaggcc aaaaggttcg agaacccttt tcttggcctg aaagactgcc tttccgaggt    4560
ttcccccgaa ggatgtgtcg tcggcgagct ctcctgaaaa ctcggcgtcc gcgtggttgt    4620
acttgaggta ggggttgtct cccgcctcaa gctgctcgtt gtacgagatg tcgtgctctc    4680
gcgcgacctc gtctgccctg ttgacaggct ctcctcgatc gagaccgttt ccgggtccga    4740
gatagttata accaggcagc acaagaccac gggcttgatc ttgatgctgc tgattgggtt    4800
ttggtttcgg tgggcccgct tcaaggccca aaaactcgcg aagaccttca ccaacttctt    4860
ccaaccaatc tggagggtga tcaacaaaag acatgactac tcgctttatt tactgttctt    4920
tattggcatc gtcaaaatcc ccaaaatctg acaagttttc cttttcccag ggggaatcc     4980 catgacaaat ttgacagtga gttacattgt gacagataca tccattttg ccccgattca     5040 aatattcaca ttcatcacat ttgttagaaa tgttgtcaaa ttgagcatga tagtcacatt    5100
tgcaatcata ccttgaattc caattgagcg gtcgcagagg agcgggatca acagtcacgt    5160
ctgaactgcg aggcgtctcg ggaacaaatg agagcctggc ccgcttctcc agactttttat   5220 agctagtatt ggtgacgtca cccagtgggc gttttagaga tttctccgcc cctttagttc    5280
ccgccaattc cctgggaact ttaaaactcgt gagtcaccgg cacctgattg acctttgccc    5340
aagcaaaaaa gtccttgact tcctgcttag taatcttgcc aaaatctggc gggagccgct    5400
tagtcagttc aaatttgaac atgcggtcct ccagcggctg ctggtgttca aggtcgtgg     5460 aattcccatc caccaccaca cacatgtttg tattggaagt tacaatgaca ggggtagaat    5520
caatttgaac agaggattta catttctgat cgaccgcac ctttgagccc cccaggatgg     5580
ccttggcgga ttcaaccacc ttgttggtca tcttttccctc ctcccaccaa atgagcattt    5640
tgtccacaca gtcattaaag ggaaagtttt cattggtcca gttcacgcag ccgtaaaagg    5700
gcacagtgtg ggcgatggcc tccgcgatgt tggtcttgcc ggtcgtggcg ggtccgtaga    5760
gccagacggt gttcctcttg ttgaaggagc gctgacacca gccgtagagg atggatcccg    5820
cgtaggccgg gtcgtagcca ttcatctcaa aaatttgcca gattctgttt tttgaaatgt    5880
cctcgggaac ggagctcccc acgaggtagt ccaccgcgct ttttgtcaga ctcataattt    5940
tggtcgcgtt gtcgagcgcg gccttgatct ggctccgaga gttgccggtg gagttgaagg    6000
agaggtagct ctcctgattt tcctggatcc actgcttctc cgaggtaatc cccttgtcca    6060
cgagccaccc gaccagctcc atgtacctgg ctgaagtttt tgatctgatc accggcgcat    6120
cagaattggg attctgattc tctttgttct gctcctgcgt ctgcgacacg tgcgtcagat    6180
gctgcgccac caaccgttta cgctccgtga gattcaaaca ggcgcttaaa tactgttcca    6240
tattagtcca cgcccactgg agctcaggct gggttttggg gagcaagtaa ttggggatgt    6300
agcactcatc caccaccttg ttcccgcctc cggcgccatt tctggtctt gtgaccgcga    6360 accagtttgg caaagtcggc tcgatcccgc ggtaaattct ctgaatcagt ttttcgcgaa    6420
tctgactcag gaaacgtccc aaaaccatgg atttcacccc ggtggttttcc acgagcacgt   6480 gcatgtggaa gtagctctct cccttctcaa attcacaaa gaaagggcc tccggggcct     6540 tactcacacg gcgccattcc gtcagaaagt cgcgctgcag cttctcggcc acggtcaggg    6600
gtgcctgctc aatcagattc agatccatgt cagaatctgg cggcaactcc cattccttct    6660
cggccaccca gttcacaaag ctgtcagaaa tgccgggcag atgctcgtca aggtcgctgg    6720
ggaccttaat cacaatctcg taaaaccccg gcatggcggc tgcgcagatc agaagttcct    6780
```
atactttcta gagaatagga acttcggaat aggaacttct gatcttccgg gggatcca      6838

<210> SEQ ID NO 25
<211> LENGTH: 816
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
ttagaaaaac tcatcgagca tcaaatgaaa ctgcaattta ttcatatcag gattatcaat        60
accatatttt tgaaaagcc gtttctgtaa tgaaggagaa aactcaccga ggcagttcca       120
taggatggca agatcctggt atcggtctgc gattccgact cgtccaacat caatacaacc      180
tattaatttc ccctcgtcaa aaataaggtt atcaagtgag aaatcaccat gagtgacgac      240
tgaatccggt gagaatggca aaagtttatg catttctttc cagacttgtt caacaggcca      300
gccattacgc tcgtcatcaa aatcactcgc atcaaccaaa ccgttattca ttcgtgattg      360
cgcctgagcg agacgaaata cgcgatcgct gttaaaagga caattacaaa caggaatcga      420
atgcaaccgg cgcaggaaca ctgccagcgc atcaacaata ttttcacctg aatcaggata      480
ttcttctaat acctggaatg ctgttttccc agggatcgca gtggtgagta accatgcatc      540
atcaggagta cggataaaat gcttgatggt cggaagaggc ataaattccg tcagccagtt      600
tagtctgacc atctcatctg taacatcatt ggcaacgcta cctttgccat gtttcagaaa      660
caactctggc gcatcgggct tcccatacaa tcgatagatt gtcgcacctg attgcccgac      720
attatcgcga gcccatttat acccatataa atcagcatcc atgttggaat taatcgcgg      780 cctagagcaa gacgtttccc gttgaatatg gctcat                                816

<210> SEQ ID NO 26
<211> LENGTH: 673
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
tgtgagcaaa aggccagcaa aaggccagga accgtaaaaa ggccgcgttg ctggcgtttt        60
tccataggct ccgcccccct gacgagcatc acaaaaatcg acgctcaagt cagaggtggc      120
gaaacccgac aggactataa agataccagg cgtttccccc tggaagctcc ctcgtgcgct      180
ctcctgttcc gaccctgccg cttaccggat acctgtccgc ctttctccct tcgggaagcg      240
tggcgctttc tcatagctca cgctgtaggt atctcagttc ggtgtaggtc gttcgctcca      300
agctgggctg tgtgcacgaa ccccccgttc agcccgaccg ctgcgcctta ccggtaact      360 atcgtcttga gtccaacccg gtaagacacg acttatcgcc actggcagca gccactggta      420
acaggattag cagagcgagg tatgtaggcg gtgctacaga gttcttgaag tggtggccta      480
actacggcta cactagaagg acagtatttg gtatctgcgc tctgctgaag ccagttacct      540
tcggaaaaag agttggtagc tcttgatccg gcaaacaaac caccgctggt agcggtggtt      600 ttttgtttg caagcagcag attacgcgca gaaaaaaagg atctcaagaa gatccttga      660 tcttttctac ggg                                                          673

<210> SEQ ID NO 27

<211> LENGTH: 143
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 27

| aattgttatc cgctcacaat tccacacaac atacgagccg gaagcataaa gtgtaaagcc | 60 |
| tggggtgcct aatgagtgag ctaactcaca ttaattgcgt tgcgctcact gcccgctttc | 120 |
| cagtcgggaa acctgtcgtg cca | 143 |

<210> SEQ ID NO 28
<211> LENGTH: 5121
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 28

| ctgaagccag ttaccttcgg aaaaagagtt ggtagctctt gatccggcaa acaaaccacc | 60 |
| gctggtagcg gtggtttttt tgtttgcaag cagcagatta cgcgcagaaa aaaggatct | 120 |
| caagaagatc ctttgatctt ttctacgggg tctgacgctc agtggaacga aaactcacgt | 180 |
| taagggattt tggtcatgtg attatcaaaa aggatcttca cctagatcct ttaaattaa | 240 |
| aaatgaagtt ttaaatcaat ctaaagtata tatgagtaaa cttggtctga cagttagaaa | 300 |
| aactcatcga gcatcaaatg aaactgcaat ttattcatat caggattatc aataccatat | 360 |
| ttttgaaaaa gccgtttctg taatgaagga gaaaactcac cgaggcagtt ccataggatg | 420 |
| gcaagatcct ggtatcggtc tgcgattccg actcgtccaa catcaataca acctattaat | 480 |
| ttcccctcgt caaaaataag gttatcaagt gagaaatcac catgagtgac gactgaatcc | 540 |
| ggtgagaatg gcaaaagttt atgcatttct ttccagactt gttcaacagg ccagccatta | 600 |
| cgctcgtcat caaaatcact cgcatcaacc aaaccgttat tcattcgtga ttgcgcctga | 660 |
| gcgagacgaa atacgcgatc gctgttaaaa ggacaattac aaacaggaat cgaatgcaac | 720 |
| cggcgcagga acactgccag cgcatcaaca atattttcac ctgaatcagg atattcttct | 780 |
| aatacctgga atgctgtttt cccagggatc gcagtggtga gtaaccatgc atcatcagga | 840 |
| gtacggataa aatgcttgat ggtcggaaga ggcataaatt ccgtcagcca gtttagtctg | 900 |
| accatctcat ctgtaacatc attggcaacg ctacctttgc catgtttcag aaacaactct | 960 |
| ggcgcatcgg gcttcccata caatcgatag attgtcgcac ctgattgccc gacattatcg | 1020 |
| cgagcccatt tatacccata taaatcagca tccatgttgg aatttaatcg cggcctagag | 1080 |
| caagacgttt cccgttgaat atggctcata ctcttccttt ttcaatatta ttgaagcatt | 1140 |
| tatcagggtt attgtctcat gagcggatac atatttgaat gtatttagaa aaataaacaa | 1200 |
| ataggggttc cgcgcacatt tccccgaaaa gtgccacctg acgtctaaga accattatt | 1260 |
| aacatgacat aacctataa aaataggcgt atcacgaggc cctttcgtct cgcgcgtttc | 1320 |
| ggtgatgacg gtgaaaacct ctgacacatg cagctcccgg agacggtcac agcttgtctg | 1380 |
| taagcggatg ccgggagcag acaagcccgt cagggcgcgt cagcgggtgt tggcgggtgt | 1440 |
| cggggctggc ttaactatgc ggcatcagag cagattgtac tgagagtgca ccatatgcgg | 1500 |
| tgtgaaatac cgcacagatg cgtaaggaga aaataccgca tcaggcgcca ttcgccattc | 1560 |
| aggctgcgca actgttggga agggcgatcg gtgcgggcct cttcgctatt acgccagctg | 1620 |

```
gcgaaagggg gatgtgctgc aaggcgatta agttgggtaa cgccagggtt ttcccagtca   1680
cgacgttgta aaacgacggc cagtgaattc gagctcggta cccgtaacaa aagcttatcg   1740
agcggccgca agaggcagta ttttactgac acgaatacac ggtttattga gggtatgcga   1800
catgaatggg ttaaagggt cggtaaggt atcggttcc gataggtctg gtggttctgt    1860
attccccggt gctgtccggg gcaaagtcca caaactgggg gtcgttgtag ttgtttgtgt   1920
actgatctc tgggttccac ctcttggagt tttccttctt gagctcccac tccatctcca    1980
cggtgacctg cccggtgctg tactgggtga tgaagctgct gacgggcacg tccgagaagc   2040
tggtgatatt tccgggcaca ggcgtgttct tgatgagcat catgggcggt gggtgtttga   2100
gtccgaatcc gcccatggcc ggagaggggt gaaagtgcgc ccccgtctct gggatcttgg   2160
cccagatggg tccttggagg tacacgtccc tctccatcca cacgctgccg ggcacgattt   2220
cctggaggtt gtacgtgccg gtcgcggggg cagtggtgga gctctggttg ttggtggcca   2280
tctgcccgcc gacgttgtac gccacgcggt tcaccggctg cgtctcgctc tcgctggtga   2340
tgagcatgtt gccctcgagg tacgtggcgg tggtgcccgg gttcgccggc tggctgttga   2400
agatcatagt gttctccagg gcataggtgt tgctgccctg gaggttgttg gtcatgccgt   2460
tcggctgcgg gggcacctgg taactcgcgc cctcgagctc catcctattg gtcgtggcga   2520
aggcgctgac actggcgcgg ttgacccccg agcccaggtt ccagccctgg gttcggccca   2580
tgggccccgg gaaccagttt ttgtaggtgt tggcgtatct cccggccagg ttcttgttga   2640
actggactcc gccagtgtta tttgtgctca cgaagcggta caagtactgg tccaccagcg   2700
ggttggccag cttgaacagg ttctgactgg gagcgaagct ggagtggaag ggcacctcct   2760
caaagttgta ggtaaactca agttgttgc ccgttctcag catcttgctg ggaaagtact    2820
ctaggcagaa gaagctgctc ctctcggtgg gattttctgt gttgtcgcgg ttcagcgtcg   2880
cgtaaccgta ctgcggcagc gtaaagacct gcggagggaa ggccggcagg catccctcgg   2940
tcccgttgcc gacgacgtag ggcagctggt agtcgtcgtc cgtaaacact tggacggtgg   3000
aggtgaggtt gttggcgatg gtggtggtgg agtcctgcac cgtgacctct ttgacttgaa   3060
tgttgaagat tttgactctg agggaccggg gtctgaagcc ccagtagttg ttgatgagtc   3120
tttgccagtc tcgggggctc cagtggctgt ggaagcggtt aaagtcaaag taccccagg    3180
gggtgctgta tccaaagtag gcgttggcgt tgcttccgtc gacggagccg cttttgatct   3240
ctcggtactg gtggttgttg tagctgggca gcacccaggt tcgggtggac ttggtgacga   3300
ctctgtcccc catccacgtg gaatcgcaat gccaatctcc cgaggcattg cccactccat   3360
cggcaccttg gttattgtcg cccaatgggc cgccacctcc cgcagacatt gtatcagctc   3420
ccaaacttga ggctggttgg gctgggattt gcagctgctg ggatccgctg gtccagctt    3480
cggcgtctga cgaggtggaa ggcttggagt cctcttcggt ccgagccttc tttctttttg   3540
gaaagtggtc gtctatccgc tttccggtag gggccgtctt agcaccctct tcaaccaggc   3600
caaaaggttc gagaacccctt ttcttggcct gaaagactgc ctttccgagg tttccccga    3660
aggatgtgtc gtcggcgagc ttctcctgaa actcggcgtc cgcgtggttg tacttgaggt   3720
aggggttgtc tcccgcctca agctgctcgt tgtacgagat gtcgtgctct cgcgcgacct   3780
cgtctgccct gttgacaggc tctcctcgat cgagaccgtt tccgggtccg agatagttat   3840
aaccaggcag cacaagacca cgggcttgat cttgatgctg ctgattgggt tttggtttcg   3900
gtgggcccgc ttcaaggccc aaaaactcgc gaagaccttc accaacttct tccaaccaat   3960
```

-continued

| | |
|---|---|
| ctggagggtg atcaacaaaa gacatgacta ctcgctttat ttactgttct ttattggcat | 4020 |
| cgtcaaaatc cccaaaatct gacaagtttt ccttttccca gggggaatc ccatgacaaa | 4080 |
| tttgacagtg agttacattg tgacagatac atccattttt gccccgattc aaatattcac | 4140 |
| attcatcaca tttgttagaa atgttgtcaa attgagcatg atagtcacat ttgcaatcat | 4200 |
| accttgaatt ccaattgagc ggtcgcagag gagcgggatc aacagtcacg tctgaactgc | 4260 |
| gaggcgtctc gggaacaaat gagagcctgg cccgcttctc cagacttta tagctagtat | 4320 |
| tggtgacgtc acccagtggg cgttttagag atttctccgc cccctttagtt cccgccaatt | 4380 |
| ccctgggaac tttaaactcg tgagtcaccg gcacctgatt gacctttgcc caagcaaaaa | 4440 |
| agtccttgac ttcctgctta gtaatcttgc caaaatctgg cgggagccgc ttagtcagtt | 4500 |
| caaatttgaa catgcggtcc tccagcggct gctggtgttc aaaggtcgtg gaattcccat | 4560 |
| ccaccaccac acacatgttt gtattggaag ttacaatgac aggggtagaa tcaatttgaa | 4620 |
| cagaggattt acatttctga tcgacccgca cctttgagcc ccccaggatg gccttggcgg | 4680 |
| attcaaccac cttgttggtc atcttccct cctcccacca aatgagcatt ttgtccacac | 4740 |
| agtcattaaa gggaaagttt tcattggtcc agttcacgca gccgtaaaaag ggcacagtgt | 4800 |
| gggcgatggc ctccgcgatg ttggtcttgc cggtcgtggc gggtccgtag agccagacgg | 4860 |
| tgttcctctt gttgaaggag cgctgacacc agccgtagag gatggatccc gcgtaggccg | 4920 |
| ggtcgtagcc attcatctca aaaatttgcc agattctgtt ttttgaaatg tcctcgggaa | 4980 |
| cggagctccc cacgaggtag tccaccgcgc ttttgtcag actcataatt ttggtcgcgt | 5040 |
| tgtcgagcgc ggccttgatc tggctccgag agttgccggt ggagttgaag gagaggtagc | 5100 |
| tctcctgatt ttcctggatc c | 5121 |

<210> SEQ ID NO 29
<211> LENGTH: 2175
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 29

| | |
|---|---|
| ttaaaggggt cgggtaaggt atcgggttcc gataggtctg gtggttctgt attccccggt | 60 |
| gctgtccggg gcaaagtcca caaactgggg gtcgttgtag ttgtttgtgt actggatctc | 120 |
| tgggttccac ctcttggagt tttccttctt gagctcccac tccatctcca cggtgacctg | 180 |
| cccgtgctg tactgggtga tgaagctgct gacgggcacg tccgagaagc tggtgatatt | 240 |
| tccgggcaca ggcgtgttct tgatgagcat catgggcggt gggtgtttga gtccgaatcc | 300 |
| gcccatggcc ggagagggt gaaagtgcgc cccgtctct gggatcttgg cccagatggg | 360 |
| tccttggagg tacacgtccc tctccatcca cacgctgccg ggcacgattt cctggaggtt | 420 |
| gtacgtgccg gtcgcggggg cagtggtgga gctctggttg ttggtggcca tctgcccgcc | 480 |
| gacgttgtac gccacgcggt tcaccggctg cgtctcgctc tcgctggtga tgagcatgtt | 540 |
| gccctcgagg tacgtggcgg tggtgccgg gttcgccggc tggctgttga agatcatagt | 600 |
| gttctccagg gcataggtgt tgctgccctg gaggttgttg gtcatgccgt tcggctgcgg | 660 |
| gggcacctgg taactcgcgc cctcgagctc catcctattg gtcgtggcga aggcgctgac | 720 |
| actggcgcgt tgaccccgg agcccaggtt ccagccctgg gttcggccca tgggcccgg | 780 |
| gaaccagttt ttgtaggtgt tggcgtatct cccggccagg ttcttgttga actggactcc | 840 |

```
gccagtgtta tttgtgctca cgaagcggta caagtactgg tccaccagcg ggttggccag      900
cttgaacagg ttctgactgg gagcgaagct ggagtggaag ggcacctcct caaagttgta      960
ggtaaactca agttgttgc ccgttctcag catcttgctg ggaaagtact ctaggcagaa      1020
gaagctgctc ctctcggtgg gattttctgt gttgtcgcgg ttcagcgtcg cgtaaccgta      1080
ctgcggcagc gtaaagacct gcggagggaa ggccggcagg catccctcgg tcccgttgcc      1140
gacgacgtag ggcagctggt agtcgtcgtc cgtaaacact tggacggtgg aggtgaggtt      1200
gttggcgatg gtggtggtgg agtcctgcac cgtgacctct ttgacttgaa tgttgaagat      1260
tttgactctg agggaccggg gtctgaagcc ccagtagttg ttgatgagtc tttgccagtc      1320 tcggggggctc cagtggctgt ggaagcggtt aaagtcaaag taccccccagg gggtgctgta      1380 tccaaagtag gcgttggcgt tgcttccgtc gacggagccg cttttgatct ctcggtactg      1440
gtggttgttg tagctgggca gcacccaggt tcgggtggac ttggtgacga ctctgtcccc      1500
catccacgtg gaatcgcaat gccaatctcc cgaggcattg cccactccat cggcaccttg      1560
gttattgtcg cccaatgggc cgccacctcc cgcagacatt gtatcagctc ccaaacttga      1620
ggctggttgg gctgggattt gcagctgctg ggatccgctg ggtccagctt cggcgtctga      1680
cgaggtggaa ggcttggagt cctcttcggt ccgagccttc tttcttttg gaaagtggtc      1740 gtctatccgc tttccggtag gggccgtctt agcaccctct tcaaccaggc caaaaggttc      1800 gagaacccctt ttcttggcct gaaagactgc cttccgagg tttcccccga aggatgtgtc      1860
gtcggcgagc ttctcctgaa actcggcgtc cgcgtggttg tacttgaggt aggggttgtc      1920
tcccgcctca agctgctcgt tgtacgagat gtcgtgctct cgcgcgacct cgtctgccct      1980
gttgacaggc tctcctcgat cgagaccgtt tccgggtccg agatagttat aaccaggcag      2040
cacaagacca cgggcttgat cttgatgctg ctgattgggt tttggtttcg gtgggcccgc      2100
ttcaaggccc aaaaactcgc gaagaccttc accaacttct tccaaccaat ctggagggtg      2160
atcaacaaaa gacat                                                      2175
```

<210> SEQ ID NO 30
<211> LENGTH: 3
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

```
cat                                                                     3
```

<210> SEQ ID NO 31
<211> LENGTH: 6980
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
ctagagtcga cctgcaggca tgcaagcttg gcgtaatcat ggtcatagct gtttcctgtg       60
tgaaattgtt atccgctcac aattccacac aacatacgag ccggaagcat aaagtgtaaa      120
gcctggggtg cctaatgagt gagctaactc acattaattg cgttgcgctc actgcccgct      180
ttccagtcgg gaaacctgtc gtgccagctg cattaatgaa tcggccaacg cgcggggaga      240
ggcggtttgc gtattgggcg ctcttccgct tcctcgctca ctgactcgct gcgctcggtc      300
```

```
gttcggctgc ggcgagcggt atcagctcac tcaaaggcgg taatacggtt atccacagaa   360
tcagggata  acgcaggaaa gaacatgtga gcaaaaggcc agcaaaaggc caggaaccgt   420
aaaaaggccg cgttgctggc gttttccat  aggctccgcc cccctgacga gcatcacaaa   480
aatcgacgct caagtcagag gtggcgaaac ccgacaggac tataaagata ccaggcgttt   540
cccctggaa  gctccctcgt gcgctctcct gttccgaccc tgccgcttac cggatacctg   600
tccgccttc  tccttcggg  aagcgtggcg ctttctcata gctcacgctg taggtatctc   660
agttcggtgt aggtcgttcg ctccaagctg ggctgtgtgc acgaaccccc cgttcagccc   720
gaccgctgcg ccttatccgg taactatcgt cttgagtcca acccggtaag acacgactta   780
tcgccactgg cagcagccac tggtaacagg attagcagag cgaggtatgt aggcggtgct   840
acagagttct tgaagtggtg gcctaactac ggctacacta aaggacagt  atttggtatc   900
tgcgctctgc tgaagccagt taccttcgga aaaagagttg gtagctcttg atccggcaaa   960
caaaccaccg ctggtagcgg tggtttttt  gtttgcaagc agcagattac gcgcagaaaa  1020
aaaggatctc aagaagatcc tttgatcttt tctacggggt ctgacgctca gtggaacgaa  1080
aactcacgtt aagggatttt ggtcatgtga ttatcaaaaa ggatcttcac ctagatcctt  1140
ttaaattaaa aatgaagttt taaatcaatc taaagtatat atgagtaaac ttggtctgac  1200
agttagaaaa actcatcgag catcaaatga aactgcaatt tattcatatc aggattatca  1260
ataccatatt tttgaaaaag ccgtttctgt aatgaaggag aaaactcacc gaggcagttc  1320
cataggatgg caagatcctg gtatcggtct gcgattccga ctcgtccaac atcaatacaa  1380
cctattaatt tcccctcgtc aaaaataagg ttatcaagtg agaaatcacc atgagtgacg  1440
actgaatccg gtgagaatgg caaaagttta tgcatttctt ccagacttg  ttcaacaggc  1500
cagccattac gctcgtcatc aaaatcactc gcatcaacca accgttatt  cattcgtgat  1560
tgcgcctgag cgagacgaaa tacgcgatcc ctgttaaaag acaattaca  aacaggaatc  1620
gaatgcaacc ggcgcaggaa cactgccagc gcatcaacaa tattttcacc tgaatcagga  1680
tattcttcta atacctggaa tgctgttttc ccagggatcg cagtggtgag taaccatgca  1740
tcatcaggag tacggataaa atgcttgatg gtcggaagag gcataaattc cgtcagccag  1800
tttagtctga ccatctcatc tgtaacatca ttggcaacgc taccttgcc  atgtttcaga  1860
aacaactctg gcgcatcggg cttcccatac aatcgataga ttgtcgcacc tgattgcccg  1920
acattatcgc gagcccattt atacccatat aaatcagcat ccatgttgga atttaatcgc  1980
ggcctagagc aagacgtttc ccgttgaata tggctcatac tcttcctttt tcaatattat  2040
tgaagcattt atcagggtta ttgtctcatg agcggataca tatttgaatg tatttagaaa  2100
aataaacaaa taggggttcc gcgcacattt ccccgaaaag tgccacctga cgtctaagaa  2160
accattatta acatgacatt aacctataaa aataggcgta tcacgaggcc ctttcgtctc  2220
gcgcgtttcg gtgatgacgg tgaaaacctc tgacacatgc agctcccgga cggtcaca    2280
gcttgtctgt aagcggatgc cgggagcaga caagcccgtc agggcgcgtc agcgggtgtt  2340
ggcgggtgtc ggggctggct taactatgcg gcatcagagc agattgtact gagagtgcac  2400
catatgcggt gtgaaatacc gcacagatgc gtaaggagaa ataccgcat  caggcgccat  2460
tcgccattca ggctgcgcaa ctgttgggaa gggcgatcgg tgcgggcctc ttcgctatta  2520
cgccagctgg cgaaaggggg atgtgctgca aggcgattaa gttgggtaac gccagggttt  2580
tcccagtcac gacgttgtaa aacgacggcc agtgaattcg agctcggtac ccgtagccat  2640
```

```
ggaaactaga taagaaagaa atacgcagag accaaagttc aactgaaacg aattaaacgg   2700
tttattgatt aacaagcaat tacagattac gagtcaggta tctggtgcca atggggcgag   2760
gctctgaata cacgccatta gtgtccacag taaagtccac attaacagac ttgttgtagt   2820
tggaagtgta ctgaatttcg ggattccagc gtttgctgtt ttccttctgc agctcccact   2880
cgatctccac gctgacctgt cccgtggagt actgtgtgat gaaggaagca aactttgccg   2940
cactgaaggt ggtcgaagga ttcgcaggta ccggggtgtt cttgatgaga atctgtggag   3000
gagggtgttt aagtccgaat ccacccatga ggggagaggg gtgaaaatgt ccgtccgtgt   3060
gtggaatctt tgcccagatg ggcccctgaa ggtacacatc tctgtcctgc cagaccatgc   3120
ctggaagaac gccttgtgtg ttgacatctg cggtagctgc ttgtctgttg cctctctgga   3180
ggttggtaga tacagaacca tactgctccg tagccacggg attggttgtc ctgatttcct   3240
cttcgtctgt aatcatgacc ttttcaatgt ccacatttgt tttctctgag ccttgcttcc   3300
caaagatgag aaccccgctc tgaggaaaaa acttttcttc atcgtccttg tggcttgcca   3360
tggccgggcc cggattcacc agagagtctc tgccattgag gtggtacttg gtagctccag   3420
tccacgagta ttcactgttg ttgttatccg cagatgtctt tgatactcgc tgctggcggt   3480
aacagggtcc aggaagccag ttcctagact ggtcccgaat gtcactcgct ccggcctgag   3540
aaaactgaag ccttgactgc gtggtggttc cacttggagt gtttgttctg ctcaagtaat   3600
acaggtactg gtcgatgaga ggattcatga acggtccag actctggctg tgagcgtagc   3660
tgctgtggaa aggaacgtcc tcaaaagtgt agctgaaggt aaagttgttt ccggtacgca   3720
gcatctgaga aggaaagtac tccaggcagt aaaatgaaga gcgtcctact gcctgactcc   3780
cgttgttcag ggtgaggtat ccatactgtg gcaccatgaa gacgtctgct gggaacggcg   3840
ggaggcatcc ttgatgcgcc gagccgagga cgtacgggga ctggtactcc gagtcagtaa   3900
acacctgaac cgtgctggta aggttattgg caatcgtcgt cgtaccgtca ttctgcgtga   3960
cctctttgac ttgaatgtta aagagcttga agttgagtct cttgggtcgg aatccccagt   4020
tgttgttgat gagtctttgc cagtcacgtg gtgaaaagtg gcagtggaat ctgttgaagt   4080
caaaataccc ccaaggggtg ctgtagccaa agtagtgatt gtcgttcgag gctcctgatt   4140
ggctggaaat ttgtttgtag aggtggttgt tgtaggtggg cagggcccag gttcgggtgc   4200
tggtggtgat gactctgtcg cccatccatg tggaatcgca atgccaattt cccgaggaat   4260
tacccactcc gtcggcgccc tcgttattgt ctgccattgg tgcgccactg cctgtagcca   4320
tcgtattagt tcccagacca gagggggctg ctggtggctg tccgagaggc tgggggtcag   4380
gtactgagtc tgcgtctcca gtctgaccaa aattcaatct ttttcttgca ggctgctggc   4440
ccgcctttcc ggttcccgag gaggagtctg gctccacagg agagtgctct accggcctct   4500 ttttttcccgg agccgtctta acaggttcct caaccaggcc cagaggttca agaaccctct   4560
ttttcgcctg gaagactgct cgtccgaggt tgccccaaaa agacgtatct tctttaaggc   4620
gctcctgaaa ctccgcgtcg gcgtggttgt acttgaggta cggggttgtct ccgctgtcga   4680 gctgccggtc gtaggctttg tcgtgctcga gggccgcggc gtctgcctcg ttgaccggct   4740
ctcccttgtc gagtccgttg aagggtccga ggtacttgta cccaggaagc acaagacccc   4800
tgctgtcgtc cttatgccgc tctgcgggct ttggtggtgg tgggccaggt ttgagcttcc   4860
accactgtct tattccttca gagagagtgt cctcgagcca atctggaaga taaccatcgg   4920
cagccatacc tgatttaaat catttattgt tcaaagatgc agtcatccaa atccacattg   4980
accagatcgc aggcagtgca agcgtctggc acctttccca tgatatgatg aatgtagcac   5040
```

```
agtttctgat acgccttttt gacgacagaa acgggttgag attctgacac gggaaagcac      5100
tctaaacagt ctttctgtcc gtgagtgaag cagatatttg aattctgatt cattctctcg      5160
cattgtctgc agggaaacag catcagattc atgcccacgt gacgagaaca tttgttttgg      5220
tacctgtctg cgtagttgat cgaagcttcc gcgtctgacg tcgatggctg cgcaactgac      5280
tcgcgcaccc gtttgggctc acttatatct gcgtcactgg gggcgggtct tttcttggct      5340
ccaccctttt tgacgtagaa ttcatgctcc acctcaacca cgtgatcctt tgcccaccgg      5400
aaaaagtctt tgacttcctg cttggtgacc ttcccaaagt catgatccag acggcgggtg      5460
agttcaaatt tgaacatccg gtcttgcaac ggctgctggt gttcgaaggt cgttgagttc      5520
ccgtcaatca cggcgcacat gttggtgttg aggtgacga tcacgggagt cgggtctatc      5580
tgggccgagg acttgcattt ctggtccacg cgcaccttgc ttcctccgag aatggctttg      5640
gccgactcca cgaccttggc ggtcatcttc ccctcctccc accagatcac catcttgtcg      5700
acacagtcgt tgaagggaaa gttctcattg gtccagttta cgcacccgta aagggcaca      5760 gtgtgggcta tggcctccgc gatgttggtc ttcccggtag ttgcaggccc aaacagccag      5820
atggtgttcc tcttgccgaa cttttttcgtg gcccatccca gaaagacgga agccgcatat      5880
tggggatcgt acccgtttag ttccaaaatt ttataaatcc gattgctgga aatgtcctcc      5940
acgggctgct ggcccaccag gtagtcgggg gcggttttag tcaggctcat aatctttccc      6000
gcattgtcca aggcagcctt gatttgggac cgcgagttgg aggccgcatt gaaggagatg      6060
tatgaggcct ggtcctcctg gatccactgc ttctccgagg taatccccttt gtccacgagc      6120 cacccgacca gctccatgta cctggctgaa gtttttgatc tgatcaccgg cgcatcagaa      6180
ttgggattct gattctcttt gttctgctcc tgcgtctgcg acacgtgcgt cagatgctgc      6240
gccaccaacc gtttacgctc cgtgagattc aaacaggcgc ttaaatactg ttccatatta      6300
gtccacgccc actggagctc aggctgggtt ttggggagca agtaattggg gatgtagcac      6360
tcatccacca ccttgttccc gcctccggcg ccatttctgg tctttgtgac cgcgaaccag      6420
tttggcaaag tcggctcgat cccgcggtaa attctctgaa tcagttttttc gcgaatctga      6480 ctcaggaaac gtcccaaaac catggatttc accccggtgg tttccacgag cacgtgcatg      6540
tggaagtagc tctctccctt ctcaaattgc acaaagaaaa gggcctccgg ggccttactc      6600
acacggcgcc attccgtcag aaagtcgcgc tgcagcttct cggccacggt cagggggtgcc      6660 tgctcaatca gattcagatc catgtcagaa tctggcggca actcccattc cttctcggcc      6720
acccagttca caaagctgtc agaaatgccg ggcagatgct cgtcaaggtc gctgggacc      6780 ttaatcacaa tctcgtaaaa ccccggcatg gcggctgcgc gttcaaacct cccgcttcaa      6840
aatggagacc ctgcgtgctc actcgggctt aaatacccag cgtgaccaca tggtgtcgca      6900
aaatgtcgca aaacactcac gtgacctcta atacaggacc tccctaaccc tatgacgtaa      6960
ttcacgtcac gactccacca                                                  6980
```

<210> SEQ ID NO 32
<211> LENGTH: 2208
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
ttacagatta cgagtcaggt atctggtgcc aatggggcga ggctctgaat acacgccatt       60
```

```
agtgtccaca gtaaagtcca cattaacaga cttgttgtag ttggaagtgt actgaatttc    120
gggattccag cgtttgctgt tttccttctg cagctcccac tcgatctcca cgctgacctg    180
tcccgtggag tactgtgtga tgaaggaagc aaactttgcc gcactgaagg tggtcgaagg    240
attcgcaggt accgggtgt tcttgatgag aatctgtgga ggagggtgtt taagtccgaa    300
tccacccatg aggggagagg ggtgaaaatg tccgtccgtg tgtggaatct tgcccagat    360 gggcccctga aggtacacat ctctgtcctg ccagaccatg cctggaagaa cgccttgtgt    420
gttgacatct gcggtagctg cttgtctgtt gcctctctgg aggttggtag atacagaacc    480
atactgctcc gtagccacgg gattggttgt cctgatttcc tcttcgtctg taatcatgac    540
cttttcaatg tccacatttg ttttctctga gccttgcttc ccaaagatga aacccccgct    600
ctgaggaaaa aacttttctt catcgtcctt gtggcttgcc atggccgggc ccggattcac    660
cagagagtct ctgccattga ggtggtactt ggtagctcca gtccacgagt attcactgtt    720
gttgttatcc gcagatgtct ttgatactcg ctgctggcgg taacagggtc caggaagcca    780
gttcctagac tggtcccgaa tgtcactcgc tccggcctga gaaaactgaa gccttgactg    840
cgtggtggtt ccacttggag tgtttgttct gctcaagtaa tacaggtact ggtcgatgag    900
aggattcatg agacggtcca gactctggct gtgagcgtag ctgctgtgga aaggaacgtc    960
ctcaaaagtg tagctgaagg taaagttgtt tccggtacgc agcatctgag aaggaaagta   1020
ctccaggcag taaaatgaag agcgtcctac tgcctgactc ccgttgttca gggtgaggta   1080
tccatactgt ggcaccatga agacgtctgc tgggaacggc gggaggcatc cttgatgcgc   1140
cgagccgagg acgtacggga gctggtactc cgagtcagta aacacctgaa ccgtgctggt   1200
aaggttattg gcaatcgtcg tcgtaccgtc attctgcgtg acctctttga cttgaatgtt   1260
aaagagcttg aagttgagtc tcttgggtcg gaatccccag ttgttgttga tgagtctttg   1320
ccagtcacgt ggtgaaaagt ggcagtggaa tctgttgaag tcaaaatacc cccaaggggt   1380
gctgtagcca aagtagtgat tgtcgttcga ggctcctgat tggctggaaa tttgtttgta   1440
gaggtggttg ttgtaggtgg gcagggccca ggttcgggtg ctggtggtga tgactctgtc   1500
gcccatccat gtggaatcgc aatgccaatt tcccgaggaa ttacccactc cgtcggcgcc   1560
ctcgttattg tctgccattg gtgcgccact gcctgtagcc atcgtattag ttcccagacc   1620 agaggggct gctggtggct gtccgagagg ctggggtca ggtactgagt ctgcgtctcc   1680
agtctgacca aaattcaatc ttttcttgc aggctgctgg cccgccttc cggttcccga   1740 ggaggagtct ggctccacag gagagtgctc taccggcctc tttttccccg gagccgtctt   1800
aacaggttcc tcaaccaggc ccagaggttc aagaaccctc tttttcgcct ggaagactgc   1860
tcgtccgagg ttgcccccaa aagacgtatc ttctttaagg cgctcctgaa actccgcgtc   1920
ggcgtggttg tacttgaggt acgggttgtc tccgctgtcg agctgccggt cgtaggcttt   1980
gtcgtgctcg agggccgcgg cgtctgcctc gttgaccggc tctcccttgt cgagtccgtt   2040
gaagggtccg aggtacttgt acccaggaag cacaagaccc ctgctgtcgt ccttatgccg   2100
ctctgcgggc tttggtggtg gtgggccagg tttgagcttc caccactgtc ttattccttc   2160
agagagagtg tcctcgagcc aatctggaag ataaccatcg gcagccat              2208
```

<210> SEQ ID NO 33
<211> LENGTH: 6893
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 33

```
ctagagtcga cctgcaggca tgcaagcttg gcgtaatcat ggtcatagct gtttcctgtg      60
tgaaattgtt atccgctcac aattccacac aacatacgag ccggaagcat aaagtgtaaa     120
gcctggggtg cctaatgagt gagctaactc acattaattg cgttgcgctc actgcccgct     180
ttccagtcgg gaaacctgtc gtgccagctg cattaatgaa tcggccaacg cgcggggaga     240
ggcggtttgc gtattgggcg ctcttccgct tcctcgctca ctgactcgct gcgctcggtc     300
gttcggctgc ggcgagcggt atcagctcac tcaaaggcgg taatacggtt atccacagaa     360
tcagggGATA acgcaggaaa gaacatgtga gcaaaaggcc agcaaaaggc caggaaccgt     420
aaaaaggccg cgttgctggc gttttttcCAT aggctccgcc cccctgacga gcatcacaaa     480
aatcgacgct caagtcagag gtggcgaaac ccgacaggac tataaagata ccaggcgttt     540
ccccctggaa gctccctcgt gcgctctcct gttccgaccc tgccgcttac cggatacctg     600
tccgcctttc tcccttcggg aagcgtggcg ctttctcata gctcacgctg taggtatctc     660
agttcggtgt aggtcgttcg ctccaagctg ggctgtgtgc acgaaccccc cgttcagccc     720
gaccgctgcg ccttatccgg taactatcgt cttgagtcca acccggtaag acacgactta     780
tcgccactgg cagcagccac tggtaacagg attagcagag cgaggtatgt aggcggtgct     840
acagagttct tgaagtggtg gcctaactac ggctacacta aggacagt atttggtatc      900
tgcgctctgc tgaagccagt taccttcgga aaaagagttg gtagctcttg atccggcaaa     960
caaaccaccg ctggtagcgg tggtttttt gtttgcaagc agcagattac gcgcagaaaa    1020
aaaggatctc aagaagatcc tttgatcttt tctacggggt ctgacgctca gtggaacgaa    1080
aactcacgtt aagggatttt ggtcatgtga ttatcaaaaa ggatcttcac ctagatcctt    1140
ttaaattaaa aatgaagttt taaatcaatc taaagtatat atgagtaaac ttggtctgac    1200
agttagaaaa actcatcgag catcaaatga aactgcaatt tattcatatc aggattatca    1260
ataccatatt tttgaaaaag ccgtttctgt aatgaaggag aaaactcacc gaggcagttc    1320
cataggatgg caagatcctg gtatcggtct gcgattccga ctcgtccaac atcaatacaa    1380
cctattaatt tcccctcgtc aaaaataagg ttatcaagtg agaaatcacc atgagtgacg    1440
actgaatccg gtgagaatgg caaaagttta tgcatttctt tccagacttg ttcaacaggc    1500
cagccattac gctcgtcatc aaaatcactc gcatcaacca accgttatt cattcgtgat    1560
tgcgcctgag cgagacgaaa tacgcgatcg ctgttaaaag acaattaca acaggaatc    1620
gaatgcaacc ggcgcaggaa cactgccagc gcatcaacaa tattttcacc tgaatcagga    1680
tattcttcta atacctggaa tgctgttttc ccagggatcg cagtggtgag taaccatgca    1740
tcatcaggag tacggataaa atgcttgatg gtcggaagag gcataaattc cgtcagccag    1800
tttagtctga ccatctcatc tgtaacatca ttggcaacgc tacctttgcc atgtttcaga    1860
aacaactctg gcgcatcggg cttcccatac aatcgataga ttgtcgcacc tgattgcccg    1920
acattatcgc gagcccattt atacccatat aaatcagcat ccatgttgga atttaatcgc    1980
ggcctagagc aagacgtttc ccgttgaata tggctcatac tcttcctttt tcaatattat    2040
tgaagcattt atcagggtta ttgtctcatg agcggataca tatttgaatg tatttagaaa    2100
aataaacaaa taggggttcc gcgcacattt ccccgaaaag tgccacctga cgtctaagaa    2160
accattatta acatgacatt aacctataaa aataggcgta tcacgaggcc ctttcgtctc    2220
```

```
gcgcgtttcg gtgatgacgg tgaaaacctc tgacacatgc agctcccgga gacggtcaca    2280
gcttgtctgt aagcggatgc cgggagcaga caagcccgtc agggcgcgtc agcgggtgtt    2340
ggcgggtgtc ggggctggct taactatgcg gcatcagagc agattgtact gagagtgcac    2400
catatgcggt gtgaaatacc gcacagatgc gtaaggagaa ataccgcat caggcgccat     2460 tcgccattca ggctgcgcaa ctgttgggaa gggcgatcgg tgcgggcctc ttcgctatta    2520
cgccagctgg cgaaaggggg atgtgctgca aggcgattaa gttgggtaac gccagggttt    2580
tcccagtcac gacgttgtaa aacgacggcc agtgaattcg agctcggtac ccgtagccat    2640
ggaaactaga taagaaagaa atacgcagag accaaagttc aactgaaacg aattaaacgg    2700
tttattgatt aacaagcaat tacagattac gagtcaggta tctggtgcca atggggcgag    2760
gctctgaata cacgccatta gtgtccacag taaagtccac attaacagac ttgttgtagt    2820
tggaagtgta ctgaatttcg ggattccagc gtttgctgtt ttccttctgc agctcccact    2880
cgatctccac gctgacctgt cccgtggagt actgtgtgat gaaggaagca aacttttgccg   2940 cactgaaggt ggtcgaagga ttcgcaggta ccggggtgtt cttgatgaga atctgtggag    3000
gagggtgttt aagtccgaat ccacccatga ggggagaggg gtgaaaatgt ccgtccgtgt    3060
gtggaatctt tgcccagatg ggcccctgaa ggtacacatc tctgtcctgc cagaccatgc    3120
ctggaagaac gccttgtgtg ttgacatctg cggtagctgc ttgtctgttg cctctctgga    3180
ggttggtaga tacagaacca tactgctccg tagccacggg attggttgtc ctgatttcct    3240
cttcgtctgt aatcatgacc ttttcaatgt ccacatttgt tttctctgag ccttgcttcc    3300
caaagatgag aaccccgctc tgaggaaaaa acttttcttc atcgtccttg tggcttgcca    3360
tggccgggcc cggattcacc agagagtctc tgccattgag gtggtacttg gtagctccag    3420
tccacgagta ttcactgttg ttgttatccg cagatgtctt tgatactcgc tgctggcggt    3480
aacagggtcc aggaagccag ttcctagact ggtcccgaat gtcactcgct ccggcctgag    3540
aaaactgaag ccttgactgc gtggtggttc cacttggagt gtttgttctg ctcaagtaat    3600
acaggtactg gtcgatgaga ggattcatga cacggtccag actctggctg tgagcgtagc    3660
tgctgtggaa aggaacgtcc tcaaaagtgt agctgaaggt aaagttgttt ccggtacgca    3720
gcatctgaga aggaaagtac tccaggcagt aaaatgaaga gcgtcctact gcctgactcc    3780
cgttgttcag ggtgaggtat ccatactgtg gcaccatgaa gacgtctgct gggaacggcg    3840
ggaggcatcc ttgatgcgcc gagccgagga cgtacgggag ctggtactcc gagtcagtaa    3900
acacctgaac cgtgctggta aggttattgg caatcgtcgt cgtaccgtca ttctgcgtga    3960
cctctttgac ttgaatgtta aagagcttga agttgagtct cttgggtcgg aatccccagt    4020
tgttgttgat gagtctttgc cagtcacgtg gtgaaaagtg gcagtggaat ctgttgaagt    4080
caaaataccc ccaaggggtg ctgtagccaa agtagtgatt gtcgttcgag gctcctgatt    4140
ggctggaaat ttgtttgtag aggtggttgt tgtaggtggg cagggcccag gttcgggtgc    4200
tggtggtgat gactctgtcg cccatccatg tggaatcgca atgccaattt cccgaggaat    4260
tacccactcc gtcggcgccc tcgttattgt ctgccattgg tgcgccactg cctgtagcca    4320
tcgtattagt tccagacca gaggggggctg ctggtggctg tccagaggc tggggggtcag    4380 gtactgagtc tgcgtctcca gtctgaccaa aattcaatct tttttcttgca ggctgctggc    4440 ccgcctttcc ggttcccgag gaggagtctg gctccacagg agagtgctct accggcctct    4500
tttttcccgg agccgtctta acaggttcct caaccaggcc cagagggttca agaaccctct    4560 ttttcgcctg gaagactgct cgtccgaggt tgccccaaa agacgtatct tctttaaggc    4620
```

-continued

```
gctcctgaaa ctccgcgtcg gcgtggttgt acttgaggta cgggttgtct ccgctgtcga    4680
gctgccggtc gtaggctttg tcgtgctcga gggccgcggc gtctgcctcg ttgaccggct    4740
ctcccttgtc gagtccgttg aagggtccga ggtacttgta cccaggaagc acaagacccc    4800
tgctgtcgtc cttatgccgc tctgcgggct ttggtggtgg tgggccaggt ttgagcttcc    4860
accactgtct tattccttca gagagagtgt cctcgagcca atctggaaga taaccatcgg    4920
cagccatacc tgatttaaat catttattgt tcaaagatgc agtcatccaa atccacattg    4980
accagatcgc aggcagtgca agcgtctggc acctttccca tgatatgatg aatgtagcac    5040
agtttctgat acgccttttt gacgacagaa acggggttgag attctgacac gggaaagcac    5100
tctaaacagt ctttctgtcc gtgagtgaag cagatatttg aattctgatt cattctctcg    5160
cattgtctgc agggaaacag catcagattc atgcccacgt gacgagaaca tttgttttgg    5220
tacctgtctg cgtagttgat cgaagcttcc gcgtctgacg tcgatggctg cgcaactgac    5280
tcgcgcaccc gtttgggctc acttatatct gcgtcactgg gggcgggtct tttcttggct    5340 ccacccttttt tgacgtagaa ttcatgctcc acctcaacca cgtgatcctt tgcccaccgg    5400
aaaaagtctt tgacttcctg cttggtgacc ttcccaaagt catgatccag acggcgggtg    5460
agttcaaatt tgaacatccg gtcttgcaac ggctgctggt gttcgaaggt cgttgagttc    5520
ccgtcaatca cggcgcacat gttggtgttg gaggtgacga tcacgggagt cgggtctatc    5580
tgggccgagg acttgcattt ctggtccacg cgcaccttgc ttcctccgag aatggctttg    5640
gccgactcca cgaccttggc ggtcatcttc ccctcctccc accagatcac catcttgtcg    5700
acacagtcgt tgaagggaaa gttctcattg gtccagttta cgcacccgta gaagggcaca    5760
gtgtgggcta tggcctccgc gatgttggtc ttcccggtag ttgcaggccc aaacagccag    5820
atggtgttcc tcttgccgaa cttttttcgtg gcccatccca gaaagacgga agccgcatat    5880 tgggatcgt accgtttag ttccaaaatt ttataaatcc gattgctgga atgtcctcc    5940 acgggctgct ggcccaccag gtagtcgggg gcggttttag tcaggctcat aatctttccc    6000
gcattgtcca aggcagcctt gatttgggac cgcgagttgg aggccgcatt gaaggagatg    6060
tatgaggcct ggtcctcctg gatccactgc ttctccgagg taatcccctt gtccacgagc    6120
cacccgacca gctccatgta cctggctgaa gttttttgatc tgatcaccgg cgcatcagaa    6180
ttgggattct gattctcttt gttctgctcc tgcgtctgcg acacgtgcgt cagatgctgc    6240
gccaccaacc gtttacgctc cgtgagattc aaacaggcgc ttaaatactg ttccatatta    6300
gtccacgccc actggagctc aggctgggtt ttggggagca agtaattggg gatgtagcac    6360
tcatccacca ccttgttccc gcctccggcg ccatttctgg tctttgtgac cgcgaaccag    6420
tttggcaaag tcggctcgat cccgcggtaa attctctgaa tcagttttttc gcgaatctga    6480 ctcaggaaac gtcccaaaac catggatttc accccggtgg tttccacgag cacgtgcatg    6540
tggaagtagc tctctccctt ctcaaattgc acaaagaaaa gggcctccgg ggccttactc    6600
acacggcgcc attccgtcag aaagtcgcgc tgcagcttct cggccacggt cagggtgcc    6660 tgctcaatca gattcagatc catgtcagaa tctggcggca actcccattc cttctcggcc    6720
acccagttca caaagctgtc agaaatgccg ggcagatgc cgtcaaggtc gctgggacc    6780 ttaatcacaa tctcgtaaaa ccccggcatg gcggctgcgc agatcagaag ttcctatact    6840
ttctagagaa taggaacttc ggaataggaa cttctgatct tccggggat cca    6893
```

<210> SEQ ID NO 34

<211> LENGTH: 179
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 34
ccccggcatg gcggctgcgc gttcaaacct cccgcttcaa aatggagacc ctgcgtgctc    60
actcgggctt aaatacccag cgtgaccaca tggtgtcgca aaatgtcgca aaacactcac   120
gtgacctcta atacaggacc tccctaaccc tatgacgtaa ttcacgtcac gactccacc    179

<210> SEQ ID NO 35
<211> LENGTH: 6989
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 35
ctagagtcga cctgcaggca tgcaagcttg gcgtaatcat ggtcatagct gtttcctgtg    60
tgaaattgtt atccgctcac aattccacac aacatacgag ccggaagcat aaagtgtaaa   120
gcctggggtg cctaatgagt gagctaactc acattaattg cgttgcgctc actgcccgct   180
ttccagtcgg gaaacctgtc gtgccagctg cattaatgaa tcggccaacg cgcgggaga    240 ggcggtttgc gtattgggcg ctcttccgct tcctcgctca ctgactcgct gcgctcggtc   300
gttcggctgc ggcgagcggt atcagctcac tcaaaggcgg taatacggtt atccacagaa   360 tcagggata acgcaggaaa gaacatgtga gcaaaaggcc agcaaaaggc caggaaccgt    420
aaaaaggccg cgttgctggc gtttttccat aggctccgcc cccctgacga gcatcacaaa   480
aatcgacgct caagtcagag gtggcgaaac ccgacaggac tataaagata ccaggcgttt   540 cccctggaa gctccctcgt gcgctctcct gttccgaccc tgccgcttac cggatacctg    600 tccgccttc tcccttcggg aagcgtggcg ctttctcata gctcacgctg taggtatctc    660
agttcggtgt aggtcgttcg ctccaagctg ggctgtgtgc acgaaccccc cgttcagccc   720
gaccgctgcg ccttatccgg taactatcgt cttgagtcca acccggtaag acacgactta   780
tcgccactgg cagcagccac tggtaacagg attagcagag cgaggtatgt aggcggtgct   840
acagagttct tgaagtggtg gcctaactac ggctacacta aaggacagt atttggtatc    900 tgcgctctgc tgaagccagt taccttcgga aaaagagttg gtagctcttg atccggcaaa   960
caaaccaccg ctggtagcgg tggtttttt gtttgcaagc agcagattac gcgcagaaaa  1020
aaaggatctc aagaagatcc tttgatcttt tctacggggt ctgacgctca gtggaacgaa   1080
aactcacgtt aagggatttt ggtcatgtga ttatcaaaaa ggatcttcac ctagatcctt   1140
ttaaattaaa aatgaagttt taatcaatc taaagtatat atgagtaaac ttggtctgac   1200
agttagaaaa actcatcgag catcaaatga aactgcaatt tattcatatc aggattatca   1260
ataccatatt tttgaaaaag ccgtttctgt aatgaaggag aaaactcacc gaggcagttc   1320
cataggatgg caagatcctg gtatcggtct gcgattccga ctcgtccaac atcaatacaa   1380
cctattaatt tcccctcgtc aaaaataagg ttatcaagtg agaaatcacc atgagtgacg   1440
actgaatccg gtgagaatgg caaaagttta tgcatttctt tccagacttg ttcaacaggc   1500
cagccattac gctcgtcatc aaaatcactc gcatcaacca aaccgttatt cattcgtgat   1560
tgcgcctgag cgagacgaaa tacgcgatcg ctgttaaaag gacaattaca aacaggaatc   1620

```
gaatgcaacc ggcgcaggaa cactgccagc gcatcaacaa tattttcacc tgaatcagga    1680
tattcttcta atacctggaa tgctgttttc ccagggatcg cagtggtgag taaccatgca    1740
tcatcaggag tacgcataaa atgcttgatg gtcggaagag gcataaattc cgtcagccag    1800
tttagtctga ccatctcatc tgtaacatca ttggcaacgc tacctttgcc atgtttcaga    1860
aacaactctg gcgcatcggg cttcccatac aatcgataga ttgtcgcacc tgattgcccg    1920
acattatcgc gagcccattt atacccatat aaatcagcat ccatgttgga atttaatcgc    1980
ggcctagagc aagacgtttc ccgttgaata tggctcatac tcttcctttt tcaatattat    2040
tgaagcattt atcagggtta ttgtctcatg agcggataca tatttgaatg tatttagaaa    2100
aataaacaaa tagggggttcc gcgcacattt ccccgaaaag tgccacctga cgtctaagaa    2160
accattatta acatgacatt aacctataaa aataggcgta tcacgaggcc ctttcgtctc    2220
gcgcgtttcg gtgatgacgg tgaaaacctc tgacacatgc agctcccgga gacggtcaca    2280
gcttgtctgt aagcggatgc cgggagcaga caagcccgtc agggcgcgtc agcgggtgtt    2340
ggcgggtgtc ggggctggct taactatgcg gcatcagagc agattgtact gagagtgcac    2400
catatgcggt gtgaaatacc gcacagatgc gtaaggagaa ataccgcat caggcgccat    2460 tcgccattca ggctgcgcaa ctgttgggaa gggcgatcgg tgcgggcctc ttcgctatta    2520
cgccagctgg cgaaaggggg atgtgctgca aggcgattaa gttgggtaac gccagggttt    2580
tcccagtcac gacgttgtaa aacgacggcc agtgaattcg agctcggtac ccgtagccat    2640
ggaaactaga taagaaagaa atacgcagag accaaagttc aactgaaacg aattaaacgg    2700
tttattgatt aacaagcaat tacagattac gggtgaggta acgggtgcca atgggcggg    2760 gttcagagta cacgccttct gtattaacag caaagtccac acttgtagat ttgtagtagt    2820
tggaggtgta ctggatctcg gggttccagc gcttgctgtt ttccttctgc agctcccatt    2880
caatttccac gctgacctgt ccggtgctgt attgcgtgat gaaagagttc agctttgact    2940
ggttgaaggt ggtcggagga tccgcaggta caggcgtgtt cttgatcagg atctgaggcg    3000
gaggatgttt caggccaaag ccgcccatca gcggagacgg gtggaagttg ccgtccgtgt    3060
gaggaatctt ggcccagatg ggaccctgca ggtacacgtc ccggttctgc cagaccatac    3120
cgggtaaggc cccctggctg ttgacagttc caatttgagg agccgtgttt tgctgctgca    3180
agttatctgc cacgataccg tattcctctg tagccacagg gttagtggtt ttgatttctt    3240
cctcgctggt gagcatgaca tcgctgtaat ccgcattgtc tctggcagca ttttgtttgc    3300
caaaaatcag gatcccgtta ctgggaaaaa aacgctcctc gtcgtctttg tgtgttgcca    3360
tagcgatgcc aggattagcc aatgaatttc ttccattcag atggtatttg gtcccagcag    3420
tccaggcaaa gttgctattg ttgttttgcc cggttgtcgt tgagacgcgt tgttggcggt    3480
aacagggtcc tggcagccag ttcttttgcct gattggccat tgtattaggc ccaccttggc    3540
tgaagcccag agtctgcgta tttgccgtgc ctcctgttgt ttgagtccga gacaagtagt    3600
acaggtactg gtcaatcaga ggattcatca gccggtccaa gctctggctg tgggcgtagc    3660
tgctgtggaa aggcacgtcc tcgaaggtgt aagtaaactg gaagttgttg ccggttctca    3720
gcatctgcga aggaaagtat tccaggcagt agaaggagga gcgtcccacg gcctgactac    3780
cgttgttgag tgttaggtag ccgtactggg gaatcatgaa cacgtccgcc gggaacggag    3840
gcaggcagcc ctggtgggca gagccgagaa cgtacgcgag ctggtactcc gagtccgtaa    3900
acacctggat ggtgctggtg aggttattgg cgatggtctt ggtgccttca ttctgcgtga    3960
```

```
cctccttgac ctggatgttg aagagcttga agctgagtct cttgggccgg aatccccagt    4020
tgttgttgat gagtcgctgc cagtcacgtg gtgaaaagtg gcagtggaat ctgttaaagt    4080
caaaataccc ccaggggtg ctgtagccga agtaggtgtt gtcgttggtg gctcctcccg     4140
atgtcccgtt ggagatttgc ttgtagaggt ggttgttgta ggtgggcagg gcccaggttc    4200
gggtgctggt ggtgatgact ctgtcgccca gccatgtgga atcgcaatgc caatttcccg    4260
aggaactacc cactccgtcg gcgccttcgt tattgtctgc cattggtgcg ccaccgcctg    4320
cagccattgt attaggtccc acaccagagg gcgctgctgg aggttctccg agaggttgag    4380
ggtctggaac tgactctgag tcgccagtct gaccaaaatt gagtcttttt ctggcgggct    4440
gttggccttt cttgccgatg cccgtagagg agtctggaga acgctggggt gatggctcta    4500 ccgtctctt ctttccagga gccgtcttag cgccttcctc aaccagaccg agaggttcga     4560
gaacccgctt cttggcctgg aagactgctc gcccgaggtt gccccaaaa gacgtatctt     4620 cttgcagacg ctcctgaaac tcggcgtcgg cgtggttata ccgcaggtac ggattgtcac    4680
ccgcctgcag ctgctggtcg taggccttgt cgtgctcgag ggccgctgcg tccgccgcgt    4740
tgacgggctc cccccttgtcg agtccgttga agggtccgag gtacttgtag ccaggaagca   4800
ccagaccccg gccgtcgtcc tgcttttgct ggttggcttt gggcttcggg gctccaggtt    4860
tcagcgccca ccactcgcga atgccctcag agaggttgtc ctcgagccaa tctggaagat    4920
aaccatcggc agccatacct gatttaaatc atttattgtt caaagatgca gtcatccaaa    4980
tccacattga ccagatcgca ggcagtgcaa gcgtctggca cctttcccat gatatgatga    5040
atgtagcaca gttctgtata cgccttttg acgacagaaa cggggttgaga ttctgacacg    5100 ggaaagcact ctaaacagtc tttctgtccg tgagtgaagc agatatttga attctgattc    5160
attctctcgc attgtctgca gggaaacagc atcagattca tgcccacgtg acgagaacat    5220
ttgttttggt acctgtctgc gtagttgatc gaagcttccg cgtctgacgt cgatggctgc    5280
gcaactgact cgcgcacccg tttgggctca cttatatctg cgtcactggg ggcgggtctt    5340
ttcttggctc cacccttttt gacgtagaat tcatgctcca cctcaaccac gtgatccttt    5400
gcccaccgga aaaagtcttt gacttcctgc ttggtgacct tcccaaagtc atgatccaga    5460
cggcgggtga gttcaaattt gaacatccgg tcttgcaacg gctgctggtg ttcgaaggtc    5520
gttgagttcc cgtcaatcac ggcgcacatg ttggtgttgg aggtgacgat cacgggagtc    5580
gggtctatct gggccgagga cttgcatttc tggtccacgc gcaccttgct tcctccgaga    5640 atggcttttgg ccgactccac gaccttggcg gtcatcttcc cctcctccca ccagatcacc   5700
atcttgtcga cacagtcgtt gaagggaaag ttctcattgg tccagtttac gcaccgtag    5760 aagggcacag tgtgggctat ggcctccgcg atgttggtct tcccggtagt tgcaggccca    5820
aacagccaga tggtgttcct cttgccgaac tttttcgtgg cccatcccag aaagacggaa    5880
gccgcatatt ggggatcgta cccgtttagt tccaaaattt tataaatccg attgctggaa    5940
atgtcctcca cgggctgctg gcccaccagg tagtcggggg cggttttagt caggctcata    6000
atctttcccg cattgtccaa ggcagccttg atttgggacc gcgagttgga ggccgcattg    6060
aaggagatgt atgaggcctg gtcctcctgg atccactgct tctccgaggt aatcccttg     6120 tccacgagcc acccgaccag ctccatgtac ctggctgaag ttttttgatct gatcaccggc   6180 gcatcagaat tgggattctg attctctttg ttctgctcct gcgtctgcga cacgtgcgtc    6240
agatgctgcg ccaccaaccg tttacgctcc gtgagattca aacaggcgct taaatactgt    6300
tccatattag tccacgccca ctggagctca ggctgggttt tggggagcaa gtaattgggg    6360
```

```
atgtagcact catccaccac cttgttcccg cctccggcgc catttctggt ctttgtgacc    6420
gcgaaccagt ttggcaaagt cggctcgatc ccgcggtaaa ttctctgaat cagttttcg    6480 cgaatctgac tcaggaaacg tcccaaaacc atggatttca ccccggtggt ttccacgagc    6540
acgtgcatgt ggaagtagct ctctcccttc tcaaattgca caaagaaaag ggcctccggg    6600
gccttactca cacggcgcca ttccgtcaga agtcgcgct gcagcttctc ggccacggtc     6660
aggggtgcct gctcaatcag attcagatcc atgtcagaat ctggcggcaa ctcccattcc    6720
ttctcggcca cccagttcac aaagctgtca gaaatgccgg gcagatgctc gtcaaggtcg    6780
ctggggacct taatcacaat ctcgtaaaac cccggcatgg cggctgcgcg ttcaaacctc    6840
ccgcttcaaa atggagaccc tgcgtgctca ctcgggctta aatacccagc gtgaccacat    6900
ggtgtcgcaa aatgtcgcaa aacactcacg tgacctctaa tacaggacct ccctaaccct    6960
atgacgtaat tcacgtcacg actccacca                                      6989

<210> SEQ ID NO 36
<211> LENGTH: 2217
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
ttacagatta cgggtgaggt aacgggtgcc aatggggcgg ggttcagagt acacgccttc      60
tgtattaaca gcaaagtcca cacttgtaga tttgtagtag ttggaggtgt actggatctc     120
ggggttccag cgcttgctgt tttccttctg cagctcccat tcaatttcca cgctgacctg    180
tccggtgctg tattgcgtga tgaaagagtt cagctttgac tggttgaagg tggtcggagg    240
atccgcaggt acaggcgtgt tcttgatcag gatctgaggc ggaggatgtt tcaggccaaa    300
gccgcccatc agcggagacg ggtggaagtt gccgtccgtg tgaggaatct tggcccagat    360
gggaccctgc aggtacacgt cccggttctg ccagaccata ccgggtaagg cccctggct    420 gttgacagtt ccaatttgag gagccgtgtt ttgctgctgc aagttatctg ccacgatacc    480
gtattcctct gtagccacag ggttagtggt tttgatttct tcctcgctgg tgagcatgac    540
atcgctgtaa tccgcattgt ctctggcagc attttgtttg ccaaaaatca ggatcccgtt    600
actgggaaaa aaacgctcct cgtcgtcttt gtgtgttgcc atagcgatgc caggattagc    660
caatgaattt cttccattca gatggtattt ggtcccagca gtccaggcaa agttgctatt    720
gttgttttgc ccggttgtcg ttgagacgcg ttgttggcgg taacagggtc ctggcagcca    780 gttcttttgcc tgattggcca ttgtattagg cccaccttgg ctgaagccca gagtctgcgt    840
atttgccgtg cctcctgttg tttgagtccg agacaagtag tacaggtact ggtcaatcag    900
aggattcatc agccggtcca agctctggct gtgggcgtag ctgctgtgga aaggcacgtc    960
ctcgaaggtg taagtaaact ggaagttgtt gccggttctc agcatctgcg aaggaaagta   1020
ttccaggcag tagaaggagg agcgtcccac ggcctgacta ccgttgttga gtgttaggta   1080
gccgtactgg ggaatcatga acacgtccgc cgggaacgga ggcaggcagc cctggtgggc   1140
agagccgaga acgtacggca gctggtactc cgagtccgta aacacctgga tggtgctggt   1200
gaggttattg gcgatggtct tggtgccttc attctgcgtg acctccttga cctggatgtt   1260
gaagagcttg aagctgagtc tcttgggccg gaatccccag ttgttgttga tgagtcgctg   1320
ccagtcacgt ggtgaaaagt ggcagtggaa tctgttaaag tcaaaatacc cccaggggt    1380
```

```
gctgtagccg aagtaggtgt tgtcgttggt ggctcctccc gatgtcccgt tggagatttg    1440
cttgtagagg tggttgttgt aggtgggcag ggcccaggtt cgggtgctgg tggtgatgac    1500
tctgtcgccc agccatgtgg aatcgcaatg ccaatttccc gaggaactac ccactccgtc    1560
ggcgccttcg ttattgtctg ccattggtgc gccaccgcct gcagccattg tattaggtcc    1620
cacaccagag ggcgctgctg gaggttctcc gagaggttga gggtctggaa ctgactctga    1680
gtcgccagtc tgaccaaaat tgagtctttt tctggcgggc tgttggcctt cttgccgat     1740 gcccgtagag gagtctggag aacgctgggg tgatggctct accgtctct tctttccagg     1800 agccgtctta gcgccttcct caaccagacc gagaggttcg agaacccgct tcttggcctg    1860
gaagactgct cgcccgaggt tgcccccaaa agacgtatct tcttgcagac gctcctgaaa    1920
ctcggcgtcg gcgtggttat accgcaggta cggattgtca cccgcctgca gctgctggtc    1980
gtaggccttg tcgtgctcga gggccgctgc gtccgccgcg ttgacgggct cccccttgtc    2040
gagtccgttg aagggtccga ggtacttgta gccaggaagc accagacccc ggccgtcgtc    2100
ctgcttttgc tggttggctt tgggcttcgg ggctccaggt ttcagcgccc accactcgcg    2160
aatgccctca gagaggttgt cctcgagcca atctggaaga taaccatcgg cagccat      2217
```

<210> SEQ ID NO 37
<211> LENGTH: 6983
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
ctagagtcga cctgcaggca tgcaagcttg gcgtaatcat ggtcatagct gtttcctgtg      60
tgaaattgtt atccgctcac aattccacac aacatacgag ccggaagcat aaagtgtaaa    120
gcctggggtg cctaatgagt gagctaactc acattaattg cgttgcgctc actgcccgct    180
ttccagtcgg gaaacctgtc gtgccagctg cattaatgaa tcggccaacg cgcggggaga    240
ggcggtttgc gtattgggcg ctcttccgct tcctcgctca ctgactcgct gcgctcggtc    300
gttcggctgc ggcgagcggt atcagctcac tcaaaggcgg taatacggtt atccacagaa    360
tcaggggata acgcaggaaa gaacatgtga gcaaaaggcc agcaaaaggc caggaaccgt    420
aaaaaggccg cgttgctggc gtttttccat aggctccgcc cccctgacga gcatcacaaa    480
aatcgacgct caagtcagag gtggcgaaac ccgacaggac tataaagata ccaggcgttt    540
ccccctggaa gctccctcgt gcgctctcct gttccgaccc tgccgcttac cggatacctg    600 tccgccttc tcccttcggg aagcgtggcg ctttctcata gctcacgctg taggtatctc    660
agttcggtgt aggtcgttcg ctccaagctg ggctgtgtgc acgaaccccc cgttcagccc    720
gaccgctgcg ccttatccgg taactatcgt cttgagtcca acccggtaag acacgactta    780
tcgccactgg cagcagccac tggtaacagg attagcagag cgaggtatgt aggcggtgct    840
acagagttct tgaagtggtg gcctaactac ggctacacta aggacagt atttggtatc      900 tgcgctctgc tgaagccagt taccttcgga aaaagagttg gtagctcttg atccggcaaa    960
caaaccaccg ctggtagcgg tggttttttt gtttgcaagc agcagattac gcgcagaaaa   1020
aaaggatctc aagaagatcc tttgatcttt tctacggggt ctgacgctca gtggaacgaa   1080
aactcacgtt aagggatttt ggtcatgtga ttatcaaaaa ggatcttcac ctagatcctt   1140
ttaaattaaa aatgaagttt taaatcaatc taaagtatat atgagtaaac ttggtctgac   1200
```

```
agttagaaaa actcatcgag catcaaatga aactgcaatt tattcatatc aggattatca    1260
ataccatatt tttgaaaaag ccgtttctgt aatgaaggag aaaactcacc gaggcagttc    1320
cataggatgg caagatcctg gtatcggtct gcgattccga ctcgtccaac atcaatacaa    1380
cctattaatt tcccctcgtc aaaaataagg ttatcaagtg agaaatcacc atgagtgacg    1440
actgaatccg gtgagaatgg caaaagttta tgcatttctt ccagacttg ttcaacaggc     1500 cagccattac gctcgtcatc aaaatcactc gcatcaacca aaccgttatt cattcgtgat    1560
tgcgcctgag cgagacgaaa tacgcgatcg ctgttaaaag acaattaca aacaggaatc     1620 gaatgcaacc ggcgcaggaa cactgccagc gcatcaacaa tattttcacc tgaatcagga    1680
tattcttcta atacctggaa tgctgttttc cagggatcg cagtggtgag taaccatgca     1740
tcatcaggag tacggataaa atgcttgatg gtcggaagag gcataaattc cgtcagccag    1800
tttagtctga ccatctcatc tgtaacatca ttggcaacgc tacctttgcc atgtttcaga    1860
aacaactctg gcgcatcggg cttcccatac aatcgataga ttgtcgcacc tgattgcccg    1920
acattatcgc gagcccattt atacccatat aaatcagcat ccatgttgga atttaatcgc    1980
ggcctagagc aagacgtttc ccgttgaata tggctcatac tcttcctttt tcaatattat    2040
tgaagcattt atcagggtta ttgtctcatg agcggataca tatttgaatg tatttagaaa    2100
aataaacaaa taggggttcc gcgcacattt ccccgaaaag tgccacctga cgtctaagaa    2160
accattatta acatgacatt aacctataaa aataggcgta tcacgaggcc ctttcgtctc    2220
gcgcgtttcg gtgatgacgg tgaaaacctc tgacacatgc agctcccgga gacggtcaca    2280
gcttgtctgt aagcggatgc cgggagcaga caagcccgtc agggcgcgtc agcgggtgtt    2340
ggcgggtgtc ggggctggct taactatgcg gcatcagagc agattgtact gagagtgcac    2400
catatgcggt gtgaaatacc gcacagatgc gtaaggagaa ataccgcat caggcgccat     2460 tcgccattca ggctgcgcaa ctgttgggaa gggcgatcgg tgcgggcctc ttcgctatta    2520
cgccagctgg cgaaaggggg atgtgctgca aggcgattaa gttgggtaac gccagggttt    2580
tcccagtcac gacgttgtaa aacgacggcc agtgaattcg agctcggtac ccgtagccat    2640
ggaaactaga taagaaagaa atacgcagag accaaagttc aactgaaacg aattaaacgg    2700
tttattgatt aacaagcaat tacagattac gagtcaggta tctggtgcca atggggcggg    2760
gttcactata tacccttca gtattaacag caaattcaac attattagac ttgtaatagt     2820
tggaagtgta ctggatctcc gggttccagc gcttgctgtt ttccttctgc agctcccact    2880
cgatctccac gctgacttgg ccagtagaat actgggtgat gaaagagttc agcttgtcct    2940
tgttgaaggc cgttggagga tccgcaggta caggtgtgtt tttgatgagg atctgaggag    3000
gcgggtgctt cattccaaac cctcccatca gcggagaagg gtgaaagttg ccgtccgtgt    3060
gaggaatttt ggcccaaatg ggtccttgca ggtacacatc tctgtcctgc aaaccatac     3120 ccggaagtat tccttggttt tgaacccagc cggtctgcgc ctgtgcttgg cactctggt     3180 ggtttgtggc cacttgtcca taggactccg ttgctaccgg gttagtagtt ttaatttctt    3240
cttcgttggt tatcatgact tgtccgcat ccacgttgtc tcttccagtt ccttgtttgc     3300
caaaaattaa agatccagac aaaggaaaga acggtcctc tccttctttg tggctggcca     3360
tagcaggtcc aggattcatc aagctattac gtccattgag agcccaagaa gaagctccag    3420
gccaagcaaa ttcgctgttg ttgttttgag tcacagtggt tgagacacgt tgttgtcggt    3480
agctgggtcc aggtatgtag tttcttccct ggacagccat gttgctgggt ccggccacac    3540
```

```
tgaatttttag cgtttgttga ttctgtccag aaccgttaat agtctttgag agatagtaca    3600
agtattggtc gatgagtgga ttcattagtc ggtccaggct ttggctgtga gcgtagctgc    3660
tatggaaagg tacgttctca aactcgtagc tgaactggaa gttgttaccc gttcttagca    3720
tttgcgacgg gaaatattcc aggcagtaaa aggacgaacg acccacggcc tggcttccat    3780
cattaagcgt cagatacccg tactgaggaa tcatgaaaac gtccgctggg aacggcggga    3840
ggcagccctc gtgagccgac ccgagcacgt acgggagctg atagtctgag tccgtgaaga    3900
cctggaccgt gctggtaagg ttattggcga tggtcttgac tccattgttg tccgtaacct    3960
ctttgacctg aatgttgaag agcttgaagt tgagtcgctt aggccggaat ccccagttgt    4020
tgttgatgag tcgctgccag tcacgtggtg agaagtggca gtggaatctg ttgaagtcaa    4080
aataccccca gggggtgctg tagccgaagt aggcgttgtc atttgaagat cctccagatg    4140
tgctgttgga gatttgcttg tagaggtgat tgttgtaggt gggcagggcc caggttcggg    4200
tgctggtggt gatgactctg tcccccagcc attgggaatc gcaatgccaa tttcccgagg    4260
aactacccac tccatcggca ccttcgttat tgtctgccac tggtgcgcca ccacctgaag    4320
ccattgtaag agatcccaca cctgaggggg ctgcggagg ttctccgatt ggttgagggt    4380
ctgggactga ctctgtgtcg ccagtctgac cgaaattgag tctcttttta gcgggctgtg    4440
cacccgattt gccataccc gcggaggagt ccggttcctg aggagactgc tctacaggcc    4500 tcttcttttcc aggagccgtc ttagccgctt cctcaaccag accaagaggt tcaagaagcc    4560 tcttttttggc ctggaagact gctcgcccga ggttgccccc aaaagacgta tcttctttga    4620
gccgctcctg gaactcggcg tcggcgtggt tgtacttgag gtacgggttg tctccggcct    4680
tgagctgctg gtcgtaggcc ttgtcgtgct cgagggccgc cgcgtctgct gcgttgaccg    4740
gctccccctt gtcgagtccg ttgccgggtc caaggtattt gtaacccgga agcacaagac    4800
ctcgagcgtt gtcttgatgt tgttgatttg ccttgggttg aggggctcca ggtttcaaag    4860
cccaccactc gcgaattcct tcactaaggt tgtcctcgag ccaatctgga agataaccat    4920
cggcagccat acctgattta aatcatttat tgttcaaaga tgcagtcatc caaatccaca    4980
ttgaccagat cgcaggcagt gcaagcgtct ggcacctttc ccatgatatg atgaatgtag    5040
cacagttcct gatacgcctt tttgacgaca gaaacgggtt gagattctga cacgggaaag    5100
cactctaaac agtcttctg tccgtgagtg aagcagatat ttgaattctg attcattctc    5160
tcgcattgtc tgcagggaaa cagcatcaga ttcatgccca cgtgacgaga acatttgttt    5220
tggtacctgt ctgcgtagtt gatcgaagct tccgcgtctg acgtcgatgg ctgcgcaact    5280
gactcgcgca cccgtttggg ctcacttata tctgcgtcac tgggggcggg tcttttcttg    5340
gctccaccct ttttgacgta gaattcatgc tccacctcaa ccacgtgatc ctttgcccac    5400
cggaaaaagt ctttgacttc ctgcttggtg accttcccaa agtcatgatc cagacggcgg    5460
gtgagttcaa atttgaacat ccggtcttgc aacggctgct ggtgttcgaa ggtcgttgag    5520
ttcccgtcaa tcacggcgca catgttggtg ttggaggtga cgatcacggg agtcgggtct    5580
atctgggccg aggacttgca tttctggtcc acgcgcacct tgcttcctcc gagaatggct    5640
ttggccgact ccacgacctt ggcggtcatc ttcccctcct cccaccagat caccatcttg    5700
tcgacacagt cgttgaaggg aaagttctca ttggtccagt ttacgcaccc gtagaagggc    5760
acagtgtggg ctatgcctc cgcgatgttg gtcttcccgg tagttgcagg cccaaacagc    5820
cagatggtgt tcctcttgcc gaactttttc gtggcccatc ccagaaagac ggaagccgca    5880
tattggggat cgtacccgtt tagttccaaa atttttataaa tccgattgct ggaaatgtcc    5940
```

```
tccacgggct gctggcccac caggtagtcg ggggcggttt tagtcaggct cataatcttt    6000
cccgcattgt ccaaggcagc cttgatttgg daccgcgagt tggaggccgc attgaaggag    6060
atgtatgagg cctggtcctc ctggatccac tgcttctccg aggtaatccc cttgtccacg    6120
agccacccga ccagctccat gtacctggct gaagttttg atctgatcac cggcgcatca    6180
gaattgggat tctgattctc tttgttctgc tcctgcgtct gcgacacgtg cgtcagatgc    6240
tgcgccacca accgtttacg ctccgtgaga ttcaaacagg cgcttaaata ctgttccata    6300
ttagtccacg cccactggag ctcaggctgg gttttgggga gcaagtaatt ggggatgtag    6360
cactcatcca ccaccttgtt cccgcctccg gcgccatttc tggtctttgt gaccgcgaac    6420
cagtttggca aagtcggctc gatcccgcgg taaattctct gaatcagttt tcgcgaatc    6480 tgactcagga aacgtcccaa aaccatggat ttcaccccgg tggtttccac gagcacgtgc    6540
atgtggaagt agctctctcc cttctcaaat tgcacaaaga aagggcctc cggggcctta    6600 ctcacacggc gccattccgt cagaaagtcg cgctgcagct tctcggccac ggtcaggggt    6660
gcctgctcaa tcagattcag atccatgtca gaatctggcg gcaactccca ttccttctcg    6720
gccacccagt tcacaaagct gtcagaaatg ccgggcagat gctcgtcaag gtcgctgggg    6780
accttaatca caatctcgta aaaccccggc atggcggctg cgcgttcaaa cctcccgctt    6840
caaaatggag accctgcgtg ctcactcggg cttaaatacc cagcgtgacc acatggtgtc    6900
gcaaaatgtc gcaaaacact cacgtgacct ctaatacagg acctccctaa ccctatgacg    6960
taattcacgt cacgactcca cca                                            6983

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
caacatacga gccggaagca taaagtgtaa a                                   31

<210> SEQ ID NO 39
<211> LENGTH: 5334
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
ggtacccaac tccatgctca acagtcccca ggtacagccc accctgcgtc gcaaccagga     60
acagctctac agcttcctgg agcgccactc gccctacttc cgcagccaca gtgcgcagat    120
taggagcgcc acttcttttt gtcacttgaa aaacatgtaa aaataatgta ctagagacac    180
tttcaataaa ggcaaatgct tttatttgta cactctcggg tgattattta ccccaccct    240 tgccgtctgc gccgtttaaa aatcaaaggg gttctgccgc gcatcgctat gcgccactgg    300
cagggacacg ttgcgatact ggtgtttagt gctccactta aactcaggca caaccatccg    360
cggcagctcg gtgaagtttt cactccacag gctgcgcacc atcaccaacg cgtttagcag    420
gtcgggcgcc gatatcttga agtcgcagtt ggggcctccg ccctgcgcgc gcgagttgcg    480
atacacaggg ttgcagcact ggaacactat cagcgccggg tggtgcacgc tggccagcac    540
```

-continued

```
gctcttgtcg gagatcagat ccgcgtccag gtcctccgcg ttgctcaggg cgaacggagt      600
caactttggt agctgccttc ccaaaaaggg cgcgtgccca ggctttgagt tgcactcgca      660
ccgtagtggc atcaaaaggt gaccgtgccc ggtctgggcg ttaggataca gcgcctgcat      720
aaaagccttg atctgcttaa aagccacctg agcctttgcg ccttcagaga agaacatgcc      780
gcaagacttg ccggaaaact gattggccgg acaggccgcg tcgtgcacgc agcaccttgc      840
gtcggtgttg gagatctgca ccacatttcg gccccaccgg ttcttcacga tcttggcctt      900
gctagactgc tccttcagcg cgcgctgccc gttttcgctc gtcacatcca tttcaatcac      960
gtgctcctta tttatcataa tgcttccgtg tagacactta agctcgcctt cgatctcagc     1020
gcagcggtgc agccacaacg cgcagcccgt gggctcgtga tgcttgtagg tcacctctgc     1080
aaacgactgc aggtacgcct gcaggaatcg ccccatcatc gtcacaaagg tcttgttgct     1140
ggtgaaggtc agctgcaacc cgcggtgctc ctcgttcagc caggtcttgc atacggccgc     1200
cagagcttcc acttggtcag gcagtagttt gaagttcgcc tttagatcgt tatccacgtg     1260
gtacttgtcc atcagcgcgc gcgcagcctc catgcccttc tcccacgcag acacgatcgg     1320
cacactcagc gggttcatca ccgtaatttc actttccgct tcgctgggct cttcctcttc     1380
ctcttgcgtc cgcataccac gcgccactgg gtcgtcttca ttcagccgcc gcactgtgcg     1440
cttacctcct ttgccatgct tgattagcac cggtgggttg ctgaaaccca ccatttgtag     1500
cgccacatct tctcttcttt cctcgctgtc cacgattacc tctggtgatg gcgggcgctc     1560
gggcttggga gaagggcgct tcttttcttt cttgggcgca atggccaaat ccgccgccga     1620
ggtcgatggc cgcgggctgg gtgtgcgcgg caccagcgcg tcttgtgatg agtcttcctc     1680
gtcctcggac tcgatacgcc gcctcatccg ctttttcggg ggcgcccggg gaggcggcgg     1740
cgacggggac ggggacgaca cgtcctccat ggttggggga cgtcgcgccg caccgcgtcc     1800
gcgctcgggg gtggtttcgc gctgctcctc ttcccgactg gccatttcct tctcctatag     1860
gcagaaaaag atcatggagt cagtcgagaa gaaggacagc ctaaccgccc cctctgagtt     1920
cgccaccacc gcctccaccg atgccgccaa cgcgcctacc accttccccg tcgaggcacc     1980
cccgcttgag gaggaggaag tgattatcga gcaggaccca ggttttgtaa gcgaagacga     2040
cgaggaccgc tcagtaccaa cagaggataa aaagcaagac caggacaacg cagaggcaaa     2100
cgaggaacaa gtcgggcggg gggacgaaag gcatggcgac tacctagatg tgggagacga     2160
cgtgctgttg aagcatctgc agcgccagtg cgccattatc tgcgacgcgt tgcaagagcg     2220
cagcgatgtg cccctcgcca tagcggatgt cagccttgcc tacgaacgcc acctattctc     2280
accgcgcgta cccccaaac gccaagaaaa cggcacatgc gagcccaacc cgcgcctcaa     2340
cttctacccc gtatttgccg tgccagaggt gcttgccacc tatcacatct tttccaaaa     2400 ctgcaagata cccctatcct gccgtgccaa ccgcagccga gcggacaagc agctggcctt     2460
gcggcagggc gctgtcatac ctgatatcgc ctcgctcaac gaagtgccaa aaatctttga     2520
gggtcttgga cgcgacgaga agcgcgcggc aaacgctctg caacaggaaa acagcgaaaa     2580
tgaaagtcac tctggagtgt tggtggaact cgagggtgac aacgcgcgcc tagccgtact     2640
aaaacgcagc atcgaggtca cccactttgc ctacccggca cttaacctac ccccaaggt      2700 catgagcaca gtcatgagtg agctgatcgt gcgccgtgcg cagcccctgg agagggatgc     2760
aaatttgcaa gaacaaacag aggagggcct acccgcagtt ggcgacgagc agctagcgcg     2820
ctggcttcaa acgcgcgagc ctgccgactt ggaggagcga cgcaaactaa tgatggccgc     2880
agtgctcgtt accgtggagc ttgagtgcat gcagcggttc tttgctgacc cggagatgca     2940
```

```
gcgcaagcta gaggaaacat tgcactacac ctttcgacag ggctacgtac gccaggcctg   3000
caagatctcc aacgtggagc tctgcaacct ggtctcctac cttggaattt tgcacgaaaa   3060
ccgccttggg caaaacgtgc ttcattccac gctcaagggc gaggcgcgcc gcgactacgt   3120
ccgcgactgc gtttacttat ttctatgcta cacctggcag acggccatgg gcgtttggca   3180
gcagtgcttg gaggagtgca acctcaagga gctgcagaaa ctgctaaagc aaaacttgaa   3240
ggacctatgg acggccttca acgagcgctc cgtggccgcg cacctggcgg acatcatttt   3300
ccccgaacgc ctgcttaaaa ccctgcaaca gggtctgcca gacttcacca gtcaaagcat   3360
gttgcagaac tttaggaact ttatcctaga gcgctcagga atcttgcccg ccacctgctg   3420
tgcacttcct agcgactttg tgcccattaa gtaccgcgaa tgcctccgc cgctttgggg   3480 ccactgctac cttctgcagc tagccaacta ccttgcctac cactctgaca taatggaaga   3540
cgtgagcggt gacggtctac tggagtgtca ctgtcgctgc aacctatgca ccccgcaccg   3600
ctccctggtt tgcaattcgc agctgcttaa cgaaagtcaa attatcggta cctttgagct   3660
gcagggtccc tcgcctgacg aaaagtccgc ggctccgggg ttgaaactca ctccggggct   3720
gtggacgtcg gcttaccttc gcaaatttgt acctgaggac taccacgccc acgagattag   3780
gttctacgaa gaccaatccc gcccgccaaa tgcggagctt accgcctgcg tcattaccca   3840
gggccacatt cttggccaat gcaagccat caacaaagcc cgccaagagt ttctgctacg   3900
aaagggacgg ggggtttact tggaccccca gtccggcgag gagctcaacc caatcccccc   3960
gccgccgcag ccctatcagc agcagccgcg ggcccttgct tcccaggatg gcacccaaaa   4020
agaagctgca gctgccgccg ccacccacgg acgaggagga atactgggac agtcaggcag   4080
aggaggtttt ggacgaggag gaggaggaca tgatggaaga ctgggagagc ctagacgagg   4140
aagcttccga ggtcgaagag gtgtcagacg aaacaccgtc accctcggtc gcattcccct   4200
cgccggcgcc ccagaaatcg gcaaccggtt ccagcatggc tacaacctcc gctcctcagg   4260
cgccgccggc actgcccgtt cgccgaccca accgtagatg ggacaccact ggaaccaggg   4320
ccggtaagtc caagcagccg ccgccgttag cccaagagca acaacagcgc caaggctacc   4380
gctcatggcg cgggcacaag aacgccatag ttgcttgctt gcaagactgt gggggcaaca   4440
tctccttcgc ccgccgcttt cttctctacc atcacggcgt ggccttcccc cgtaacatcc   4500
tgcattacta ccgtcatctc tacagcccat actgcaccgg cggcagcggc agcggcagca   4560
acagcagcgg ccacacagaa gcaaaggcga ccggatagca agactctgac aaagcccaag   4620
aaatccacag cggcggcagc agcaggagga ggagcgctgc gtctggcgcc aacgaaccc   4680 gtatcgaccc gcgagcttag aaacaggatt tttcccactc tgtatgctat atttcaacag   4740 agcagggcc aagaacaaga gctgaaaata aaaaacaggt ctctgcgatc cctcacccgc   4800
agctgcctgt atcacaaaag cgaagatcag cttcggcgca cgctggaaga gcgcggaggct   4860 ctcttcagta aatactgcgc gctgactctt aaggactagt ttcgcgccct ttctcaaatt   4920
taagcgcgaa aactacgtca tctccagcgg ccacacccgg cgccagcacc tgtcgtcagc   4980
gccattatga gcaaggaaat tcccacgccc tacatgtgga gttaccagcc acaaatggga   5040
cttgcggctg gagctgccca agactactca acccgaataa actacatgag gcgcgggaccc   5100 cacatgatat cccgggtcaa cggaatccgc gcccaccgaa accgaattct cttggaacag   5160
gcggctatta ccaccacacc tcgtaataac cttaatcccc gtagttggcc cgctgccctg   5220
gtgtaccagg aaagtcccgc tcccaccact gtggtacttc ccagagacgc ccaggccgaa   5280
```

```
gttcagatga ctaactcagg ggcgcagctt gcgggcggct ttcgtcacag ggtg       5334
```

<210> SEQ ID NO 40
<211> LENGTH: 3201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
tacactaaac ggtacacagg aaacaggaga cacaactcca agtgcatact ctatgtcatt    60
ttcatgggac tggtctggcc acaactacat taatgaaata tttgccacat cctcttacac   120
tttttcatac attgcccaag aataaagaat cgtttgtgtt atgtttcaac gtgtttattt   180
ttcaattgca gaaatttca agtcattttt cattcagtag tatagcccca ccaccacata    240
gcttatacag atcaccgtac cttaatcaaa ctcacagaac cctagtattc aacctgccac   300
ctccctccca acacacagag tacacagtcc tttctccccg gctggcctta aaaagcatca   360
tatcatgggt aacagacata ttcttaggtg ttatattcca cacggtttcc tgtcgagcca   420
aacgctcatc agtgatatta ataaactccc cgggcagctc acttaagttc atgtcgctgt   480
ccagctgctg agccacaggc tgctgtccaa cttgcggttg cttaacgggc ggcgaaggag   540
aagtccacgc ctacatgggg gtagagtcat aatcgtgcat caggatagggcggtggtgct    600
gcagcagcgc gcgaataaac tgctgccgcc gccgctccgt cctgcaggaa tacaacatgg   660
cagtggtctc ctcagcgatg attcgcaccg cccgcagcat aaggcgcctt gtcctccggg   720
cacagcagcg caccctgatc tcacttaaat cagcacagta actgcagcac agcaccacaa   780
tattgttcaa atcccacag tgcaaggcgc tgtatccaaa gctcatggcg gggaccacag    840
aacccacgtg gccatcatac cacaagcgca ggtagattaa gtggcgaccc ctcataaaca   900
cgctggacat aaacattacc tcttttggca tgttgtaatt caccacctcc cggtaccata   960
taaacctctg attaaacatg gcgccatcca ccaccatcct aaaccagctg gccaaaacct  1020
gcccgccggc tatacactgc agggaaccgg gactggaaca atgacagtgg agagcccagg  1080
actcgtaacc atggatcatc atgctcgtca tgatatcaat gttggcacaa cacaggcaca  1140
cgtgcataca cttcctcagg attacaagct cctcccgcgt tagaaccata tcccagggaa  1200
caacccattc ctgaatcagc gtaaatccca cactgcaggg aagacctcgc acgtaactca  1260
cgttgtgcat tgtcaaagtg ttacattcgg gcagcagcgg atgatcctcc agtatggtag  1320
cgcgggtttc tgtctcaaaa ggaggtagac gatccctact gtacgagtgc gccgagaca    1380
accgagatcg tgttggtcgt agtgtcatgc caaatggaac gccggacgta gtcatatttc  1440
ctgaagcaaa accaggtgcg ggcgtgacaa acagatctgc gtctccggtc tcgccgctta  1500
gatcgctctg tgtagtagtt gtagtatatc cactctctca aagcatccag gcgcccctg   1560
gcttcgggtt ctatgtaaac tccttcatgc gccgctgccc tgataacatc caccaccgca  1620
gaataagcca cacccagcca acctacacat tcgttctgcg agtcacacac gggaggagcg  1680
ggaagagctg gaagaaccat gttttttttt ttattccaaa agattatcca aaacctcaaa  1740
atgaagatct attaagtgaa cgcgctcccc tccggtggcg tggtcaaact ctacagccaa  1800
agaacagata atggcatttg taagatgttg cacaatggct tccaaaaggc aaacggccct  1860
cacgtccaag tggacgtaaa ggctaaaccc ttcagggtga atctcctcta taaacattcc  1920
agcaccttca accatgccca aataattctc atctcgccac cttctcaata tatctctaag  1980
```

```
caaatcccga atattaagtc cggccattgt aaaaatctgc tccagagcgc cctccacctt    2040
cagcctcaag cagcgaatca tgattgcaaa aattcaggtt cctcacagac ctgtataaga    2100
ttcaaaagcg gaacattaac aaaaataccg cgatcccgta ggtcccttcg cagggccagc    2160
tgaacataat cgtgcaggtc tgcacggacc agcgcggcca cttccccgcc aggaaccatg    2220
acaaaagaac ccacactgat tatgacacgc atactcggag ctatgctaac cagcgtagcc    2280
ccgatgtaag cttgttgcat gggcggcgat ataaatgca aggtgctgct caaaaaatca     2340
ggcaaagcct cgcgcaaaaa agaaagcaca tcgtagtcat gctcatgcag ataaaggcag    2400
gtaagctccg gaaccaccac agaaaaagac accattttc tctcaaacat gtctgcgggt     2460
ttctgcataa acacaaaata aataacaaa aaacattta acattagaa gcctgtctta       2520 caacaggaaa acaaccctt ataagcataa gacggactac ggccatgccg gcgtgaccgt     2580
aaaaaaactg gtcaccgtga ttaaaaagca ccaccgacag ctcctcggtc atgtccggag    2640
tcataatgta agactcggta acacatcag gttgattcac atcggtcagt gctaaaaagc     2700
gaccgaaata gcccggggga atacataccc gcaggcgtag agacaacatt acagccccca    2760
taggaggtat aacaaaatta ataggagaga aaaacacata aacacctgaa aaaccctcct    2820
gcctaggcaa aatagcaccc tcccgctcca gaacaacata cagcgcttcc acagcggcag    2880
ccataacagt cagccttacc agtaaaaaag aaaacctatt aaaaaaacac cactcgacac    2940
ggcaccagct caatcagtca cagtgtaaaa aagggcaag tgcagagcga gtatatatag    3000
gactaaaaaa tgacgtaacg gttaaagtcc acaaaaaaca cccagaaaac cgcacgcgaa    3060
cctacgccca gaaacgaaag ccaaaaaacc cacaacttcc tcaaatcgtc acttccgttt    3120
tcccacgtta cgtaacttcc cattttaaga aaactacaat tcccaacaca tacaagttac    3180
tccgccctaa aacctacgtc a                                              3201

<210> SEQ ID NO 41
<211> LENGTH: 6896
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
ctagagtcga cctgcaggca tgcaagcttg gcgtaatcat ggtcatagct gtttcctgtg     60
tgaaattgtt atccgctcac aattccacac aacatacgag ccggaagcat aaagtgtaaa    120
gcctggggtg cctaatgagt gagctaactc acattaattg cgttgcgctc actgcccgct    180
ttccagtcgg gaaacctgtc gtgccagctg cattaatgaa tcggccaacg cgcggggaga    240
ggcggtttgc gtattgggcg ctcttccgct tcctcgctca ctgactcgct gcgctcggtc    300
gttcggctgc ggcgagcggt atcagctcac tcaaaggcgg taatacggtt atccacagaa    360 tcagggggata acgcaggaaa gaacatgtga gcaaaaggcc agcaaaaggc caggaaccgt    420
aaaaaggccg cgttgctggc gtttttccat aggctccgcc cccctgacga gcatcacaaa    480
aatcgacgct caagtcagag gtggcgaaac ccgacaggac tataaagata ccaggcgttt    540
ccccctggaa gctccctcgt gcgctctcct gttccgaccc tgccgcttac cggatacctg    600
tccgcctttc tcccttcggg aagcgtggcg ctttctcata gctcacgctg taggtatctc    660
agttcggtgt aggtcgttcg ctccaagctg ggctgtgtgc acgaaccccc cgttcagccc    720
gaccgctgcg ccttatccgg taactatcgt cttgagtcca acccggtaag acacgactta    780
```

```
tcgccactgg cagcagccac tggtaacagg attagcagag cgaggtatgt aggcggtgct      840
acagagttct tgaagtggtg gcctaactac ggctacacta gaaggacagt atttggtatc      900
tgcgctctgc tgaagccagt taccttcgga aaaagagttg gtagctcttg atccggcaaa      960
caaaccaccg ctggtagcgg tggttttttt gtttgcaagc agcagattac gcgcagaaaa     1020
aaaggatctc aagaagatcc tttgatcttt tctacggggt ctgacgctca gtggaacgaa     1080
aactcacgtt aagggatttt ggtcatgtga ttatcaaaaa ggatcttcac ctagatcctt     1140
ttaaattaaa aatgaagttt taaatcaatc taaagtatat atgagtaaac ttggtctgac     1200
agttagaaaa actcatcgag catcaaatga actgcaatt tattcatatc aggattatca     1260
ataccatatt tttgaaaaag ccgtttctgt aatgaaggag aaaactcacc gaggcagttc     1320
cataggatgg caagatcctg gtatcggtct gcgattccga ctcgtccaac atcaatacaa     1380
cctattaatt tcccctcgtc aaaaataagg ttatcaagtg agaaatcacc atgagtgacg     1440
actgaatccg gtgagaatgg caaaagttta tgcatttctt tccagacttg ttcaacaggc     1500
cagccattac gctcgtcatc aaaatcactc gcatcaacca aaccgttatt cattcgtgat     1560
tgcgcctgag cgagacgaaa tacgcgatcg ctgttaaaag gacaattaca aacaggaatc     1620
gaatgcaacc ggcgcaggaa cactgccagc gcatcaacaa tattttcacc tgaatcagga     1680
tattcttcta atacctggaa tgctgttttc ccagggatcg cagtggtgag taaccatgca     1740
tcatcaggag tacggataaa atgcttgatg gtcggaagag gcataaattc cgtcagccag     1800
tttagtctga ccatctcatc tgtaacatca ttggcaacgc taccttttgcc atgtttcaga     1860 aacaactctg gcgcatcggg cttcccatac aatcgataga ttgtcgcacc tgattgcccg     1920
acattatcgc gagcccattt atacccatat aaatcagcat ccatgttgga atttaatcgc     1980
ggcctagagc aagacgtttc ccgttgaata tggctcatac tcttcctttt tcaatattat     2040
tgaagcattt atcagggtta ttgtctcatg agcggataca tatttgaatg tatttagaaa     2100
aataaacaaa taggggttcc gcgcacattt ccccgaaaag tgccacctga cgtctaagaa     2160
accattatta acatgacatt aacctataaa aataggcgta tcacgaggcc ctttcgtctc     2220
gcgcgtttcg gtgatgacgg tgaaaacctc tgacacatgc agctcccgga gacggtcaca     2280
gcttgtctgt aagcggatgc cgggagcaga caagcccgtc agggcgcgtc agcgggtgtt     2340
ggcgggtgtc ggggctggct taactatgcg gcatcagagc agattgtact gagagtgcac     2400
catatgcggt gtgaaatacc gcacagatgc gtaaggagaa aataccgcat caggcgccat     2460
tcgccattca ggctgcgcaa ctgttgggaa gggcgatcgg tgcgggcctc ttcgctatta     2520
cgccagctgg cgaaaggggg atgtgctgca aggcgattaa gttgggtaac gccagggttt     2580
tcccagtcac gacgttgtaa aacgacggcc agtgaattcg agctcggtac ccgtagccat     2640
ggaaactaga taagaaagaa atacgcagag accaaagttc aactgaaacg aattaaacgg     2700
tttattgatt aacaagcaat tacagattac gagtcaggta tctggtgcca atggggcggg     2760
gttcactata tacaccttca gtattaacag caaattcaac attattagac ttgtaatagt     2820
tggaagtgta ctggatctcc gggttccagc gcttgctgtt ttccttctgc agctcccact     2880
cgatctccac gctgacttgg ccagtagaat actgggtgat gaaagagttc agcttgtcct     2940
tgttgaaggc cgttggagga tccgcaggta caggtgtgtt tttgatgagg atctgaggag     3000
gcgggtgctt cattccaaac cctcccatca gcggagaagg gtgaaagttg ccgtccgtgt     3060
gaggaatttt ggcccaaatg ggtccttgca ggtacacatc tctgtcctgc aaaccatac     3120 ccggaagtat tccttggttt tgaacccagc cggtctgcgc ctgtgcttgg gcactctggt     3180
```

```
ggtttgtggc cacttgtcca taggactccg ttgctaccgg gttagtagtt ttaatttctt    3240
cttcgttggt tatcatgact ttgtccgcat ccacgttgtc tcttccagtt ccttgtttgc    3300
caaaaattaa agatccagac aaaggaaaga acggtcctc tccttctttg tggctggcca     3360
tagcaggtcc aggattcatc aagctattac gtccattgag agcccaagaa gaagctccag    3420
gccaagcaaa ttcgctgttg ttgttttgag tcacagtggt tgagacacgt tgttgtcggt    3480
agctgggtcc aggtatgtag tttcttccct ggacagccat gttgctgggt ccggccacac    3540
tgaattttag cgtttgttga ttctgtccag aaccgttaat agtctttgag agatagtaca    3600
agtattggtc gatgagtgga ttcattagtc ggtccaggct ttggctgtga gcgtagctgc    3660
tatggaaagg tacgttctca aactcgtagc tgaactggaa gttgttaccc gttcttagca    3720
tttgcgacgg gaaatattcc aggcagtaaa aggacgaacg acccacggcc tggcttccat    3780
cattaagcgt cagataccccg tactgaggaa tcatgaaaac gtccgctggg aacggcggga   3840
ggcagccctc gtgagccgac ccagcacgt acggagctg atagtctgag tccgtgaaga     3900
cctggaccgt gctggtaagg ttattggcga tggtcttgac tccattgttg tccgtaacct    3960
ctttgacctg aatgttgaag agcttgaagt tgagtcgctt aggccggaat ccccagttgt    4020
tgttgatgag tcgctgccag tcacgtggtg agaagtggca gtggaatctg ttgaagtcaa    4080 aatacccca gggggtgctg tagccgaagt aggcgttgtc atttgaagat cctccagatg    4140
tgctgttgga gatttgcttg tagaggtgat tgttgtaggt gggcagggcc caggttcggg    4200
tgctggtggt gatgactctg tcccccagcc attgggaatc gcaatgccaa tttcccgagg    4260
aactacccac tccatcggca ccttcgttat tgtctgccac tggtgcgcca ccacctgaag    4320
ccattgtaag agatcccaca cctgaggggg ctgcgggagg ttctccgatt ggttgagggt    4380
ctgggactga ctctgtgtcg ccagtctgac cgaaattgag tctcttttta gcgggctgtg    4440
cacccgattt gccaataccc gcggaggagt ccggttcctg aggagactgc tctacaggcc    4500 tcttcttcc aggagccgtc ttagccgctt cctcaaccag accaagaggt tcaagaagcc    4560 tcttttggc ctggaagact gctcgcccga ggttgccccc aaaagacgta tcttctttga    4620
gccgctcctg gaactcggcg tcggcgtggt tgtacttgag gtacgggttg tctccggcct    4680
tgagctgctg gtcgtaggcc ttgtcgtgct cgagggccgc cgcgtctgct gcgttgaccg    4740
gctccccctt gtcgagtccg ttgccgggtc caaggtattt gtaacccgga agcacaagac    4800
ctcgagcgtt gtcttgatgt tgttgatttg ccttgggttg aggggctcca ggtttcaaag    4860
cccaccactc gcgaattcct tcactaaggt tgtcctcgag ccaatctgga agataaccat    4920
cggcagccat acctgattta aatcatttat tgttcaaaga tgcagtcatc caaatccaca    4980
ttgaccagat cgcaggcagt gcaagcgtct ggcacctttc ccatgatatg atgaatgtag    5040
cacagtttct gatacgcctt tttgacgaca gaaacgggtt gagattctga cacgggaaag    5100
cactctaaac agtctttctg tccgtgagtg aagcagatat ttgaattctg attcattctc    5160
tcgcattgtc tgcagggaaa cagcatcaga ttcatgccca cgtgacgaga acatttgttt    5220
tggtacctgt ctgcgtagtt gatcgaagct tccgcgtctg acgtcgatgg ctgcgcaact    5280
gactcgcgca cccgtttggg ctcacttata tctgcgtcac tgggggcggg tcttttcttg    5340
gctccaccct ttttgacgta gaattcatgc tccacctcaa ccacgtgatc ctttgcccac    5400
cggaaaaagt ctttgacttc ctgcttggtg accttcccaa agtcatgatc cagacggcgg    5460
gtgagttcaa atttgaacat ccggtcttgc aacggctgct ggtgttcgaa ggtcgttgag    5520
```

```
ttcccgtcaa tcacggcgca catgttggtg ttggaggtga cgatcacggg agtcgggtct      5580
atctgggccg aggacttgca tttctggtcc acgcgcacct tgcttcctcc gagaatggct      5640
ttggccgact ccacgacctt ggcggtcatc ttcccctcct cccaccagat caccatcttg      5700
tcgacacagt cgttgaaggg aaagttctca ttggtccagt ttacgcaccc gtagaagggc      5760
acagtgtggg ctatggcctc cgcgatgttg gtcttcccgg tagttgcagg cccaaacagc      5820
cagatggtgt tcctcttgcc gaactttttc gtggcccatc ccagaaagac ggaagccgca      5880
tattggggat cgtacccgtt tagttccaaa attttataaa tccgattgct ggaaatgtcc      5940
tccacgggct gctggcccac caggtagtcg ggggcggttt tagtcaggct cataatcttt      6000
cccgcattgt ccaaggcagc cttgatttgg gaccgcgagt tggaggccgc attgaaggag      6060
atgtatgagg cctggtcctc ctggatccac tgcttctccg aggtaatccc cttgtccacg      6120
agccacccga ccagctccat gtacctggct gaagttttg atctgatcac cggcgcatca      6180
gaattgggat tctgattctc tttgttctgc tcctgcgtct gcgacacgtg cgtcagatgc      6240
tgcgccacca accgtttacg ctccgtgaga ttcaaacagg cgcttaaata ctgttccata      6300
ttagtccacg cccactggag ctcaggctgg gttttgggga gcaagtaatt ggggatgtag      6360
cactcatcca ccaccttgtt cccgcctccg gcgccatttc tggtctttgt gaccgcgaac      6420
cagtttggca aagtcggctc gatcccgcgg taaattctct gaatcagttt tcgcgaatc       6480 tgactcagga acgtcccaa aaccatggat ttcaccccgg tggtttccac gagcacgtgc       6540
atgtggaagt agctctctcc cttctcaaat tgcacaaaga aaagggcctc cggggcctta      6600
ctcacacggc gccattccgt cagaaagtcg cgctgcagct tctcggccac ggtcaggggt      6660
gcctgctcaa tcagattcag atccatgtca gaatctggcg gcaactccca ttccttctcg      6720
gccacccagt tcacaaagct gtcagaaatg ccgggcagat gctcgtcaag gtcgctgggg      6780
accttaatca caatctcgta aaaccccggc atggcggctg cgcagatcag aagttcctat      6840
actttctaga gaataggaac ttcggaatag gaacttctga tcttccgggg gatcca         6896
```

<210> SEQ ID NO 42
<211> LENGTH: 8469
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (4155)..(4254)
<223> OTHER INFORMATION: a, c, t, g, unknown or other
<220> FEATURE:
<221> NAME/KEY: misc_feature
<222> LOCATION: (4155)..(4254)
<223> OTHER INFORMATION: This region may encompass 60-100 nucleotides

<400> SEQUENCE: 42

```
tagggaaata ggccaggttt tcaccgtaac acgccacatc ttgcgaatat atgtgtagaa        60
actgccggaa atcgtcgtgt gcactcatgg aaaacggtgt aacaagggtg aacactatcc       120
catatcacca gctcaccgtc tttcattgcc atacggaact ccggatgagc attcatcagg       180
cgggcaagaa tgtgaataaa ggccggataa aacttgtgct tattttctt tacggtctttt       240 aaaaaggccg taatatccag ctgaacggtc tggttatagg tacattgagc aactgactga       300
aatgcctcaa aatgttcttt acgatgccat tgggatatat caacggtggt atatccagtg      360 attttttct ccattttttt ttcctccttt agaaaaactc atcgagcatc aaatgaaact       420
```

```
gcaatttatt catatcagga ttatcaatac catattttg aaaaagccgt ttctgtaatg    480
aaggagaaaa ctcaccgagg cagttccata ggatggcaag atcctggtat cggtctgcga    540
ttccgactcg tccaacatca atacaaccta ttaatttccc ctcgtcaaaa ataaggttat    600
caagtgagaa atcaccatga gtgacgactg aatccggtga aatggcaaa agtttatgca    660 tttctttcca gacttgttca acaggccagc cattacgctc gtcatcaaaa tcactcgcat    720
caaccaaacc gttattcatt cgtgattgcg cctgagcgag gcgaaatacg cgatcgctgt    780
taaaaggaca attacaaaca ggaatcgagt gcaaccggcg caggaacact gccagcgcat    840
caacaatatt ttcacctgaa tcaggatatt cttctaatac ctggaacgct gttttttccgg   900 ggatcgcagt ggtgagtaac catgcatcat caggagtacg ataaaatgc ttgatggtcg    960 gaagtggcat aaattccgtc agccagttta gtctgaccat ctcatctgta acatcattgg   1020
caacgctacc tttgccatgt ttcagaaaca actctggcgc atcgggcttc ccatacaagc   1080
gatagattgt cgcacctgat tgcccgacat tatcgcgagc ccatttatac ccatataaat   1140
cagcatccat gttggaattt aatcgcggcc tcgacgtttc ccgttgaata tggctcattt   1200 tttttttcctc ctttaccaat gcttaatcag tgaggcacct atctcagcga tctgtctatt   1260
tcgttcatcc atagttgcct gactccccgt cgtgtagata actacgatac gggagggctt   1320
accatctggc cccagcgctg cgatgatacc gcgagaacca cgctcaccgg ctccggattt   1380
atcagcaata accagccag ccggaagggc cgagcgcaga agtggtcctg caactttatc   1440
cgcctccatc cagtctatta attgttgccg ggaagctaga gtaagtagtt cgccagttaa   1500
tagtttgcgc aacgttgttg ccatcgctac aggcatcgtg gtgtcacgct cgtcgtttgg   1560
tatggcttca ttcagctccg gttcccaacg atcaaggcga gttacatgat cccccatgtt   1620
gtgcacgttg tcagaagtaa gttggccgca gtgttatcac tcatggttat ggcagcactg   1680
cataattctc ttactgtcat gccatccgta agatgctttt ctgtgactgg tgagtactca   1740
accaagtcat tctgagaata gtgtatgcgg cgaccgagtt gctcttgccc ggcgtcaata   1800
cgggataata ccgcgccaca tagcagaact ttaaaagtgc tcatcattgg aaaacgttct   1860
tcggggcgaa aactctcaag gatcttaccg ctgttgagat ccagttcgat gtaacccact   1920
cgtgcaccca actgatcttc agcatctttt actttcacca gcgtttctgg gtgagcaaaa   1980
acaggaaggc aaaatgccgc aaaaaaggga taagggcga cacggaaatg ttgaatactc   2040
atattcttcc ttttttcaata ttattgaagc atttatcagg gttattgtct catgagcgga   2100
tacatatttg aatgtattta gaaaaataaa caaatagggg tcagtgttac aaccaattaa   2160
ccaattctga acattatcgc gagcccattt atacctgaat atggctcata cacccccttg   2220
tttgcctggc ggcagtagcg cggtggtccc acctgacccc atgccgaact cagaagtgaa   2280
acgccgtagc gccgatggta gtgtggggac tccccatgcg agagtaggga actgccaggc   2340
atcaaataaa acgaaaggct cagtcgaaag actgggcctt tcgcccgggc taattgaggg   2400
gtgtcgccct tattcgactc ggggctcgag cagcagctgc gcgctcgctc gctcactgag   2460
gccgcccggg caaagcccgg gcgtcgggcg acctttggtc gcccggcctc agtgagcgag   2520
cgagcgcgca gagggagt gggttttaa ttaaacgcgt ttacataact tacggtaaat   2580
ggcccgcctg gctgaccgcc caacgacccc cgcccattga cgtcaataat gacgtatgtt   2640
cccatagtaa cgccaatagg gactttccat tgacgtcaat gggtggacta tttacggtaa   2700
actgcccact tggcagtaca tcaagtgtat catatgccaa gtacgccccc tattgacgtc   2760
aatgacggta atgggcccgc ctggcattat gcccagtaca tgaccttatg gactttcct   2820
```

| | |
|---|---|
| acttggcagt acatctacgt attagtcatc gctattacca tggtgatgcg gttttggcag | 2880 |
| tacatcaatg ggcgtggata gcggtttgac tcacggggat ttccaagtct ccaccccatt | 2940 |
| gacgtcaatg ggagtttgtt ttggcaccaa aatcaacggg actttccaaa atgtcgtaac | 3000 |
| aactccgccc cattgacgca aatgggcggt aggcgtgtac ggtgggaggt ctatataggc | 3060 |
| gcgccgaact gaaaaaccag aaagttaact ggtaagttta gtcttttgt cttttatttc | 3120 |
| aggtcccgga tccggtggtg gtgcaaatca aagaactgct cctcagtgga tgttgccttt | 3180 |
| acttctaggc ctgtacggaa gtgttacttc tgctctaaaa gctcctgcag ggaattcgcc | 3240 |
| accatggtga gcaagggcga ggagctgttc accggggtgg tgcccatcct ggtcgagctg | 3300 |
| gacggcgacg taaacggcca caagttcagc gtgtccggcg agggcgaggg cgatgccacc | 3360 |
| tacggcaagc tgaccctgaa gttcatctgc accaccggca agctgcccgt gccctggccc | 3420 |
| accctcgtga ccaccctgac ctacggcgtg cagtgcttca gccgctaccc cgaccacatg | 3480 |
| aagcagcacg acttcttcaa gtccgccatg cccgaaggct acgtccagga gcgcaccatc | 3540 |
| ttcttcaagg acgacggcaa ctacaagacc cgcgccgagg tgaagttcga gggcgacacc | 3600 |
| ctggtgaacc gcatcgagct gaagggcatc gacttcaagg aggacggcaa catcctgggg | 3660 |
| cacaagctgg agtacaacta caacagccac aacgtctata tcatggccga caagcagaag | 3720 |
| aacggcatca aggtgaactt caagatccgc cacaacatcg aggacggcag cgtgcagctc | 3780 |
| gccgaccact accagcagaa cacccccatc ggcgacggcc ccgtgctgct gcccgacaac | 3840 |
| cactacctga gcacccagtc cgccctgagc aaagacccca acgagaagcg cgatcacatg | 3900 |
| gtcctgctgg agttcgtgac cgccgccggg atcactctcg gcatggacga gctgtacaag | 3960 |
| taatagacta gtgtcgacag atcttttaaa aaacctccca cacaattgtt gttgttaact | 4020 |
| tgtttattgc agcttataat ggttacaaat aaagcaatag catcacaaat ttcacaaata | 4080 |
| aagcattttt ttcactgcat tctagttgtg gtttgtccaa actcatcaat gtatcttatc | 4140 |
| atgtctgttt aaacnnnnnn nnnnnnnnnn nnnnnnnnnn nnnnnnnnnn nnnnnnnnnn | 4200 |
| nnnnnnnnnn nnnnnnnnnn nnnnnnnnnn nnnnnnnnnn nnnnnnnnnn nnnnatttaa | 4260 |
| ataggaaccc ctagtgatgg agttggccac tccctctctg cgcgctcgct cgctcactga | 4320 |
| ggccgggcga ccaaaggtcg cccgacgccc gggctttgcc cggcggcct cagtgagcga | 4380 |
| gcgagcgcgc agagagtata catcgatgtg agttcgcggg tggctggggg gccctgggct | 4440 |
| gcgaccgccc ccgaaccgcg tctacgagcc ttgcgggctc cgggtctttg cagtcgtatg | 4500 |
| ggggcagggt agctgttccc cgcaaggaga gctcaaggtc agcgctcgga cctggcggag | 4560 |
| ccccgcaccc aggctgtggc gccctgtgca gctccgccct tgcggcgcca tctgcccgga | 4620 |
| gcctccttcc cctagtcccc agaaacagga ggtccctact cccgcccgag atcccgaccc | 4680 |
| ggacccctag gtggggacg ctttctttcc tttcgcgctc tgcggggtca cgtgtcgcag | 4740 |
| aggagccccct cccccacggc ctccggcacc gcaggcccg ggatgctagt gcgcagcggg | 4800 |
| tgcatccctg tccggatgct gcgcctgcgg tagagcggcc gccatgttgc aaccgggaag | 4860 |
| gaaatgaatg ggcagccgtt aggaaagcct gccggtgact aaccctgcgc tcctgcctcg | 4920 |
| atgggtggag tcgcgtgtgg cggggaagtc aggtggagcg aggctagctg gcccgatttc | 4980 |
| tcctccgggt gatgcttttc ctagattatt ctctggtaaa tcaaagaagt gggtttatgg | 5040 |
| aggtcctctt gtgtccccctc cccgcagagg tgtggtggcg gtggcatggt gccaagccgg | 5100 |
| gagaagctga gtcatgggta gttggaaaag gacatttcca ccgcaaaatg gcccctctgg | 5160 |

```
tggtggcccc ttcctgcagc gccggctcac ctcacggccc cgcccttccc ctgccagcct    5220
agcgttgacc cgaccccaaa ggccaggctg taaatgtcac cgggaggatt gggtgtctgg    5280
gcgcctcggg gaacctgccc ttctccccat tccgtcttcc ggaaaccaga tctcccaccg    5340
caccctggtc tgaggttaaa tatagctgct gacctttctg tagctggggg cctgggctgg    5400
ggctctctcc catcccttct ccccacacac atgcacttac ctgtgctccc actcctgatt    5460
tctggaaaag agctaggaag gacaggcaac ttggcaaatc aaagccctgg gactagggga    5520
ttaaaataca gcttcccctc ttcccacccg ccccagtctc tgtcccttt gtaggaggga    5580 cttagagaag gggtgggctt gccctgtcca gttaatttct gacctttact cctgcccttt    5640
gagtttgatg atgctgagtg tacaagcgtt ttctccctaa agggtgcagc tgagctaggc    5700
agcagcaagc attcctgggg tggcatagtg gggtggtgaa taccatgtac aaagcttgtg    5760
cccagactgt gggtggcagt gccccacatg gccgcttctc ctggaagggc ttcgtatgac    5820
tgggggtgtt gggcagccct ggagccttca gttgcagcca tgccttaagc caggccagcc    5880
tggcagggaa gctcaaggga gataaaattc aacctcttgg gccctcctgg gggtaaggag    5940
atgctgcatt cgccctctta atggggaggt ggcctagggc tgctcacata ttctggagga    6000
gcctcccctc ctcatgcctt cttgcctctt gtctcttagg catgcaaaag agtcgaataa    6060
gggcgacaca aaatttattc taaatgcata ataaatactg ataacatctt atagtttgta    6120
ttatattttg tattatcgtt gacatgtata attttgatat caaaaactga ttttcccttt    6180
attattttcg agatttattt tcttaattct ctttaacaaa ctagaaatat tgtatataca    6240
aaaaatcata aataatagat gaatagttta attataggtg ttcatcaatc gaaaaagcaa    6300
cgtatcttat ttaaagtgcg ttgctttttt ctcatttata aggttaaata attctcatat    6360
atcaagcaaa gtgacaggcg cccttaaata ttctgacaaa tgctctttcc ctaaactccc    6420
cccataaaaa aacccgccga agcgggtttt tacgttattt gcggattaac gattactcgt    6480
tatcagaacc gcccaggggg cccgagctta agactggccg tcgttttaca acacagaaag    6540
agtttgtaga aacgcaaaaa ggccatccgt caggggcctt ctgcttagtt tgatgcctgg    6600
cagttcccta ctctcgcctt ccgcttcctc gctcactgac tcgctgcgct cggtcgttcg    6660
gctgcggcga gcggtatcag ctcactcaaa ggcggtaata cggttatcca cagaatcagg    6720
ggataacgca ggaaagaaca tgtgagcaaa aggccagcaa aaggccagga accgtaaaaa    6780
ggccgcgttg ctggcgtttt tccataggct ccgcccccct gacgagcatc acaaaaatcg    6840
acgctcaagt cagaggtggc gaaacccgac aggactataa agataccagg cgtttccccc    6900
tggaagctcc ctcgtgcgct ctcctgttcc gaccctgccg cttaccggat acctgtccgc    6960
ctttctccct tcgggaagcg tggcgctttc tcatagctca cgctgtaggt atctcagttc    7020
ggtgtaggtc gttcgctcca agctgggctg tgtgcacgaa ccccccgttc agcccgaccg    7080
ctgcgcctta tccggtaact atcgtcttga gtccaacccg gtaagacacg acttatcgcc    7140
actggcagca gccactggta acaggattag cagagcgagg tatgtaggcg gtgctacaga    7200
gttcttgaag tggtgggcta actacggcta cactagaaga acagtatttg gtatctgcgc    7260
tctgctgaag ccagttacct tcggaaaaag agttggtagc tcttgatccg gcaaacaaac    7320
caccgctggt agcggtggtt tttttgtttg caagcagcag attacgcgca gaaaaaaagg    7380
atctcaagaa gatcctttga tcttttctac ggggtctgac gctcagtgga acgacgcgcg    7440
cgtaactcac gttaagggat tttggtcatg agcttgcgcc gtcccgtcaa gtcagcgtaa    7500
tgctctgctt aggtggcggt acttgggtcg atatcaaagt gcatcacttc ttcccgtatg    7560
```

```
cccaactttg tatagagagc cactgcggga tcgtcaccgt aatctgcttg cacgtagatc    7620
acataagcac caagcgcgtt ggcctcatgc ttgaggagat tgatgagcgc ggtggcaatg    7680
ccctgcctcc ggtgctcgcc ggagactgcg agatcataga tatagatctc actacgcggc    7740
tgctcaaact tgggcagaac gtaagccgcg agagcgccaa caaccgcttc ttggtcgaag    7800
gcagcaagcg cgatgaatgt cttactacgg agcaagttcc cgaggtaatc ggagtccggc    7860
tgatgttggg agtaggtggc tacgtcaccg aactcacgac cgaaaagatc aagagcagcc    7920
cgcatggatt tgacttggtc agggccgagc ctacatgtgc gaatgatgcc catacttgag    7980
ccacctaact ttgttttagg gcgactgccc tgctgcgtaa catcgttgct gctccataac    8040
atcaaacatc gacccacggc gtaacgcgct tgctgcttgg atgcccgagg catagactgt    8100
acaaaaaaac agtcataaca agccatgaaa accgccactg cgccgttacc accgctgcgt    8160
tcggtcaagg ttctggacca gttgcgtgag cgcattttt  tttcctcctc ggcgtttacg    8220
ccccgccctg ccactcatcg cagtactgtt gtaattcatt aagcattctg ccgacatgga    8280
agccatcaca gacggcatga tgaacctgaa tcgccagcgg catcagcacc ttgtcgcctt    8340
gcgtataata tttgcccata gtgaaaacgg gggcgaagaa gttgtccata ttggccacgt    8400
ttaaatcaaa actggtgaaa ctcacccagg gattggcgct gacgaaaaac atattctcaa    8460
taaacccctt                                                          8469

<210> SEQ ID NO 43
<211> LENGTH: 116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
cagcagctgc gcgctcgctc gctcactgag gccgcccggg caaagcccgg gcgtcgggcg     60
acctttggtc gcccggcctc agtgagcgag cgagcgcgca gagagggagt ggggtt        116

<210> SEQ ID NO 44
<211> LENGTH: 534
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
ttaggtggcg gtacttgggt cgatatcaaa gtgcatcact tcttcccgta tgcccaactt     60
tgtatagaga gccactgcgg gatcgtcacc gtaatctgct tgcacgtaga tcacataagc    120
accaagcgcg ttggcctcat gcttgaggag attgatgagc gcggtggcaa tgccctgcct    180
ccggtgctcg ccggagactg cgagatcata gatatagatc tcactacgcg gctgctcaaa    240
cttgggcaga acgtaagccg cgagagcgcc aacaaccgct tcttggtcga aggcagcaag    300
cgcgatgaat gtcttactac ggagcaagtt cccgaggtaa tcggagtccg gctgatgttg    360
ggagtaggtg gctacgtcac cgaactcacg accgaaaaga tcaagagcag cccgcatgga    420
tttgacttgg tcagggccga gcctacatgt gcgaatgatg cccatacttg agccacctaa    480
ctttgtttta gggcgactgc cctgctgcgt aacatcgttg ctgctccata acat          534

<210> SEQ ID NO 45
```

<211> LENGTH: 11635
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 45

| | | | | | |
|---|---|---|---|---|---|
| ggtacccaac | tccatgctta | acagtcccca | ggtacagccc | accctgcgtc | gcaaccagga | 60 |
| acagctctac | agcttcctgg | agcgccactc | gccctacttc | cgcagccaca | gtgcgcagat | 120 |
| taggagcgcc | acttctttt | gtcacttgaa | aaacatgtaa | aaataatgta | ctaggagaca | 180 |
| ctttcaataa | aggcaaatgt | ttttatttgt | acactctcgg | gtgattattt | accccccacc | 240 |
| cttgccgtct | gcgccgttta | aaaatcaaag | gggttctgcc | gcgcatcgct | atgcgccact | 300 |
| ggcagggaca | cgttgcgata | ctggtgttta | gtgctccact | aaaactcagg | cacaaccatc | 360 |
| cgcggcagct | cggtgaagtt | ttcactccac | aggctgcgca | ccatcaccaa | cgcgtttagc | 420 |
| aggtcgggcg | ccgatatctt | gaagtcgcag | ttggggcctc | cgccctgcgc | gcgcgagttg | 480 |
| cgatacacag | ggttgcagca | ctggaacact | atcagcgccg | ggtggtgcac | gctggccagc | 540 |
| acgtcttgt | cggagatcag | atccgcgtcc | aggtcctccg | cgttgctcag | ggcgaacgga | 600 |
| gtcaactttg | gtagctgcct | tcccaaaaag | ggtgcatgcc | caggctttga | gttgcactcg | 660 |
| caccgtagtg | gcatcagaag | gtgaccgtgc | ccggtctggg | cgttaggata | cagcgcctgc | 720 |
| atgaaagcct | tgatctgctt | aaaagccacc | tgagcctttg | cgccttcaga | gaagaacatg | 780 |
| ccgcaagact | tgccggaaaa | ctgattggcc | ggacaggccg | cgtcatgcac | gcagcacctt | 840 |
| gcgtcggtgt | tggagatctg | caccacattt | cggcccacc | ggttcttcac | gatcttggcc | 900 |
| ttgctagact | gctccttcag | cgcgcgctgc | ccgttttcgc | tcgtcacatc | catttcaatc | 960 |
| acgtgctcct | tatttatcat | aatgctcccg | tgtagacact | taagctcgcc | ttcgatctca | 1020 |
| gcgcagcggt | gcagccacaa | cgcgcagccc | gtgggctcgt | ggtgcttgta | ggttaccctct | 1080 |
| gcaaacgact | gcaggtacgc | ctgcaggaat | cgccccatca | tcgtcacaaa | ggtcttgttg | 1140 |
| ctggtgaagg | tcagctgcaa | cccgcggtgc | tcctcgttta | gccaggtctt | gcatacggcc | 1200 |
| gccagagctt | ccacttggtc | aggcagtagc | ttgaagtttg | cctttagatc | gttatccacg | 1260 |
| tggtacttgt | ccatcaacgc | gcgcgcagcc | tccatgccct | tctcccacgc | agacacgatc | 1320 |
| ggcaggctca | gcgggtttat | caccgtgctt | tcactttccg | cttcactgga | ctcttccttt | 1380 |
| tcctcttgcg | tccgcatacc | ccgcgccact | gggtcgtctt | cattcagccg | ccgcaccgtg | 1440 |
| cgcttacctc | ccttgccgtg | cttgattagc | accggtgggt | tgctgaaacc | caccatttgt | 1500 |
| agcgccacat | cttctctttc | ttcctcgctg | tccacgatca | cctctgggga | tggcgggcgc | 1560 |
| tcgggcttgg | gagaggggcg | cttctttttc | tttttggacg | caatggccaa | atccgccgtc | 1620 |
| gaggtcgatg | gccgcgggct | gggtgtgcgc | ggcaccagcg | catcttgtga | cgagtcttct | 1680 |
| tcgtcctcgg | actcgagacg | ccgcctcagc | cgcttttttg | ggggcgcgcg | gggaggcggc | 1740 |
| ggcgacggcg | acgggacga | cacgtcctcc | atggttggtg | gacgtcgcgc | cgcaccgcgt | 1800 |
| ccgcgctcgg | gggtggttc | gcgctgctcc | tcttcccgac | tggccatttc | cttctcctat | 1860 |
| aggcagaaaa | agatcatgga | gtcagtcgag | aaggaggaca | gcctaaccgc | cccctttgag | 1920 |
| ttcgccacca | ccgcctccac | cgatgccgcc | aacgcgccta | ccaccttccc | cgtcgaggca | 1980 |
| cccccgcttg | aggaggagga | agtgattatc | gagcaggacc | caggttttgt | aagcgaagac | 2040 |
| gacgaggatc | gctcagtacc | aacagaggat | aaaaagcaag | accaggacga | cgcagaggca | 2100 |

```
aacgaggaac aagtcgggcg gggggaccaa aggcatggcg actacctaga tgtgggagac   2160
gacgtgctgt tgaagcatct gcagcgccag tgcgccatta tctgcgacgc gttgcaagag   2220
cgcagcgatg tgcccctcgc catagcggat gtcagccttg cctacgaacg ccacctgttc   2280
tcaccgcgcg tacccccaa acgccaagaa aacggcacat gcgagcccaa cccgcgcctc    2340
aacttctacc ccgtatttgc cgtgccagag gtgcttgcca cctatcacat cttttttccaa  2400 aactgcaaga taccctatc ctgccgtgcc aaccgcagcc gagcggacaa gcagctggcc    2460
ttgcggcagg gcgctgtcat acctgatatc gcctcgctcg acgaagtgcc aaaaatcttt   2520
gagggtcttg gacgcgacga gaaacgcgcg gcaaacgctc tgcaacaaga aaacagcgaa   2580
aatgaaagtc actgtggagt gctggtggaa cttgagggtg acaacgcgcg cctagccgtg   2640
ctgaaacgca gcatcgaggt cacccacttt gcctacccgg cacttaacct accccccaag   2700
gttatgagca cagtcatgag cgagctgatc gtgcgccgtg cacgacccct ggagagggat   2760
gcaaacttgc aagaacaaac cgaggagggc ctacccgcag ttggcgatga gcagctggcg   2820
cgctggcttg agacgcgcga gcctgccgac ttggaggagc gacgcaagct aatgatggcc   2880
gcagtgcttg ttaccgtgga gcttgagtgc atgcagcggt tctttgctga cccggagatg   2940
cagcgcaagc tagaggaaac gttgcactac acctttcgcc agggctacgt gcgccaggcc   3000
tgcaaaattt ccaacgtgga gctctgcaac ctggtctcct accttggaat tttgcacgaa   3060
aaccgcctcg gcaaaacgt gcttcattcc acgtcaagg gcgaggcgcg ccgcgactac     3120
gtccgcgact gcgtttactt atttctgtgc tacacctggc aaacggccat gggcgtgtgg   3180
cagcaatgcc tggaggagcg caacctaaag gagctgcaga agctgctaaa gcaaaacttg   3240
aaggacctat ggacggcctt caacgagcgc tccgtggccg cgcacctggc ggacattatc   3300
ttccccgaac gcctgcttaa aaccctgcaa cagggtctgc cagacttcac cagtcaaagc   3360
atgttgcaaa actttaggaa ctttatccta gagcgttcag gaattctgcc cgccacctgc   3420
tgtgcgcttc ctagcgactt tgtgcccatt aagtaccgtg aatgccctcc gccgctttgg   3480
ggtcactgct accttctgca gctagccaac taccttgcct accactccga catcatggaa   3540
gacgtgagcg gtgacggcct actggagtgt cactgtcgct gcaacctatg cacccccgcac  3600 cgctccctgg tctgcaattc gcaactgctt agcgaaagtc aaattatcgg tacctttgag   3660
ctgcagggtc cctcgcctga cgaaaagtcc gcggctccgg ggttgaaact cactccgggg   3720
ctgtggacgt cggcttacct tcgcaaattt gtacctgagg actaccacgc ccacgagatt   3780
aggttctacg aagaccaatc ccgccgcca aatgcggagc ttaccgcctg cgtcattacc    3840
cagggccaca tccttggcca attgcaagcc atcaacaaag cccgccaaga gtttctgcta   3900
cgaaagggac gggggttta cctggacccc cagtccggcg aggagctcaa cccaatcccc    3960
ccgccgccgc agccctatca gcagccgcgg gcccttgctt cccaggatgg cacccaaaaa   4020
gaagctgcag ctgccgccgc cgccaccac ggacgaggag gaatactggg acagtcaggc    4080
agaggaggtt ttggacgagg aggaggagat gatggaagac tgggacagcc tagacgaagc   4140
ttccgaggcc gaagaggtgt cagacgaaac accgtcaccc tcggtcgcat tcccctcgcc   4200
ggcgccccag aaattggcaa ccgttccag catcgctaca acctccgctc tcaggcgcc    4260 gccggcactg cctgttcgcc gacccaaccg tagatgggac accactggaa ccagggccgg   4320
taagtctaag cagccgccgc cgttagccca agagcaacaa cagcgccaag gctaccgctc   4380
gtggcgcggg cacaagaacg ccatagttgc ttgcttgcaa gactgtgggg gcaacatctc   4440
cttcgcccgc cgctttcttc tctaccatca cggcgtggcc ttccccccgta acatcctgca  4500
```

```
ttactaccgt catctctaca gcccctactg caccggcggc agcggcagcg gcagcaacag    4560
cagcggtcac acagaagcaa aggcgaccgg atagcaagac tctgacaaag cccaagaaat    4620
ccacagcggc ggcagcagca ggaggaggag cgctgcgtct ggcgcccaac gaacccgtat    4680
cgacccgcga gcttagaaat aggatttttc ccactctgta tgctatattt caacaaagca    4740
ggggccaaga acaagagctg aaaataaaaa acaggtctct gcgctccctc acccgcagct    4800
gcctgtatca caaagcgaa gatcagcttc ggcgcacgct ggaagacgcg gaggctctct     4860
tcagcaaata ctgcgcgctg actcttaagg actagtttcg cgccctttct caaatttaag    4920
cgcgaaaact acgtcatctc cagcggccac acccggcgcc agcacctgtc gtcagcgcca    4980
ttatgagcaa ggaaattccc acgccctaca tgtggagtta ccagccacaa atgggacttg    5040
cggctggagc tgcccaagac tactcaaccc gaataaacta catgagcgcg gaccccaca     5100
tgatatcccg ggtcaacgga atccgcgccc accgaaaccg aattctcctc gaacaggcgg    5160
ctattaccac cacacctcgt aataaccttra atccccgtag ttggcccgct gccctggtgt    5220
accaggaaag tcccgctccc accactgtgg tacttcccag agacgcccag gccgaagttc    5280
agatgactaa ctcaggggcg cagcttgcgg cggcttttcg tcacagggtg cggtcgcccg    5340
ggcgttttag ggcggagtaa cttgcatgta ttgggaattg tagtttttttt aaaatgggaa    5400
gtgacgtatc gtgggaaaac ggaagtgaag atttgaggaa gttgtgggtt ttttggcttt    5460
cgtttctggg cgtaggttcg cgtgcggttt tctgggtgtt ttttgtggac tttaaccgtt    5520
acgtcatttt ttagtcctat atatactcgc tctgtacttg gccctttta cactgtgact      5580
gattgagctg gtgccgtgtc gagtggtgtt ttttaatagg tttttttact ggtaaggctg    5640
actgttatgg ctgccgctgt ggaagcgctg tatgttgttc tggagcggga gggtgctatt    5700
ttgcctaggc aggagggttt ttcaggtgtt tatgtgtttt tctctcctat taattttgtt    5760
atacctccta tgggggctgt aatgttgtct ctacgcctgc gggtatgtat tcccccgggc    5820
tatttcggtc gctttttagc actgaccgat gttaaccaac ctgatgtgtt taccgagtct    5880
tacattatga ctccggacat gaccgaggaa ctgtcggtgg tgcttttaa tcacggtgac     5940
cagtttttt acggtcacgc cggcatggcc gtagtccgtc ttatgcttat aagggttgtt    6000
tttcctgttg taagacaggc ttctaatgtt taaatgtttt ttttttttgtt attttatttt    6060
gtgtttaatg caggaacccg cagacatgtt tgagagaaaa atggtgtctt tttctgtggt    6120
ggttccggaa cttacctgcc tttatctgca tgagcatgac tacgatgtgc ttgctttttt    6180
gcgcgaggct ttgcctgatt ttttgagcag caccttgcat tttatatcgc cgcccatgca    6240
acaagcttac ataggggcta cgctggttag catagctccg agtatgcgtg tcataatcag    6300
tgtgggttct tttgtcatgg ttcctggcgg ggaagtggcc gcgctggtcc gtgcagacct    6360
gcacgattat gttcagctgg ccctgcgaag ggacctacgg gatcgcggta ttttgttaa     6420
tgttccgctt ttgaatctta tacaggtctg tgaggaacct gaattttgc aatcatgatt     6480
cgctgcttga ggctgaaggt ggagggcgct ctggagcaga ttttttacaat ggccggactt   6540
aatattcggg atttgcttag agacatattg ataaggtggc gagatgaaaa ttatttgggc    6600
atggttgaag gtgctggaat gtttatagag gagattcacc ctgaagggtt tagccttrtac   6660
gtccacttgg acgtgagggc agtttgcctt ttggaagcca ttgtgcaaca tcttacaaat    6720
gccattatct gttctttggc tgtagagttt gaccacgcca ccggagggga gcgcgttcac    6780
ttaatagatc ttcattttga ggtttttggat aatctttttgg aataaaaaaa aaaaaacatg   6840
```

```
gttcttccag ctcttcccgc tcctcccgtg tgtgactcgc agaacgaatg tgtaggttgg    6900
ctgggtgtgg cttattctgc ggtggtggat gttatcaggg cagcggcgca tgaaggagtt    6960
tacatagaac ccgaagccag ggggcgcctg gatgctttga gagagtggat atactacaac    7020
tactacacag agcgagctaa gcgacgagac cggagacgca gatctgtttg tcacgcccgc    7080
acctggtttt gcttcaggaa atatgactac gtccggcgtt ccatttggca tgacactacg    7140
accaacacga tctcggttgt ctcggcgcac tccgtacagt agggatcgcc tacctccttt    7200
tgagacagag accgcgcta ccatactgga ggatcatccg ctgctgcccg aatgtaacac    7260
tttgacaatg cacaacgtga gttacgtgcg aggtcttccc tgcagtgtgg gatttacgct    7320
gattcaggaa tgggttgttc cctgggatat ggttctgacg cgggaggagc ttgtaatcct    7380
gaggaagtgt atgcacgtgt gcctgtgttg tgccaacatt gatatcatga cgagcatgat    7440
gatccatggt tacgagtcct gggctctcca ctgtcattgt tccagtcccg gttcctgca    7500 gtgcatagcc ggcgggcagg ttttggccag ctggtttagg atggtggtgg atggcgccat    7560
gtttaatcag aggtttatat ggtaccggga ggtggtgaat tacaacatgc caaaagaggt    7620
aatgtttatg tccagcgtgt ttatgagggg tcgccactta atctacctgc gcttgtggta    7680
tgatggccac gtgggttctg tggtcccgc catgagcttt ggatacagcg ccttgcactg    7740
tgggattttg aacaatattg tggtgctgtg ctgcagttac tgtgctgatt aagtgagat    7800 cagggtgcgc tgctgtgccc ggaggacaag gcgtctcatg ctgcgggcgg tgcgaatcat    7860
cgctgaggag accactgcca tgttgtattc ctgcaggacg gagcggcggc ggcagcagtt    7920
tattcgcgcg ctgctgcagc accaccgccc tatcctgatg cacgattatg actctacccc    7980
catgtaggcg tggacttccc cttcgccgcc cgttgagcaa ccgcaagttg dacagcagcc    8040
tgtggctcag cagctggaca gcgacatgaa cttaagcgag ctgcccgggg agtttattaa    8100
tatcactgat gagcgtttgg ctcgacagga aaccgtgtgg aatataacac ctaagaatat    8160
gtctgttacc catgatatga tgcttttta ggccagccgg ggagaaagga ctgtgtactc    8220
tgtgtgttgg gagggaggtg gcaggttgaa tactagggtt ctgtgagttt gattaaggta    8280
cggtgatcaa tataagctat gtggtggtgg ggctatacta ctgaatgaaa atgacttga    8340 aattttctgc aattgaaaaa taaacacgtt gaaacataac atgcaacagg ttcacgattc    8400
tttattcctg ggcaatgtag gagaaggtgt aagagttggt agcaaaagtt tcagtggtgt    8460 atttccact ttcccaggac catgtaaaag acatagagta agtgcttacc tcgctagttt    8520
ctgtggattc actagaatcg atgtaggatg ttgcccctcc tgacgcggta ggagaagggg    8580
agggtgccct gcatgtctgc cgctgctctt gctcttgccg ctgctgagga gggggggcgca    8640 tctgccgcag caccgatgc atctgggaaa agcaaaaaag gggctcgtcc ctgtttccgg    8700
aggaatttgc aagcgggtc ttgcatgacg gggaggcaaa cccccgttcg ccgcagtccg    8760
gccggcccga gactcgaacc gggggtcctg cgactcaacc cttggaaaat aaccctccgg    8820
ctacagggag cgagccactt aatgctttcg ctttccagcc taaccgctta cgccgcgcgc    8880
ggccagtggc caaaaaagct agcgcagcag ccgccgcgcc tggaaggaag ccaaaaggag    8940
cgctcccccg ttgtctgacg tcgcacacct gggttcgaca cgcgggcggt aaccgcatgg    9000
atcacggcgg acggccggat ccggggttcg aaccccggtc gtccgccatg ataccccttgc    9060 gaatttatcc accagaccac ggaagagtgc ccgcttacag gctctccttt tgcacggtct    9120
agagcgtcaa cgactgcgca cgcctcaccg gccagagcgt cccgaccatg gagcactttt    9180
tgccgctgcg caacatctgg aaccgcgtcc gcgactttcc gcgcgcctcc accaccgccg    9240
```

```
ccggcatcac ctggatgtcc aggtacatct acggattacg tcgacgttta aaccatatga   9300
tcagctcact caaaggcggt aatacggtta tccacagaat caggggataa cgcaggaaag   9360
aacatgtgag caaaaggcca gcaaaaggcc aggaaccgta aaaaggccgc gttgctggcg   9420 ttttccata ggctccgccc ccctgacgag catcacaaaa atcgacgctc aagtcagagg    9480
tggcgaaacc cgacaggact ataaagatac caggcgtttc ccctggaag ctccctcgtg    9540 cgctctcctg ttccgaccct gccgcttacc ggatacctgt ccgcctttct ccttcggga    9600 agcgtggcgc tttctcatag ctcacgctgt aggtatctca gttcggtgta ggtcgttcgc   9660
tccaagctgg gctgtgtgca cgaacccccc gttcagcccg accgctgcgc cttatccggt   9720
aactatcgtc ttgagtccaa cccggtaaga cacgacttat cgccactggc agcagccact   9780
ggtaacagga ttagcagagc gaggtatgta ggcggtgcta cagagttctt gaagtggtgg   9840
cctaactacg gctacactag aagaacagta tttggtatct gcgctctgct gaagccagtt   9900
accttcggaa aaagagttgg tagctcttga tccggcaaac aaaccaccgc tggtagcggt   9960
ggtttttttg tttgcaagca gcagattacg cgcagaaaaa aaggatctca agaagatcct  10020
ttgatctttt ctacggggtc tgacgctcag tggaacgaaa actcacgtta agggattttg  10080
gtcatgagat tatcaaaaag gatcttcacc tagatccttt taaattaaaa atgaagtttt  10140
aaatcaatct aaagtatata tgagtaaact tggtctgaca gttaccaatg cttaatcagt  10200
gaggcaccta tctcagcgat ctgtctattt cgttcatcca tagttgcctg actccccgtc  10260
gtgtagataa ctacgatacg ggagggctta ccatctggcc ccagtgctgc aatgataccg  10320
cgagacccac gctcaccggc tccagattta tcagcaataa accagccagc cggaagggcc  10380
gagcgcagaa gtggtcctgc aactttatcc gcctccatcc agtctattaa ttgttgccgg  10440
gaagctagag taagtagttc gccagttaat agtttgcgca acgttgttgc cattgctaca  10500
ggcatcgtgg tgtcacgctc gtcgtttggt atggcttcat tcagctccgg ttcccaacga  10560
tcaaggcgag ttacatgatc ccccatgttg tgcaaaaaag cggttagctc cttcggtcct  10620
ccgatcgttg tcagaagtaa gttggccgca gtgttatcac tcatggttat ggcagcactg  10680
cataattctc ttactgtcat gccatccgta agatgctttt ctgtgactgg tgagtactca  10740
accaagtcat tctgagaata gtgtatgcgg cgaccgagtt gctcttgccc ggcgtcaata  10800
cgggataata ccgcgccaca tagcagaact ttaaaagtgc tcatcattgg aaaacgttct  10860
tcggggcgaa aactctcaag gatcttaccg ctgttgagat ccagttcgat gtaacccact  10920
cgtgcaccca actgatcttc agcatctttt actttcacca gcgtttctgg gtgagcaaaa  10980
acaggaaggc aaaatgccgc aaaaaaggga ataaggcga cacggaaatg ttgaatactc   11040
atactcttcc ttttcaata ttattgaagc atttatcagg gttattgtct catgagcgga   11100
tacatatttg aatgtattta gaaaaataaa caaatagggg ttccgcgcac atttccccga   11160
aaagtgccac ctaaattgta agcgttaata ttttgttaaa attcgcgtta aattttgtt    11220 aaatcagctc attttttaac caataggccg aaatcggcaa aatcccttat aaatcaaaag   11280
aatagaccga gatagggttg agtgttgttc cagtttggaa caagagtcca ctattaaaga   11340
acgtggactc caacgtcaaa gggcgaaaaa ccgtctatca gggcgatggc ccactacgtg   11400
aaccatcacc ctaatcaagt tttttggggt cgaggtgccg taaagcacta atcggaacc    11460 ctaaagggag cccccgattt agagcttgac ggggaaagcc ggcgaacgtg gcgagaaagg   11520
aagggaagaa agcgaaagga gcgggcgcta gggcgctggc aagtgtagcg gtcacgctgc   11580
```
gcgtaaccac cacacccgcc gcgcttaatg cgccgctaca gggcgcgatg gatcc    11635

<210> SEQ ID NO 46
<211> LENGTH: 5336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
ggtacccaac tccatgctta acagtcccca ggtacagccc accctgcgtc gcaaccagga      60
acagctctac agcttcctgg agcgccactc gccctacttc cgcagccaca gtgcgcagat     120
taggagcgcc acttcttttt gtcacttgaa aaacatgtaa aataatgta ctaggagaca      180
cttctcaataa aggcaaatgt ttttatttgt acactctcgg gtgattattt accccccacc    240
cttgccgtct gcgccgttta aaaatcaaag gggttctgcc gcgcatcgct atgcgccact    300
ggcagggaca cgttgcgata ctggtgttta gtgctccact taaactcagg cacaaccatc    360
cgcggcagct cggtgaagtt ttcactccac aggctgcgca ccatcaccaa cgcgtttagc    420
aggtcgggcg ccgatatctt gaagtcgcag ttggggcctc cgccctgcgc gcgcgagttg    480
cgatacacag ggttgcagca ctggaacact atcagcgccg ggtggtgcac gctggccagc    540
acgtcttgt cggagatcag atccgcgtcc aggtcctccg cgttgctcag ggcgaacgga    600
gtcaactttg gtagctgcct tcccaaaaag ggtgcatgcc caggctttga gttgcactcg    660
caccgtagtg gcatcagaag gtgaccgtgc ccggtctggg cgttaggata cagcgcctgc    720
atgaaagcct tgatctgctt aaaagccacc tgagcctttg cgccttcaga gaagaacatg    780
ccgcaagact tgccggaaaa ctgattggcc ggacaggccg cgtcatgcac gcagcacctt    840
gcgtcggtgt tggagatctg caccacattt cggcccacc ggttcttcac gatcttggcc    900
ttgctagact gctccttcag cgcgcgctgc ccgttttcgc tcgtcacatc catttcaatc    960
acgtgctcct tatttatcat aatgctcccg tgtagacact taagctcgcc ttcgatctca   1020
gcgcagcggt gcagccacaa cgcgcagccc gtgggctcgt ggtgcttgta ggttacctct   1080
gcaaacgact gcaggtacgc ctgcaggaat cgccccatca tcgtcacaaa ggtcttgttg   1140
ctggtgaagg tcagctgcaa cccgcggtgc tcctcgttta gccaggtctt gcatacggcc   1200
gccagagctt ccacttggtc aggcagtagc ttgaagtttg cctttagatc gttatccacg   1260
tggtacttgt ccatcaacgc gcgcgcagcc tccatgccct tctcccacgc agacacgatc   1320
ggcaggctca gcgggtttat caccgtgctt tcactttccg cttcactgga ctcttccttt   1380
tcctcttgcg tccgcatacc ccgcgccact gggtcgtctt cattcagccg ccgcaccgtg   1440
cgcttacctc ccttgccgtg cttgattagc accgtgggt tgctgaaacc caccatttgt    1500
agcgccacat cttctctttc ttcctcgctg tccacgatca cctctgggga tggcgggcgc   1560
tcgggcttgg gagaggggcg cttcttttc tttttggacg caatggccaa atccgccgtc   1620
gaggtcgatg gccgcgggct gggtgtgcgc ggcaccagcg catcttgtga cgagtcttct   1680
tcgtcctcgg actcgagacg ccgcctcagc cgctttttg ggggcgcgcg gggaggcggc   1740
ggcgacggcg acgggacga cacgtcctcc atggttggtg gacgtcgcgc cgcaccgcgt    1800
ccgcgctcgg gggtggtttc gcgctgctcc tcttcccgac tggccatttc cttctcctat   1860
aggcagaaaa agatcatgga gtcagtcgag aaggaggaca gcctaaccgc cccctttgag   1920
ttcgccacca ccgcctccac cgatgccgcc aacgcgccta ccaccttccc cgtcgaggca   1980
```

```
cccccgcttg aggaggagga agtgattatc gagcaggacc caggttttgt aagcgaagac    2040
gacgaggatc gctcagtacc aacagaggat aaaaagcaag accaggacga cgcagaggca    2100
aacgaggaac aagtcgggcg gggggaccaa aggcatggcg actacctaga tgtgggagac    2160
gacgtgctgt tgaagcatct gcagcgccag tgcgccatta tctgcgacgc gttgcaagag    2220
cgcagcgatg tgcccctcgc catagcggat gtcagccttg cctacgaacg ccacctgttc    2280
tcaccgcgcg tacccccaa acgccaagaa aacggcacat gcgagcccaa cccgcgcctc     2340
aacttctacc ccgtatttgc cgtgccagag gtgcttgcca cctatcacat cttttttccaa   2400 aactgcaaga taccoctate ctgcogtgcc aaccgcagcc gagcggacaa gcagctggcc    2460
ttgcggcagg gcgctgtcat acctgatatc gcctcgctcg acgaagtgcc aaaaatcttt    2520
gagggtcttg gacgcgacga gaaacgcgcg gcaaacgctc tgcaacaaga aaacagcgaa    2580
aatgaaagtc actgtggagt gctggtggaa cttgagggtg acaacgcgcg cctagccgtg    2640
ctgaaacgca gcatcgaggt cacccacttt gcctacccgg cacttaacct accccccaag    2700
gttatgagca cagtcatgag cgagctgatc gtgcgccgtg cacgacccct ggagagggat    2760
gcaaacttgc aagaacaaac cgaggagggc ctaccgcag ttggcgatga gcagctggcg      2820
cgctggcttg agacgcgcga gcctgccgac ttggaggagc gacgcaagct aatgatggcc    2880
gcagtgcttg ttaccgtgga gcttgagtgc atgcagcggt tctttgctga cccggagatg    2940
cagcgcaagc tagaggaaac gttgcactac acctttcgcc agggctacgt gcgccaggcc    3000
tgcaaaattt ccaacgtgga gctctgcaac ctggtctcct accttggaat tttgcacgaa    3060
aaccgcctcg ggcaaaacgt gcttcattcc acgctcaagg gcgaggcgcg ccgcgactac    3120
gtccgcgact gcgtttactt atttctgtgc tacacctggc aaacggccat gggcgtgtgg    3180
cagcaatgcc tggaggagcg caacctaaag gagctgcaga agctgctaaa gcaaaacttg    3240
aaggacctat ggacggcctt caacgagcgc tccgtggccg cgcacctggc ggacattatc    3300
ttccccgaac gcctgcttaa aaccctgcaa cagggtctgc cagacttcac cagtcaaagc    3360
atgttgcaaa actttaggaa ctttatccta gagcgttcag gaattctgcc cgccacctgc    3420
tgtgcgcttc ctagcgactt tgtgcccatt aagtaccgtg aatgccctcc gccgctttgg    3480
ggtcactgct accttctgca gctagccaac taccttgcct accactccga catcatggaa    3540
gacgtgagcg gtgacggcct actggagtgt cactgtcgct gcaacctatg caccccgcac    3600
cgctccctgg tctgcaattc gcaactgctt agcgaaagtc aaattatcgg tacctttgag    3660
ctgcagggtc cctcgcctga cgaaaagtcc gcggctccgg ggttgaaact cactccgggg    3720
ctgtggacgt cggcttacct tcgcaaattt gtacctgagg actaccacgc ccacgagatt    3780
aggttctacg aagaccaatc ccgcccgcca aatgcggagc ttaccgcctg cgtcattacc    3840
cagggccaca tccttggcca attgcaagcc atcaacaaag cccgccaaga gtttctgcta    3900
cgaaagggac ggggggttta cctggacccc cagtccggcg aggagctcaa cccaatcccc    3960
ccgccgccgc agccctatca gcagccgcgg gcccttgctt cccaggatgg cacccaaaaa    4020
gaagctgcag ctgccgccgc cgccaccac ggacgaggag gaatactggg acagtcaggc     4080
agaggaggtt ttggacgagg aggaggagat gatggaagac tggacagcc tagacgaagc     4140 ttccgaggcc gaagaggtgt cagacgaaac accgtcaccc tcggtcgcat tcccctcgcc    4200
ggcgccccag aaaattggcaa ccgttcccag catcgctaca acctccgctc ctcaggcgcc   4260 gccgcactg cctgttcgcc gacccaaccg tagatgggac accactggaa ccagggccgg     4320
taagtctaag cagccgccgc cgttagccca agagcaacaa cagcgccaag gctaccgctc    4380
```

```
gtggcgcggg cacaagaacg ccatagttgc ttgcttgcaa gactgtgggg gcaacatctc    4440
cttcgcccgc cgctttcttc tctaccatca cggcgtggcc ttcccccgta acatcctgca    4500
ttactaccgt catctctaca gcccctactg caccggcggc agcggcagcg gcagcaacag    4560
cagcggtcac acagaagcaa aggcgaccgg atagcaagac tctgacaaag cccaagaaat    4620
ccacagcggc ggcagcagca ggaggaggag cgctgcgtct ggcgcccaac gaacccgtat    4680
cgacccgcga gcttagaaat aggattttc ccactctgta tgctatattt caacaaagca    4740
ggggccaaga acaagagctg aaaataaaaa acaggtctct gcgctccctc acccgcagct    4800
gcctgtatca aaaagcgaa gatcagcttc ggcgcacgct ggaagacgcg gaggctctct    4860
tcagcaaata ctgcgcgctg actcttaagg actagtttcg cgccctttct caaatttaag    4920
cgcgaaaact acgtcatctc cagcggccac acccggcgcc agcacctgtc gtcagcgcca    4980
ttatgagcaa ggaaattccc acgccctaca tgtggagtta ccagccacaa atgggacttg    5040
cggctggagc tgcccaagac tactcaaccc gaataaacta catgagcgcg gaccccaca    5100 tgatatcccg ggtcaacgga atccgcgccc accgaaaccg aattctcctc gaacaggcgg    5160
ctattaccac cacacctcgt aataaccta atccccgtag ttggcccgct gccctggtgt    5220
accaggaaag tcccgctccc accactgtgg tacttcccag agacgcccag gccgaagttc    5280
agatgactaa ctcaggggcg cagcttgcgg gcggctttcg tcacagggtg cggtcg        5336

<210> SEQ ID NO 47
<211> LENGTH: 3201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
cccgggcgtt tagggcgga gtaacttgca tgtattggga attgtagttt ttttaaaatg        60
ggaagtgacg tatcgtggga aaacggaagt gaagatttga ggaagttgtg ggttttttgg      120
ctttcgtttc tgggcgtagg ttcgcgtgcg gttttctggg tgttttttgt ggactttaac      180
cgttacgtca tttttagtc ctatatatac tcgctctgta cttggcccct tttacactgt      240
gactgattga gctggtgccg tgtcgagtgg tgttttttaa taggtttttt tactggtaag      300
gctgactgtt atggctgccg ctgtggaagc gctgtatgtt gttctggagc gggagggtgc      360
tattttgcct aggcaggagg gttttcagg tgtttatgtg ttttctctc ctattaattt       420 tgttataccct cctatggggg ctgtaatgtt gtctctacgc ctgcgggtat gtattccccc    480
gggctatttc ggtcgctttt tagcactgac cgatgttaac caacctgatg tgttaccga       540 gtcttacatt atgactccgg acatgaccga ggaactgtcg gtggtgcttt ttaatcacgg      600
tgaccagttt ttttacggtc acgccggcat ggccgtagtc cgtcttatgc ttataagggt      660
tgtttttcct gttgtaagac aggcttctaa tgtttaaatg ttttttttt tgttattta        720 ttttgtgttt aatgcaggaa cccgcagaca tgtttgagag aaaaatggtg tcttttttctg     780 tggtggttcc ggaacttacc tgcctttatc tgcatgagca tgactacgat gtgcttgctt      840
ttttgcgcga ggctttgcct gattttttga gcagcaccct gcatttata tcgccgccca       900 tgcaacaagc ttacatagg gctacgctgg ttagcatagc tccgagtatg cgtgtcataa       960
tcagtgtggg ttcttttgtc atggttcctg gcggggaagt ggccgcgctg gtccgtgcag     1020
acctgcacga ttatgttcag ctggccctgc gaagggacct acgggatcgc ggtattttg     1080
```

```
ttaatgttcc gcttttgaat cttatacagg tctgtgagga acctgaattt ttgcaatcat    1140
gattcgctgc ttgaggctga aggtggaggg cgctctggag cagatttta caatggccgg    1200 acttaatatt cgggatttgc ttagagacat attgataagg tggcgagatg aaaattattt    1260
gggcatggtt gaaggtgctg gaatgtttat agaggagatt caccctgaag ggtttagcct    1320
ttacgtccac ttggacgtga gggcagtttg ccttttggaa gccattgtgc aacatcttac    1380
aaatgccatt atctgttctt tggctgtaga gtttgaccac gccaccggag gggagcgcgt    1440
tcacttaata gatcttcatt ttgaggtttt ggataatctt ttggaataaa aaaaaaaaaa    1500
catggttctt ccagctcttc ccgctcctcc cgtgtgtgac tcgcagaacg aatgtgtagg    1560
ttggctgggt gtggcttatt ctgcggtggt ggatgttatc agggcagcgg cgcatgaagg    1620
agtttacata gaacccgaag ccaggggggcg cctggatgct ttgagagagt ggatatacta    1680
caactactac acagagcgag ctaagcgacg agaccggaga cgcagatctg tttgtcacgc    1740
ccgcacctgg ttttgcttca ggaaatatga ctacgtccgg cgttccattt ggcatgacac    1800
tacgaccaac acgatctcgg ttgtctcggc gcactccgta cagtagggat cgcctacctc    1860
cttttgagac agagaccccgc gctaccatac tggaggatca tccgctgctg cccgaatgta    1920
acactttgac aatgcacaac gtgagttacg tgcgaggtct tccctgcagt gtgggattta    1980
cgctgattca ggaatgggtt gttccctggg atatggttct gacgcgggag gagcttgtaa    2040
tcctgaggaa gtgtatgcac gtgtgcctgt gttgtgccaa cattgatatc atgacgagca    2100
tgatgatcca tggttacgag tcctgggctc tccactgtca ttgttccagt cccggttccc    2160
tgcagtgcat agccggcggg caggttttgg ccagctggtt taggatggtg gtggatggcg    2220
ccatgtttaa tcagaggttt atatggtacc gggaggtggt gaattacaac atgccaaaag    2280
aggtaatgtt tatgtccagc gtgtttatga ggggtcgcca cttaatctac ctgcgcttgt    2340
ggtatgatgg ccacgtgggt tctgtggtcc ccgccatgag cttggatac agcgccttgc    2400 actgtgggat tttgaacaat attgtggtgc tgtgctgcag ttactgtgct gatttaagtg    2460
agatcagggt gcgctgctgt gcccggagga caaggcgtct catgctgcgg gcggtgcgaa    2520
tcatcgctga ggagaccact gccatgttgt attcctgcag gacggagcgg cggcggcagc    2580
agtttattcg cgcgctgctg cagcaccacc gccctatcct gatgcacgat tatgactcta    2640
cccccatgta ggcgtggact tccccttcgc cgcccgttga gcaaccgcaa gttggacagc    2700
agcctgtggc tcagcagctg gacagcgaca tgaacttaag cgagctgccc ggggagttta    2760
ttaatatcac tgatgagcgt ttggctcgac aggaaaccgt gtggaatata acctaaga    2820 atatgtctgt tacccatgat atgatgcttt ttaaggccag ccggggagaa aggactgtgt    2880
actctgtgtg ttgggaggga ggtggcaggt tgaatactag ggttctgtga gttttgattaa    2940 ggtacggtga tcaatataag ctatgtggtg gtggggctat actactgaat gaaaaatgac    3000
ttgaaatttt ctgcaattga aaataaaca cgttgaaaca taacatgcaa caggttcacg    3060
attctttatt cctgggcaat gtaggagaag gtgtaagagt tggtagcaaa agtttcagtg    3120
gtgtattttc cactttccca ggaccatgta aaagacatag agtaagtgct tacctcgcta    3180
gtttctgtgg attcactaga a                                            3201
```

<210> SEQ ID NO 48
<211> LENGTH: 743
<212> TYPE: DNA
<213> ORGANISM: Artificial Sequence
<220> FEATURE:

<223> OTHER INFORMATION: Description of Artificial Sequence: Synthetic
     polynucleotide

<400> SEQUENCE: 48
tcgatgtagg atgttgcccc tcctgacgcg gtaggagaag gggagggtgc cctgcatgtc    60
tgccgctgct cttgctcttg ccgctgctga ggaggggggc gcatctgccg cagcaccgga   120
tgcatctggg aaaagcaaaa aagggggctcg tccctgtttc cggaggaatt tgcaagcggg  180
gtcttgcatg acggggaggc aaaccccgt tcgccgcagt ccggccggcc cgagactcga   240
accgggggtc ctgcgactca acccttggaa aataaccctc cggctacagg gagcgagcca   300
cttaatgctt tcgctttcca gcctaaccgc ttacgccgcg cgcggccagt ggccaaaaaa   360
gctagcgcag cagccgccgc gcctggaagg aagccaaaag gagcgctccc ccgttgtctg   420
acgtcgcaca cctgggttcg acacgcgggc ggtaaccgca tggatcacgg cggacggccg   480
gatccggggt tcgaaccccg gtcgtccgcc atgataccct tgcgaattta tccaccagac   540
cacggaagag tgcccgctta caggctctcc ttttgcacgg tctagagcgt caacgactgc   600
gcacgcctca ccggccagag cgtcccgacc atggagcact ttttgccgct gcgcaacatc   660
tggaaccgcg tccgcgactt tccgcgcgcc tccaccaccg ccgccggcat cacctggatg   720
tccaggtaca tctacggatt acg                                           743

<210> SEQ ID NO 49
<211> LENGTH: 160
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 49
aaggggctcg tccctgtttc cggaggaatt tgcaagcggg gtcttgcatg acggggaggc    60 aaaccccgt tcgccgcagt ccggccggcc cgagactcga accgggggtc ctgcgactca   120
acccttggaa aataaccctc cggctacagg gagcgagcca                         160

<210> SEQ ID NO 50
<211> LENGTH: 162
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 50
aaaggagcgc tcccccgttg tctgacgtcg cacacctggg ttcgacacgc gggcggtaac    60
cgcatggatc acggcggacg gccggatccg gggttcgaac cccggtcgtc cgccatgata  120
cccttgcgaa tttatccacc agaccacgga agagtgcccg ct                      162

<210> SEQ ID NO 51
<211> LENGTH: 1590
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 51
ttaaaaatca aaggggttct gccgcgcatc gctatgcgcc actggcaggg acacgttgcg    60
atactggtgt ttagtgctcc acttaaactc aggcacaacc atccgcggca gctcggtgaa  120

```
gttttcactc cacaggctgc gcaccatcac caacgcgttt agcaggtcgg gcgccgatat     180
cttgaagtcg cagttggggc ctccgccctg cgcgcgcgag ttgcgataca cagggttgca     240
gcactggaac actatcagcg ccgggtggtg cacgctggcc agcacgctct tgtcggagat     300
cagatccgcg tccaggtcct ccgcgttgct cagggcgaac ggagtcaact ttggtagctg     360
ccttcccaaa aagggtgcat gcccaggctt tgagttgcac tcgcaccgta gtggcatcag     420
aaggtgaccg tgcccggtct gggcgttagg atacagcgcc tgcatgaaag ccttgatctg     480
cttaaaagcc acctgagcct tgcgccttc agagaagaac atgccgcaag acttgccgga      540
aaactgattg gccggacagg ccgcgtcatg cacgcagcac cttgcgtcgg tgttggagat     600
ctgcaccaca tttcggcccc accggttctt cacgatcttg gccttgctag actgctcctt     660
cagcgcgcgc tgcccgtttt cgctcgtcac atccatttca atcacgtgct ccttatttat     720
cataatgctc ccgtgtagac acttaagctc gccttcgatc tcagcgcagc ggtgcagcca     780
caacgcgcag cccgtgggct cgtggtgctt gtaggttacc tctgcaaacg actgcaggta     840
cgcctgcagg aatcgcccca tcatcgtcac aaaggtcttg ttgctggtga aggtcagctg     900
caacccgcgc tgctcctcgt ttagccaggt cttgcatacg gccgcagag cttccacttg      960 gtcaggcagt agcttgaagt tgcctttag atcgttatcc acgtggtact tgtccatcaa      1020
cgcgcgcgca gcctccatgc ccttctccca cgcagacacg atcggcaggc tcagcgggtt    1080
tatcaccgtg ctttcacttt ccgcttcact ggactcttcc ttttcctctt gcgtccgcat     1140
accccgcgcc actgggtcgt cttcattcag ccgccgcacc gtgcgcttac ctcccttgcc     1200
gtgcttgatt agcaccggtg ggttgctgaa acccaccatt tgtagcgcca catcttctct     1260
ttcttcctcg ctgtccacga tcacctctgg ggatggcggg cgctcgggct tgggagaggg     1320
gcgcttcttt ttcttttgg acgcaatggc caaatccgcc gtcgaggtcg atggccgcgg      1380
gctgggtgtg cgcggcacca gcgcatcttg tgacgagtct tcttcgtcct cggactcgag    1440
acgccgcctc agccgctttt ttggggggcgc gcggggaggc ggcggcgacg cgacggga     1500 cgacacgtcc tccatggttg gtggacgtcg cgccgcaccg cgtccgcgct cggggtggt     1560 ttcgcgctgc tcctcttccc gactggccat                                      1590
```

<210> SEQ ID NO 52
<211> LENGTH: 2446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
ttccttctcc tataggcaga aaagatcat ggagtcagtc gagaaggagg acagcctaac       60
cgcccccttt gagttcgcca ccaccgcctc caccgatgcc gccaacgcgc ctaccacctt     120
ccccgtcgag gcaccccgc ttgaggagga ggaagtgatt atcgagcagg acccaggttt     180
tgtaagcgaa gacgacgagg atcgctcagt accaacagag gataaaaagc aagaccagga    240
cgacgcagag gcaaacgagg aacaagtcgg gcgggggga caaaggcatg gcgactacct    300
agatgtggga gacgacgtgc tgttgaagca tctgcagcgc cagtgcgcca ttatctgcga     360
cgcgttgcaa gagcgcagcg atgtgcccct cgccatagcg gatgtcagcc ttgcctacga    420
acgccacctg ttctcaccgc gcgtaccccc caaacgccaa gaaaacggca catgcgagcc     480
caacccgcgc ctcaacttct accccgtatt tgccgtgcca gaggtgcttg ccacctatca     540
```

```
catcttttc caaaactgca agatacccct atcctgccgt gccaaccgca gccgagcgga    600
caagcagctg gccttgcggc agggcgctgt catacctgat atcgcctcgc tcgacgaagt    660
gccaaaaatc tttgagggtc ttggacgcga cgagaaacgc gcggcaaacg ctctgcaaca    720
agaaaacagc gaaaatgaaa gtcactgtgg agtgctggtg aacttgagg gtgacaacgc     780 gcgcctagcc gtgctgaaac gcagcatcga ggtcacccac tttgcctacc cggcacttaa    840 cctaccccc aaggttatga gcacagtcat gagcgagctg atcgtgcgcc gtgcacgacc     900
cctggagagg gatgcaaact gcaagaaca aaccgaggag ggcctacccg cagttggcga     960
tgagcagctg gcgcgctggc ttgagacgcg cgagcctgcc gacttggagg agcgacgcaa   1020
gctaatgatg gccgcagtgc ttgttaccgt ggagcttgag tgcatgcagc ggttctttgc   1080
tgacccggag atgcagcgca agctagagga aacgttgcac tacacctttc gcagggcta    1140 cgtgcgccag gcctgcaaaa tttccaacgt ggagctctgc aacctggtct cctaccttgg   1200 aatttttgcac gaaaaccgcc tcgggcaaaa cgtgcttcat tccacgctca agggcgaggc   1260
gcgccgcgac tacgtccgcg actgcgttta cttatttctg tgctacacct ggcaaacggc   1320
catgggcgtg tggcagcaat gcctggagga gcgcaaccta aaggagctgc agaagctgct   1380
aaagcaaaac ttgaaggacc tatggacggc cttcaacgag cgctccgtgg ccgcgcacct   1440
ggcggacatt atcttccccg aacgcctgct taaaaccctg caacagggtc tgccagactt   1500
caccagtcaa agcatgttgc aaaactttag gaactttatc ctagagcgtt caggaattct   1560
gcccgccacc tgctgtgcgc ttcctagcga cttttgtgccc attaagtacc gtgaatgccc   1620
tccgccgctt tggggtcact gctaccttct gcagctagcc aactaccttg cctaccactc   1680
cgacatcatg gaagacgtga gcggtgacgg cctactggag tgtcactgtc gctgcaacct   1740
atgcaccccg caccgctccc tggtctgcaa ttcgcaactg cttagcgaaa gtcaaattat   1800
cggtaccttt gagctgcagg gtccctcgcc tgacgaaaag tccgcggctc cggggttgaa   1860
actcactccg gggctgtgga cgtcggctta ccttcgcaaa tttgtacctg aggactacca   1920
cgcccacgag attaggttct acgaagacca atcccgcccg ccaaatgcgg agcttaccgc   1980
ctgcgtcatt acccagggcc acatccttgg ccaattgcaa gccatcaaca aagcccgcca   2040
agagtttctg ctacgaaagg gacgggggt ttacctggac ccccagtccg gcgaggagct    2100
caacccaatc cccccgccgc cgcagcccta tcagcagccg cgggcccttg cttcccagga   2160
tggcacccaa aaagaagctg cagctgccgc cgccgccacc cacggacgag gaggaatact   2220
gggacagtca ggcagaggag gttttggacg aggaggagga gatgatgaa gactgggaca    2280 gcctagacga agcttccgag gccgaagagg tgtcagacga aacaccgtca ccctcggtcg   2340 cattccctc gccggcgccc cagaaattgg caaccgttcc cagcatcgct acaacctccg   2400
ctcctcaggc gccgccggca ctgcctgttc gccgacccaa ccgtag                  2446
```

<210> SEQ ID NO 53
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
gccccctactg caccggcggc agcggcagcg gcagcaacag cagcggtcac acagaagcaa    60
aggcgaccgg atagcaagac tctgacaaag cccaagaaat ccacagcggc ggcagcagca   120
```

```
ggaggaggag cgctgcgtct ggcgcccaac gaacccgtat cgaccgcga gcttagaaat      180 aggatttttc ccactctgta tgctatattt caacaaagca ggggccaaga acaagagctg      240
aaaataaaaa acaggtctct gcgctccctc acccgcagct gcctgtatca caaaagcgaa      300
gatcagcttc ggcgcacgct ggaagacgcg gaggctctct tcagcaaata ctgcgcgctg      360
actcttaagg actag                                                       375

<210> SEQ ID NO 54
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atgagcaagg aaattcccac gccctacatg tggagttacc agccacaaat gggacttgcg       60
gctggagctg cccaagacta ctcaacccga ataaactaca tgagcgcggg accccacatg      120
atatcccggg tcaacggaat ccgcgcccac cgaaaccgaa ttctcctcga acaggcggct      180
attaccacca cacctcgtaa taaccttaat ccccgtagtt ggcccgctgc cctggtgtac      240
caggaaagtc ccgctcccac cactgtggta cttcccagag acgcccaggc cgaagttcag      300
atgactaact caggggcgca gcttgcgggc ggctttcgtc acagggtgcg gtcg            354

<210> SEQ ID NO 55
<211> LENGTH: 1164
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
atgactacgt ccggcgttcc atttggcatg acactacgac caacacgatc tcggttgtct       60
cggcgcactc cgtacagtag ggatcgccta cctccttttg agacagagac ccgcgctacc      120
atactggagg atcatccgct gctgcccgaa tgtaacactt tgacaatgca caacgtgagt      180
tacgtgcgag tcttccctg cagtgtggga tttacgctga ttcaggaatg ggttgttccc      240
tgggatatgg ttctgacgcg ggaggagctt gtaatcctga ggaagtgtat gcacgtgtgc      300
ctgtgttgtg ccaacattga tatcatgacg agcatgatga tccatggtta cgagtcctgg      360
gctctccact gtcattgttc cagtcccggt tccctgcagt gcatagccgg cgggcaggtt      420
ttggccagct ggtttaggat ggtggtggat ggcgccatgt ttaatcagag gtttatatgg      480
taccgggagg tggtgaatta caacatgcca aaagaggtaa tgtttatgtc cagcgtgttt      540 atgagggtc gccacttaat ctacctgcgc ttgtggtatg atggccacgt gggttctgtg      600
gtccccgcca tgagctttgg atacagcgcc ttgcactgtg ggattttgaa caatattgtg      660
gtgctgtgct gcagttactg tgctgattta agtgagatca gggtgcgctg ctgtgcccgg      720
aggacaaggc gtctcatgct gcgggcggtg cgaatcatcg ctgaggagac cactgccatg      780
ttgtattcct gcaggacgga gcggcggcgg cagcagttta ttcgcgcgct gctgcagcac      840
caccgcccta tcctgatgca cgattatgac tctaccccca tgtaggcgtg gacttcccct      900
tcgccgcccg ttgagcaacc gcaagttgga cagcagcctg tggctcagca gctggacagc      960
gacatgaact taagcgagct gcccggggag tttattaata tcactgatga gcgtttggct     1020
```

```
cgacaggaaa ccgtgtggaa tataacacct aagaatatgt ctgttaccca tgatatgatg      1080 cttttttaagg ccagccgggg agaaaggact gtgtactctg tgtgttggga gggaggtggc    1140
aggttgaata ctagggttct gtga                                              1164

<210> SEQ ID NO 56
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
atggttcttc cagctcttcc cgctcctccc gtgtgtgact cgcagaacga atgtgtaggt        60
tggctgggtg tggcttattc tgcggtggtg gatgttatca gggcagcggc gcatgaagga      120
gtttacatag aacccgaagc caggggggcgc ctggatgctt tgagagagtg gatatactac     180
aactactaca cagagcgagc taagcgacga gaccggagac gcagatctgt tgtcacgcc      240 cgcacctggt tttgcttcag gaaatatgac tacgtccggc gttccatttg gcatgacact     300
acgaccaaca cgatctcggt tgtctcggcg cactccgtac agtag                      345

<210> SEQ ID NO 57
<211> LENGTH: 319
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
atgattcgct gcttgaggct gaaggtggag ggcgctctgg agcagatttt tacaatggcc        60
ggacttaata ttcgggattt gcttagagac atattgataa ggtggcgaga tgaaaattat     120
ttgggcatgg ttgaaggtgc tggaatgttt atagaggaga ttcaccctga agggtttagc    180
ctttacgtcc acttggacgt gagggcagtt tgccttttgg aagccattgt gcaacatctt    240
acaaatgcca ttatctgttc tttggctgta gagtttgacc acgccaccgg aggggagcgc    300
gttcacttaa tagatcttc                                                   319

<210> SEQ ID NO 58
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
atgcaggaac ccgcagacat gtttgagaga aaaatggtgt cttttttctgt ggtggttccg      60 gaacttacct gcctttatct gcatgagcat gactacgatg tgcttgcttt tttgcgcgag    120
gctttgcctg atttttttgag cagcaccttg cattttatat cgccgcccat gcaacaagct   180 tacataggg ctacgctggt tagcatagct ccgagtatgc gtgtcataat cagtgtgggt     240
tcttttgtca tggttcctgg cggggaagtg gccgcgctgg tccgtgcaga cctgcacgat    300
tatgttcagc tggccctgcg aagggaccta cgggatcgcg gtattttgtt taatgttccg    360
cttttgaatc ttatacaggt ctgtgaggaa cctgaatttt tgcaatcatg a               411

<210> SEQ ID NO 59
```

<211> LENGTH: 7327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

| | | | | | |
|---|---|---|---|---|---|
| gcgcgccgat | atcgttaacg | ccccgcgccg | gccgctctag | aactagtgga | tccccggaa | 60 |
| gatcagaagt | tcctattccg | aagttcctat | tctctagaaa | gtataggaac | ttctgatctg | 120 |
| cgcagccgcc | atgccggggt | tttacgagat | tgtgattaag | gtccccagcg | accttgacga | 180 |
| gcatctgccc | ggcatttctg | acagctttgt | gaactgggtg | gccagaaagg | aatgggagtt | 240 |
| gccgccagat | tctgacatgg | atctgaatct | gattgagcag | gcacccctga | ccgtggccga | 300 |
| gaagctgcag | cgcgactttc | tgacggaatg | gcgccgtgtg | agtaaggccc | cggaggccct | 360 |
| tttctttgtg | caatttgaga | agggagagag | ctacttccac | atgcacgtgc | tcgtggaaac | 420 |
| caccggggtg | aaatccatgg | ttttgggacg | tttcctgagt | cagattcgcg | aaaaactgat | 480 |
| tcagagaatt | taccgcggga | tcgagccgac | tttgccaaac | tggttcgcgg | tcacaaagac | 540 |
| cagaaatggc | gccggaggcg | ggaacaaggt | ggtggatgag | tgctacatcc | ccaattactt | 600 |
| gctccccaaa | acccagcctg | agctccagtg | ggcgtggact | aatatggaac | agtatttaag | 660 |
| cgcctgtttg | aatctcacgg | agcgtaaacg | gttggtggcg | cagcatctga | cgcacgtgtc | 720 |
| gcagacgcag | gagcagaaca | aagagaatca | gaatcccaat | tctgatgcgc | cggtgatcag | 780 |
| atcaaaaact | tcagccaggt | acatggagct | ggtcgggtgg | ctcgtggaca | gggattac | 840 |
| ctcggagaag | cagtggatcc | aggaggacca | ggcctcatac | atctccttca | atgcggcctc | 900 |
| caactcgcgg | tcccaaatca | aggctgcctt | ggacaatgcg | ggaaagatta | tgagcctgac | 960 |
| taaaaccgcc | cccgactacc | tggtgggcca | gcagcccgtg | gaggacattt | ccagcaatcg | 1020 |
| gatttataaa | attttggaac | taaacgggta | cgatccccaa | tatgcggctt | ccgtctttct | 1080 |
| gggatgggcc | acgaaaaagt | tcggcaagag | gaacaccatc | tggctgtttg | gcctgcaac | 1140 |
| taccgggaag | accaacatcg | cggaggccat | agcccacact | gtgcccttct | acgggtgcgt | 1200 |
| aaactggacc | aatgagaact | ttcccttcaa | cgactgtgtc | gacaagatgg | tgatctggtg | 1260 |
| ggaggagggg | aagatgaccg | ccaaggtcgt | ggagtcggcc | aaagccattc | tcggaggaag | 1320 |
| caaggtgcgc | gtggaccaga | aatgcaagtc | ctcggcccag | atagacccga | ctcccgtgat | 1380 |
| cgtcacctcc | aacaccaaca | tgtgcgccgt | gattgacggg | aactcaacga | ccttcgaaca | 1440 |
| ccagcagccg | ttgcaagacc | ggatgttcaa | atttgaactc | acccgccgtc | tggatcatga | 1500 |
| ctttgggaag | gtcaccaagc | aggaagtcaa | agactttttc | cggtgggcaa | aggatcacgt | 1560 |
| ggttgaggtg | gagcatgaat | tctacgtcaa | aagggtgga | gccaagaaaa | gacccgcccc | 1620 |
| cagtgacgca | gatataagtg | agcccaaacg | ggtgcgcgag | tcagttgcgc | agccatcgac | 1680 |
| gtcagacgcg | gaagcttcga | tcaactacgc | agacaggtac | caaaacaaat | gttctcgtca | 1740 |
| cgtgggcatg | aatctgatgc | tgtttccctg | cagacaatgc | gagagaatga | atcagaattc | 1800 |
| aaatatctgc | ttcactcacg | gacagaaaga | ctgtttagag | tgctttcccg | tgtcagaatc | 1860 |
| tcaacccgtt | tctgtcgtca | aaaggcgta | tcagaaactg | tgctacattc | atcatatcat | 1920 |
| gggaaaggtg | ccagacgctt | gcactgcctg | cgatctggtc | aatgtggatt | tggatgactg | 1980 |
| catctttgaa | caataaatga | tttaaatcag | gtatggctgc | cgatggttat | cttccagatt | 2040 |
| ggctcgagga | cactctctct | gaaggaataa | gacagtggtg | gaagctcaaa | cctggcccac | 2100 |

```
caccaccaaa gcccgcagag cggcataagg acgacagcag gggtcttgtg cttcctgggt    2160
acaagtacct cggacccttc aacggactcg acaagggaga gccggtcaac gaggcagacg    2220
ccgcggccct cgagcacgac aaagcctacg accggcagct cgacagcgga gacaacccgt    2280
acctcaagta caaccacgcc gacgcggagt tcaggagcg ccttaaagaa gatacgtctt      2340
ttgggggcaa cctcggacga gcagtcttcc aggcgaaaaa gagggttctt gaacctctgg    2400
gcctggttga ggaacctgtt aagacggctc cgggaaaaaa gaggccggta gagcactctc    2460
ctgtggagcc agactcctcc tcgggaaccg gaaaggcggg ccagcagcct gcaagaaaaa    2520
gattgaattt tggtcagact ggagacgcag actcagtacc tgaccccag cctctcggac      2580
agccaccagc agcccctct ggtctgggaa ctaatacgat ggctacaggc agtggcgcac      2640
caatggcaga caataacgag ggcgccgacg gagtgggtaa ttcctcggga aattggcatt    2700
gcgattccac atggatgggc gacagagtca tcaccaccag cacccgaacc tgggccctgc    2760
ccacctacaa caaccacctc tacaaacaaa tttccagcca atcaggagcc tcgaacgaca    2820
atcactactt tggctacagc acccttgggg gtattttga cttcaacaga ttccactgcc      2880
acttttcacc acgtgactgg caaagactca tcaacaacaa ctggggattc cgacccaaga    2940
gactcaactt caagctcttt aacattcaag tcaaagaggt cacgcagaat gacggtacga    3000
cgacgattgc caataacctt accagcacgg ttcaggtgtt tactgactcg gagtaccagc    3060
tcccgtacgt cctcggctcg gcgcatcaag gatgcctccc gccgttccca gcagacgtct    3120
tcatggtgcc acagtatgga tacctcaccc tgaacaacgg gagtcaggca gtaggacgct    3180
cttcattta ctgcctggag tactttcctt ctcagatgct gcgtaccgga aacaacttta      3240
ccttcagcta cacttttgag gacgttcctt tccacagcag ctacgctcac agccagagtc    3300
tggaccgtct catgaatcct ctcatcgacc agtacctgta ttacttgagc agaacaaaca    3360
ctccaagtgg aaccaccacg cagtcaaggc ttcagttttc tcaggccgga gcgagtgaca    3420
ttcgggacca gtctaggaac tggcttcctg gaccctgtta ccgccagcag cgagtatcaa    3480
agacatctgc ggataacaac aacagtgaat actcgtggac tggagctacc aagtaccacc    3540
tcaatggcag agactctctg gtgaatccgg gcccggccat ggcaagccac aaggacgatg    3600
aagaaaagtt ttttcctcag agcggggttc tcatctttgg gaagcaaggc tcagagaaaa    3660
caaatgtgga cattgaaaag gtcatgatta cagacgaaga ggaaatcagg acaaccaatc    3720
ccgtggctac ggagcagtat ggttctgtat ctaccaacct ccagagaggc aacagacaag    3780
cagctaccgc agatgtcaac acacaaggcg ttcttccagg catggtctgg caggacagag    3840
atgtgtacct tcagggccc atctgggcaa agattccaca cacggacgga cattttcacc      3900
cctctcccct catgggtgga ttcggactta aacaccctcc tccacagatt ctcatcaaga    3960
acacccgt acctgcgaat ccttcgacca ccttcagtgc ggcaaagttt gcttccttca        4020
tcacacagta ctccacggga caggtcagcg tggagatcga gtgggagctg cagaaggaaa    4080
acagcaaacg ctggaatccc gaaattcagt acacttccaa ctacaacaag tctgttaatg    4140
tggactttac tgtggacact aatggcgtgt attcagagcc tcgccccatt ggcaccagat    4200
acctgactcg taatctgtaa ttgcttgtta atcaataaac cgtttaattc gtttcagttg    4260
aactttggtc tctgcgtatt tctttcttat ctagtttcca tggctacgta gataagtagc    4320
atggcgggtt aatcattaac tacagcccgg gcgtttaaac agcgggcgga ggggtggagt    4380
cgtgacgtga attacgtcat agggttaggg aggtcctgta ttagaggtca cgtgagtgtt    4440
ttgcgacatt ttgcgacacc atgtggtctc gctgggggg ggggcccgag tgagcacgca      4500
```

```
gggtctccat tttgaagcgg gaggtttgaa cgagcgctgg cgcgctcact ggccgtcgtt    4560
ttacaacgtc gtgactggga aaccctggc gttacccaac ttaatcgcct tgcagcacat    4620 cccccttcg ccagctggcg taatagcgaa gaggcccgca ccgatcgccc ttcccaacag    4680
ttgcgcagcc tgaatggcga atggaaattg taagcgttaa tattttgtta aaattcgcgt    4740 taaattttg ttaaatcagc tcattttttt aaccaatagg ccgaaatcgg caaatccct    4800 tataaatcaa agaatagac cgagataggg ttgagtgttg ttccagtttg gaacaagagt    4860
ccactattaa gaacgtggac tccaacgtca aagggcgaaa aaccgtctat cagggcgatg    4920
gcccactacg tgaaccatca ccctaatcaa gttttttggg gtcgaggtgc cgtaaagcac    4980
taaatcggaa ccctaaaggg agcccccgat ttagagcttg acggggaaag ccggcgaacg    5040
tggcgagaaa ggaagggaag aaagcgaaag gagcgggcgc tagggcgctg gcaagtgtag    5100
cggtcacgct gcgcgtaacc accacacccg ccgcgcttaa tgcgccgcta cagggcgcgt    5160
caggtggcac ttttcgggga aatgtgcgcg gaaccctat ttgtttatt ttctaaatac    5220 attcaaatat gtatccgctc atgagacaat aaccctgata aatgcttcaa taatattgaa    5280
aaaggaagag tatgagtatt caacatttcc gtgtcgccct tattccctt tttgcggcat    5340 tttgccttcc tgtttttgct cacccagaaa cgctggtgaa agtaaaagat gctgaagatc    5400
agttgggtgc acgagtgggt tacatcgaac tggatctcaa cagcggtaag atccttgaga    5460
gtttcgcccc gaagaacgt tttccaatga tgagcacttt taaagttctg ctatgtggcg    5520
cggtattatc ccgtattgac gccgggcaag agcaactcgg tcgccgcata cactattctc    5580
agaatgactt ggttgagtac tcaccagtca cagaaaagca tcttacggat ggcatgacag    5640
taagagaatt atgcagtgct gccataacca tgagtgataa cactgcggcc aacttacttc    5700
tgacaacgat cggaggaccg aaggagctaa ccgcttttt gcacaacatg ggggatcatg    5760
taactcgcct tgatcgttgg gaaccggagc tgaatgaagc cataccaaac gacgagcgtg    5820
acaccacgat gcctgtagca atggcaacaa cgttgcgcaa actattaact ggcgaactac    5880
ttactctagc ttcccggcaa caattaatag actggatgga ggcggataaa gttgcaggac    5940
cacttctgcg ctcggccctt ccggctggct ggtttattgc tgataaatct ggagccggtg    6000
agcgtgggtc tcgcggtatc attgcagcac tggggccaga tggtaagccc tcccgtatcg    6060
tagttatcta cacgacgggg agtcaggcaa ctatggatga acgaaataga cagatcgctg    6120
agataggtgc ctcactgatt aagcattggt aactgtcaga ccaagtttac tcatatatac    6180
tttagattga tttaaaactt catttttaat ttaaaaggat ctaggtgaag atcctttttg    6240
ataatctcat gaccaaaatc ccttaacgtg agttttcgtt ccactgagcg tcagaccccg    6300
tagaaaagat caaaggatct tcttgagatc cttttttct gcgcgtaatc tgctgcttgc    6360
aaacaaaaaa accaccgcta ccagcggtgg tttgtttgcc ggatcaagag ctaccaactc    6420
tttttccgaa ggtaactggc ttcagcagag cgcagatacc aaatactgtt cttctagtgt    6480
agccgtagtt aggccaccac ttcaagaact ctgtagcacc gcctacatac ctcgctctgc    6540
taatcctgtt accagtggct gctgccagtg gcgataagtc gtgtcttacc gggttggact    6600
caagacgata gttaccggat aaggcgcagc ggtcgggctg aacggggggt tcgtgcacac    6660
agcccagctt ggagcgaacg acctacaccg aactgagata cctacagcgt gagctatgag    6720
aaagcgccac gcttcccgaa gggagaaagg cggacaggta tccggtaagc ggcagggtcg    6780
gaacaggaga gcgcacgagg gagcttccag ggggaaacgc ctggtatctt tatagtcctg    6840
```

```
tcgggtttcg ccacctctga cttgagcgtc gattttgtg atgctcgtca ggggggcgga       6900
gcctatggaa aaacgccagc aacgcggcct ttttacggtt cctggccttt tgctggcctt       6960
ttgctcacat gttctttcct gcgttatccc ctgattctgt ggataaccgt attaccgcct       7020
ttgagtgagc tgataccgct cgccgcagcc gaacgaccga gcgcagcgag tcagtgagcg       7080
aggaagcgga agagcgccca atacgcaaac cgcctctccc cgcgcgttgg ccgattcatt       7140
aatgcagctg gcacgacagg tttcccgact ggaaagcggg cagtgagcgc aacgcaatta       7200
atgtgagtta gctcactcat taggcacccc aggctttaca ctttatgctt ccggctcgta       7260
tgttgtgtgg aattgtgagc ggataacaat ttcacacagg aaacagctat gaccatgatt       7320
acgccaa                                                                  7327
```

<210> SEQ ID NO 60
<211> LENGTH: 6902
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60

```
ctagagtcga cctgcaggca tgcaagcttg gcgtaatcat ggtcatagct gtttcctgtg         60
tgaaattgtt atccgctcac aattccacac aacatacgag ccggaagcat aaagtgtaaa        120
gcctggggtg cctaatgagt gagctaactc acattaattg cgttgcgctc actgcccgct        180
ttccagtcgg gaaacctgtc gtgccagctg cattaatgaa tcggccaacg cgcgggggaga       240
ggcggtttgc gtattgggcg ctcttccgct tcctcgctca ctgactcgct gcgctcggtc        300
gttcggctgc ggcgagcggt atcagctcac tcaaaggcgg taatacggtt atccacagaa        360
tcaggggata acgcaggaaa gaacatgtga gcaaaaggcc agcaaaaggc caggaaccgt        420
aaaaaggccg cgttgctggc gttttttccat aggctccgcc cccctgacga gcatcacaaa      480
aatcgacgct caagtcagag gtggcgaaac ccgacaggac tataaagata ccaggcgttt        540
ccccctggaa gctccctcgt gcgctctcct gttccgaccc tgccgcttac cggatacctg        600
tccgcctttc tcccttcggg aagcgtggcg ctttctcata gctcacgctg taggtatctc        660
agttcggtgt aggtcgttcg ctccaagctg ggctgtgtgc acgaaccccc cgttcagccc        720
gaccgctgcg ccttatccgg taactatcgt cttgagtcca acccggtaag acacgactta        780
tcgccactgg cagcagccac tggtaacagg attagcagag cgaggtatgt aggcggtgct        840
acagagttct tgaagtggtg gcctaactac ggctacacta aggacagt atttggtatc          900
tgcgctctgc tgaagccagt taccttcgga aaaagagttg gtagctcttg atccggcaaa        960
caaaccaccg ctggtagcgg tggtttttttt gtttgcaagc agcagattac gcgcagaaaa     1020
aaaggatctc aagaagatcc tttgatcttt tctacggggt ctgacgctca gtggaacgaa       1080
aactcacgtt aagggatttt ggtcatgtga ttatcaaaaa ggatcttcac ctagatcctt       1140
ttaaattaaa aatgaagttt taaatcaatc taaagtatat atgagtaaac ttggtctgac       1200
agttagaaaa actcatcgag catcaaatga aactgcaatt tattcatatc aggattatca       1260
ataccatatt tttgaaaaag ccgtttctgt aatgaaggag aaaactcacc gaggcagttc       1320
cataggatgg caagatcctg gtatcggtct gcgattccga ctcgtccaac atcaatacaa       1380
cctattaatt tcccctcgtc aaaaataagg ttatcaagtg agaaatcacc atgagtgacg       1440
actgaatccg gtgagaatgg caaaagttta tgcatttctt ccagacttg ttcaacaggc        1500
```

```
cagccattac gctcgtcatc aaaatcactc gcatcaacca aaccgttatt cattcgtgat      1560
tgcgcctgag cgagacgaaa tacgcgatcg ctgttaaaag gacaattaca aacaggaatc      1620
gaatgcaacc ggcgcaggaa cactgccagc gcatcaacaa tattttcacc tgaatcagga      1680
tattcttcta atacctggaa tgctgttttc ccagggatcg cagtggtgag taaccatgca      1740
tcatcaggag tacggataaa atgcttgatg gtcggaagag gcataaattc cgtcagccag      1800
tttagtctga ccatctcatc tgtaacatca ttggcaacgc tacctttgcc atgtttcaga      1860
aacaactctg gcgcatcggg cttcccatac aatcgataga ttgtcgcacc tgattgcccg      1920
acattatcgc gagcccattt atacccatat aaatcagcat ccatgttgga atttaatcgc      1980
ggcctagagc aagacgtttc ccgttgaata tggctcatac tcttcctttt tcaatattat      2040
tgaagcattt atcagggtta ttgtctcatg agcggataca tatttgaatg tatttagaaa      2100
aataaacaaa taggggttcc gcgcacattt ccccgaaaag tgccacctga cgtctaagaa      2160
accattatta acatgacatt aacctataaa aataggcgta tcacgaggcc ctttcgtctc      2220
gcgcgtttcg gtgatgacgg tgaaaacctc tgacacatgc agctcccgga gacggtcaca      2280
gcttgtctgt aagcggatgc cgggagcaga caagcccgtc agggcgcgtc agcgggtgtt      2340
ggcgggtgtc ggggctggct taactatgcg gcatcagagc agattgtact gagagtgcac      2400
catatgcggt gtgaaatacc gcacagatgc gtaaggagaa aataccgcat caggcgccat      2460
tcgccattca ggctgcgcaa ctgttgggaa gggcgatcgg tgcgggcctc ttcgctatta      2520
cgccagctgg cgaaaggggg atgtgctgca aggcgattaa gttgggtaac gccagggttt      2580
tcccagtcac gacgttgtaa aacgacggcc agtgaattcg agctcggtac ccgtagccat      2640
ggaaactaga taagaaagaa atacgcagag accaaagttc aactgaaacg aattaaacgg      2700
tttattgatt aacaagcaat tacagattac gggtgaggta acgggtgcca atggggcggg      2760
gttcagagta cacgccttct gtattaacag caaagtccac acttgtagat ttgtagtagt      2820
tggaggtgta ctggatctcg gggttccagc gcttgctgtt ttccttctgc agctcccatt      2880
caatttccac gctgacctgt ccggtgctgt attgcgtgat gaaagagttc agctttgact      2940
ggttgaaggt ggtcggagga tccgcaggta caggcgtgtt cttgatcagg atctgaggcg      3000
gaggatgttt caggccaaag ccgcccatca gcggagacgg gtggaagttg ccgtccgtgt      3060
gaggaatctt ggcccagatg ggaccctgca ggtacacgtc ccggttctgc cagaccatac      3120
cgggtaaggc cccctggctg ttgacagttc caatttgagg agccgtgttt tgctgctgca      3180
agttatctgc cacgataccg tattcctctg tagccacagg gttagtggtt ttgatttctt      3240
cctcgctggt gagcatgaca tcgctgtaat ccgcattgtc tctggcagca ttttgtttgc      3300
caaaaatcag gatcccgtta ctgggaaaaa aacgctcctc gtcgtctttg tgtgttgcca      3360
tagcgatgcc aggattagcc aatgaatttc ttccattcag atggtatttg gtcccagcag      3420
tccaggcaaa gttgctattg ttgttttgcc cggttgtcgt tgagacgcgt tgttggcggt      3480
aacagggtcc tggcagccag ttctttgcct gattggccat tgtattaggc ccaccttggc      3540
tgaagcccag agtctgcgta tttgccgtgc ctcctgttgt ttgagtccga acaagtagt      3600 acaggtactg gtcaatcaga ggattcatca gccggtccaa gctctggctg tgggcgtagc      3660
tgctgtggaa aggcacgtcc tcgaaggtgt aagtaaactg gaagttgttg ccggttctca      3720
gcatctgcga aggaaagtat tccaggcagt agaaggagga gcgtcccacg gcctgactac      3780
cgttgttgag tgttaggtag ccgtactggg gaatcatgaa cacgtccgcc gggaacggag      3840
gcaggcagcc ctggtgggca gagccgagaa cgtacggcag ctggtactcc gagtccgtaa      3900
```

```
acacctggat ggtgctggtg aggttattgg cgatggtctt ggtgccttca ttctgcgtga   3960
cctccttgac ctggatgttg aagagcttga agctgagtct cttgggccgg aatccccagt   4020
tgttgttgat gagtcgctgc cagtcacgtg gtgaaaagtg gcagtggaat ctgttaaagt   4080
caaaataccc ccaggggggtg ctgtagccga agtaggtgtt gtcgttggtg gctcctcccg   4140
atgtcccgtt ggagatttgc ttgtagaggt ggttgttgta ggtgggcagg gcccaggttc   4200
gggtgctggt ggtgatgact ctgtcgccca gccatgtgga atcgcaatgc caatttcccg   4260
aggaactacc cactccgtcg gcgccttcgt tattgtctgc cattggtgcg ccaccgcctg   4320
cagccattgt attaggtccc acaccagagg gcgctgctgg aggttctccg agaggttgag   4380
ggtctggaac tgactctgag tcgccagtct gaccaaaatt gagtcttttt ctggcgggct   4440
gttggccttt cttgccgatg cccgtagagg agtctggaga acgctggggt gatggctcta   4500
ccggtctctt ctttccagga gccgtcttag cgccttcctc aaccagaccg agaggttcga   4560
gaacccgctt cttggcctgg aagactgctc gcccgaggtt gcccccaaaa gacgtatctt   4620
cttgcagacg ctcctgaaac tcggcgtcgg cgtggttata ccgcaggtac ggattgtcac   4680
ccgcctgcag ctgctggtcg taggccttgt cgtgctcgag ggccgctgcg tccgccgcgt   4740
tgacgggctc ccccttgtcg agtccgttga agggtccgag gtacttgtag ccaggaagca   4800
ccagaccccg gccgtcgtcc tgcttttgct ggttggcttt gggcttcggg gctccaggtt   4860
tcagcgccca ccactcgcga atgccctcag agaggttgtc ctcgagccaa tctggaagat   4920
aaccatcggc agccatacct gatttaaatc atttattgtt caaagatgca gtcatccaaa   4980
tccacattga ccagatcgca ggcagtgcaa gcgtctggca cctttcccat gatatgatga   5040
atgtagcaca gtttctgata cgccttttg acgacagaaa cggggttgaga ttctgacacg   5100 ggaaagcact ctaaacagtc tttctgtccg tgagtgaagc agatatttga attctgattc   5160
attctctcgc attgtctgca gggaaacagc atcagattca tgcccacgtg acgagaacat   5220
ttgttttggt acctgtctgc gtagttgatc gaagcttccg cgtctgacgt cgatggctgc   5280
gcaactgact cgcgcacccg tttgggctca cttatatctg cgtcactggg ggcgggtctt   5340
ttcttggctc cacccttttt gacgtagaat tcatgctcca cctcaaccac gtgatcctt   5400 gcccaccgga aaaagtcttt gacttcctgc ttggtgacct tcccaaagtc atgatccaga   5460
cggcgggtga gttcaaattt gaacatccgg tcttgcaacg gctgctggtg ttcgaaggtc   5520
gttgagttcc cgtcaatcac ggcgcacatg ttggtgttgg aggtgacgat cacgggagtc   5580
gggtctatct gggccgagga cttgcatttc tggtccacgc gcaccttgct tcctccgaga   5640
atggctttgg ccgactccac gaccttggcg gtcatcttcc cctcctccca ccagatcacc   5700
atcttgtcga cacagtcgtt gaagggaaag ttctcattgg tccagtttac gcacccgtag   5760
aagggcacag tgtgggctat ggcctccgcg atgttggtct tcccggtagt tgcaggccca   5820
aacagccaga tggtgttcct cttgccgaac ttttcgtgg cccatcccag aaagacggaa   5880
gccgcatatt ggggatcgta cccgtttagt tccaaaattt tataaatccg attgctggaa   5940
atgtcctcca cgggctgctg gcccaccagg tagtcggggg cggttttagt caggctcata   6000
atctttcccg cattgtccaa ggcagccttg atttgggacc gcgagttgga ggccgcattg   6060
aaggagatgt atgaggcctg gtcctcctgg atccactgct tctccgaggt aatccccttg   6120
tccacgagcc acccgaccag ctccatgtac ctggctgaag ttttttgatct gatcaccggc   6180 gcatcagaat tgggattctg attctctttg ttctgctcct gcgtctgcga cacgtgcgtc   6240
```

```
agatgctgcg ccaccaaccg tttacgctcc gtgagattca aacaggcgct taaatactgt    6300
tccatattag tccacgccca ctggagctca ggctgggttt tggggagcaa gtaattgggg    6360
atgtagcact catccaccac cttgttcccg cctccggcgc catttctggt ctttgtgacc    6420
gcgaaccagt ttggcaaagt cggctcgatc ccgcggtaaa ttctctgaat cagttttcg     6480 cgaatctgac tcaggaaacg tcccaaaacc atggatttca ccccggtggt ttccacgagc    6540
acgtgcatgt ggaagtagct ctctcccttc tcaaattgca caagaaaag gggcctccggg    6600 gccttactca cacggcgcca ttccgtcaga aagtcgcgct gcagcttctc ggccacggtc    6660
aggggtgcct gctcaatcag attcagatcc atgtcagaat ctggcggcaa ctcccattcc    6720
ttctcggcca cccagttcac aaagctgtca gaaatgccgg gcagatgctc gtcaaggtcg    6780
ctggggacct taatcacaat ctcgtaaaac cccggcatgg cggctgcgca gatcagaagt    6840
tcctatactt tctagagaat aggaacttcg gaataggaac ttctgatctt ccgggggatc    6900
ca                                                                   6902
```

<210> SEQ ID NO 61
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
ttagaccgtg ccatggctag ttgggtacca ggtcacccgt gctcgacttc cggtcttcat      60
ggagaactgg tgaccggtaa ccgaccgtaa gattgggaat                            100
```

<210> SEQ ID NO 62
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

```
tgtcaagaat acgatcggaa aggactcgac aattgatggg cctgtagcgc caacgttgta      60
ctttatccaa ggtgagctca ggagtgttat cataaatacg                            100
```

<210> SEQ ID NO 63
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
tctcctgttc atccgacaac cacactccct agttcaggga ggtcactcga gttagagctg      60
aaaccccact agctcacgct cgttatcaac ccgggtaagt                            100
```

<210> SEQ ID NO 64
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
gtggctcctt taaggtctcg cctgttcgat tgttcgtcgc tgccgcggat cagcaaagtt    60
gcttccgtcc taattcggcc taaggatccg ctagtgcgcg                         100
```

<210> SEQ ID NO 65
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
actgcgcttc tgtggctcct gaacaacgca aagcttcggt cgcctagtcc agtggatggg    60
ccaaggacaa ttgcagtgct tatctccact gctgaaaccc                         100
```

<210> SEQ ID NO 66
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

```
gtgaaagatg aggagtgagt ttacgcactc acgaagccct aattacccga gtatcgtaag    60
ccaatatcgt agcccagttc ctgtacaggg tcgcgtataa                         100
```

<210> SEQ ID NO 67
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67

```
acgatttccg tcgttcatat gagccaccag gcttgtctct tcgcgcaatt tgacacgcaa    60
cacccgctgc cattccgagg tcgttagggc ttttggattt                         100
```

<210> SEQ ID NO 68
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
aacctatttg attgtacagc gtgagtacga agcgaatagg ctagtaacac tgccctatgc    60
aaagacgcct tggttgattc tagagctggg attggtacga                         100
```

<210> SEQ ID NO 69
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
tgaggtcatc tcctttccat ccgtgtccta acgcttcgat ccttctgcag gctcctctta    60
tggatgtttt atcaccctgt cgagcgtgca cgatggtgga                         100
```

<210> SEQ ID NO 70
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
gaactccgcg tgcagcgcgg agttgacacg gaaggccagg gagccaattt ccactgtcct      60
gagctagacc ccttgatagc acttgctgtg catggttgct                          100

<210> SEQ ID NO 71
<211> LENGTH: 10150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (5875)..(5974)
<223> OTHER INFORMATION: a, c, t, g, unknown or other
<220> FEATURE:
<221> NAME/KEY: misc_feature
<222> LOCATION: (5875)..(5974)
<223> OTHER INFORMATION: This region may encompass 60-100 nucleotides

<400> SEQUENCE: 71
tagggaaata ggccaggttt tcaccgtaac acgccacatc ttgcgaatat atgtgtagaa      60
actgccggaa atcgtcgtgt gcactcatgg aaaacggtgt aacaagggtg aacactatcc    120
catatcacca gctcaccgtc tttcattgcc atacggaact ccggatgagc attcatcagg    180
cgggcaagaa tgtgaataaa ggccggataa aacttgtgct tatttttctt tacggtcttt    240
aaaaaggccg taatatccag ctgaacggtc tggttatagg tacattgagc aactgactga    300
aatgcctcaa aatgttcttt acgatgccat tgggatatat caacggtggt atatccagtg    360
atttttttct ccattttttt ttcctccttt agaaaaactc atcgagcatc aaatgaaact    420
gcaatttatt catatcagga ttatcaatac catatttttg aaaaagccgt ttctgtaatg    480
aaggagaaaa ctcaccgagg cagttccata ggatggcaag atcctggtat cggtctgcga    540
ttccgactcg tccaacatca atacaaccta ttaatttccc ctcgtcaaaa ataaggttat    600
caagtgagaa atcaccatga gtgacgactg aatccggtga gaatggcaaa agtttatgca    660
tttctttcca gacttgttca acaggccagc cattacgctc gtcatcaaaa tcactcgcat    720
caaccaaacc gttattcatt cgtgattgcg cctgagcgag gcgaaatacg cgatcgctgt    780
taaaaggaca attacaaaca ggaatcgagt gcaaccggcg caggaacact gccagcgcat    840
caacaatatt ttcacctgaa tcaggatatt cttctaatac ctggaacgct gttttttccgg    900 ggatcgcagt ggtgagtaac catgcatcat caggagtacg gataaaatgc ttgatggtcg    960
gaagtggcat aaattccgtc agccagttta gtctgaccat ctcatctgta acatcattgg   1020
caacgctacc tttgccatgt ttcagaaaca actctggcgc atcgggcttc ccatacaagc   1080
gatagattgt cgcacctgat tgcccgacat tatcgcgagc ccatttatac ccatataaat   1140
cagcatccat gttggaattt aatcgcggcc tcgacgtttc ccgttgaata tggctcattt   1200 tttttttcctc ctttaccaat gcttaatcag tgaggcacct atctcagcga tctgtctatt   1260
tcgttcatcc atagttgcct gactccccgt cgtgtagata actacgatac gggagggctt   1320

```
accatctggc cccagcgctg cgatgatacc gcgagaacca cgctcaccgg ctccggattt      1380
atcagcaata aaccagccag ccggaagggc cgagcgcaga agtggtcctg caactttatc      1440
cgcctccatc cagtctatta attgttgccg ggaagctaga gtaagtagtt cgccagttaa      1500
tagtttgcgc aacgttgttg ccatcgctac aggcatcgtg gtgtcacgct cgtcgtttgg      1560
tatggcttca ttcagctccg gttcccaacg atcaaggcga gattcttcct ttttcaatat      1620
tattgaagca tttatcaggg ttattgtctc atgagcggat acatatttga atgtatttag      1680
aaaaataaac aaataggggt cagtgttaca accaattaac caattctgaa cattatcgcg      1740
agcccattta tacctgaata tggctcataa caccccttgt ttgcctggcg gcagtagcgc      1800
ggtggtccca cctgacccca tgccgaactc agaagtgaaa cgccgtagcg ccgatggtag      1860
tgtggggact ccccatgcga gagtagggaa ctgccaggca tcaaataaaa cgaaaggctc      1920
agtcgaaaga ctgggccttt cgcccgggct aattgagggg tgtcgccctt attcgactcg      1980
gggctcgagc tgcgcgctcg ctcgctcact gaggccgccc gggcaaagcc cgggcgtcgg      2040
gcgacctttg gtcgcccggc ctcagtgagc gagcgagcgc gcagagaggg agtggccaac      2100
tccatcacta ggggttcctt taattaaacg cgtttacata acttacggta aatggcccgc      2160
ctggctgacc gcccaacgac ccccgcccat tgacgtcaat aatgacgtat gttcccatag      2220
taacgccaat agggactttc cattgacgtc aatgggtgga ctatttacgg taaactgccc      2280
acttggcagt acatcaagtg tatcatatgc caagtacgcc ccctattgac gtcaatgacg      2340
gtaaatggcc cgcctggcat tatgcccagt acatgacctt atgggacttt cctacttggc      2400
agtacatcta cgtattagtc atcgctatta ccatggtgat gcggttttgg cagtacatca      2460
atgggcgtgg atagcggttt gactcacggg gatttccaag tctccacccc attgacgtca      2520
atgggagttt gttttggcac caaaatcaac gggactttcc aaaatgtcgt aacaactccg      2580
ccccattgac gcaaatgggc ggtaggcgtg tacggtggga ggtctatata ggcgcgccga      2640
actgaaaaac cagaaagtta actggtaagt ttagtctttt tgtctttat ttcaggtccc       2700
ggatccggtg gtggtgcaaa tcaaagaact gctcctcagt ggatgttgcc tttacttcta      2760
ggcctgtacg gaagtgttac ttctgctcta aaagctcctg cagggaattc gccaccatgg      2820
tgagcaaggg cgaggagctg ttcaccgggg tggtgcccat cctggtcgag ctggacggcg      2880
acgtaaacgg ccacaagttc agcgtgtccg gcgagggcga gggcgatgcc acctacggca      2940
agctgaccct gaagttcatc tgcaccaccg gcaagctgcc cgtgccctgg cccaccctcg      3000
tgaccaccct gacctacggc gtgcagtgct tcagccgcta ccccgaccac atgaagcagc      3060
acgacttctt caagtccgcc atgcccgaag gctacgtcca ggagcgcacc atcttcttca      3120
aggacgacgg caactacaag acccgcgccg aggtgaagtt cgagggcgac accctggtga      3180
accgcatcga gctgaagggc atcgacttca aggaggacgg caacatcctg gggcacaagc      3240
tggagtacaa ctacaacagc cacaacgtct atatcatggc cgacaagcag aagaacggca      3300
tcaaggtgaa cttcaagatc cgccacaaca tcgaggacgg cagcgtgcag ctcgccgacc      3360
actaccagca gaacaccccc atcggcgacg gccccgtgct gctgcccgac aaccactacc      3420
tgagcaccca gtccgccctg agcaaagacc ccaacgagaa gcgcgatcac atggtcctgc      3480
tggagttcgt gaccgccgcc gggatcactc tcggcatgga cgagctgtac aagtaataga      3540
ctagtgcccc tctccctccc ccccccctaa cgttactggc cgaagccgct tggaataagg      3600
ccggtgtgcg tttgtctata tgttattttc caccatattg ccgtctttg gcaatgtgag      3660
ggcccggaaa cctggccctg tcttcttgac gagcattcct aggggtcttt ccctctcgc      3720
```

-continued

```
caaaggaatg caaggtctgt tgaatgtcgt gaaggaagca gttcctctgg aagcttcttg    3780
aagacaaaca acgtctgtag cgacccttttg caggcagcgg aacccccac ctggcgacag    3840 gtgcctctgc ggccaaaagc cacgtgtata agatacacct gcaaaggcgg cacaacccca    3900
gtgccacgtt gtgagttgga tagttgtgga aagagtcaaa tggctcacct caagcgtatt    3960
caacaagggg ctgaaggatg cccagaaggt accccattgt atgggatctg atctggggcc    4020
tcggtgcaca tgctttacat gtgtttagtc gaggttaaaa aacgtctagg ccccccgaac    4080
cacggggacg tggttttcct ttgaaaaaca cgatgataat accggtgcca ccatgctgct    4140
gctgctgctg ctgctgggcc tgaggctaca gctctccctg ggcatcatcc cagttgagga    4200
ggagaacccg gacttctgga accgcgaggc agccgaggcc ctgggtgccg ccaagaagct    4260
gcagcctgca cagacagccg ccaagaacct catcatcttc ctgggcgatg ggatgggggt    4320
gtctacggtg acagctgcca ggatcctaaa agggcagaag aaggacaaac tggggcctga    4380
gatacccctg gccatggacc gcttcccata tgtggctctg tccaagacat acaatgtaga    4440
caaacatgtg ccagacagtg gagccacagc cacggcctac ctgtgcgggg tcaagggcaa    4500
cttccagacc attggcttga gtgcagccgc ccgcttaac cagtgcaaca cgacacgcgg    4560
caacgaggtc atctccgtga tgaatcgggc caagaaagca gggaagtcag tgggagtggt    4620
aaccaccaca cgagtgcagc acgcctcgcc agccggcacc tacgcccaca cggtgaaccg    4680
caactggtac tcggacgccg acgtgcctgc ctcggcccgc caggagggggt gccaggacat    4740 cgctacgcag ctcatctcca acatggacat tgacgtgatc ctaggtggag gccgaaagta    4800
catgtttcgc atgggaaccc cagaccctga gtacccagat gactacagcc aaggtgggac    4860
caggctggac gggaagaatc tggtgcagga atggctggcg aagcgccagg gtgcccggta    4920
tgtgtggaac cgcactgagc tcatgcaggc ttccctggac ccgtctgtga cccatctcat    4980
gggtctcttt gagcctggag acatgaaata cgagatccac cgagactcca cactggaccc    5040
ctccctgatg gagatgacag aggctgccct gcgcctgctg agcaggaacc cccgcggctt    5100
cttcctcttc gtggagggtg gtcgcatcga ccatggtcat catgaaagca gggcttaccg    5160
ggcactgact gagacgatca tgttcgacga cgccattgag agggcgggcc agctcaccag    5220
cgaggaggac acgctgagcc tcgtcactgc cgaccactcc cacgtcttct ccttcggagg    5280
ctaccccctg cgagggagct ccatcttcgg gctggcccct ggcaaggccc gggacaggaa    5340
ggcctacacg gtcctcctat acggaaacgg tccaggctat gtgctcaagg acggcgcccg    5400
gccggatgtt accgagagcg agagcgggag ccccgagtat cggcagcagt cagcagtgcc    5460
cctggacgaa gagacccacg caggcgagga cgtggcggtg ttcgcgcgcg gcccgcaggc    5520
gcacctggtt cacggcgtgc aggagcagac cttcatagcg cacgtcatgg ccttcgccgc    5580
ctgcctggag ccctacaccg cctgcgacct ggcgcccccc gccggcacca ccgacgccgc    5640
gcacccgggt tactctagag tcggggcggc cggccgcttc gagcagacat gagtcgacag    5700
atcttttaaa aaacctccca cacaattgtt gttgttaact tgtttattgc agcttataat    5760
ggttacaaat aaagcaatag catcacaaat ttcacaaata aagcattttt ttcactgcat    5820
tctagttgtg gtttgtccaa actcatcaat gtatcttatc atgtctgttt aaacnnnnnn    5880
nnnnnnnnnn nnnnnnnnnn nnnnnnnnnn nnnnnnnnnn nnnnnnnnnn nnnnnnnnnn    5940
nnnnnnnnnn nnnnnnnnnn nnnnnnnnnn nnnatttaa ataggaaccc ctagtgatgg    6000
agttggccac tccctctctg cgcgctcgct cgctcactga ggccgggcga ccaaaggtcg    6060
```

-continued

```
cccgacgccc gggctttgcc cgggcggcct cagtgagcga gcgagcgcgc agagagtata  6120
catcgatgtg agttcgcggg tggctggggg ccctgggct gcgaccgccc ccgaaccgcg   6180
tctacgagcc ttgcgggctc cgggtctttg cagtcgtatg ggggcagggt agctgttccc  6240
cgcaaggaga gctcaaggtc agcgctcgga cctggcggag ccccgcaccc aggctgtggc  6300
gccctgtgca gctccgccct tgcggcgcca tctgcccgga gcctccttcc cctagtcccc  6360
agaaacagga ggtccctact cccgcccgag atcccgaccc ggaccctag gtgggggacg   6420
cttctcttcc tttcgcgctc tgcggggtca cgtgtcgcag aggagcccct ccccacggc   6480
ctccggcacc gcaggcccg ggatgctagt gcgcagcggg tgcatccctg tccgatgct    6540
gcgcctgcgg tagagcggcc gccatgttgc aaccgggaag gaaatgaatg ggcagccgtt  6600
aggaaagcct gccggtgact aaccctgcgc tcctgcctcg atgggtggag tcgcgtgtgg  6660
cggggaagtc aggtggagcg aggctagctg cccgatttc cctccgggt gatgcttttc    6720
ctagattatt ctctggtaaa tcaaagaagt gggtttatgg aggtcctctt gtgtcccctc  6780
cccgcagagg tgtggtggct gtggcatggt gccaagccgg agaagctga gtcatgggta   6840
gttggaaaag gacatttcca ccgcaaaatg gcccctctgg tggtggcccc ttcctgcagc  6900
gccggctcac ctcacggccc cgcccttccc ctgccagcct agcgttgacc cgaccccaaa  6960
ggccaggctg taaatgtcac cgggaggatt gggtgtctgg gcgcctcggg gaacctgccc  7020
ttctccccat tccgtcttcc ggaaaccaga tctcccaccg caccctggtc tgaggttaaa  7080
tatagctgct gacctttctg tagctggggg cctgggctgg ggctctctcc catcccttct  7140
ccccacacac atgcacttac ctgtgctccc actcctgatt tctggaaaag agctaggaag  7200
gacaggcaac ttggcaaatc aaagccctgg gactaggggg ttaaaataca gcttcccctc  7260
ttcccacccg ccccagtctc tgtccctttt gtaggaggga cttagagaag gggtgggctt  7320
gccctgtcca gttaatttct gacctttact cctgcccttt gagtttgatg atgctgagtg  7380
tacaagcgtt ttctccctaa agggtgcagc tgagctaggc agcagcaagc attcctgggg  7440
tggcatagtg gggtggtgaa taccatgtac aaagcttgtg cccagactgt gggtggcagt  7500
gccccacatg gccgcttctc ctggaagggc ttcgtatgac tgggggtgtt gggcagccct  7560
ggagccttca gttgcagcca tgccttaagc caggccagcc tggcagggaa gctcaaggga  7620
gataaaattc aacctcttgg gccctcctgg gggtaaggag atgctgcatt cgccctctta  7680
atggggaggt ggcctagggc tgctcacata ttctggagga gcctcccctc ctcatgcctt  7740
cttgcctctt gtctcttagg catgcaaaag agtcgaataa gggcgacaca aaatttattc  7800
taaatgcata ataaatactg ataacatctt atagtttgta ttatattttg tattatcgtt  7860
gacatgtata attttgatat caaaaactga ttttcccttt attattttcg agatttattt  7920
tcttaattct ctttaacaaa ctagaaatat tgtatataca aaaatcata aataatagat  7980
gaatagttta attataggtg ttcatcaatc gaaaaagcaa cgtatcttat ttaaagtgcg  8040
ttgcttttttt ctcatttata aggttaaata attctcatat atcaagcaaa gtgacaggcg  8100
cccttaaata ttctgacaaa tgctctttcc ctaaactccc cccataaaaa aacccgccga  8160
agcgggtttt tacgttattt gcggattaac gattactcgt tatcagaacc gcccaggggg  8220
cccgagctta agactggccg tcgttttaca acacagaaag agtttgtaga aacgcaaaaa  8280
ggccatccgt caggggcctt ctgcttagtt tgatgcctgg cagttcccta ctctcgcctt  8340
ccgcttcctc gctcactgac tcgctgcgct cggtcgttcg gctgcggcga gcggtatcag  8400
ctcactcaaa ggcggtaata cggttatcca cagaatcagg ggataacgca ggaaagaaca  8460
```

```
tgtgagcaaa aggccagcaa aaggccagga accgtaaaaa ggccgcgttg ctggcgtttt    8520
tccataggct ccgcccccct gacgagcatc acaaaaatcg acgctcaagt cagaggtggc    8580
gaaacccgac aggactataa agataccagg cgtttccccc tggaagctcc ctcgtgcgct    8640
ctcctgttcc gaccctgccg cttaccggat acctgtccgc ctttctccct tcgggaagcg    8700
tggcgctttc tcatagctca cgctgtaggt atctcagttc ggtgtaggtc gttcgctcca    8760
agctgggctg tgtgcacgaa ccccccgttc agcccgaccg ctgcgcctta tccggtaact    8820
atcgtcttga gtccaacccg gtaagacacg acttatcgcc actggcagca gccactggta    8880
acaggattag cagagcgagg tatgtaggcg gtgctacaga gttcttgaag tggtgggcta    8940
actacggcta cactagaaga acagtatttg gtatctgcgc tctgctgaag ccagttacct    9000
tcggaaaaag agttggtagc tcttgatccg gcaaacaaac caccgctggt agcggtggtt    9060
tttttgtttg caagcagcag attacgcgca gaaaaaaagg atctcaagaa gatcctttga    9120
tcttttctac ggggtctgac gctcagtgga acgacgcgcg cgtaactcac gttaagggat    9180
tttggtcatg agcttgcgcc gtcccgtcaa gtcagcgtaa tgctacactt cttcccgtat    9240
gcccaacttt gtatagagag ccactgcggg atcgtcaccg taatctgctt gcacgtagat    9300
ttataaagca ccaagcgcgt tggccttag cttgaggaga ttgatgagcg cggtggcaat    9360
gccctgcctc cggtgctcgc cggagactgc gagatttaag atatagatct cactacgcgg    9420
ctgctcaaac ttgggcagaa cgtaagccgc gagagcgcca caaccgctt cttggtcgaa    9480 ggcagcaagc gcgatgaatg tcttactacg gagcaagttc ccgaggtaat cggagtccgg    9540
ctgatgttgg gagtaggtgg ctacgtcacc gaactcacga ccgaaaagat caagagcagc    9600
ccgttaggat ttgacttggt cagggccgag cctattagtg cgaatgatgc cttaacttga    9660
gccacctaac tttgttttag ggcgactgcc ctgctgcgta attacgttgc tgctcttaaa    9720
ttacaaacat cgacccacgg cgtaacgcgc ttgctgcttg gatgcccgag gcatagactg    9780
tacaaaaaaa cagtcataac aagccatgaa aaccgccact gcgccgttac caccgctgcg    9840
ttcggtcaag gttctggacc agttgcgtga gcgcattttt ttttcctcct cggcgtttac    9900
gccccgccct gccactcatc gcagtactgt tgtaattcat taagcattct gccgacatgg    9960
aagccatcac agacggcatg atgaacctga atcgccagcg gcatcagcac cttgtcgcct   10020
tgcgtataat atttgcccat agtgaaaacg ggggcgaaga agttgtccat attggccacg   10080
tttaaatcaa aactggtgaa actcacccag ggattggcgc tgacgaaaaa catattctca   10140
ataaaccctt                                                          10150
```

<210> SEQ ID NO 72
<211> LENGTH: 498
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

```
cacttcttcc cgtatgccca actttgtata gagagccact gcgggatcgt caccgtaatc      60
tgcttgcacg tagatttata aagcaccaag cgcgttggcc tttagcttga ggagattgat     120
gagcgcggtg gcaatgccct gcctccggtg ctcgccggag actgcgagat ttaagatata     180
gatctcacta cgcggctgct caaacttggg cagaacgtaa gccgcgagag cgccaacaac     240
cgcttcttgg tcgaaggcag caagcgcgat gaatgtctta ctacggagca agttcccgag     300
```

```
gtaatcggag tccggctgat gttgggagta ggtggctacg tcaccgaact cacgaccgaa    360
aagatcaaga gcagcccgtt aggatttgac ttggtcaggg ccgagcctat tagtgcgaat    420
gatgccttaa cttgagccac ctaactttgt tttagggcga ctgccctgct gcgtaattac    480
gttgctgctc ttaaatta                                                  498
```

<210> SEQ ID NO 73
<211> LENGTH: 7989
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (3714)..(3813)
<223> OTHER INFORMATION: a, c, t, g, unknown or other
<220> FEATURE:
<221> NAME/KEY: misc_feature
<222> LOCATION: (3714)..(3813)
<223> OTHER INFORMATION: This region may encompass 60-100 nucleotides

<400> SEQUENCE: 73

```
tagggaaata ggccaggttt tcaccgtaac acgccacatc ttgcgaatat atgtgtagaa      60
actgccggaa atcgtcgtgt gcactcatgg aaaacggtgt aacaagggtg aacactatcc     120
catatcacca gctcaccgtc tttcattgcc atacggaact ccggatgagc attcatcagg     180
cgggcaagaa tgtgaataaa ggccggataa aacttgtgct tatttttctt tacggtctttt    240 aaaaaggccg taatatccag ctgaacggtc tggttatagg tacattgagc aactgactga     300
aatgcctcaa aatgttcttt acgatgccat gggatatat caacggtggt atatccagtg      360 attttttttct ccattttttt ttcctccttt agaaaaactc atcgagcatc aaatgaaact    420
gcaatttatt catatcagga ttatcaatac catattttg aaaaagccgt ttctgtaatg     480
aaggagaaaa ctcaccgagg cagttccata ggatggcaag atcctggtat cggtctgcga    540
ttccgactcg tccaacatca atacaaccta ttaatttccc ctcgtcaaaa ataaggttat    600
caagtgagaa atcaccatga gtgacgactg aatccggtga gaatggcaaa agtttatgca    660
tttctttcca gacttgttca acaggccagc cattacgctc gtcatcaaaa tcactcgcat    720
caaccaaacc gttattcatt cgtgattgcg cctgagcgag gcgaaatacg cgatcgctgt    780
taaaaggaca attacaaaca ggaatcgagt gcaaccggcg caggaacact gccagcgcat    840
caacaatatt ttcacctgaa tcaggatatt cttctaatac ctggaacgct gtttttccgg    900
ggatcgcagt ggtgagtaac catgcatcat caggagtacg gataaaatgc ttgatggtcg    960
gaagtggcat aaaattccgtc agccagttta gtctgaccat ctcatctgta acatcattgg   1020
caacgctacc tttgccatgt ttcagaaaca actctggcgc atcgggcttc ccatacaagc   1080
gatagattgt cgcacctgat tgcccgacat tatcgcgagc ccatttatac ccatataaat   1140
cagcatccat gttggaattt aatcgcggcc tcgacgtttc ccgttgaata tggctcattt   1200
ttttttcctc ctttaccaat gcttaatcag tgaggcacct atctcagcga tctgtctatt   1260
tcgttcatcc atagttgcct gactcccgt cgtgtagata actacgatac gggagggctt   1320
accatctggc cccagcgctg cgatgatacc gcgagaacca cgctcaccgg ctccggattt   1380
atcagcaata aaccagccag ccggaagggc cgagcgcaga agtggtcctg caactttatc   1440
cgcctccatc cagtctatta attgttgccg ggaagctaga gtaagtagtt cgccagttaa   1500
tagtttcgcg aacgttgttg ccatcgctac aggcatcgtg gtgtcacgct cgtcgtttgg   1560
```

```
tatggcttca ttcagctccg gttcccaacg atcaaggcga gattcttcct ttttcaatat    1620
tattgaagca tttatcaggg ttattgtctc atgagcggat acatatttga atgtatttag    1680
aaaaataaac aaatagggt cagtgttaca accaattaac caattctgaa cattatcgcg     1740
agcccattta tacctgaata tggctcataa cacccccttgt ttgcctggcg gcagtagcgc   1800
ggtggtccca cctgacccca tgccgaactc agaagtgaaa cgccgtagcg ccgatggtag    1860
tgtgggact ccccatgcga gagtagggaa ctgccaggca tcaaataaaa cgaaaggctc     1920
agtcgaaaga ctgggccttt cgcccgggct aattgagggg tgtcgcccctt attcgactcg   1980
gggctcgagc agcagctgcg cgctcgctcg ctcactgagg ccgcccgggc aaagcccggg    2040
cgtcgggcga cctttggtcg cccggcctca gtgagcgagc gagcgcgcag agagggagtg    2100
gggttttaat taaacgcgtt tacataactt acggtaaatg gcccgcctgg ctgaccgccc    2160
aacgacccc gcccattgac gtcaataatg acgtatgttc ccatagtaac gccaataggg     2220
actttccatt gacgtcaatg ggtggactat ttacggtaaa ctgcccactt ggcagtacat    2280
caagtgtatc atatgccaag tacgcccct attgacgtca atgacggtaa atggcccgcc     2340
tggcattatg cccagtacat gaccttatgg gactttccta cttggcagta catctacgta    2400
ttagtcatcg ctattaccat ggtgatgcgg ttttggcagt acatcaatgg gcgtggatag    2460
cggtttgact cacggggatt tccaagtctc cacccccattg acgtcaatgg gagtttgttt   2520
tggcaccaaa atcaacggga cttttccaaaa tgtcgtaaca actccgcccc attgacgcaa   2580
atgggcggta ggcgtgtacg gtgggaggtc tatataggcg cgccgaactg aaaaaccaga   2640
aagttaactg gtaagtttag tcttttttgtc ttttatttca ggtcccggat ccggtggtgg   2700
tgcaaatcaa agaactgctc ctcagtggat gttgccttta cttctaggcc tgtacggaag   2760
tgttacttct gctctaaaag ctcctgcagg gaattcgcca ccatggtgag caagggcgag   2820
gagctgttca ccggggtggt gcccatcctg gtcgagctgg acggcgacgt aaacggccac   2880
aagttcagcg tgtccggcga gggcgagggc gatgccacct acggcaagct gaccctgaag   2940
ttcatctgca ccaccggcaa gctgcccgtg ccctggccca cctcgtgac cacccctgacc   3000
tacggcgtgc agtgcttcag ccgctacccc gaccacatga agcagcacga cttcttcaag   3060
tccgccatgc ccgaaggcta cgtccaggag cgcaccatct tcttcaagga cgacggcaac   3120
tacaagaccc gcgccgaggt gaagttcgag ggcgacaccc tggtgaaccg catcgagctg   3180
aagggcatcg acttcaagga ggacggcaac atcctggggc acaagctgga gtacaactac   3240
aacagccaca acgtctatat catggccgac aagcagaaga cggcatcaa ggtgaacttc    3300
aagatccgcc acaacatcga ggacggcagc gtgcagctcg ccgaccacta ccagcagaac   3360
accccccatcg cgacggccc cgtgctgctg cccgacaacc actacctgag cacccagtcc   3420
gccctgagca agacccccaa cgagaagcgc gatcacatgg tcctgctgga gttcgtgacc   3480
gccgccggga tcactctcgg catggacgag ctgtacaagt aatagactag tgtcgacaga   3540
tcttttaaaa aacctcccac acaattgttg ttgttaactt gtttattgca gcttataatg   3600
gttacaaata aagcaatagc atcacaaatt tcacaaataa agcattttt tcactgcatt    3660
ctagttgtgg tttgtccaaa ctcatcaatg tatcttatca tgtctgttta aacnnnnnnn   3720
nnnnnnnnnn nnnnnnnnnn nnnnnnnnnn nnnnnnnnnn nnnnnnnnnn nnnnnnnnnn   3780
nnnnnnnnnn nnnnnnnnnn nnnnnnnnnn nnnatttaaa taggaaccccc tagtgatgga   3840
gttggccact ccctctctgc gcgctcgctc gctcactgag gccgggcgac caaaggtcgc   3900
```

```
ccgacgcccg ggctttgccc gggcggcctc agtgagcgag cgagcgcgca gagagtatac   3960
atcgatgtga gttcgcgggt ggctggggg ccctgggctg cgaccgcccc cgaaccgcgt    4020
ctacgagcct tgcgggctcc gggtctttgc agtcgtatgg gggcagggta gctgttcccc   4080
gcaaggagag ctcaaggtca gcgctcggac ctggcggagc cccgcaccca ggctgtggcg   4140
ccctgtgcag ctccgccctt gcggcgccat ctgcccggag cctccttccc ctagtcccca   4200
gaaacaggag gtccctactc ccgcccgaga tcccgacccg gaccctaggt tgggggacgc   4260
tttcttttcct ttcgcgctct gcggggtcac gtgtcgcaga ggagcccctc ccccacggcc  4320
tccggcaccg caggcccggg gatgctagtg cgcagcgggt gcatccctgt ccggatgctg   4380
cgcctgcggt agagcggccg ccatgttgca accgggaagg aaatgaatgg gcagccgtta   4440
ggaaagcctg ccggtgacta accctgcgct cctgcctcga tgggtggagt cgcgtgtggc   4500
ggggaagtca ggtggagcga ggctagctgg cccgatttct cctccgggtg atgctttcc    4560
tagattattc tctggtaaat caaagaagtg ggtttatgga ggtcctcttg tgtcccctcc   4620
ccgcagaggt gtggtggctg tggcatggtg ccaagccggg agaagctgag tcatgggtag   4680
ttggaaaagg acatttccac cgcaaaatgg ccctctggt ggtggcccct tcctgcagcg    4740
ccggctcacc tcacggcccc gcccttcccc tgccagccta cgttgaccc gaccccaaag    4800
gccaggctgt aaatgtcacc gggaggattg ggtgtctggg cgcctcgggg aacctgccct   4860
tctccccatt ccgtcttccg gaaaccagat ctcccaccgc accctggtct gaggttaaat   4920
atagctgctg accttctgt agctgggggc ctgggctggg gctctctccc atcccttctc    4980
cccacacaca tgcacttacc tgtgctccca ctcctgattt ctggaaaaga gctaggaagg   5040
acaggcaact tggcaaatca aagccctggg actaggggt taaaatacag cttcccctct    5100
tcccacccgc cccagtctct gtccctttg taggagggac ttagagaagg ggtgggcttg    5160
ccctgtccag ttaatttctg acctttactc ctgcccttg agtttgatga tgctgagtgt    5220
acaagcgttt tctccctaaa gggtgcagct gagctaggca gcagcaagca ttcctggggt   5280
ggcatagtgg ggtggtgaat accatgtaca aagcttgtgc ccagactgtg ggtggcagtg   5340
ccccacatgg ccgcttctcc tggaagggct tcgtatgact gggggtgttg ggcagccctg   5400
gagccttcag ttgcagccat gccttaagcc aggccagcct ggcagggaag ctcaagggag   5460
ataaaattca acctcttggg ccctcctggg ggtaaggaga tgctgcattc gccctcttaa   5520
tggggaggtg gcctagggct gctcacatat tctggaggag cctcccctcc tcatgccttc   5580
ttgcctcttg tctcttaggc atgcaaaaga gtcgaataag ggcgacacaa aatttattct    5640
aaatgcataa taaatactga taacatctta tagtttgtat tatattttgt attatcgttg   5700
acatgtataa ttttgatatc aaaaactgat tttcccttta ttattttcga gatttatttt   5760
cttaattctc tttaacaaac tagaaatatt gtatatacaa aaaatcataa ataatagatg   5820
aatagtttaa ttataggtgt tcatcaatcg aaaaagcaac gtatcttatt taaagtgcgt   5880
tgcttttttc tcatttataa ggttaaataa ttctcatata tcaagcaaag tgacaggcgc   5940
ccttaaatat tctgacaaat gctctttccc taaactcccc ccataaaaaa acccgccgaa   6000
gcgggttttt acgttatttg cggattaacg attactcgtt atcagaaccg ccaggggc    6060
ccgagcttaa gactggccgt cgttttacaa cacagaaaga gtttgtagaa acgcaaaaag   6120
gccatccgtc aggggccttc tgcttagttt gatgcctggc agttccctac tctcgccttc   6180
cgcttcctcg ctcactgact cgctgcgctc ggtcgttcgg ctgcggcgag cggtatcagc   6240
tcactcaaag gcggtaatac ggttatccac agaatcaggg gataacgcag gaaagaacat   6300
```

```
gtgagcaaaa ggccagcaaa aggccaggaa ccgtaaaaag gccgcgttgc tggcgttttt    6360
ccataggctc cgccccctg acgagcatca caaaaatcga cgctcaagtc agaggtggcg     6420
aaacccgaca ggactataaa gataccaggc gtttccccct ggaagctccc tcgtgcgctc    6480
tcctgttccg accctgccgc ttaccggata cctgtccgcc tttctccctt cgggaagcgt    6540
ggcgctttct catagctcac gctgtaggta tctcagttcg gtgtaggtcg ttcgctccaa    6600
gctgggctgt gtgcacgaac ccccgttca gcccgaccgc tgcgccttat ccggtaacta    6660
tcgtcttgag tccaacccgg taagacacga cttatcgcca ctggcagcag ccactggtaa    6720
caggattagc agagcgaggt atgtaggcgg tgctacagag ttcttgaagt ggtgggctaa    6780
ctacggctac actagaagaa cagtatttgg tatctgcgct ctgctgaagc cagttacctt    6840
cggaaaaaga gttggtagct cttgatccgg caaacaaacc accgctggta gcggtggttt    6900
ttttgtttgc aagcagcaga ttacgcgcag aaaaaaagga tctcaagaag atcctttgat    6960
cttttctacg gggtctgacg ctcagtggaa cgacgcgcgc gtaactcacg ttaagggatt    7020
ttggtcatga gcttgcgccg tcccgtcaag tcagcgtaat gctacacttc ttcccgtatg    7080
cccaactttg tatagagagc cactgcggga tcgtcaccgt aatctgcttg cacgtagatt    7140
tataaagcac caagcgcgtt ggcctttagc ttgaggagat tgatgagcgc ggtggcaatg    7200
ccctgcctcc ggtgctcgcc ggagactgcg agatttaaga tatagatctc actacgcggc    7260
tgctcaaact tgggcagaac gtaagccgcg agagcgccaa caaccgcttc ttggtcgaag    7320
gcagcaagcg cgatgaatgt cttactacgg agcaagttcc cgaggtaatc ggagtccggc    7380
tgatgttggg agtaggtggc tacgtcaccg aactcacgac cgaaaagatc aagagcagcc    7440
cgttaggatt tgacttggtc agggccgagc ctattagtgc gaatgatgcc ttaacttgag    7500
ccacctaact ttgttttagg gcgactgccc tgctgcgtaa ttacgttgct gctcttaaat    7560
tacaaacatc gacccacggc gtaacgcgct tgctgcttgg atgcccgagg catagactgt    7620
acaaaaaaac agtcataaca agccatgaaa accgccactg cgccgttacc accgctgcgt    7680
tcggtcaagg ttctggacca gttgcgtgag cgcattttt tttcctcctc ggcgtttacg    7740
ccccgccctg ccactcatcg cagtactgtt gtaattcatt aagcattctg ccgacatgga    7800
agccatcaca gacggcatga tgaacctgaa tcgccagcgg catcagcacc ttgtcgcctt    7860
gcgtataata tttgcccata gtgaaaacgg gggcgaagaa gttgtccata ttggccacgt    7920
ttaaatcaaa actggtgaaa ctcacccagg gattggcgct gacgaaaaac atattctcaa    7980
taaacccctt                                                           7989
```

<210> SEQ ID NO 74
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MISC_FEATURE
<222> LOCATION: (1)..(3)
<223> OTHER INFORMATION: This region may or may not be present

<400> SEQUENCE: 74

Gly Ser Gly Glu Gly Arg Gly Ser Leu Leu Thr Cys Gly Asp Val Glu
1               5                   10                  15

Glu Asn Pro Gly Pro
            20

```
<210> SEQ ID NO 75
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(3)
<223> OTHER INFORMATION: This region may or may not be present

<400> SEQUENCE: 75

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 76
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(3)
<223> OTHER INFORMATION: This region may or may not be present

<400> SEQUENCE: 76

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(3)
<223> OTHER INFORMATION: This region may or may not be present

<400> SEQUENCE: 77

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```